US008829279B2

(12) United States Patent
Carozzi et al.

(10) Patent No.: US 8,829,279 B2
(45) Date of Patent: Sep. 9, 2014

(54) FAMILY OF PESTICIDAL PROTEINS AND METHODS FOR THEIR USE

(75) Inventors: Nadine Carozzi, Raleigh, NC (US); Michael G. Koziel, Raleigh, NC (US); Nicholas Duck, Apex, NC (US); Nalini M. Desai, Chapel Hill, NC (US); Rong Guo, Cary, NC (US); Daniel John Tomso, Bahama, NC (US); Rebekah Deter, Urbana, IL (US); Tracy Hargiss, Chapel Hill, NC (US)

(73) Assignee: Athenix Corporation, Morrisville, NC (US)

( * ) Notice: Subject to any disclaimer, the term of this patent is extended or adjusted under 35 U.S.C. 154(b) by 105 days.

(21) Appl. No.: 13/168,454

(22) Filed: Jun. 24, 2011

(65) Prior Publication Data

US 2011/0263488 A1 Oct. 27, 2011

Related U.S. Application Data

(63) Continuation of application No. 11/763,947, filed on Jun. 15, 2007, now abandoned.

(60) Provisional application No. 60/814,007, filed on Jun. 15, 2006, provisional application No. 60/813,859, filed on Jun. 15, 2006, provisional application No. 60/814,420, filed on Jun. 16, 2006, provisional application No. 60/814,212, filed on Jun. 16, 2006, provisional application No. 60/814,989, filed on Jun. 20, 2006.

(51) Int. Cl.

| | |
|---|---|
| ***A01H 5/00*** | (2006.01) |
| ***C12N 15/82*** | (2006.01) |
| ***C07K 14/325*** | (2006.01) |
| ***A01N 37/18*** | (2006.01) |

(52) U.S. Cl.

CPC .......... *C07K 14/325* (2013.01); *C12N 15/8286* (2013.01)

USPC .................... 800/302; 435/320.1; 435/252.3; 435/418; 514/4.5; 536/23.71

(58) Field of Classification Search

None

See application file for complete search history.

(56) References Cited

U.S. PATENT DOCUMENTS

2005/0049410 A1 3/2005 Carozzi et al.

FOREIGN PATENT DOCUMENTS

| | | |
|---|---|---|
| EP | 0382990 | 8/1990 |
| WO | 9308693 | 5/1993 |
| WO | 9535378 | 12/1995 |
| WO | 2007045160 | 4/2007 |

OTHER PUBLICATIONS

Chan et a1,1996, J. Biol. Chem. 271:14183-14187.*
Liu et al, 1996, Appl. Environ. Microbiol. 62:2174-2176.*
Guo et al (2004, Proc. Natl. Acad. Sci. USA 101:9205-9210.*
Argôlo-Filho et al, 2014, Insects 5:62-91.*
Partial European Search Report for European Patent Application 11173104.8, mailed Apr. 3, 2012.
NCBI Database Report for Accession No. AAB36661, Direct Submission Dec. 6, 1995.
NCBI Database Report for Accession No. AAC44124, Direct Submission Jan. 26, 1996.
NCBI Database Report for Accession No. AAF76376, Direct Submission Dec. 10, 1997.
NCBI Database Report for Accession No. AAO86513, Direct Submission Feb. 27, 2003.
NCBI Database Report for Accession No. AAV70918, Direct Submission Nov. 10, 2004.
NCBI Database Report for Accession No. CAA63374, Direct Submission Oct. 31, 1995.
NCBI Database Report for Accession No. CAA67205, Direct Submission Jun. 21, 1996.
NCBI Database Report for Accession No. CAA73761, Direct Submission May 20, 1997.
NCBI Database Report for Accession No. CAD30104, Direct Submission Apr. 19, 2002.
NCBI Database Report for Accession No. Q45729, Direct Submission Mar. 15, 2005.
NCBI Database Report for Accession No. ZP_00741579, Direct Submission Sep. 1, 2005.
UNIPROT Database Report for Accession No. Q58H99, Apr. 26, 2005.
Guo et al., (2004, Proc. Natl. Acad. Sci. USA 101:9205-9210).
Chan et al., 1996, J. Biol. Chem. 271:14183-14187.
Liu et al., Appl. Environ. Microbiol. 62:2174-2176, 1996.

* cited by examiner

*Primary Examiner* — Anne Kubelik

(57) ABSTRACT

Compositions and methods for conferring pesticidal activity to bacteria, plants, plant cells, tissues and seeds are provided. Compositions comprising a coding sequence for pesticidal polypeptides are provided. The coding sequences can be used in DNA constructs or expression cassettes for transformation and expression in plants and bacteria. Compositions also comprise transformed bacteria, plants, plant cells, tissues, and seeds. In particular, isolated pesticidal nucleic acid molecules are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2, 4, 6, 7, 9, 11, 13, 15, 17, 19, 21, 23, 25, 27, 29, 31, 33, 35, 37 or 61, the nucleotide sequence set forth in SEQ ID NO:1, 3, 5, 8, 10, 12, 14, 16, 18, 20, 22, 24, 26, 28, 30, 32, 34, 36, or 60, or the nucleotide sequence deposited in a bacterial host as Accession No. NRRL B-30961, B-30955, B-30956, B-30957, B-30958, B-30942, B-30939, B-30941, B-50047, B-30959, B-30960, B-30943, or B-50048, as well as variants and fragments thereof.

21 Claims, 4 Drawing Sheets

```
                    *        20         *        40         *        60         *
Axmi022   : MKRMKKKLASVVTCTLLAPMFLNGNVDTVFADSKTNQISSTQENQKN-EMDRKGLLGYYFKGKDFNNLTIFAPTR :  74
iotaB     : MNIQIKNVFSFLTLTAMISQTLSYNVYAQTTTQNDTNQKEEITNENT--LSSNGLMGYYFADEHFKDLELMAPIK :  73
Isp1a     : MKYMKKGLSSVVIGTLFASMFLNGNVNAVYANSKTNQIATTTQASKDNQIDREGLLGYYFKGKDFNDLTLFAPTR :  75
Isp1b     : MTYMKKKLVSVVTCALLAPMFLNGNVNPVYADNQTNQLSTAQENQEK-EVDRKGLLGYYFKGKEFNHLTLFAPTR :  74
vip1A(b)  : MKNMKKKLASVVTCMLLAPMFLNGNVNAVNADSKINQISTTQENQQK-EMDRKGLLGYYFKGKDFNNLTMFAPTR :  74
vip1A(c)  : MKNMKKKLASVVTCTLLAPMFLNGNVNAVYADSKTNQISTTQKNQQK-EMDRKGLLGYYFKGKDFSNLTMFAPTR :  74

               80         *       100         *       120         *       140         *
Axmi022   : ENTLIYDLETANSLLDKQQQTYQSIRWIGLIKSKKAGDFTFQLSDDEHAIIEIDGKVISQKGQKKQVVHLEKDKL : 149
iotaB     : NGDLKFEEKKVDKLLTEDNSSIKSIRWTGRIIPSEDGEYILST-DRNDVLMQINAKGDIAKTLK---VNMKKGQA : 144
Isp1a     : DNTLIYDQQTANTLVDQKHQEYHSIRWIGLIQSSATGDFTFKLSDDENAIIELDGKVISEKGNNKQSVHLEKGQL : 150
Isp1b     : DNTLIYDQQTVDFLLDKKQQEYQSIRWIGLIQSKETGDFTFNLSDDKNAIIEIDGKTISHKGQNKQVVHLEKGKL : 149
vip1A(b)  : DNTLMYDQQTANALLDKKQQEYQSIRWIGLIQRKETGDFTFNLSKDEQAIIEIDGKIISNKGKEKQVVHLEKEKL : 149
vip1A(c)  : DNTLIYDQQTANKLLDKKQQQYQSIRWIGLIQSKEKGDFTFNLSEDEQAIIEIDGKIISNKGKEKQVVHLEKEKL : 149

                   160         *       180         *       200         *       220
Axmi022   : VPIKIEYQSDKALNPDSQMFKELKLFKINSQKQSQQVQQDELRNPEFGKEKTQTYLKKASKSSLFSNKSKRDIDE : 224
iotaB     : YNIRIEIQDKNLGSIDNLSVPKLYWELNGNKTVIP---EENLFFRDYSKIDENDPFIP--NNNFFDVRFFSAAWE : 214
Isp1a     : VQIKIEYQSDDALHIDNKIFKELKLFKIDSQNHSQQVQQDELRNPEFNKKETQVFLKKASKTNLFTQKTKRDIDE : 225
Isp1b     : VPIKIEYQSDQIVNRDSKIFKEFKLFKVDSQQQSHQVQLDELRNPEFNKKETQQFLEKASKTNIFTQNMKRDEDA : 224
vip1A(b)  : VPIKIEYQSDTKFNIDSKTFKELKLFKIDSQNQSQ---QVQLRNPEFNKKESQEFLAKASKTNLFKQKMKRDIDE : 221
vip1A(c)  : VPIKIEYQSDTKFNIDSKTFKEFKLFKIDSQNQSQQVKRDELRNPEFNKKESREFLAKASKTNFFMQKMKRDIDE : 224

               *       240         *       260         *       280         *       300
Axmi022   : DIDEDTDTDGDAIPDVWEENGYTIKGRVAVKWDEGLADKGYKKFVSNPFRQHTAGDPYSDYEKASKDLDLSNAKE : 299
iotaB     : D--EDLDTDNDNIPDAYEKNGYTIKDSIAVKWNDSFAEQGYKKYVSSYLESNTAGDPYTDYQKASGSIDKAIKLE : 287
Isp1a     : D----TDTDGDSIPDVWEENGYTIQNKVAVKWDDSLASKGYQKFTSNPLEAHTVGDPYSDYEKAARDMPLSNAKE : 296
Isp1b     : -----TDTDGDSIPDLWEENGYTIQNKVAVKWDDSFAAKGYTKFVSNPFDSHTVGDPYTDYEKAARDLDLANAKE : 294
vip1A(b)  : D----TDTDGDSIPDLWEENGYTIQNKVAVKWDDSLASKGYTKFVSNPLDSHTVGDPYTDYEKAARDLDLSNAKE : 292
vip1A(c)  : D----TDTDGDSIPDLWEENGYTIQNKVAVKWDDKFAQQGYVKYLSSPYQAHTVGDPYTDWEKAAGDIPKSNAAA : 295

                    *       320         *       340         *       360         *
Axmi022   : TFNPLVAAFPSVNVSLENVTISKDENKTAEIASTSS----NNWSYTNTEGASIEAGIGPEG--LLSFGVSANYQH : 368
iotaB     : ARDPLVAAYPVVGVGMENLIISTNEHASSDQGKTVSRATTNSKTDANTVGVSISAGYQNGFTGNITTSYSHTTDN : 362
Isp1a     : TFNPLVAAFPSVNVSLEKVILSKNEDLSHSVESSQS----TNWSYTNTEGVNVNAGWSGL---GPSFGVSVNYQH : 364
Isp1b     : TFNPLVAAFPSVNVNLEKVILSPNEDLSNSVESHSS----TNWSYTNTEGASIEAGSGPL---GISYGVSANYQH : 362
vip1A(b)  : TFNPLVAAFPSVNVSMEKVILSPNENLSNSVESHSS----TNWSYTNTEGASIEAGGGPL---GLSFGVSVTYQH : 360
vip1A(c)  : TRNPLVAAFPSINVDMRKMILSKDSNLSNSAEAHSN----NSYTYANSEGASIEAGFGPK---GFSFGVSANYQH : 363
```

FIG. 1

```
                  380         *        400         *        420         *        440         *
Axmi022   : SETVAKEWGTTKGDATQYNTASAGYLNANVRYNNVGTAAIYDVKPTTNFVLDKTTLATIKAKENATADHIIPGNS :  443
iotaB     : STAVQDSNGESWNTGLSINKGESAYINANVRYYNTGTAPMYKVTPTTNLVLDGETLATIKAQDNQIGNNLSPNET :  437
Isp1a     : SETVANEWGSATNDGTHINGAESAYLNANVRYNNVGTGAIYETKPTTSFILDGTTIGTIKAKENTTALTILPDQS :  439
Isp1b     : SETVAKEWGTSTGNTSQFNTASAGYLNANVRYNNVGTGAIYEVKPTTGFVLDNDTVATITAKSNSTALSISPGES :  437
vip1A(b)  : SETVAQEWGTSTGNTSQFNTASAGYLNANVRYNNVGTGAIYDVKPTTSFVLNNNTIATITAKSNSTALRISPGDS :  435
vip1A(c)  : TETVGSDWGNSKSNTEQFNSASAGYLNANVHYNNVGTGGIYDAQPTTSFILQDSTIATITAKSNATALSIPSGDR :  438

                      460         *        480         *        500         *        520
Axmi022   : YPEKGKNGIAITTMDDFNSHPITLNKQQLDKLLYNVTPLMLETTQVEGTYKKKDVDGNIITGG-TWSGVTQQIEA :  517
iotaB     : YPKKGLSPLALNTMDQFNARLIPINYDQLKKLDSGK-QIKLETTQVSGNYGTKNSQGQIITEGNSWSNYISQIDS :  511
Isp1a     : YPEKGKNGIAINTMDDFNSRPIPLNKEQLNTYLSNKKPILLETDQVEGKYAIKDTNGNITIAG-DWNGITDEISA :  513
Isp1b     : YPKKGQNGIAINTMDDFNSHPITLNKQQLDQIFNNK-PLMLETNQADGVYKIKDTSGNIVTGG-EWNGVIQQIQA :  510
vip1A(b)  : YPEIGENAIAITSMDDFNSHPITLNKQQVNQLINNK-PIMLETDQTDGVYKIRDTHGNIVTGG-EWNGVTQQIKA :  508
vip1A(c)  : YPAS-KEGISLKTMDDFNSHPITLNKPQLDAVLNNE-VIKINTDQTDGRYGIIGVDGKAEIGD-RWSPIIDEIKG :  510

                *         540         *        560         *        580         *        600
Axmi022   : QTASIIVDTGE-GVSEKRIAAKDYDDPEDKTPSLTLKDALKIGYPEEIEE-KNDLLYYKGK---------IISES :  581
iotaB     : VSASIILDTGS-QTFERRVAAKEQGNPEDKTPEITIGEAIKKAFSATKNG---ELLYFNGIP---------IDES :  573
Isp1a     : KTASIIVDNGN-QMSEKRVAAKDYTNPEDKTPNLSVKEALKLAYPDEIEE-KDGLLFYNDQ---------PIFEA :  577
Isp1b     : KTASIIVDTGE-GVSEKRVAAKDYDNPEDKTPSLSLKEALKLGYPEEIKE-KDGLLYYNDK---------PIYES :  574
vip1A(b)  : KTASIIVDDGK-QVAEKRVAAKDYGHPEDKTPPLTLKDTLKLSYPDEIKE-TNGLLYYDDK---------PIYES :  572
vip1A(c)  : RTASIIIDPADGKALETRIAAKDYKNPEDKTPSLTIKEGLKIAYPESISEDKDGILFYEYKNDEGKVTKKQLSEE :  585

                    *         620         *        640         *        660         *
Axmi022   : SVMTFLDNGTSEKVKKQIEDKTGKFKDVQHLYDVKLTPGMNFTIKLASIYDSVDNFSG--------SQ-SLGALN :  647
iotaB     : CVELIFDDNTSEIIKEQLKYLDD----KK-IYNVKLERGMNILIKVPSYFTNFDEYNN--------FPASWSNID :  635
Isp1a     : SVQSYVDEYTAKQIRKQLNDSTGSFKDVKNLYDVKLEPKMNFTIKTSTLYDGGESDNT--------KIGNWYYTY :  644
Isp1b     : SVMTYLDENTAKEVKEQLNDITGKFKDVKQLFDVKLTPKMNFTIKLATLYDGAEDGSSPTDVGISSPLGEWAFKP :  649
vip1A(b)  : SVMTYLDENTAKEVKKQINDTTGKFKDVNHLYDVKLTPKMNFTIKMASLYDGAENNHN--------SLGTWYLTY :  639
vip1A(c)  : NIMPYLDEDTSKEFERQLSDGS-----AKGLYDIKLTPKMNITIRLATVTLGFDDQFS-----------AYPWEN :  644

                  680         *        700         *        720         *        740         *
Axmi022   : SISKVAGGNTGKNQYQSSSSN-----AYISLSSSTKGELNKNTTYYLSMYMRADADTEPTIELKGEKS-TIKSQK :  716
iotaB     : TKN-----QDGLQSVANKLSG--------ETKIIIPMSKLKPYKRYVFSGYSKDPSTSNSITVNIKSK--EQKTD :  695
Isp1a     : VVN---GGNTGKKQYRSANKG-----AFTELSTESKNKLKKNIDYYVSLYMKADSKVSVDIEIDGKQE-SIVTDN :  710
Isp1b     : DINNVEGGNTGKRQYQLSKNKDGYYYGMLALSPEVSNKLKKNYQYYISMSIKADAGVEPTVTVMDNLLNGIVDKK :  724
vip1A(b)  : NVA---GGNTGKRQYRSAHS-----CAHVALSSEAKKKLNQNANYYLSMYMKADSTTEPTIEVAGEKS-AITSKK :  705
vip1A(c)  : ATWSDKFGNLRLGSLAIPQES-----KYTIPKDKVKPNYDYLITGYIKHDFTTDNESLGIVAFTKKDNFEMWNMG :  714
```

FIG. 2

```
                   760         *       780         *       800         *       820
Axmi022   : VKLMNKG----YQRVDILVENTESNPIHQIYVHG--------MNKTNVYWDDVSLTEVSAIKQELPDISDKEIQR :  779
iotaB     : YLVPEKD----YTKFSYEFETTGKDSSDIEITLT---------SSGVIFLDNLSITELNSTPEILK--------- :  748
Isp1a     : ITLDHVG----YQRINILVPNLEGNEINTISIKG--------DGQTNVYWDDVSFVEVGAEEIEY---------- :  763
Isp1b     : LKLSSNG----YQRFDILVDNSESHPINVMVIDLGVSSQDYNNYSKNIYIDDITITEVSAMKVKN---------- :  785
vip1A(b)  : VKLMNQN----YQRVDILVKNSERNPMDKIYIRG--------NGTTNVYGDDVTIPEVSAINPAS---------- :  758
vip1A(c)  : TSIFSQNSGGEFKKFTIKTQNISGDYILDSIQLMK---RNNDVNKIDSYLDDISIIPIGPNKSR----------- :  775

                *       840         *       860         *       880         *       900
Axmi022   : AHTFKKEQLSLDGKYMNELTLHVDSLKDKNNKPVQFSYKVKDGEKDLGTKSYTPDKQGNININFLDYNRGFGISK :  854
iotaB     : ---------E--------------------------------------PEIKVPSDQEILDAHNKYYADIKLDTN :  776
Isp1a     : --------------------------------------------------KDPVPQFDIIEGDFDFFGDPLAVKY :  788
Isp1b     : --------------------------------------------------------------------------- :    -
vip1A(b)  : --------------------------------------------------LSDEEIQEIFKDSTIEYGNPSFVAD :  783
vip1A(c)  : --------------------------------------------------------------------------- :    -

                    *       920         *       940         *       960         *
Axmi022   : DHKIQIYAVRKDQEVKVAELKNYNMSGTIRFSNDGESGLPEIYGYIFMTPEGQYPVSPVGGIHQIWSRYYTSTYK :  929
iotaB     : TGNTYIDGIYFEPTQTNKEALDYIQKYRVEATLQYSG-----------------FKDIGTKDKEIRNYLGDQNQP :  834
Isp1a     : H---------DATYFIDSPLITQTPGTFSFTYKVIGE--------------------------QTKTVLDSGSGK :  828
Isp1b     : --------------------------------------------------------------------------- :    -
vip1A(b)  : ----------AVTFKNIKPLQNYVKEYEIYHKSHR---------------------------------YEKKTVF :  815
vip1A(c)  : --------------------------------------------------------------------------- :    -

             980         *       1000        *       1020        *       1040
Axmi022   : WSTQYSYDFASFNSDIKTVHFNGYVKELDDTNGDDILAYLENKYESHGLEGSVVLEGDERGSNVTVEYHIKLK- : 1002
iotaB     : KTNYINFRSYFTSGENVMTYKKLRIYAVTPDNRELLVLSVN--------------------------------- :  875
Isp1a     : NANRINLDFKNVKSDRSFLYTLSCKDDLWGSTRTAVVRIFAVD------------------------------- :  871
Isp1b     : -------------------------------------------------------------------------- :    -
vip1A(b)  : DIMGVHYEYSIAREQKKAA------------------------------------------------------- :  834
vip1A(c)  : -------------------------------------------------------------------------- :    -
```

FIG. 3

```
                       *        20         *        40         *        60         *        80
Axmi023          : -----------------MHKQTIKNLSICIATVSLLGQYFISSTTVYAAENQINSLNLKVEQILDFGRDKEKAKEWADTYF :  64
isp2a            : ---MIVIIFTNVKGGNELKKNFYKNLICMSALLLAMPISSNVTYAYGSE--KVDYLVKTTNNTEDFKEDKEKAKEWGKE-- :  74
Vip2Ab-AAO86513  : MKRMEGKLFMVSTKLQAVTKAVLLSTVLSISLLNNEVIKAEQLNMNSQNKYTNFENLKITDKVEDFKEDKEKAKEWGKE-- :  79
iotaA            : --------------MKKVNKSISVFLILYLILTSSFPSYTYAQDLQIAS--NYITDRAFIERPEDFLKDKENAIQWEKKEA :  65
axmi041          : -------------------------------------------------------MNKLIKVEENKTPQTQTIYTSFN-A :  24

                       *       100         *       120         *       140         *       160
Axmi023          : KDWKKTINNEQK---KLLNDIKRLTQLNEKIGKFDQNSEMFSKKDKEDIDKIDKALNNKNAKLTKSLNVYKNLNGKDLGYV : 142
isp2a            : KEKEWKLTVTEKTRMNNFLDNKNDIKKNYKEITFSMAGSFED--EIKDLKEIDKMFDK--ANLSSSIVTYKNVEPSTIGFN : 151
Vip2Ab-AAO86513  : KEKEWKLTATEKGKMNNFLDNKNDIKTNYKEITFSMAGSFED--EIKDLKEIDKIFDK--ANLSSPIITYKNVEPATIGFN : 156
iotaA            : ERVEKNLDTLEKEALELYKKDSEQISNYSQTRQYFYDYQIESNPREKEYKNLRNAISK--NKIDKPINVYYFESPEKFAFN : 144
axmi041          : TDIGFASNSDIKDGFLNFDEQKINTIIKYLKMGNFPDFRVGNLLPSEPHSTVNAFFTQ--RRILIELEVPAGTYLAHLGNG : 103

                       *       180         *       200         *       220         *       240
Axmi023          : EGYFNVPNSPNKIDRTKYNKLVNEFKYGAINTFMNTDLTQDTTNKSTPILLSLKLPKGTK----IG-----QLNEEHIITD : 214
isp2a            : KPLTEG--NTINTDVQAQFKEQFLGKDIKFDSYLDTHLTAQNVSSKERIILQVTVPSGKGSTIPTKAGVILNNNEYKMLID : 230
Vip2Ab-AAO86513  : KSLTEG--NTINSDAMAQFKEQFLDRDIKFDSYLDTHLTVQQVSSKERVILKVKVPSGKGSTTPTKAGIILNNSEYKMLID : 235
iotaA            : KEIRTENQNEISLEKFNELKETIQDKLFKQDGFKDVSLYEPGNGDEKPTPLLIHLKLPKN----TGMLPYINSNDVKTLIE : 221
axmi041          : QTIFPLDYGMKLTDQAGTIIGKQVLKLKALVVPKDDILKETNVQMFILYKSISNILRSKG--FDEKDIESLKAQCMFIFSG : 182

                       *       260         *       280         *       300         *       320
Axmi023          : RNLGIEIKKTSIIVEKGREVIKLEGDVVPKTKIQEKVKKAESDLNQKFKEITGLKQNLLSLKIDNLYTSASIDR-TETVIK : 294
isp2a            : NGYVLHVDNISKVVKKGYECLQIQGTLKKSLDFKNDINAEAHRWGMKNYEGWAKNLTDPQREALDGYARQDYKQINDYLRN : 311
Vip2Ab-AAO86513  : NGYMVHVDKVSKVVKKGVECLQVEGTLKKSLDFKNDINAGAHSWGMKNYEEWAKDLTDLQREALDGYARQDYKEINNYLRN : 316
iotaA            : QDYSIKIDKIVRIVIEGKQYIKAEASIVNSLDFKDDVSKG-DLWGKENYSDWSNKLTPNELADVNDYMRGGYTAINNYLIS : 301
axmi041          : PNVLLAIENSQSAMLDLLTNEYIPNNLLRDTLLKLKQHAGIAFLSVPICMDKAIAGSTS---------FP----------K : 244

                       *       340         *       360         *       380         *       400
Axmi023          : QLVSNVPNNLLLNIMKNMNNKT-LFTITDKILIPGKEGVLGYYDTISKTLFIQIDHLGHKNNEGNDTNTLLHEFGHAVDHL : 374
isp2a            : QG--GSGNEKLDTQIKNISEALEKQPIPENITVYRWCGMAEFGYQISDP------LPSLKEMEEKFLNTMKEDKGYMSTSL : 384
Vip2Ab-AAO86513  : QG--GNGNEKLDAQIKNISDALGKKPIPENITVYRWCGMPEFGYQISDP------LPSLKDFEEQFLNTIKEDKGYMSTSL : 389
iotaA            : NGPLNNPNPELDSKVNNIENALKLTPIPSNLIVYRRSGPQEFGLTLTSPEYDFNKIENIDAFKEKWEGKVITYPNFISTSI : 382
axmi041          : NG--DKPNMSIIPTHQSLLSQLDEHISTSRTLHHEFGHVIDREILNGISS-----TPEFKALFEKEKNNITEINTYANYAK : 318

                       *       420         *       440         *       460         *       480
Axmi023          : AKGEIQSKSS-KFIEIFNRERGNITIEPYIKQDAAEFFAGVFNYLYSPKISDREQIQKEAPDACKFIRNLIHGLH-  : 448
isp2a            : SSERLSAFGSRKFILRLQVPKGSTGAYLSAIGGFASEKEILIDKDSNYHIDKITEVVIKGVKRYVVDATLLTK---  : 457
Vip2Ab-AAO86513  : SSERLAAFGSRKIILRLQVPKGSTGAYLSAIGGFANEKEILLDKDSKYHIDKVTEVIIKGVKRYVVDATLLTN---  : 462
iotaA            : GSVNMSAFAKRKIILRINIPKDSPGAYLSAIPGYAGEYEVLLNHGSKFKINKVDSYKDGTVTKLILDATLIN----  : 454
axmi041          : TNSQEFFAEVFKSMVSMGNEKYPSSYYRDSIEKEAPETVRFIKDKLKEKGYVL-----------------------  : 371
```

FIG. 4

SEQUENCE LISTING

```
<160> NUMBER OF SEQ ID NOS: 63

<210> SEQ ID NO 1
<211> LENGTH: 957
<212> TYPE: DNA
<213> ORGANISM: Bacillus thuringiensis
<220> FEATURE:
<221> NAME/KEY: CDS
<222> LOCATION: (1)...(957)

<400> SEQUENCE: 1

atg aat aaa aaa cct atg gta gcg ttg ata tta gcc act tcg att ggt      48
Met Asn Lys Lys Pro Met Val Ala Leu Ile Leu Ala Thr Ser Ile Gly
 1               5                  10                  15

ata cct tgt aca ttt aca cct gga agt gca tta gca gca gaa aat att      96
Ile Pro Cys Thr Phe Thr Pro Gly Ser Ala Leu Ala Ala Glu Asn Ile
            20                  25                  30

cag act agt gtt aat gaa aat gta aaa gtt ggt att aca gat gtt caa     144
Gln Thr Ser Val Asn Glu Asn Val Lys Val Gly Ile Thr Asp Val Gln
        35                  40                  45

tct gaa ttg aat aag ata gga gac tat tat tat agt aat aac tta gca     192
Ser Glu Leu Asn Lys Ile Gly Asp Tyr Tyr Tyr Ser Asn Asn Leu Ala
    50                  55                  60

aat acg act ata aaa cct cct cat cat tgg gat tat aca ctt aaa aaa     240
Asn Thr Thr Ile Lys Pro Pro His His Trp Asp Tyr Thr Leu Lys Lys
65                  70                  75                  80

aat cct gat aaa gtt gga aca aat ttg gat ttt agt att act ggt act     288
Asn Pro Asp Lys Val Gly Thr Asn Leu Asp Phe Ser Ile Thr Gly Thr
                85                  90                  95

gct agt aaa cta aat tat gat agt gta act cct ata tac att ggg cat     336
Ala Ser Lys Leu Asn Tyr Asp Ser Val Thr Pro Ile Tyr Ile Gly His
            100                 105                 110

aat gaa ttt aat aat gat tca gat cag cct caa aaa ttt aca act tct     384
Asn Glu Phe Asn Asn Asp Ser Asp Gln Pro Gln Lys Phe Thr Thr Ser
        115                 120                 125

aaa ttt act aaa gct gta aca gag gga aca aca agt acc gta aca aat     432
```

-continued

```
Lys Phe Thr Lys Ala Val Thr Glu Gly Thr Thr Ser Thr Val Thr Asn
    130                 135                 140

gga ttt aga tta gga aat cca ggt tta aac tta ttt act att cca tta      480
Gly Phe Arg Leu Gly Asn Pro Gly Leu Asn Leu Phe Thr Ile Pro Leu
145                 150                 155                 160

att tta agt gat ggt atg aaa att aat gcg gaa ttt aac tct tct act      528
Ile Leu Ser Asp Gly Met Lys Ile Asn Ala Glu Phe Asn Ser Ser Thr
                165                 170                 175

tca gaa tct caa caa aaa tcg gaa aca aaa aca ata gaa gca tca cct      576
Ser Glu Ser Gln Gln Lys Ser Glu Thr Lys Thr Ile Glu Ala Ser Pro
            180                 185                 190

caa aac ata gaa gtt cca gca cat aaa aaa tat aaa gta gat gtt gta      624
Gln Asn Ile Glu Val Pro Ala His Lys Lys Tyr Lys Val Asp Val Val
        195                 200                 205

ttg gaa caa aca agc tat tgg gca gat gtt aca ttt aca ggt gaa gga      672
Leu Glu Gln Thr Ser Tyr Trp Ala Asp Val Thr Phe Thr Gly Glu Gly
    210                 215                 220

att aat ctt aat act act ata aat gca act gga ata cat act ggg cat      720
Ile Asn Leu Asn Thr Thr Ile Asn Ala Thr Gly Ile His Thr Gly His
225                 230                 235                 240

atg gga atg cag gag tca aga aaa ttt tct tgg aac aaa aat acc att      768
Met Gly Met Gln Glu Ser Arg Lys Phe Ser Trp Asn Lys Asn Thr Ile
                245                 250                 255

gaa tta ttt aat gga cta aaa caa gag caa aaa aat aat ata cat ggg      816
Glu Leu Phe Asn Gly Leu Lys Gln Glu Gln Lys Asn Asn Ile His Gly
            260                 265                 270

att aaa ttt agt aat ggg aaa atg aat gca aac gga aca ggt aaa gtt      864
Ile Lys Phe Ser Asn Gly Lys Met Asn Ala Asn Gly Thr Gly Lys Val
        275                 280                 285

gaa ggt att ttt ggt agt aat cta gtt gta aag gta aat gat gtt aca      912
Glu Gly Ile Phe Gly Ser Asn Leu Val Val Lys Val Asn Asp Val Thr
    290                 295                 300

gat cca tta aat cct atc cta gta atg act aaa agt tta aaa taa          957
Asp Pro Leu Asn Pro Ile Leu Val Met Thr Lys Ser Leu Lys
305                 310                 315


<210> SEQ ID NO 2
<211> LENGTH: 318
<212> TYPE: PRT
<213> ORGANISM: Bacillus thuringiensis

<400> SEQUENCE: 2

Met Asn Lys Lys Pro Met Val Ala Leu Ile Leu Ala Thr Ser Ile Gly
 1               5                  10                  15

Ile Pro Cys Thr Phe Thr Pro Gly Ser Ala Leu Ala Ala Glu Asn Ile
            20                  25                  30

Gln Thr Ser Val Asn Glu Asn Val Lys Val Gly Ile Thr Asp Val Gln
        35                  40                  45

Ser Glu Leu Asn Lys Ile Gly Asp Tyr Tyr Tyr Ser Asn Asn Leu Ala
    50                  55                  60

Asn Thr Thr Ile Lys Pro Pro His His Trp Asp Tyr Thr Leu Lys Lys
65                  70                  75                  80

Asn Pro Asp Lys Val Gly Thr Asn Leu Asp Phe Ser Ile Thr Gly Thr
                85                  90                  95

Ala Ser Lys Leu Asn Tyr Asp Ser Val Thr Pro Ile Tyr Ile Gly His
            100                 105                 110

Asn Glu Phe Asn Asn Asp Ser Asp Gln Pro Gln Lys Phe Thr Thr Ser
        115                 120                 125
```

```
Lys Phe Thr Lys Ala Val Thr Glu Gly Thr Thr Ser Thr Val Thr Asn
    130                 135                 140

Gly Phe Arg Leu Gly Asn Pro Gly Leu Asn Leu Phe Thr Ile Pro Leu
145                 150                 155                 160

Ile Leu Ser Asp Gly Met Lys Ile Asn Ala Glu Phe Asn Ser Ser Thr
                165                 170                 175

Ser Glu Ser Gln Gln Lys Ser Glu Thr Lys Thr Ile Glu Ala Ser Pro
            180                 185                 190

Gln Asn Ile Glu Val Pro Ala His Lys Lys Tyr Lys Val Asp Val Val
        195                 200                 205

Leu Glu Gln Thr Ser Tyr Trp Ala Asp Val Thr Phe Thr Gly Glu Gly
    210                 215                 220

Ile Asn Leu Asn Thr Thr Ile Asn Ala Thr Gly Ile His Thr Gly His
225                 230                 235                 240

Met Gly Met Gln Glu Ser Arg Lys Phe Ser Trp Asn Lys Asn Thr Ile
                245                 250                 255

Glu Leu Phe Asn Gly Leu Lys Gln Glu Gln Lys Asn Asn Ile His Gly
            260                 265                 270

Ile Lys Phe Ser Asn Gly Lys Met Asn Ala Asn Gly Thr Gly Lys Val
        275                 280                 285

Glu Gly Ile Phe Gly Ser Asn Leu Val Val Lys Val Asn Asp Val Thr
    290                 295                 300

Asp Pro Leu Asn Pro Ile Leu Val Met Thr Lys Ser Leu Lys
305                 310                 315


<210> SEQ ID NO 3
<211> LENGTH: 927
<212> TYPE: DNA
<213> ORGANISM: Bacillus thuringiensis
<220> FEATURE:
<221> NAME/KEY: CDS
<222> LOCATION: (1)...(927)

<400> SEQUENCE: 3

atg att aat gta aac agt ggt aag gtt ata gat ata tca gga aat tca       48
Met Ile Asn Val Asn Ser Gly Lys Val Ile Asp Ile Ser Gly Asn Ser
 1               5                  10                  15

aca gca aat att caa caa tat gag tgg cgt ggt gat tta cca tct gaa       96
Thr Ala Asn Ile Gln Gln Tyr Glu Trp Arg Gly Asp Leu Pro Ser Glu
            20                  25                  30

tat tgg tac ttt cat cgt gaa gcg gat ggg tat tat gtt att gaa tca      144
Tyr Trp Tyr Phe His Arg Glu Ala Asp Gly Tyr Tyr Val Ile Glu Ser
        35                  40                  45

aaa ctt agt gga aag gta tta gac ata aaa gga aat tca aca gca aat      192
Lys Leu Ser Gly Lys Val Leu Asp Ile Lys Gly Asn Ser Thr Ala Asn
     50                  55                  60

aat gca aat gtt cag caa tat caa ttt ata caa aat gca cct gct gaa      240
Asn Ala Asn Val Gln Gln Tyr Gln Phe Ile Gln Asn Ala Pro Ala Glu
 65                  70                  75                  80

aga ttt gct gct gaa gaa gcg gga agc gtc tct ctc cca tca ata aat      288
Arg Phe Ala Ala Glu Glu Ala Gly Ser Val Ser Leu Pro Ser Ile Asn
                85                  90                  95

acg aaa cca tta tca cca gta cca gaa tat aaa acg att aat gat caa      336
Thr Lys Pro Leu Ser Pro Val Pro Glu Tyr Lys Thr Ile Asn Asp Gln
            100                 105                 110

ctt cca gaa gaa acg gaa cgt gta gta aca gct ttt aca ata gtt ccg      384
Leu Pro Glu Glu Thr Glu Arg Val Val Thr Ala Phe Thr Ile Val Pro
        115                 120                 125
```

```
tgt atc tca gta aaa gat cca cat tat ggt gga gat act gct aaa caa      432
Cys Ile Ser Val Lys Asp Pro His Tyr Gly Gly Asp Thr Ala Lys Gln
    130                 135                 140

ata aga gaa aat cct tat tac atg gtt gta aaa aaa caa tgg tgg aaa      480
Ile Arg Glu Asn Pro Tyr Tyr Met Val Val Lys Lys Gln Trp Trp Lys
145                 150                 155                 160

aaa caa gaa tct tat gtt tta gct cct agt gaa acg tat act ttt gaa      528
Lys Gln Glu Ser Tyr Val Leu Ala Pro Ser Glu Thr Tyr Thr Phe Glu
                165                 170                 175

aca aaa act ggt ata aaa gta att gat caa gaa act gct aca agg aca      576
Thr Lys Thr Gly Ile Lys Val Ile Asp Gln Glu Thr Ala Thr Arg Thr
            180                 185                 190

gta agt tgg agc att ggt gct gat atg gga ttt agt ttc aaa gga ttt      624
Val Ser Trp Ser Ile Gly Ala Asp Met Gly Phe Ser Phe Lys Gly Phe
        195                 200                 205

tca tta gga atg tcc act caa tat tca aca caa tta cag act act ata      672
Ser Leu Gly Met Ser Thr Gln Tyr Ser Thr Gln Leu Gln Thr Thr Ile
    210                 215                 220

agt cat aca act gaa caa tta aaa gaa gaa aca aac agg cac gaa ata      720
Ser His Thr Thr Glu Gln Leu Lys Glu Glu Thr Asn Arg His Glu Ile
225                 230                 235                 240

aag aat cca ttt tca gag aga atg gcg tat tct aga tat gta tta gcg      768
Lys Asn Pro Phe Ser Glu Arg Met Ala Tyr Ser Arg Tyr Val Leu Ala
                245                 250                 255

aca gaa tat tct gtc caa aga aaa aat ggt aca atc gta aat tct cct      816
Thr Glu Tyr Ser Val Gln Arg Lys Asn Gly Thr Ile Val Asn Ser Pro
            260                 265                 270

tgg act atg acc gat aag aca aaa gca cat gct gta act ttt cca aaa      864
Trp Thr Met Thr Asp Lys Thr Lys Ala His Ala Val Thr Phe Pro Lys
        275                 280                 285

tcc aca gga aat gca tta gat gaa aat aca aag gaa cta tca aat agt      912
Ser Thr Gly Asn Ala Leu Asp Glu Asn Thr Lys Glu Leu Ser Asn Ser
    290                 295                 300

gaa agt gta aac taa                                                  927
Glu Ser Val Asn
305


<210> SEQ ID NO 4
<211> LENGTH: 308
<212> TYPE: PRT
<213> ORGANISM: Bacillus thuringiensis

<400> SEQUENCE: 4

Met Ile Asn Val Asn Ser Gly Lys Val Ile Asp Ile Ser Gly Asn Ser
 1               5                  10                  15

Thr Ala Asn Ile Gln Gln Tyr Glu Trp Arg Gly Asp Leu Pro Ser Glu
            20                  25                  30

Tyr Trp Tyr Phe His Arg Glu Ala Asp Gly Tyr Tyr Val Ile Glu Ser
        35                  40                  45

Lys Leu Ser Gly Lys Val Leu Asp Ile Lys Gly Asn Ser Thr Ala Asn
    50                  55                  60

Asn Ala Asn Val Gln Gln Tyr Gln Phe Ile Gln Asn Ala Pro Ala Glu
65                  70                  75                  80

Arg Phe Ala Ala Glu Glu Ala Gly Ser Val Ser Leu Pro Ser Ile Asn
                85                  90                  95

Thr Lys Pro Leu Ser Pro Val Pro Glu Tyr Lys Thr Ile Asn Asp Gln
            100                 105                 110

Leu Pro Glu Glu Thr Glu Arg Val Val Thr Ala Phe Thr Ile Val Pro
        115                 120                 125
```

-continued

```
Cys Ile Ser Val Lys Asp Pro His Tyr Gly Gly Asp Thr Ala Lys Gln
    130                 135                 140

Ile Arg Glu Asn Pro Tyr Tyr Met Val Val Lys Lys Gln Trp Trp Lys
145                 150                 155                 160

Lys Gln Glu Ser Tyr Val Leu Ala Pro Ser Glu Thr Tyr Thr Phe Glu
                165                 170                 175

Thr Lys Thr Gly Ile Lys Val Ile Asp Gln Glu Thr Ala Thr Arg Thr
            180                 185                 190

Val Ser Trp Ser Ile Gly Ala Asp Met Gly Phe Ser Phe Lys Gly Phe
        195                 200                 205

Ser Leu Gly Met Ser Thr Gln Tyr Ser Thr Gln Leu Gln Thr Thr Ile
    210                 215                 220

Ser His Thr Thr Glu Gln Leu Lys Glu Glu Thr Asn Arg His Glu Ile
225                 230                 235                 240

Lys Asn Pro Phe Ser Glu Arg Met Ala Tyr Ser Arg Tyr Val Leu Ala
                245                 250                 255

Thr Glu Tyr Ser Val Gln Arg Lys Asn Gly Thr Ile Val Asn Ser Pro
            260                 265                 270

Trp Thr Met Thr Asp Lys Thr Lys Ala His Ala Val Thr Phe Pro Lys
        275                 280                 285

Ser Thr Gly Asn Ala Leu Asp Glu Asn Thr Lys Glu Leu Ser Asn Ser
    290                 295                 300

Glu Ser Val Asn
305


<210> SEQ ID NO 5
<211> LENGTH: 1017
<212> TYPE: DNA
<213> ORGANISM: Bacillus thuringiensis
<220> FEATURE:
<221> NAME/KEY: CDS
<222> LOCATION: (1)...(1017)

<400> SEQUENCE: 5

atg gat aaa aaa ata aca aaa gca gcg tta agc atg ata atg ggt ata       48
Met Asp Lys Lys Ile Thr Lys Ala Ala Leu Ser Met Ile Met Gly Ile
 1               5                  10                  15

agt gtt tta tca tct cct tta gct gta gcc gca aaa aca gag aat aat       96
Ser Val Leu Ser Ser Pro Leu Ala Val Ala Ala Lys Thr Glu Asn Asn
            20                  25                  30

aaa gaa caa cac gta att aca cag ttt aat cag aga gaa aat aag ttc      144
Lys Glu Gln His Val Ile Thr Gln Phe Asn Gln Arg Glu Asn Lys Phe
        35                  40                  45

cct gat gta gga cag ggg att caa tgg tta tct caa ttt tat gga aaa      192
Pro Asp Val Gly Gln Gly Ile Gln Trp Leu Ser Gln Phe Tyr Gly Lys
     50                  55                  60

tct tta agg aat aat ggt gaa gga tac tcc tta ggt cag gat gta atg      240
Ser Leu Arg Asn Asn Gly Glu Gly Tyr Ser Leu Gly Gln Asp Val Met
 65                  70                  75                  80

agc tat ttt cta gaa gta aaa aat tct tat ggt caa ttg gca atg gaa      288
Ser Tyr Phe Leu Glu Val Lys Asn Ser Tyr Gly Gln Leu Ala Met Glu
                85                  90                  95

cct caa gta ata agc act aca cct ctt tgg gct ggc caa agt gac ttg      336
Pro Gln Val Ile Ser Thr Thr Pro Leu Trp Ala Gly Gln Ser Asp Leu
            100                 105                 110

gaa aat gca act gat gat gaa caa act tta aat tcc aca gaa ttt aaa      384
Glu Asn Ala Thr Asp Asp Glu Gln Thr Leu Asn Ser Thr Glu Phe Lys
        115                 120                 125
```

```
aaa acg tat tct aat aca aca acc acc tct aca gaa aat gga ttt atg      432
Lys Thr Tyr Ser Asn Thr Thr Thr Thr Ser Thr Glu Asn Gly Phe Met
    130                 135                 140

ata ggg cag gaa acc gaa ggg aaa gtt ggt ata ccc ttt gtc gca gaa      480
Ile Gly Gln Glu Thr Glu Gly Lys Val Gly Ile Pro Phe Val Ala Glu
145                 150                 155                 160

gga aaa gtc acc ata aaa act gaa tat aat ttt aat cat act aat ggg      528
Gly Lys Val Thr Ile Lys Thr Glu Tyr Asn Phe Asn His Thr Asn Gly
                165                 170                 175

tat gaa aca tct gag agt gta gag tat att gct cct tct caa tct att      576
Tyr Glu Thr Ser Glu Ser Val Glu Tyr Ile Ala Pro Ser Gln Ser Ile
            180                 185                 190

aag gta cca ccg cat act att gcc cga gtg aca gca tta tta gat gtg      624
Lys Val Pro Pro His Thr Ile Ala Arg Val Thr Ala Leu Leu Asp Val
        195                 200                 205

aaa aaa att aaa ggg aag atg cat cta tat tca gaa att gga ctt aat      672
Lys Lys Ile Lys Gly Lys Met His Leu Tyr Ser Glu Ile Gly Leu Asn
    210                 215                 220

aaa gat tat ggt tac gat atg gta cca ctt gtt tat aaa tat gga ggt      720
Lys Asp Tyr Gly Tyr Asp Met Val Pro Leu Val Tyr Lys Tyr Gly Gly
225                 230                 235                 240

cca ttt aaa tat gta acc tta ggt aca tta tat gac gag ggc tat aag      768
Pro Phe Lys Tyr Val Thr Leu Gly Thr Leu Tyr Asp Glu Gly Tyr Lys
                245                 250                 255

cag gca aaa tta gat tat tct aat atg gga aat gtt ata ccg gaa gaa      816
Gln Ala Lys Leu Asp Tyr Ser Asn Met Gly Asn Val Ile Pro Glu Glu
            260                 265                 270

att gag act gtt tcg aaa agt aac aat ccc aac cat tta tta gca agt      864
Ile Glu Thr Val Ser Lys Ser Asn Asn Pro Asn His Leu Leu Ala Ser
        275                 280                 285

gga gta gga atc ttt gaa tca gaa tac gga agt gta ttt aat gtt aaa      912
Gly Val Gly Ile Phe Glu Ser Glu Tyr Gly Ser Val Phe Asn Val Lys
    290                 295                 300

gtt gaa tat ata gat att aaa aat aaa aag att aaa aaa aca gag aat      960
Val Glu Tyr Ile Asp Ile Lys Asn Lys Lys Ile Lys Lys Thr Glu Asn
305                 310                 315                 320

ttc act atc gaa ccg aca ata gtc cct gtt gaa cag aag aat acg aat     1008
Phe Thr Ile Glu Pro Thr Ile Val Pro Val Glu Gln Lys Asn Thr Asn
                325                 330                 335

aca aaa taa                                                         1017
Thr Lys


<210> SEQ ID NO 6
<211> LENGTH: 338
<212> TYPE: PRT
<213> ORGANISM: Bacillus thuringiensis

<400> SEQUENCE: 6

Met Asp Lys Lys Ile Thr Lys Ala Ala Leu Ser Met Ile Met Gly Ile
 1               5                  10                  15

Ser Val Leu Ser Ser Pro Leu Ala Val Ala Ala Lys Thr Glu Asn Asn
            20                  25                  30

Lys Glu Gln His Val Ile Thr Gln Phe Asn Gln Arg Glu Asn Lys Phe
        35                  40                  45

Pro Asp Val Gly Gln Gly Ile Gln Trp Leu Ser Gln Phe Tyr Gly Lys
    50                  55                  60

Ser Leu Arg Asn Asn Gly Glu Gly Tyr Ser Leu Gly Gln Asp Val Met
65                  70                  75                  80
```

```
Ser Tyr Phe Leu Glu Val Lys Asn Ser Tyr Gly Gln Leu Ala Met Glu
                85                  90                  95

Pro Gln Val Ile Ser Thr Thr Pro Leu Trp Ala Gly Gln Ser Asp Leu
            100                 105                 110

Glu Asn Ala Thr Asp Asp Glu Gln Thr Leu Asn Ser Thr Glu Phe Lys
        115                 120                 125

Lys Thr Tyr Ser Asn Thr Thr Thr Thr Ser Thr Glu Asn Gly Phe Met
    130                 135                 140

Ile Gly Gln Glu Thr Glu Gly Lys Val Gly Ile Pro Phe Val Ala Glu
145                 150                 155                 160

Gly Lys Val Thr Ile Lys Thr Glu Tyr Asn Phe Asn His Thr Asn Gly
                165                 170                 175

Tyr Glu Thr Ser Glu Ser Val Glu Tyr Ile Ala Pro Ser Gln Ser Ile
            180                 185                 190

Lys Val Pro Pro His Thr Ile Ala Arg Val Thr Ala Leu Leu Asp Val
        195                 200                 205

Lys Lys Ile Lys Gly Lys Met His Leu Tyr Ser Glu Ile Gly Leu Asn
    210                 215                 220

Lys Asp Tyr Gly Tyr Asp Met Val Pro Leu Val Tyr Lys Tyr Gly Gly
225                 230                 235                 240

Pro Phe Lys Tyr Val Thr Leu Gly Thr Leu Tyr Asp Glu Gly Tyr Lys
                245                 250                 255

Gln Ala Lys Leu Asp Tyr Ser Asn Met Gly Asn Val Ile Pro Glu Glu
            260                 265                 270

Ile Glu Thr Val Ser Lys Ser Asn Asn Pro Asn His Leu Leu Ala Ser
        275                 280                 285

Gly Val Gly Ile Phe Glu Ser Glu Tyr Gly Ser Val Phe Asn Val Lys
    290                 295                 300

Val Glu Tyr Ile Asp Ile Lys Asn Lys Lys Ile Lys Lys Thr Glu Asn
305                 310                 315                 320

Phe Thr Ile Glu Pro Thr Ile Val Pro Val Glu Gln Lys Asn Thr Asn
                325                 330                 335

Thr Lys


<210> SEQ ID NO 7
<211> LENGTH: 296
<212> TYPE: PRT
<213> ORGANISM: Bacillus thuringiensis

<400> SEQUENCE: 7

Gln Arg Glu Asn Lys Phe Pro Asp Val Gly Gln Gly Ile Gln Trp Leu
 1               5                  10                  15

Ser Gln Phe Tyr Gly Lys Ser Leu Arg Asn Asn Gly Glu Gly Tyr Ser
            20                  25                  30

Leu Gly Gln Asp Val Met Ser Tyr Phe Leu Glu Val Lys Asn Ser Tyr
        35                  40                  45

Gly Gln Leu Ala Met Glu Pro Gln Val Ile Ser Thr Thr Pro Leu Trp
    50                  55                  60

Ala Gly Gln Ser Asp Leu Glu Asn Ala Thr Asp Asp Glu Gln Thr Leu
65                  70                  75                  80

Asn Ser Thr Glu Phe Lys Lys Thr Tyr Ser Asn Thr Thr Thr Thr Ser
                85                  90                  95

Thr Glu Asn Gly Phe Met Ile Gly Gln Glu Thr Glu Gly Lys Val Gly
            100                 105                 110
```

```
Ile Pro Phe Val Ala Glu Gly Lys Val Thr Ile Lys Thr Glu Tyr Asn
        115                 120                 125

Phe Asn His Thr Asn Gly Tyr Glu Thr Ser Glu Ser Val Glu Tyr Ile
    130                 135                 140

Ala Pro Ser Gln Ser Ile Lys Val Pro Pro His Thr Ile Ala Arg Val
145                 150                 155                 160

Thr Ala Leu Leu Asp Val Lys Lys Ile Lys Gly Lys Met His Leu Tyr
                165                 170                 175

Ser Glu Ile Gly Leu Asn Lys Asp Tyr Gly Tyr Asp Met Val Pro Leu
            180                 185                 190

Val Tyr Lys Tyr Gly Gly Pro Phe Lys Tyr Val Thr Leu Gly Thr Leu
        195                 200                 205

Tyr Asp Glu Gly Tyr Lys Gln Ala Lys Leu Asp Tyr Ser Asn Met Gly
    210                 215                 220

Asn Val Ile Pro Glu Glu Ile Glu Thr Val Ser Lys Ser Asn Asn Pro
225                 230                 235                 240

Asn His Leu Leu Ala Ser Gly Val Gly Ile Phe Glu Ser Glu Tyr Gly
                245                 250                 255

Ser Val Phe Asn Val Lys Val Glu Tyr Ile Asp Ile Lys Asn Lys Lys
            260                 265                 270

Ile Lys Lys Thr Glu Asn Phe Thr Ile Glu Pro Thr Ile Val Pro Val
        275                 280                 285

Glu Gln Lys Asn Thr Asn Thr Lys
    290                 295


<210> SEQ ID NO 8
<211> LENGTH: 1422
<212> TYPE: DNA
<213> ORGANISM: Bacillus thuringiensis
<220> FEATURE:
<221> NAME/KEY: CDS
<222> LOCATION: (1)...(1422)

<400> SEQUENCE: 8

atg gtt gat cgt aac ggc atg cca aca ata gat aga agc gga ttt act       48
Met Val Asp Arg Asn Gly Met Pro Thr Ile Asp Arg Ser Gly Phe Thr
 1               5                  10                  15

gtt aat cga act gtt aat tac aca aat aca aat tgg atg gct aat att       96
Val Asn Arg Thr Val Asn Tyr Thr Asn Thr Asn Trp Met Ala Asn Ile
            20                  25                  30

gat aat tct cgt agg atc agt gaa tta tca att cca gga aca cat gga      144
Asp Asn Ser Arg Arg Ile Ser Glu Leu Ser Ile Pro Gly Thr His Gly
        35                  40                  45

tca atg gca ctt cat ggt gga gtt gct gga act ata gga gat ata gct      192
Ser Met Ala Leu His Gly Gly Val Ala Gly Thr Ile Gly Asp Ile Ala
     50                  55                  60

atc aat caa aca atg aac ctt gaa act caa tta aac tca gga atc cga      240
Ile Asn Gln Thr Met Asn Leu Glu Thr Gln Leu Asn Ser Gly Ile Arg
 65                  70                  75                  80

tat att gat att cga tgt agg cat tat cat aat aat ttt gct atc cat      288
Tyr Ile Asp Ile Arg Cys Arg His Tyr His Asn Asn Phe Ala Ile His
                85                  90                  95

cat gga cag ata tac cag cac gca ttt ttt ggt tct cat gtt tta gag      336
His Gly Gln Ile Tyr Gln His Ala Phe Phe Gly Ser His Val Leu Glu
            100                 105                 110

ccc gtg ata aga ttt tta agg caa aat ccc agt gaa aca att tta atg      384
Pro Val Ile Arg Phe Leu Arg Gln Asn Pro Ser Glu Thr Ile Leu Met
        115                 120                 125
```

-continued

```
cgt att caa caa gaa tac aat cca aca ggt aat aca aga act ttt gct      432
Arg Ile Gln Gln Glu Tyr Asn Pro Thr Gly Asn Thr Arg Thr Phe Ala
    130                 135                 140

gaa act ttt gaa tcc ttc tgg act cca aat caa cgt tat ttt tgg tct      480
Glu Thr Phe Glu Ser Phe Trp Thr Pro Asn Gln Arg Tyr Phe Trp Ser
145                 150                 155                 160

cct act agt aat aat cca aca tta gga gac gtc cga gga aga att att      528
Pro Thr Ser Asn Asn Pro Thr Leu Gly Asp Val Arg Gly Arg Ile Ile
                165                 170                 175

cta tta caa caa ttc ccc tct gat aga gga tgg ttt ggt att aat tgg      576
Leu Leu Gln Gln Phe Pro Ser Asp Arg Gly Trp Phe Gly Ile Asn Trp
            180                 185                 190

ggc tcg tta gcc ata caa gat cag tgg gag gta gca ggt ctt aat ggc      624
Gly Ser Leu Ala Ile Gln Asp Gln Trp Glu Val Ala Gly Leu Asn Gly
        195                 200                 205

ata tac aga aaa tgg ata gct att aaa aat cat ttt ttt aac aca ata      672
Ile Tyr Arg Lys Trp Ile Ala Ile Lys Asn His Phe Phe Asn Thr Ile
    210                 215                 220

aat aat aga aat cga atc cat att aat cat tta agt gga act ggt ggt      720
Asn Asn Arg Asn Arg Ile His Ile Asn His Leu Ser Gly Thr Gly Gly
225                 230                 235                 240

ttc ggt gaa cca aga ccc tgg ttt tta gca agt ggc tat aat agt cga      768
Phe Gly Glu Pro Arg Pro Trp Phe Leu Ala Ser Gly Tyr Asn Ser Arg
                245                 250                 255

aat gac aat agt atg tta agg tct gca tcg aga ggt cct agt gat gga      816
Asn Asp Asn Ser Met Leu Arg Ser Ala Ser Arg Gly Pro Ser Asp Gly
            260                 265                 270

tgg cca gat ttc cca cgt cat agg ccc aca gga gat ata tat ttt gga      864
Trp Pro Asp Phe Pro Arg His Arg Pro Thr Gly Asp Ile Tyr Phe Gly
        275                 280                 285

gga atg aat atc ctt gca act aga aga att cga gac cgt aga ttt act      912
Gly Met Asn Ile Leu Ala Thr Arg Arg Ile Arg Asp Arg Arg Phe Thr
    290                 295                 300

cat aca gga att gtt gct gct gat ttc cct gga aga gga tta att gaa      960
His Thr Gly Ile Val Ala Ala Asp Phe Pro Gly Arg Gly Leu Ile Glu
305                 310                 315                 320

cgc aca att gcg tta aat ttc cct ata tca cca cct cac ttt cct ggt     1008
Arg Thr Ile Ala Leu Asn Phe Pro Ile Ser Pro Pro His Phe Pro Gly
                325                 330                 335

tac tct caa att gtg aca gct tta aat agt agt agt gta att gat cta     1056
Tyr Ser Gln Ile Val Thr Ala Leu Asn Ser Ser Ser Val Ile Asp Leu
            340                 345                 350

aat cct aat cgt aat gtc aca tta tgg tcg aat cat cga gga ctt aat     1104
Asn Pro Asn Arg Asn Val Thr Leu Trp Ser Asn His Arg Gly Leu Asn
        355                 360                 365

caa agg tgg cgc att caa cat att tct gga aat tca tat tca ata ttg     1152
Gln Arg Trp Arg Ile Gln His Ile Ser Gly Asn Ser Tyr Ser Ile Leu
    370                 375                 380

cca aat ctt cca gtt tta ggt tta cct tat gtt tta act ggg aat gtt     1200
Pro Asn Leu Pro Val Leu Gly Leu Pro Tyr Val Leu Thr Gly Asn Val
385                 390                 395                 400

tat aat ctt aat tct aat gta ttt ctt gct cga tct aac gga ttg cct     1248
Tyr Asn Leu Asn Ser Asn Val Phe Leu Ala Arg Ser Asn Gly Leu Pro
                405                 410                 415

gag caa cag tgg ctt ctg gaa gaa ttt ttt gac ggt gac tat ata att     1296
Glu Gln Gln Trp Leu Leu Glu Glu Phe Phe Asp Gly Asp Tyr Ile Ile
            420                 425                 430

aaa aat aga aga aat ccg aat ctg gtt tta gat gta tcc aga agc agc     1344
Lys Asn Arg Arg Asn Pro Asn Leu Val Leu Asp Val Ser Arg Ser Ser
        435                 440                 445
```

-continued

```
act agt aat ggc tca ggt att att tta agt aca aga cac aat gga aat      1392
Thr Ser Asn Gly Ser Gly Ile Ile Leu Ser Thr Arg His Asn Gly Asn
    450                 455                 460

aat caa aga ttt ttt atc aga cca ttt taa                              1422
Asn Gln Arg Phe Phe Ile Arg Pro Phe
465                 470


<210> SEQ ID NO 9
<211> LENGTH: 473
<212> TYPE: PRT
<213> ORGANISM: Bacillus thuringiensis

<400> SEQUENCE: 9

Met Val Asp Arg Asn Gly Met Pro Thr Ile Asp Arg Ser Gly Phe Thr
 1               5                  10                  15

Val Asn Arg Thr Val Asn Tyr Thr Asn Thr Asn Trp Met Ala Asn Ile
            20                  25                  30

Asp Asn Ser Arg Arg Ile Ser Glu Leu Ser Ile Pro Gly Thr His Gly
        35                  40                  45

Ser Met Ala Leu His Gly Gly Val Ala Gly Thr Ile Gly Asp Ile Ala
    50                  55                  60

Ile Asn Gln Thr Met Asn Leu Glu Thr Gln Leu Asn Ser Gly Ile Arg
65                  70                  75                  80

Tyr Ile Asp Ile Arg Cys Arg His Tyr His Asn Asn Phe Ala Ile His
                85                  90                  95

His Gly Gln Ile Tyr Gln His Ala Phe Phe Gly Ser His Val Leu Glu
            100                 105                 110

Pro Val Ile Arg Phe Leu Arg Gln Asn Pro Ser Glu Thr Ile Leu Met
        115                 120                 125

Arg Ile Gln Gln Glu Tyr Asn Pro Thr Gly Asn Thr Arg Thr Phe Ala
    130                 135                 140

Glu Thr Phe Glu Ser Phe Trp Thr Pro Asn Gln Arg Tyr Phe Trp Ser
145                 150                 155                 160

Pro Thr Ser Asn Asn Pro Thr Leu Gly Asp Val Arg Gly Arg Ile Ile
                165                 170                 175

Leu Leu Gln Gln Phe Pro Ser Asp Arg Gly Trp Phe Gly Ile Asn Trp
            180                 185                 190

Gly Ser Leu Ala Ile Gln Asp Gln Trp Glu Val Ala Gly Leu Asn Gly
        195                 200                 205

Ile Tyr Arg Lys Trp Ile Ala Ile Lys Asn His Phe Phe Asn Thr Ile
    210                 215                 220

Asn Asn Arg Asn Arg Ile His Ile Asn His Leu Ser Gly Thr Gly Gly
225                 230                 235                 240

Phe Gly Glu Pro Arg Pro Trp Phe Leu Ala Ser Gly Tyr Asn Ser Arg
                245                 250                 255

Asn Asp Asn Ser Met Leu Arg Ser Ala Ser Arg Gly Pro Ser Asp Gly
            260                 265                 270

Trp Pro Asp Phe Pro Arg His Arg Pro Thr Gly Asp Ile Tyr Phe Gly
        275                 280                 285

Gly Met Asn Ile Leu Ala Thr Arg Arg Ile Arg Asp Arg Arg Phe Thr
    290                 295                 300

His Thr Gly Ile Val Ala Ala Asp Phe Pro Gly Arg Gly Leu Ile Glu
305                 310                 315                 320

Arg Thr Ile Ala Leu Asn Phe Pro Ile Ser Pro Pro His Phe Pro Gly
                325                 330                 335
```

```
Tyr Ser Gln Ile Val Thr Ala Leu Asn Ser Ser Ser Val Ile Asp Leu
            340                 345                 350

Asn Pro Asn Arg Asn Val Thr Leu Trp Ser Asn His Arg Gly Leu Asn
        355                 360                 365

Gln Arg Trp Arg Ile Gln His Ile Ser Gly Asn Ser Tyr Ser Ile Leu
    370                 375                 380

Pro Asn Leu Pro Val Leu Gly Leu Pro Tyr Val Leu Thr Gly Asn Val
385                 390                 395                 400

Tyr Asn Leu Asn Ser Asn Val Phe Leu Ala Arg Ser Asn Gly Leu Pro
                405                 410                 415

Glu Gln Gln Trp Leu Leu Glu Glu Phe Phe Asp Gly Asp Tyr Ile Ile
            420                 425                 430

Lys Asn Arg Arg Asn Pro Asn Leu Val Leu Asp Val Ser Arg Ser Ser
        435                 440                 445

Thr Ser Asn Gly Ser Gly Ile Ile Leu Ser Thr Arg His Asn Gly Asn
    450                 455                 460

Asn Gln Arg Phe Phe Ile Arg Pro Phe
465                 470


<210> SEQ ID NO 10
<211> LENGTH: 1053
<212> TYPE: DNA
<213> ORGANISM: Bacillus thuringiensis
<220> FEATURE:
<221> NAME/KEY: CDS
<222> LOCATION: (1)...(1053)

<400> SEQUENCE: 10

atg aaa tct tat aaa aaa ata tta cta gtt gcc cca tta gca tgt acc        48
Met Lys Ser Tyr Lys Lys Ile Leu Leu Val Ala Pro Leu Ala Cys Thr
 1               5                  10                  15

tta gca acg gga gtt ttt aca aca cct cat gca gca ttt gca gca tct        96
Leu Ala Thr Gly Val Phe Thr Thr Pro His Ala Ala Phe Ala Ala Ser
            20                  25                  30

tca gtg ggc atg cag gcg aat gca aag gat act ctt gca ttt aat gat       144
Ser Val Gly Met Gln Ala Asn Ala Lys Asp Thr Leu Ala Phe Asn Asp
        35                  40                  45

caa caa tta aaa aaa gat tta tca gat cga cta aca tct gcc gtg aga       192
Gln Gln Leu Lys Lys Asp Leu Ser Asp Arg Leu Thr Ser Ala Val Arg
     50                  55                  60

aat agg cca gat tta ttt ggg ata acc aca cca gtc ctc gtt aat aac       240
Asn Arg Pro Asp Leu Phe Gly Ile Thr Thr Pro Val Leu Val Asn Asn
 65                  70                  75                  80

att aaa aac atg aat ttc aaa tta aca gat atg aac gcg act tat ggg       288
Ile Lys Asn Met Asn Phe Lys Leu Thr Asp Met Asn Ala Thr Tyr Gly
                85                  90                  95

tat aca aat aat gga aca att caa acg gat gcg aag gtg gat cat tat       336
Tyr Thr Asn Asn Gly Thr Ile Gln Thr Asp Ala Lys Val Asp His Tyr
            100                 105                 110

ggt gat ggg gga caa gtg gag tta tta agc tat cgg aat gat acc tct       384
Gly Asp Gly Gly Gln Val Glu Leu Leu Ser Tyr Arg Asn Asp Thr Ser
        115                 120                 125

gtg aat caa act ttc aat acc cca gaa aaa agc tta aaa aca tca gaa       432
Val Asn Gln Thr Phe Asn Thr Pro Glu Lys Ser Leu Lys Thr Ser Glu
    130                 135                 140

agt ttt acc tat tca aat cag gaa ggg gta aaa ttg ggg gta gcc tcg       480
Ser Phe Thr Tyr Ser Asn Gln Glu Gly Val Lys Leu Gly Val Ala Ser
145                 150                 155                 160
```

```
gaa act aaa gtc ggt gta gat att ccc ttt ata ggt ggg gct gac gaa      528
Glu Thr Lys Val Gly Val Asp Ile Pro Phe Ile Gly Gly Ala Asp Glu
                165                 170                 175

acg att aag att tcc agc gag ttt tct tat aac cat act agt tca aat      576
Thr Ile Lys Ile Ser Ser Glu Phe Ser Tyr Asn His Thr Ser Ser Asn
            180                 185                 190

act agc aca aaa gaa gaa acg act aca ttt aaa tca caa ccg gtt att      624
Thr Ser Thr Lys Glu Glu Thr Thr Thr Phe Lys Ser Gln Pro Val Ile
        195                 200                 205

tgt gta gca gga tat aca aca caa ttt tca gga agc gta caa aat gct      672
Cys Val Ala Gly Tyr Thr Thr Gln Phe Ser Gly Ser Val Gln Asn Ala
    210                 215                 220

gtc ttt tct ggg tca ttt agt ggc act gca gaa gcg tca ggt gat gtg      720
Val Phe Ser Gly Ser Phe Ser Gly Thr Ala Glu Ala Ser Gly Asp Val
225                 230                 235                 240

aaa ttc caa gaa gtg aac gag ttg ttc cgt gta gat acg tct tta ggt      768
Lys Phe Gln Glu Val Asn Glu Leu Phe Arg Val Asp Thr Ser Leu Gly
                245                 250                 255

gac aat cca aat att aaa gga cac gca tta tac aat gtc ttt aaa tat      816
Asp Asn Pro Asn Ile Lys Gly His Ala Leu Tyr Asn Val Phe Lys Tyr
            260                 265                 270

tcg ggc atg cct gtt cca tca tat gta aaa tta gat gat acg aat aaa      864
Ser Gly Met Pro Val Pro Ser Tyr Val Lys Leu Asp Asp Thr Asn Lys
        275                 280                 285

aga gct tta att gaa aat gtg aca tcc acg tat agt gga gtt ggt ggt      912
Arg Ala Leu Ile Glu Asn Val Thr Ser Thr Tyr Ser Gly Val Gly Gly
    290                 295                 300

cat tat tca cgc gta gaa gtt aaa gtg ttc cca aat acg cgt agt aat      960
His Tyr Ser Arg Val Glu Val Lys Val Phe Pro Asn Thr Arg Ser Asn
305                 310                 315                 320

gaa gat gca atc aca ata cca tat gca aaa tat atg caa aaa gta aaa     1008
Glu Asp Ala Ile Thr Ile Pro Tyr Ala Lys Tyr Met Gln Lys Val Lys
                325                 330                 335

gat ggt aca cta cag aaa gaa tta gaa cag cat tat aaa aaa gct         1053
Asp Gly Thr Leu Gln Lys Glu Leu Glu Gln His Tyr Lys Lys Ala
            340                 345                 350


<210> SEQ ID NO 11
<211> LENGTH: 351
<212> TYPE: PRT
<213> ORGANISM: Bacillus thuringiensis

<400> SEQUENCE: 11

Met Lys Ser Tyr Lys Lys Ile Leu Leu Val Ala Pro Leu Ala Cys Thr
 1               5                  10                  15

Leu Ala Thr Gly Val Phe Thr Thr Pro His Ala Ala Phe Ala Ala Ser
            20                  25                  30

Ser Val Gly Met Gln Ala Asn Ala Lys Asp Thr Leu Ala Phe Asn Asp
        35                  40                  45

Gln Gln Leu Lys Lys Asp Leu Ser Asp Arg Leu Thr Ser Ala Val Arg
    50                  55                  60

Asn Arg Pro Asp Leu Phe Gly Ile Thr Thr Pro Val Leu Val Asn Asn
65                  70                  75                  80

Ile Lys Asn Met Asn Phe Lys Leu Thr Asp Met Asn Ala Thr Tyr Gly
                85                  90                  95

Tyr Thr Asn Asn Gly Thr Ile Gln Thr Asp Ala Lys Val Asp His Tyr
            100                 105                 110

Gly Asp Gly Gly Gln Val Glu Leu Leu Ser Tyr Arg Asn Asp Thr Ser
        115                 120                 125
```

```
Val Asn Gln Thr Phe Asn Thr Pro Glu Lys Ser Leu Lys Thr Ser Glu
    130                 135                 140

Ser Phe Thr Tyr Ser Asn Gln Glu Gly Val Lys Leu Gly Val Ala Ser
145                 150                 155                 160

Glu Thr Lys Val Gly Val Asp Ile Pro Phe Ile Gly Gly Ala Asp Glu
                165                 170                 175

Thr Ile Lys Ile Ser Ser Glu Phe Ser Tyr Asn His Thr Ser Ser Asn
            180                 185                 190

Thr Ser Thr Lys Glu Glu Thr Thr Thr Phe Lys Ser Gln Pro Val Ile
        195                 200                 205

Cys Val Ala Gly Tyr Thr Thr Gln Phe Ser Gly Ser Val Gln Asn Ala
    210                 215                 220

Val Phe Ser Gly Ser Phe Ser Gly Thr Ala Glu Ala Ser Gly Asp Val
225                 230                 235                 240

Lys Phe Gln Glu Val Asn Glu Leu Phe Arg Val Asp Thr Ser Leu Gly
                245                 250                 255

Asp Asn Pro Asn Ile Lys Gly His Ala Leu Tyr Asn Val Phe Lys Tyr
            260                 265                 270

Ser Gly Met Pro Val Pro Ser Tyr Val Lys Leu Asp Asp Thr Asn Lys
        275                 280                 285

Arg Ala Leu Ile Glu Asn Val Thr Ser Thr Tyr Ser Gly Val Gly Gly
    290                 295                 300

His Tyr Ser Arg Val Glu Val Lys Val Phe Pro Asn Thr Arg Ser Asn
305                 310                 315                 320

Glu Asp Ala Ile Thr Ile Pro Tyr Ala Lys Tyr Met Gln Lys Val Lys
                325                 330                 335

Asp Gly Thr Leu Gln Lys Glu Leu Glu Gln His Tyr Lys Lys Ala
            340                 345                 350


<210> SEQ ID NO 12
<211> LENGTH: 1062
<212> TYPE: DNA
<213> ORGANISM: Unknown
<220> FEATURE:
<221> NAME/KEY: CDS
<222> LOCATION: (1)...(1062)
<223> OTHER INFORMATION: Isolated from soil sample

<400> SEQUENCE: 12

atg tca gga ttt gaa gaa tta ttt tac cca gat aat acc aac cgt aga       48
Met Ser Gly Phe Glu Glu Leu Phe Tyr Pro Asp Asn Thr Asn Arg Arg
 1               5                  10                  15

agc aga gta gaa caa tta atg gct caa tgt aca gat tta act aac caa       96
Ser Arg Val Glu Gln Leu Met Ala Gln Cys Thr Asp Leu Thr Asn Gln
            20                  25                  30

att aag aat gat aga aaa gac att gat gac ctt ttt cga aat aat gat      144
Ile Lys Asn Asp Arg Lys Asp Ile Asp Asp Leu Phe Arg Asn Asn Asp
        35                  40                  45

cca att atc aaa gaa aag ctt aaa ggt aag cta ata tta agc att cct      192
Pro Ile Ile Lys Glu Lys Leu Lys Gly Lys Leu Ile Leu Ser Ile Pro
    50                  55                  60

aat aaa tat ttt gat ata tcc aaa aat tcc ata gat gat att tta aat      240
Asn Lys Tyr Phe Asp Ile Ser Lys Asn Ser Ile Asp Asp Ile Leu Asn
 65                  70                  75                  80

tat gct tta ggt cca gtt cct gct gct att gta ggg gct gat aat aga      288
Tyr Ala Leu Gly Pro Val Pro Ala Ala Ile Val Gly Ala Asp Asn Arg
                 85                  90                  95
```

-continued

```
aca tta tat caa aaa ata att aaa gaa ttg gtg aaa att cgt att gag      336
Thr Leu Tyr Gln Lys Ile Ile Lys Glu Leu Val Lys Ile Arg Ile Glu
            100                 105                 110

tta aag tat ata gaa tta aag act att tat gat aaa atg gtt att agt      384
Leu Lys Tyr Ile Glu Leu Lys Thr Ile Tyr Asp Lys Met Val Ile Ser
        115                 120                 125

gcc gtt ata aaa gag att act cgg att aaa aaa aca gcc caa aaa cat      432
Ala Val Ile Lys Glu Ile Thr Arg Ile Lys Lys Thr Ala Gln Lys His
    130                 135                 140

aac tgg act aat gaa ata cta gca gaa att act cag gaa atc att gaa      480
Asn Trp Thr Asn Glu Ile Leu Ala Glu Ile Thr Gln Glu Ile Ile Glu
145                 150                 155                 160

aac act att gaa acg ata gaa aca att aat gta gaa cct tct aga gaa      528
Asn Thr Ile Glu Thr Ile Glu Thr Ile Asn Val Glu Pro Ser Arg Glu
                165                 170                 175

tta gct gta gat aaa tta caa gaa att gat gaa aat ctt gca gct tgg      576
Leu Ala Val Asp Lys Leu Gln Glu Ile Asp Glu Asn Leu Ala Ala Trp
            180                 185                 190

atc aat gaa gat cca tct aat caa aaa att act atg gaa ttg aat gca      624
Ile Asn Glu Asp Pro Ser Asn Gln Lys Ile Thr Met Glu Leu Asn Ala
        195                 200                 205

tta gat gaa gta tat aaa gtt att tcg cct tta aat aat aaa agc gtg      672
Leu Asp Glu Val Tyr Lys Val Ile Ser Pro Leu Asn Asn Lys Ser Val
    210                 215                 220

tta gat ttt tct cgc tca aat aat aat gcg att tta tgg gat gac cat      720
Leu Asp Phe Ser Arg Ser Asn Asn Asn Ala Ile Leu Trp Asp Asp His
225                 230                 235                 240

gat ggt gaa aat caa aaa tgg aaa ttt gaa tac aat gca aag cac aca      768
Asp Gly Glu Asn Gln Lys Trp Lys Phe Glu Tyr Asn Ala Lys His Thr
                245                 250                 255

gca tac caa att aaa agt ctg gta aat aaa gac ttt gtt tta gca tgg      816
Ala Tyr Gln Ile Lys Ser Leu Val Asn Lys Asp Phe Val Leu Ala Trp
            260                 265                 270

gat gac ggt aat aaa tta aag aat gtg ttt gtt aca aaa aat caa tac      864
Asp Asp Gly Asn Lys Leu Lys Asn Val Phe Val Thr Lys Asn Gln Tyr
        275                 280                 285

aaa gaa gaa cat ttt tgg att tta gaa aag aca gaa gat gac aat tat      912
Lys Glu Glu His Phe Trp Ile Leu Glu Lys Thr Glu Asp Asp Asn Tyr
    290                 295                 300

att ata aaa aat aaa aaa tcc cta att tta ata tta gag gtc gat agg      960
Ile Ile Lys Asn Lys Lys Ser Leu Ile Leu Ile Leu Glu Val Asp Arg
305                 310                 315                 320

gct caa act aat aat gga gca aac att aaa tta aat gaa caa aac cgt     1008
Ala Gln Thr Asn Asn Gly Ala Asn Ile Lys Leu Asn Glu Gln Asn Arg
                325                 330                 335

ata gat aaa cgg tta att aat gct caa aaa ttc aaa tta gca aag tgt     1056
Ile Asp Lys Arg Leu Ile Asn Ala Gln Lys Phe Lys Leu Ala Lys Cys
            340                 345                 350

tat taa                                                             1062
Tyr
```

```
<210> SEQ ID NO 13
<211> LENGTH: 353
<212> TYPE: PRT
<213> ORGANISM: Unknown
<220> FEATURE:
<223> OTHER INFORMATION: Isolated from soil sample

<400> SEQUENCE: 13

Met Ser Gly Phe Glu Glu Leu Phe Tyr Pro Asp Asn Thr Asn Arg Arg
 1               5                  10                  15
```

-continued

```
Ser Arg Val Glu Gln Leu Met Ala Gln Cys Thr Asp Leu Thr Asn Gln
            20                  25                  30

Ile Lys Asn Asp Arg Lys Asp Ile Asp Asp Leu Phe Arg Asn Asn Asp
        35                  40                  45

Pro Ile Ile Lys Glu Lys Leu Lys Gly Lys Leu Ile Leu Ser Ile Pro
    50                  55                  60

Asn Lys Tyr Phe Asp Ile Ser Lys Asn Ser Ile Asp Asp Ile Leu Asn
65                  70                  75                  80

Tyr Ala Leu Gly Pro Val Pro Ala Ala Ile Val Gly Ala Asp Asn Arg
                85                  90                  95

Thr Leu Tyr Gln Lys Ile Ile Lys Glu Leu Val Lys Ile Arg Ile Glu
            100                 105                 110

Leu Lys Tyr Ile Glu Leu Lys Thr Ile Tyr Asp Lys Met Val Ile Ser
        115                 120                 125

Ala Val Ile Lys Glu Ile Thr Arg Ile Lys Lys Thr Ala Gln Lys His
    130                 135                 140

Asn Trp Thr Asn Glu Ile Leu Ala Glu Ile Thr Gln Glu Ile Ile Glu
145                 150                 155                 160

Asn Thr Ile Glu Thr Ile Glu Thr Ile Asn Val Glu Pro Ser Arg Glu
                165                 170                 175

Leu Ala Val Asp Lys Leu Gln Glu Ile Asp Glu Asn Leu Ala Ala Trp
            180                 185                 190

Ile Asn Glu Asp Pro Ser Asn Gln Lys Ile Thr Met Glu Leu Asn Ala
        195                 200                 205

Leu Asp Glu Val Tyr Lys Val Ile Ser Pro Leu Asn Asn Lys Ser Val
    210                 215                 220

Leu Asp Phe Ser Arg Ser Asn Asn Asn Ala Ile Leu Trp Asp Asp His
225                 230                 235                 240

Asp Gly Glu Asn Gln Lys Trp Lys Phe Glu Tyr Asn Ala Lys His Thr
                245                 250                 255

Ala Tyr Gln Ile Lys Ser Leu Val Asn Lys Asp Phe Val Leu Ala Trp
            260                 265                 270

Asp Asp Gly Asn Lys Leu Lys Asn Val Phe Val Thr Lys Asn Gln Tyr
        275                 280                 285

Lys Glu Glu His Phe Trp Ile Leu Glu Lys Thr Glu Asp Asp Asn Tyr
    290                 295                 300

Ile Ile Lys Asn Lys Lys Ser Leu Ile Leu Ile Leu Glu Val Asp Arg
305                 310                 315                 320

Ala Gln Thr Asn Asn Gly Ala Asn Ile Lys Leu Asn Glu Gln Asn Arg
                325                 330                 335

Ile Asp Lys Arg Leu Ile Asn Ala Gln Lys Phe Lys Leu Ala Lys Cys
            340                 345                 350

Tyr


<210> SEQ ID NO 14
<211> LENGTH: 942
<212> TYPE: DNA
<213> ORGANISM: Bacillus thuringiensis
<220> FEATURE:
<221> NAME/KEY: CDS
<222> LOCATION: (1)...(942)

<400> SEQUENCE: 14

atg aaa aaa ata gga ttc gtt agt ggc atg aca tct tta gct att tta       48
Met Lys Lys Ile Gly Phe Val Ser Gly Met Thr Ser Leu Ala Ile Leu
```

-continued

```
 1               5                  10                  15

gct agt gct ttt gga gga gaa atc aaa cct gca tct gcg agc act tct        96
Ala Ser Ala Phe Gly Gly Glu Ile Lys Pro Ala Ser Ala Ser Thr Ser
            20                  25                  30

gct tta tcc caa caa tct act ctt cat tct aca caa caa gct gtt cag       144
Ala Leu Ser Gln Gln Ser Thr Leu His Ser Thr Gln Gln Ala Val Gln
        35                  40                  45

aaa cat aat ttt gat gca atc gtt aat gag atc att cat gca tgg att       192
Lys His Asn Phe Asp Ala Ile Val Asn Glu Ile Ile His Ala Trp Ile
    50                  55                  60

aaa aaa aat aat cct ggt gga cat tat cca ttt att gat agt aaa aat       240
Lys Lys Asn Asn Pro Gly Gly His Tyr Pro Phe Ile Asp Ser Lys Asn
65                  70                  75                  80

atc tca caa att aaa gaa tcc cgt tta aac att ggt gct cct aaa cga       288
Ile Ser Gln Ile Lys Glu Ser Arg Leu Asn Ile Gly Ala Pro Lys Arg
                85                  90                  95

att gga aat att gaa aat cga aca tta gtt aca act att cct tct aga       336
Ile Gly Asn Ile Glu Asn Arg Thr Leu Val Thr Thr Ile Pro Ser Arg
            100                 105                 110

att tac aat aat aca aat gca tct gta tta aaa cca gca act tca acc       384
Ile Tyr Asn Asn Thr Asn Ala Ser Val Leu Lys Pro Ala Thr Ser Thr
        115                 120                 125

gaa tta aaa aca agt cac agt agc tct ttt act aat tta aca gaa atc       432
Glu Leu Lys Thr Ser His Ser Ser Ser Phe Thr Asn Leu Thr Glu Ile
    130                 135                 140

aca cat aca ggt ggc atc aca aca aaa gcg gaa gtg aaa ttt aaa cca       480
Thr His Thr Gly Gly Ile Thr Thr Lys Ala Glu Val Lys Phe Lys Pro
145                 150                 155                 160

aaa ggc ctt gtt gca gat ggt gaa gtt tct aca ggt cta gaa tta aaa       528
Lys Gly Leu Val Ala Asp Gly Glu Val Ser Thr Gly Leu Glu Leu Lys
                165                 170                 175

tat gaa tat agt aat aca cag gga acc aat caa acc caa aca aca acc       576
Tyr Glu Tyr Ser Asn Thr Gln Gly Thr Asn Gln Thr Gln Thr Thr Thr
            180                 185                 190

aat gaa tta agt ttt aaa gtc gat aca cct gtt gaa gtt cct cca cgg       624
Asn Glu Leu Ser Phe Lys Val Asp Thr Pro Val Glu Val Pro Pro Arg
        195                 200                 205

tca tct ata gaa gta ata aca aat att tat aaa gac aaa gta aga tat       672
Ser Ser Ile Glu Val Ile Thr Asn Ile Tyr Lys Asp Lys Val Arg Tyr
    210                 215                 220

gaa tat aca gga tat agt gaa ttc aca ggt gaa gtc aca ttc caa tat       720
Glu Tyr Thr Gly Tyr Ser Glu Phe Thr Gly Glu Val Thr Phe Gln Tyr
225                 230                 235                 240

aga ttg aat gca tct gac aca cca aaa aca gta aca aga gaa att ggt       768
Arg Leu Asn Ala Ser Asp Thr Pro Lys Thr Val Thr Arg Glu Ile Gly
                245                 250                 255

acc atg atg tat gaa ata gat gat gaa acg tac aat aaa tta gct gac       816
Thr Met Met Tyr Glu Ile Asp Asp Glu Thr Tyr Asn Lys Leu Ala Asp
            260                 265                 270

aga gga att aca gta aaa ggc gca gta gat tct cca gat gtc tta cgt       864
Arg Gly Ile Thr Val Lys Gly Ala Val Asp Ser Pro Asp Val Leu Arg
        275                 280                 285

att aaa gga aca gct att ttg gat gta gat gag gca tat agc acg gaa       912
Ile Lys Gly Thr Ala Ile Leu Asp Val Asp Glu Ala Tyr Ser Thr Glu
    290                 295                 300

gta att gca aga gat att gca cct att cag                               942
Val Ile Ala Arg Asp Ile Ala Pro Ile Gln
305                 310
```

-continued

<210> SEQ ID NO 15
<211> LENGTH: 314
<212> TYPE: PRT
<213> ORGANISM: Bacillus thuringiensis

<400> SEQUENCE: 15

```
Met Lys Lys Ile Gly Phe Val Ser Gly Met Thr Ser Leu Ala Ile Leu
 1               5                  10                  15

Ala Ser Ala Phe Gly Gly Glu Ile Lys Pro Ala Ser Ala Ser Thr Ser
            20                  25                  30

Ala Leu Ser Gln Gln Ser Thr Leu His Ser Thr Gln Gln Ala Val Gln
        35                  40                  45

Lys His Asn Phe Asp Ala Ile Val Asn Glu Ile Ile His Ala Trp Ile
    50                  55                  60

Lys Lys Asn Asn Pro Gly Gly His Tyr Pro Phe Ile Asp Ser Lys Asn
65                  70                  75                  80

Ile Ser Gln Ile Lys Glu Ser Arg Leu Asn Ile Gly Ala Pro Lys Arg
                85                  90                  95

Ile Gly Asn Ile Glu Asn Arg Thr Leu Val Thr Thr Ile Pro Ser Arg
            100                 105                 110

Ile Tyr Asn Asn Thr Asn Ala Ser Val Leu Lys Pro Ala Thr Ser Thr
        115                 120                 125

Glu Leu Lys Thr Ser His Ser Ser Ser Phe Thr Asn Leu Thr Glu Ile
    130                 135                 140

Thr His Thr Gly Gly Ile Thr Thr Lys Ala Glu Val Lys Phe Lys Pro
145                 150                 155                 160

Lys Gly Leu Val Ala Asp Gly Glu Val Ser Thr Gly Leu Glu Leu Lys
                165                 170                 175

Tyr Glu Tyr Ser Asn Thr Gln Gly Thr Asn Gln Thr Gln Thr Thr Thr
            180                 185                 190

Asn Glu Leu Ser Phe Lys Val Asp Thr Pro Val Glu Val Pro Pro Arg
        195                 200                 205

Ser Ser Ile Glu Val Ile Thr Asn Ile Tyr Lys Asp Lys Val Arg Tyr
    210                 215                 220

Glu Tyr Thr Gly Tyr Ser Glu Phe Thr Gly Glu Val Thr Phe Gln Tyr
225                 230                 235                 240

Arg Leu Asn Ala Ser Asp Thr Pro Lys Thr Val Thr Arg Glu Ile Gly
                245                 250                 255

Thr Met Met Tyr Glu Ile Asp Asp Glu Thr Tyr Asn Lys Leu Ala Asp
            260                 265                 270

Arg Gly Ile Thr Val Lys Gly Ala Val Asp Ser Pro Asp Val Leu Arg
        275                 280                 285

Ile Lys Gly Thr Ala Ile Leu Asp Val Asp Glu Ala Tyr Ser Thr Glu
    290                 295                 300

Val Ile Ala Arg Asp Ile Ala Pro Ile Gln
305                 310
```

<210> SEQ ID NO 16
<211> LENGTH: 3552
<212> TYPE: DNA
<213> ORGANISM: Bacillus thuringiensis
<220> FEATURE:
<221> NAME/KEY: CDS
<222> LOCATION: (1)...(3552)

<400> SEQUENCE: 16

```
atg tgt ttt cta tgt cat aga aga cac ata gga gat tgt tta ttc aat       48
```

-continued

```
Met Cys Phe Leu Cys His Arg Arg His Ile Gly Asp Cys Leu Phe Asn
 1               5                  10                  15

tta ata tac ttt ttg gag gta aat tat atg gat ata aga aat cag aag       96
Leu Ile Tyr Phe Leu Glu Val Asn Tyr Met Asp Ile Arg Asn Gln Lys
            20                  25                  30

aaa tca gaa gaa ata cac ccc aca tta aat gaa tca tct tct aat aca      144
Lys Ser Glu Glu Ile His Pro Thr Leu Asn Glu Ser Ser Ser Asn Thr
        35                  40                  45

aca tca aag tat cca ctt gca agt gat cta atc aaa caa tat caa aat      192
Thr Ser Lys Tyr Pro Leu Ala Ser Asp Leu Ile Lys Gln Tyr Gln Asn
    50                  55                  60

atg aat tat aaa gat agt tta aat ata atc gag gag aat aat gta atc      240
Met Asn Tyr Lys Asp Ser Leu Asn Ile Ile Glu Glu Asn Asn Val Ile
65                  70                  75                  80

gat cct gta tct gga act gcc gct ttg gta act gca agg aaa att ggt      288
Asp Pro Val Ser Gly Thr Ala Ala Leu Val Thr Ala Arg Lys Ile Gly
                85                  90                  95

ggt aag ata att aag aag tta gga gag gca gct ctg tct aaa att ttg      336
Gly Lys Ile Ile Lys Lys Leu Gly Glu Ala Ala Leu Ser Lys Ile Leu
            100                 105                 110

aaa gag atc ttg ggt tat tta tgg ccg act tca gga gaa gac gat tca      384
Lys Glu Ile Leu Gly Tyr Leu Trp Pro Thr Ser Gly Glu Asp Asp Ser
        115                 120                 125

tgg aca gat atg atg acg gca gta gaa gaa ctt att gat caa aaa ata      432
Trp Thr Asp Met Met Thr Ala Val Glu Glu Leu Ile Asp Gln Lys Ile
    130                 135                 140

cag gaa cag gta gaa ttg gat gca ctt acg gag ttg gaa aaa ata ggt      480
Gln Glu Gln Val Glu Leu Asp Ala Leu Thr Glu Leu Glu Lys Ile Gly
145                 150                 155                 160

gaa gcc gtg gag gca tat tat atc gca tta gac gat tgg gaa cca gta      528
Glu Ala Val Glu Ala Tyr Tyr Ile Ala Leu Asp Asp Trp Glu Pro Val
                165                 170                 175

cct gaa gat atg ttt agt cta agc gaa gta ata aaa cga tac gat ttt      576
Pro Glu Asp Met Phe Ser Leu Ser Glu Val Ile Lys Arg Tyr Asp Phe
            180                 185                 190

gcg cag caa ctt gca aga gct tca atg cca gaa ttc aag aag aaa ggt      624
Ala Gln Gln Leu Ala Arg Ala Ser Met Pro Glu Phe Lys Lys Lys Gly
        195                 200                 205

tat gaa att ccc ttg tta gca aca tat gca aat gct gca aat gtt cat      672
Tyr Glu Ile Pro Leu Leu Ala Thr Tyr Ala Asn Ala Ala Asn Val His
    210                 215                 220

ttg ctt tta atg aga gat atg caa ata tac ggg gaa aga tgg gga ata      720
Leu Leu Leu Met Arg Asp Met Gln Ile Tyr Gly Glu Arg Trp Gly Ile
225                 230                 235                 240

cct aaa gaa gat ata gag ctc tac tta tct gaa caa gaa aat ttt acc      768
Pro Lys Glu Asp Ile Glu Leu Tyr Leu Ser Glu Gln Glu Asn Phe Thr
                245                 250                 255

tct gaa tat aca gat cat tgc gta aaa tat tat aat gag gga tta aat      816
Ser Glu Tyr Thr Asp His Cys Val Lys Tyr Tyr Asn Glu Gly Leu Asn
            260                 265                 270

caa ttg aaa aat aaa agt ggc gta agt ggt tta gtt tgg gag aat tat      864
Gln Leu Lys Asn Lys Ser Gly Val Ser Gly Leu Val Trp Glu Asn Tyr
        275                 280                 285

aac cgt ttc cgt aca gaa atg aca atc ctg gtg tta gat att gtg gct      912
Asn Arg Phe Arg Thr Glu Met Thr Ile Leu Val Leu Asp Ile Val Ala
    290                 295                 300

gta ttt cca cgc tac aat gta atc gaa tat cct ata gat tca aca gta      960
Val Phe Pro Arg Tyr Asn Val Ile Glu Tyr Pro Ile Asp Ser Thr Val
305                 310                 315                 320
```

-continued

```
gaa tta aca aga aca att tat cta gat cca ctt ggt tac aca ggg aat      1008
Glu Leu Thr Arg Thr Ile Tyr Leu Asp Pro Leu Gly Tyr Thr Gly Asn
                325                 330                 335

tcc aat gac gag cat ccc gaa tat tat gcg tct aca aaa tca ttt tca      1056
Ser Asn Asp Glu His Pro Glu Tyr Tyr Ala Ser Thr Lys Ser Phe Ser
            340                 345                 350

tca ata gag agt aga gcc ata cct gca ccc aca tta ttc cag tgg atc      1104
Ser Ile Glu Ser Arg Ala Ile Pro Ala Pro Thr Leu Phe Gln Trp Ile
        355                 360                 365

act gaa ctt caa gta tat tca gca aaa ggc tct cat ggt tct acc tat      1152
Thr Glu Leu Gln Val Tyr Ser Ala Lys Gly Ser His Gly Ser Thr Tyr
    370                 375                 380

act aca tgg tgg act gga cat aaa gtg act gct aag cct act aat ggt      1200
Thr Thr Trp Trp Thr Gly His Lys Val Thr Ala Lys Pro Thr Asn Gly
385                 390                 395                 400

ggt ctt gaa agt aaa tat gat ttc gga agt tct tca ggt tct cag aac      1248
Gly Leu Glu Ser Lys Tyr Asp Phe Gly Ser Ser Ser Gly Ser Gln Asn
                405                 410                 415

aag gat gtt ttt gct ctt gat ggc aag gat gta tat gat tca caa agt      1296
Lys Asp Val Phe Ala Leu Asp Gly Lys Asp Val Tyr Asp Ser Gln Ser
            420                 425                 430

atg tta aca tcg att agt tat tcc ggt att aga tat ttt ggg tgt cct      1344
Met Leu Thr Ser Ile Ser Tyr Ser Gly Ile Arg Tyr Phe Gly Cys Pro
        435                 440                 445

cag ttt aag tta aat tgg ata aat aag aat aat gag cta gca gaa cag      1392
Gln Phe Lys Leu Asn Trp Ile Asn Lys Asn Asn Glu Leu Ala Glu Gln
    450                 455                 460

ata ttt aat tat tca agt aat gtt ggt tca tct ttc agt gag tat agg      1440
Ile Phe Asn Tyr Ser Ser Asn Val Gly Ser Ser Phe Ser Glu Tyr Arg
465                 470                 475                 480

tat agc aag gat gaa tta cca ata gaa ttg ttg gcg agc cct att tat      1488
Tyr Ser Lys Asp Glu Leu Pro Ile Glu Leu Leu Ala Ser Pro Ile Tyr
                485                 490                 495

gga gat att gag gaa tac agt cat agg tta agt cac gtt tca gag gta      1536
Gly Asp Ile Glu Glu Tyr Ser His Arg Leu Ser His Val Ser Glu Val
            500                 505                 510

att aaa gat tat ggg cag gga ata att cct gta tta ggt ttc aca cat      1584
Ile Lys Asp Tyr Gly Gln Gly Ile Ile Pro Val Leu Gly Phe Thr His
        515                 520                 525

gta agt gta agt cgt gac aat aga att tat tca gat aag att acg caa      1632
Val Ser Val Ser Arg Asp Asn Arg Ile Tyr Ser Asp Lys Ile Thr Gln
    530                 535                 540

att cca gct gtg aaa atg tat gaa tta gta agc cca gcc gtt gtt gta      1680
Ile Pro Ala Val Lys Met Tyr Glu Leu Val Ser Pro Ala Val Val Val
545                 550                 555                 560

aaa ggg cct gga tct aca ggt gga gat tta gtt aag aga ggg agt agt      1728
Lys Gly Pro Gly Ser Thr Gly Gly Asp Leu Val Lys Arg Gly Ser Ser
                565                 570                 575

ggt aat ata gga tct atg aat gtt acc gta aac tca cca ctt tct caa      1776
Gly Asn Ile Gly Ser Met Asn Val Thr Val Asn Ser Pro Leu Ser Gln
            580                 585                 590

aaa tat cgt gtc aga gtt cga tat gcc act aat gct tct ggc cag tta      1824
Lys Tyr Arg Val Arg Val Arg Tyr Ala Thr Asn Ala Ser Gly Gln Leu
        595                 600                 605

aac gtg agt att aac gat aaa tta aca ctt caa aaa cct ttt gaa aga      1872
Asn Val Ser Ile Asn Asp Lys Leu Thr Leu Gln Lys Pro Phe Glu Arg
    610                 615                 620

acc gga aca aca ata ggt gaa gga aca gat ttg tcc tat gat tca ttt      1920
Thr Gly Thr Thr Ile Gly Glu Gly Thr Asp Leu Ser Tyr Asp Ser Phe
625                 630                 635                 640
```

-continued

```
gga tat tta gaa tat tct acg acg att caa ttt ccg aat gag cac cca     1968
Gly Tyr Leu Glu Tyr Ser Thr Thr Ile Gln Phe Pro Asn Glu His Pro
                645                 650                 655

aaa atc act ttt aat tta tcc cat tgg agc ggc agt gga gca ttt tat     2016
Lys Ile Thr Phe Asn Leu Ser His Trp Ser Gly Ser Gly Ala Phe Tyr
            660                 665                 670

ata gat aaa atc gaa ttt atc cct gta gat gaa aat tac gat gaa aga     2064
Ile Asp Lys Ile Glu Phe Ile Pro Val Asp Glu Asn Tyr Asp Glu Arg
        675                 680                 685

gta aca cta gaa aaa gca cag aaa gcc gtg aat gcc ttg ttt aca gcg     2112
Val Thr Leu Glu Lys Ala Gln Lys Ala Val Asn Ala Leu Phe Thr Ala
    690                 695                 700

gga aga aat gca ctc caa aaa gat gtg aca gat ttt aaa gta gat cag     2160
Gly Arg Asn Ala Leu Gln Lys Asp Val Thr Asp Phe Lys Val Asp Gln
705                 710                 715                 720

gtt tcc att tta gtg gat tgt ata cca ggg gaa ttg tat cca aat gag     2208
Val Ser Ile Leu Val Asp Cys Ile Pro Gly Glu Leu Tyr Pro Asn Glu
                725                 730                 735

aaa cgc gaa cta cta agt tta gtc aaa tac gca aaa cgg ttg agt tat     2256
Lys Arg Glu Leu Leu Ser Leu Val Lys Tyr Ala Lys Arg Leu Ser Tyr
            740                 745                 750

tcc cgt aat tta ctc cta gac cca aca ttc gat tct atc aat tca cca     2304
Ser Arg Asn Leu Leu Leu Asp Pro Thr Phe Asp Ser Ile Asn Ser Pro
        755                 760                 765

gat gag aat ggc tgg tac ggg agt aat ggt att gca att gga aat ggg     2352
Asp Glu Asn Gly Trp Tyr Gly Ser Asn Gly Ile Ala Ile Gly Asn Gly
    770                 775                 780

aac ttt gta ttc aaa gga aac tat tta att ttc tca ggt acc aat gat     2400
Asn Phe Val Phe Lys Gly Asn Tyr Leu Ile Phe Ser Gly Thr Asn Asp
785                 790                 795                 800

aca caa tac cca acg tat ctc tat caa aaa att gat gaa tcc aag ctc     2448
Thr Gln Tyr Pro Thr Tyr Leu Tyr Gln Lys Ile Asp Glu Ser Lys Leu
                805                 810                 815

aaa gaa tat aca cgc tat aaa ctg aga ggt ttt atc gag agt agt cag     2496
Lys Glu Tyr Thr Arg Tyr Lys Leu Arg Gly Phe Ile Glu Ser Ser Gln
            820                 825                 830

gat tta gag gca tat gtg att cgc tat gat gca aaa cat gaa aca ttg     2544
Asp Leu Glu Ala Tyr Val Ile Arg Tyr Asp Ala Lys His Glu Thr Leu
        835                 840                 845

gat gta tcc aat aat cta ttc cca gat att tct cct gtg aat gca tgc     2592
Asp Val Ser Asn Asn Leu Phe Pro Asp Ile Ser Pro Val Asn Ala Cys
    850                 855                 860

gga gaa cca aat cgt tgt gcg gca cta caa tac ctg gat gaa aac cca     2640
Gly Glu Pro Asn Arg Cys Ala Ala Leu Gln Tyr Leu Asp Glu Asn Pro
865                 870                 875                 880

agg tta gaa tgt agt tcg ata caa gat ggc att tta tct gat tcg cat     2688
Arg Leu Glu Cys Ser Ser Ile Gln Asp Gly Ile Leu Ser Asp Ser His
                885                 890                 895

tca ttt tct ctc aat ata gat aca ggt tct att gat tac gat gag aac     2736
Ser Phe Ser Leu Asn Ile Asp Thr Gly Ser Ile Asp Tyr Asp Glu Asn
            900                 905                 910

gta ggt att tgg gtg ttg ttt aaa att tcc aca ccg gaa ggg tat gcg     2784
Val Gly Ile Trp Val Leu Phe Lys Ile Ser Thr Pro Glu Gly Tyr Ala
        915                 920                 925

aaa ttt gga aac cta gaa gtg att gaa gat ggc cta gtc att gga gaa     2832
Lys Phe Gly Asn Leu Glu Val Ile Glu Asp Gly Leu Val Ile Gly Glu
    930                 935                 940

gca tta gcc cgt gtg aaa cgt caa gaa acg aag tgg aga aac aag ttg     2880
Ala Leu Ala Arg Val Lys Arg Gln Glu Thr Lys Trp Arg Asn Lys Leu
```

-continued

```
945                 950                 955                 960

aca caa ctg cga acg gaa aca caa gcg att tat aca cga gca aaa caa      2928
Thr Gln Leu Arg Thr Glu Thr Gln Ala Ile Tyr Thr Arg Ala Lys Gln
                965                 970                 975

gcc att gat aat tta ttc aca aat gca cag gac tct cac tta aaa ata      2976
Ala Ile Asp Asn Leu Phe Thr Asn Ala Gln Asp Ser His Leu Lys Ile
            980                 985                 990

ggt gct aca ttc gcg tca att gtg gcc gcg cga aag att gtc caa tca      3024
Gly Ala Thr Phe Ala Ser Ile Val Ala Ala Arg Lys Ile Val Gln Ser
        995                 1000                1005

ata cgt gaa gcg tat atg tca tgg tta tct atc gtc cca agt gta aat      3072
Ile Arg Glu Ala Tyr Met Ser Trp Leu Ser Ile Val Pro Ser Val Asn
    1010                1015                1020

tat cct att ttc aca gag ttg aat gaa aga gta cag cga gca ttt cga      3120
Tyr Pro Ile Phe Thr Glu Leu Asn Glu Arg Val Gln Arg Ala Phe Arg
1025                1030                1035                1040

tta tat gat gta cga aat gtc gta cgt aat ggc cga ttc ttg agt gga      3168
Leu Tyr Asp Val Arg Asn Val Val Arg Asn Gly Arg Phe Leu Ser Gly
                1045                1050                1055

gta tcg gat tgg att gtg aca tct gat gta aag gta caa gaa gaa aat      3216
Val Ser Asp Trp Ile Val Thr Ser Asp Val Lys Val Gln Glu Glu Asn
            1060                1065                1070

ggg aac aac gta tta gtt ctt tcc aat tgg gat gca caa gta tta caa      3264
Gly Asn Asn Val Leu Val Leu Ser Asn Trp Asp Ala Gln Val Leu Gln
        1075                1080                1085

tgt ctg aat ctc tac gaa gac cat ggg tat atc tta cgc gta aca gca      3312
Cys Leu Asn Leu Tyr Glu Asp His Gly Tyr Ile Leu Arg Val Thr Ala
    1090                1095                1100

cgt aag gaa gga ctc gga gaa gga tat ata aca atc act gat gaa gaa      3360
Arg Lys Glu Gly Leu Gly Glu Gly Tyr Ile Thr Ile Thr Asp Glu Glu
1105                1110                1115                1120

ggg cat aca gat caa ttg aca ttt ggt gga tgt gag gag ata gat tca      3408
Gly His Thr Asp Gln Leu Thr Phe Gly Gly Cys Glu Glu Ile Asp Ser
                1125                1130                1135

tcc aat tct ttc gta tct aca ggt tat att aca aaa gag cta gaa ttc      3456
Ser Asn Ser Phe Val Ser Thr Gly Tyr Ile Thr Lys Glu Leu Glu Phe
            1140                1145                1150

ttc cca gat aca gag aaa gtg cgc atc gaa att gga gaa aca gaa gga      3504
Phe Pro Asp Thr Glu Lys Val Arg Ile Glu Ile Gly Glu Thr Glu Gly
        1155                1160                1165

aca ttc cag gta gaa agt gtg gaa tta ttt ttg atg gaa gac ata tgc      3552
Thr Phe Gln Val Glu Ser Val Glu Leu Phe Leu Met Glu Asp Ile Cys
    1170                1175                1180


<210> SEQ ID NO 17
<211> LENGTH: 1184
<212> TYPE: PRT
<213> ORGANISM: Bacillus thuringiensis

<400> SEQUENCE: 17

Met Cys Phe Leu Cys His Arg Arg His Ile Gly Asp Cys Leu Phe Asn
 1               5                  10                  15

Leu Ile Tyr Phe Leu Glu Val Asn Tyr Met Asp Ile Arg Asn Gln Lys
            20                  25                  30

Lys Ser Glu Glu Ile His Pro Thr Leu Asn Glu Ser Ser Ser Asn Thr
        35                  40                  45

Thr Ser Lys Tyr Pro Leu Ala Ser Asp Leu Ile Lys Gln Tyr Gln Asn
    50                  55                  60

Met Asn Tyr Lys Asp Ser Leu Asn Ile Ile Glu Glu Asn Asn Val Ile
```

```
65                  70                  75                  80

Asp Pro Val Ser Gly Thr Ala Ala Leu Val Thr Ala Arg Lys Ile Gly
                85                  90                  95

Gly Lys Ile Ile Lys Lys Leu Gly Glu Ala Ala Leu Ser Lys Ile Leu
            100                 105                 110

Lys Glu Ile Leu Gly Tyr Leu Trp Pro Thr Ser Gly Glu Asp Asp Ser
        115                 120                 125

Trp Thr Asp Met Met Thr Ala Val Glu Glu Leu Ile Asp Gln Lys Ile
    130                 135                 140

Gln Glu Gln Val Glu Leu Asp Ala Leu Thr Glu Leu Glu Lys Ile Gly
145                 150                 155                 160

Glu Ala Val Glu Ala Tyr Tyr Ile Ala Leu Asp Asp Trp Glu Pro Val
                165                 170                 175

Pro Glu Asp Met Phe Ser Leu Ser Glu Val Ile Lys Arg Tyr Asp Phe
            180                 185                 190

Ala Gln Gln Leu Ala Arg Ala Ser Met Pro Glu Phe Lys Lys Lys Gly
        195                 200                 205

Tyr Glu Ile Pro Leu Leu Ala Thr Tyr Ala Asn Ala Ala Asn Val His
    210                 215                 220

Leu Leu Leu Met Arg Asp Met Gln Ile Tyr Gly Glu Arg Trp Gly Ile
225                 230                 235                 240

Pro Lys Glu Asp Ile Glu Leu Tyr Leu Ser Glu Gln Glu Asn Phe Thr
                245                 250                 255

Ser Glu Tyr Thr Asp His Cys Val Lys Tyr Tyr Asn Glu Gly Leu Asn
            260                 265                 270

Gln Leu Lys Asn Lys Ser Gly Val Ser Gly Leu Val Trp Glu Asn Tyr
        275                 280                 285

Asn Arg Phe Arg Thr Glu Met Thr Ile Leu Val Leu Asp Ile Val Ala
    290                 295                 300

Val Phe Pro Arg Tyr Asn Val Ile Glu Tyr Pro Ile Asp Ser Thr Val
305                 310                 315                 320

Glu Leu Thr Arg Thr Ile Tyr Leu Asp Pro Leu Gly Tyr Thr Gly Asn
                325                 330                 335

Ser Asn Asp Glu His Pro Glu Tyr Tyr Ala Ser Thr Lys Ser Phe Ser
            340                 345                 350

Ser Ile Glu Ser Arg Ala Ile Pro Ala Pro Thr Leu Phe Gln Trp Ile
        355                 360                 365

Thr Glu Leu Gln Val Tyr Ser Ala Lys Gly Ser His Gly Ser Thr Tyr
    370                 375                 380

Thr Thr Trp Trp Thr Gly His Lys Val Thr Ala Lys Pro Thr Asn Gly
385                 390                 395                 400

Gly Leu Glu Ser Lys Tyr Asp Phe Gly Ser Ser Ser Gly Ser Gln Asn
                405                 410                 415

Lys Asp Val Phe Ala Leu Asp Gly Lys Asp Val Tyr Asp Ser Gln Ser
            420                 425                 430

Met Leu Thr Ser Ile Ser Tyr Ser Gly Ile Arg Tyr Phe Gly Cys Pro
        435                 440                 445

Gln Phe Lys Leu Asn Trp Ile Asn Lys Asn Asn Glu Leu Ala Glu Gln
    450                 455                 460

Ile Phe Asn Tyr Ser Ser Asn Val Gly Ser Ser Phe Ser Glu Tyr Arg
465                 470                 475                 480

Tyr Ser Lys Asp Glu Leu Pro Ile Glu Leu Leu Ala Ser Pro Ile Tyr
                485                 490                 495
```

-continued

```
Gly Asp Ile Glu Glu Tyr Ser His Arg Leu Ser His Val Ser Glu Val
            500                 505                 510

Ile Lys Asp Tyr Gly Gln Gly Ile Ile Pro Val Leu Gly Phe Thr His
        515                 520                 525

Val Ser Val Ser Arg Asp Asn Arg Ile Tyr Ser Asp Lys Ile Thr Gln
    530                 535                 540

Ile Pro Ala Val Lys Met Tyr Glu Leu Val Ser Pro Ala Val Val Val
545                 550                 555                 560

Lys Gly Pro Gly Ser Thr Gly Gly Asp Leu Val Lys Arg Gly Ser Ser
                565                 570                 575

Gly Asn Ile Gly Ser Met Asn Val Thr Val Asn Ser Pro Leu Ser Gln
            580                 585                 590

Lys Tyr Arg Val Arg Val Arg Tyr Ala Thr Asn Ala Ser Gly Gln Leu
        595                 600                 605

Asn Val Ser Ile Asn Asp Lys Leu Thr Leu Gln Lys Pro Phe Glu Arg
    610                 615                 620

Thr Gly Thr Thr Ile Gly Glu Gly Thr Asp Leu Ser Tyr Asp Ser Phe
625                 630                 635                 640

Gly Tyr Leu Glu Tyr Ser Thr Thr Ile Gln Phe Pro Asn Glu His Pro
                645                 650                 655

Lys Ile Thr Phe Asn Leu Ser His Trp Ser Gly Ser Gly Ala Phe Tyr
            660                 665                 670

Ile Asp Lys Ile Glu Phe Ile Pro Val Asp Glu Asn Tyr Asp Glu Arg
        675                 680                 685

Val Thr Leu Glu Lys Ala Gln Lys Ala Val Asn Ala Leu Phe Thr Ala
    690                 695                 700

Gly Arg Asn Ala Leu Gln Lys Asp Val Thr Asp Phe Lys Val Asp Gln
705                 710                 715                 720

Val Ser Ile Leu Val Asp Cys Ile Pro Gly Glu Leu Tyr Pro Asn Glu
                725                 730                 735

Lys Arg Glu Leu Leu Ser Leu Val Lys Tyr Ala Lys Arg Leu Ser Tyr
            740                 745                 750

Ser Arg Asn Leu Leu Leu Asp Pro Thr Phe Asp Ser Ile Asn Ser Pro
        755                 760                 765

Asp Glu Asn Gly Trp Tyr Gly Ser Asn Gly Ile Ala Ile Gly Asn Gly
    770                 775                 780

Asn Phe Val Phe Lys Gly Asn Tyr Leu Ile Phe Ser Gly Thr Asn Asp
785                 790                 795                 800

Thr Gln Tyr Pro Thr Tyr Leu Tyr Gln Lys Ile Asp Glu Ser Lys Leu
                805                 810                 815

Lys Glu Tyr Thr Arg Tyr Lys Leu Arg Gly Phe Ile Glu Ser Ser Gln
            820                 825                 830

Asp Leu Glu Ala Tyr Val Ile Arg Tyr Asp Ala Lys His Glu Thr Leu
        835                 840                 845

Asp Val Ser Asn Asn Leu Phe Pro Asp Ile Ser Pro Val Asn Ala Cys
    850                 855                 860

Gly Glu Pro Asn Arg Cys Ala Ala Leu Gln Tyr Leu Asp Glu Asn Pro
865                 870                 875                 880

Arg Leu Glu Cys Ser Ser Ile Gln Asp Gly Ile Leu Ser Asp Ser His
                885                 890                 895

Ser Phe Ser Leu Asn Ile Asp Thr Gly Ser Ile Asp Tyr Asp Glu Asn
            900                 905                 910
```

```
Val Gly Ile Trp Val Leu Phe Lys Ile Ser Thr Pro Glu Gly Tyr Ala
        915                 920                 925

Lys Phe Gly Asn Leu Glu Val Ile Glu Asp Gly Leu Val Ile Gly Glu
    930                 935                 940

Ala Leu Ala Arg Val Lys Arg Gln Glu Thr Lys Trp Arg Asn Lys Leu
945                 950                 955                 960

Thr Gln Leu Arg Thr Glu Thr Gln Ala Ile Tyr Thr Arg Ala Lys Gln
                965                 970                 975

Ala Ile Asp Asn Leu Phe Thr Asn Ala Gln Asp Ser His Leu Lys Ile
            980                 985                 990

Gly Ala Thr Phe Ala Ser Ile Val Ala Ala Arg Lys Ile Val Gln Ser
        995                 1000                1005

Ile Arg Glu Ala Tyr Met Ser Trp Leu Ser Ile Val Pro Ser Val Asn
    1010                1015                1020

Tyr Pro Ile Phe Thr Glu Leu Asn Glu Arg Val Gln Arg Ala Phe Arg
1025                1030                1035                1040

Leu Tyr Asp Val Arg Asn Val Val Arg Asn Gly Arg Phe Leu Ser Gly
                1045                1050                1055

Val Ser Asp Trp Ile Val Thr Ser Asp Val Lys Val Gln Glu Glu Asn
            1060                1065                1070

Gly Asn Asn Val Leu Val Leu Ser Asn Trp Asp Ala Gln Val Leu Gln
        1075                1080                1085

Cys Leu Asn Leu Tyr Glu Asp His Gly Tyr Ile Leu Arg Val Thr Ala
    1090                1095                1100

Arg Lys Glu Gly Leu Gly Glu Gly Tyr Ile Thr Ile Thr Asp Glu Glu
1105                1110                1115                1120

Gly His Thr Asp Gln Leu Thr Phe Gly Gly Cys Glu Glu Ile Asp Ser
                1125                1130                1135

Ser Asn Ser Phe Val Ser Thr Gly Tyr Ile Thr Lys Glu Leu Glu Phe
            1140                1145                1150

Phe Pro Asp Thr Glu Lys Val Arg Ile Glu Ile Gly Glu Thr Glu Gly
        1155                1160                1165

Thr Phe Gln Val Glu Ser Val Glu Leu Phe Leu Met Glu Asp Ile Cys
    1170                1175                1180


<210> SEQ ID NO 18
<211> LENGTH: 3477
<212> TYPE: DNA
<213> ORGANISM: Bacillus thuringiensis
<220> FEATURE:
<221> NAME/KEY: CDS
<222> LOCATION: (1)...(3477)

<400> SEQUENCE: 18

atg gat ata aga aat cag aag aaa tca gaa gaa ata cac ccc aca tta       48
Met Asp Ile Arg Asn Gln Lys Lys Ser Glu Glu Ile His Pro Thr Leu
 1               5                  10                  15

aat gaa tca tct tct aat aca aca tca aag tat cca ctt gca agt gat       96
Asn Glu Ser Ser Ser Asn Thr Thr Ser Lys Tyr Pro Leu Ala Ser Asp
            20                  25                  30

cta atc aaa caa tat caa aat atg aat tat aaa gat agt tta aat ata      144
Leu Ile Lys Gln Tyr Gln Asn Met Asn Tyr Lys Asp Ser Leu Asn Ile
         35                  40                  45

atc gag gag aat aat gta atc gat cct gta tct gga act gcc gct ttg      192
Ile Glu Glu Asn Asn Val Ile Asp Pro Val Ser Gly Thr Ala Ala Leu
     50                  55                  60

gta act gca agg aaa att ggt ggt aag ata att aag aag tta gga gag      240
```

-continued

```
Val Thr Ala Arg Lys Ile Gly Gly Lys Ile Ile Lys Lys Leu Gly Glu
 65                  70                  75                  80

gca gct ctg tct aaa att ttg aaa gag atc ttg ggt tat tta tgg ccg      288
Ala Ala Leu Ser Lys Ile Leu Lys Glu Ile Leu Gly Tyr Leu Trp Pro
                 85                  90                  95

act tca gga gaa gac gat tca tgg aca gat atg atg acg gca gta gaa      336
Thr Ser Gly Glu Asp Asp Ser Trp Thr Asp Met Met Thr Ala Val Glu
            100                 105                 110

gaa ctt att gat caa aaa ata cag gaa cag gta gaa ttg gat gca ctt      384
Glu Leu Ile Asp Gln Lys Ile Gln Glu Gln Val Glu Leu Asp Ala Leu
        115                 120                 125

acg gag ttg gaa aaa ata ggt gaa gcc gtg gag gca tat tat atc gca      432
Thr Glu Leu Glu Lys Ile Gly Glu Ala Val Glu Ala Tyr Tyr Ile Ala
    130                 135                 140

tta gac gat tgg gaa cca gta cct gaa gat atg ttt agt cta agc gaa      480
Leu Asp Asp Trp Glu Pro Val Pro Glu Asp Met Phe Ser Leu Ser Glu
145                 150                 155                 160

gta ata aaa cga tac gat ttt gcg cag caa ctt gca aga gct tca atg      528
Val Ile Lys Arg Tyr Asp Phe Ala Gln Gln Leu Ala Arg Ala Ser Met
                165                 170                 175

cca gaa ttc aag aag aaa ggt tat gaa att ccc ttg tta gca aca tat      576
Pro Glu Phe Lys Lys Lys Gly Tyr Glu Ile Pro Leu Leu Ala Thr Tyr
            180                 185                 190

gca aat gct gca aat gtt cat ttg ctt tta atg aga gat atg caa ata      624
Ala Asn Ala Ala Asn Val His Leu Leu Leu Met Arg Asp Met Gln Ile
        195                 200                 205

tac ggg gaa aga tgg gga ata cct aaa gaa gat ata gag ctc tac tta      672
Tyr Gly Glu Arg Trp Gly Ile Pro Lys Glu Asp Ile Glu Leu Tyr Leu
    210                 215                 220

tct gaa caa gaa aat ttt acc tct gaa tat aca gat cat tgc gta aaa      720
Ser Glu Gln Glu Asn Phe Thr Ser Glu Tyr Thr Asp His Cys Val Lys
225                 230                 235                 240

tat tat aat gag gga tta aat caa ttg aaa aat aaa agt ggc gta agt      768
Tyr Tyr Asn Glu Gly Leu Asn Gln Leu Lys Asn Lys Ser Gly Val Ser
                245                 250                 255

ggt tta gtt tgg gag aat tat aac cgt ttc cgt aca gaa atg aca atc      816
Gly Leu Val Trp Glu Asn Tyr Asn Arg Phe Arg Thr Glu Met Thr Ile
            260                 265                 270

ctg gtg tta gat att gtg gct gta ttt cca cgc tac aat gta atc gaa      864
Leu Val Leu Asp Ile Val Ala Val Phe Pro Arg Tyr Asn Val Ile Glu
        275                 280                 285

tat cct ata gat tca aca gta gaa tta aca aga aca att tat cta gat      912
Tyr Pro Ile Asp Ser Thr Val Glu Leu Thr Arg Thr Ile Tyr Leu Asp
    290                 295                 300

cca ctt ggt tac aca ggg aat tcc aat gac gag cat ccc gaa tat tat      960
Pro Leu Gly Tyr Thr Gly Asn Ser Asn Asp Glu His Pro Glu Tyr Tyr
305                 310                 315                 320

gcg tct aca aaa tca ttt tca tca ata gag agt aga gcc ata cct gca     1008
Ala Ser Thr Lys Ser Phe Ser Ser Ile Glu Ser Arg Ala Ile Pro Ala
                325                 330                 335

ccc aca tta ttc cag tgg atc act gaa ctt caa gta tat tca gca aaa     1056
Pro Thr Leu Phe Gln Trp Ile Thr Glu Leu Gln Val Tyr Ser Ala Lys
            340                 345                 350

ggc tct cat ggt tct acc tat act aca tgg tgg act gga cat aaa gtg     1104
Gly Ser His Gly Ser Thr Tyr Thr Thr Trp Trp Thr Gly His Lys Val
        355                 360                 365

act gct aag cct act aat ggt ggt ctt gaa agt aaa tat gat ttc gga     1152
Thr Ala Lys Pro Thr Asn Gly Gly Leu Glu Ser Lys Tyr Asp Phe Gly
    370                 375                 380
```

-continued

```
agt tct tca ggt tct cag aac aag gat gtt ttt gct ctt gat ggc aag     1200
Ser Ser Ser Gly Ser Gln Asn Lys Asp Val Phe Ala Leu Asp Gly Lys
385                 390                 395                 400

gat gta tat gat tca caa agt atg tta aca tcg att agt tat tcc ggt     1248
Asp Val Tyr Asp Ser Gln Ser Met Leu Thr Ser Ile Ser Tyr Ser Gly
                405                 410                 415

att aga tat ttt ggg tgt cct cag ttt aag tta aat tgg ata aat aag     1296
Ile Arg Tyr Phe Gly Cys Pro Gln Phe Lys Leu Asn Trp Ile Asn Lys
            420                 425                 430

aat aat gag cta gca gaa cag ata ttt aat tat tca agt aat gtt ggt     1344
Asn Asn Glu Leu Ala Glu Gln Ile Phe Asn Tyr Ser Ser Asn Val Gly
        435                 440                 445

tca tct ttc agt gag tat agg tat agc aag gat gaa tta cca ata gaa     1392
Ser Ser Phe Ser Glu Tyr Arg Tyr Ser Lys Asp Glu Leu Pro Ile Glu
    450                 455                 460

ttg ttg gcg agc cct att tat gga gat att gag gaa tac agt cat agg     1440
Leu Leu Ala Ser Pro Ile Tyr Gly Asp Ile Glu Glu Tyr Ser His Arg
465                 470                 475                 480

tta agt cac gtt tca gag gta att aaa gat tat ggg cag gga ata att     1488
Leu Ser His Val Ser Glu Val Ile Lys Asp Tyr Gly Gln Gly Ile Ile
                485                 490                 495

cct gta tta ggt ttc aca cat gta agt gta agt cgt gac aat aga att     1536
Pro Val Leu Gly Phe Thr His Val Ser Val Ser Arg Asp Asn Arg Ile
            500                 505                 510

tat tca gat aag att acg caa att cca gct gtg aaa atg tat gaa tta     1584
Tyr Ser Asp Lys Ile Thr Gln Ile Pro Ala Val Lys Met Tyr Glu Leu
        515                 520                 525

gta agc cca gcc gtt gtt gta aaa ggg cct gga tct aca ggt gga gat     1632
Val Ser Pro Ala Val Val Val Lys Gly Pro Gly Ser Thr Gly Gly Asp
    530                 535                 540

tta gtt aag aga ggg agt agt ggt aat ata gga tct atg aat gtt acc     1680
Leu Val Lys Arg Gly Ser Ser Gly Asn Ile Gly Ser Met Asn Val Thr
545                 550                 555                 560

gta aac tca cca ctt tct caa aaa tat cgt gtc aga gtt cga tat gcc     1728
Val Asn Ser Pro Leu Ser Gln Lys Tyr Arg Val Arg Val Arg Tyr Ala
                565                 570                 575

act aat gct tct ggc cag tta aac gtg agt att aac gat aaa tta aca     1776
Thr Asn Ala Ser Gly Gln Leu Asn Val Ser Ile Asn Asp Lys Leu Thr
            580                 585                 590

ctt caa aaa cct ttt gaa aga acc gga aca aca ata ggt gaa gga aca     1824
Leu Gln Lys Pro Phe Glu Arg Thr Gly Thr Thr Ile Gly Glu Gly Thr
        595                 600                 605

gat ttg tcc tat gat tca ttt gga tat tta gaa tat tct acg acg att     1872
Asp Leu Ser Tyr Asp Ser Phe Gly Tyr Leu Glu Tyr Ser Thr Thr Ile
    610                 615                 620

caa ttt ccg aat gag cac cca aaa atc act ttt aat tta tcc cat tgg     1920
Gln Phe Pro Asn Glu His Pro Lys Ile Thr Phe Asn Leu Ser His Trp
625                 630                 635                 640

agc ggc agt gga gca ttt tat ata gat aaa atc gaa ttt atc cct gta     1968
Ser Gly Ser Gly Ala Phe Tyr Ile Asp Lys Ile Glu Phe Ile Pro Val
                645                 650                 655

gat gaa aat tac gat gaa aga gta aca cta gaa aaa gca cag aaa gcc     2016
Asp Glu Asn Tyr Asp Glu Arg Val Thr Leu Glu Lys Ala Gln Lys Ala
            660                 665                 670

gtg aat gcc ttg ttt aca gcg gga aga aat gca ctc caa aaa gat gtg     2064
Val Asn Ala Leu Phe Thr Ala Gly Arg Asn Ala Leu Gln Lys Asp Val
        675                 680                 685

aca gat ttt aaa gta gat cag gtt tcc att tta gtg gat tgt ata cca     2112
Thr Asp Phe Lys Val Asp Gln Val Ser Ile Leu Val Asp Cys Ile Pro
    690                 695                 700
```

-continued

```
ggg gaa ttg tat cca aat gag aaa cgc gaa cta cta agt tta gtc aaa      2160
Gly Glu Leu Tyr Pro Asn Glu Lys Arg Glu Leu Leu Ser Leu Val Lys
705                 710                 715                 720

tac gca aaa cgg ttg agt tat tcc cgt aat tta ctc cta gac cca aca      2208
Tyr Ala Lys Arg Leu Ser Tyr Ser Arg Asn Leu Leu Leu Asp Pro Thr
                725                 730                 735

ttc gat tct atc aat tca cca gat gag aat ggc tgg tac ggg agt aat      2256
Phe Asp Ser Ile Asn Ser Pro Asp Glu Asn Gly Trp Tyr Gly Ser Asn
            740                 745                 750

ggt att gca att gga aat ggg aac ttt gta ttc aaa gga aac tat tta      2304
Gly Ile Ala Ile Gly Asn Gly Asn Phe Val Phe Lys Gly Asn Tyr Leu
        755                 760                 765

att ttc tca ggt acc aat gat aca caa tac cca acg tat ctc tat caa      2352
Ile Phe Ser Gly Thr Asn Asp Thr Gln Tyr Pro Thr Tyr Leu Tyr Gln
    770                 775                 780

aaa att gat gaa tcc aag ctc aaa gaa tat aca cgc tat aaa ctg aga      2400
Lys Ile Asp Glu Ser Lys Leu Lys Glu Tyr Thr Arg Tyr Lys Leu Arg
785                 790                 795                 800

ggt ttt atc gag agt agt cag gat tta gag gca tat gtg att cgc tat      2448
Gly Phe Ile Glu Ser Ser Gln Asp Leu Glu Ala Tyr Val Ile Arg Tyr
                805                 810                 815

gat gca aaa cat gaa aca ttg gat gta tcc aat aat cta ttc cca gat      2496
Asp Ala Lys His Glu Thr Leu Asp Val Ser Asn Asn Leu Phe Pro Asp
            820                 825                 830

att tct cct gtg aat gca tgc gga gaa cca aat cgt tgt gcg gca cta      2544
Ile Ser Pro Val Asn Ala Cys Gly Glu Pro Asn Arg Cys Ala Ala Leu
        835                 840                 845

caa tac ctg gat gaa aac cca agg tta gaa tgt agt tcg ata caa gat      2592
Gln Tyr Leu Asp Glu Asn Pro Arg Leu Glu Cys Ser Ser Ile Gln Asp
    850                 855                 860

ggc att tta tct gat tcg cat tca ttt tct ctc aat ata gat aca ggt      2640
Gly Ile Leu Ser Asp Ser His Ser Phe Ser Leu Asn Ile Asp Thr Gly
865                 870                 875                 880

tct att gat tac gat gag aac gta ggt att tgg gtg ttg ttt aaa att      2688
Ser Ile Asp Tyr Asp Glu Asn Val Gly Ile Trp Val Leu Phe Lys Ile
                885                 890                 895

tcc aca ccg gaa ggg tat gcg aaa ttt gga aac cta gaa gtg att gaa      2736
Ser Thr Pro Glu Gly Tyr Ala Lys Phe Gly Asn Leu Glu Val Ile Glu
            900                 905                 910

gat ggc cta gtc att gga gaa gca tta gcc cgt gtg aaa cgt caa gaa      2784
Asp Gly Leu Val Ile Gly Glu Ala Leu Ala Arg Val Lys Arg Gln Glu
        915                 920                 925

acg aag tgg aga aac aag ttg aca caa ctg cga acg gaa aca caa gcg      2832
Thr Lys Trp Arg Asn Lys Leu Thr Gln Leu Arg Thr Glu Thr Gln Ala
    930                 935                 940

att tat aca cga gca aaa caa gcc att gat aat tta ttc aca aat gca      2880
Ile Tyr Thr Arg Ala Lys Gln Ala Ile Asp Asn Leu Phe Thr Asn Ala
945                 950                 955                 960

cag gac tct cac tta aaa ata ggt gct aca ttc gcg tca att gtg gcc      2928
Gln Asp Ser His Leu Lys Ile Gly Ala Thr Phe Ala Ser Ile Val Ala
                965                 970                 975

gcg cga aag att gtc caa tca ata cgt gaa gcg tat atg tca tgg tta      2976
Ala Arg Lys Ile Val Gln Ser Ile Arg Glu Ala Tyr Met Ser Trp Leu
            980                 985                 990

tct atc gtc cca agt gta aat tat cct att ttc aca gag ttg aat gaa      3024
Ser Ile Val Pro Ser Val Asn Tyr Pro Ile Phe Thr Glu Leu Asn Glu
        995                 1000                1005

aga gta cag cga gca ttt cga tta tat gat gta cga aat gtc gta cgt      3072
Arg Val Gln Arg Ala Phe Arg Leu Tyr Asp Val Arg Asn Val Val Arg
```

```
    1010                1015                1020

aat ggc cga ttc ttg agt gga gta tcg gat tgg att gtg aca tct gat     3120
Asn Gly Arg Phe Leu Ser Gly Val Ser Asp Trp Ile Val Thr Ser Asp
1025                1030                1035                1040

gta aag gta caa gaa gaa aat ggg aac aac gta tta gtt ctt tcc aat     3168
Val Lys Val Gln Glu Glu Asn Gly Asn Asn Val Leu Val Leu Ser Asn
                1045                1050                1055

tgg gat gca caa gta tta caa tgt ctg aat ctc tac gaa gac cat ggg     3216
Trp Asp Ala Gln Val Leu Gln Cys Leu Asn Leu Tyr Glu Asp His Gly
            1060                1065                1070

tat atc tta cgc gta aca gca cgt aag gaa gga ctc gga gaa gga tat     3264
Tyr Ile Leu Arg Val Thr Ala Arg Lys Glu Gly Leu Gly Glu Gly Tyr
        1075                1080                1085

ata aca atc act gat gaa gaa ggg cat aca gat caa ttg aca ttt ggt     3312
Ile Thr Ile Thr Asp Glu Glu Gly His Thr Asp Gln Leu Thr Phe Gly
    1090                1095                1100

gga tgt gag gag ata gat tca tcc aat tct ttc gta tct aca ggt tat     3360
Gly Cys Glu Glu Ile Asp Ser Ser Asn Ser Phe Val Ser Thr Gly Tyr
1105                1110                1115                1120

att aca aaa gag cta gaa ttc ttc cca gat aca gag aaa gtg cgc atc     3408
Ile Thr Lys Glu Leu Glu Phe Phe Pro Asp Thr Glu Lys Val Arg Ile
                1125                1130                1135

gaa att gga gaa aca gaa gga aca ttc cag gta gaa agt gtg gaa tta     3456
Glu Ile Gly Glu Thr Glu Gly Thr Phe Gln Val Glu Ser Val Glu Leu
            1140                1145                1150

ttt ttg atg gaa gac ata tgc                                         3477
Phe Leu Met Glu Asp Ile Cys
        1155


<210> SEQ ID NO 19
<211> LENGTH: 1159
<212> TYPE: PRT
<213> ORGANISM: Bacillus thuringiensis

<400> SEQUENCE: 19

Met Asp Ile Arg Asn Gln Lys Lys Ser Glu Glu Ile His Pro Thr Leu
 1               5                   10                  15

Asn Glu Ser Ser Ser Asn Thr Thr Ser Lys Tyr Pro Leu Ala Ser Asp
            20                  25                  30

Leu Ile Lys Gln Tyr Gln Asn Met Asn Tyr Lys Asp Ser Leu Asn Ile
        35                  40                  45

Ile Glu Glu Asn Asn Val Ile Asp Pro Val Ser Gly Thr Ala Ala Leu
    50                  55                  60

Val Thr Ala Arg Lys Ile Gly Gly Lys Ile Ile Lys Lys Leu Gly Glu
65                  70                  75                  80

Ala Ala Leu Ser Lys Ile Leu Lys Glu Ile Leu Gly Tyr Leu Trp Pro
                85                  90                  95

Thr Ser Gly Glu Asp Asp Ser Trp Thr Asp Met Met Thr Ala Val Glu
            100                 105                 110

Glu Leu Ile Asp Gln Lys Ile Gln Glu Gln Val Glu Leu Asp Ala Leu
        115                 120                 125

Thr Glu Leu Glu Lys Ile Gly Glu Ala Val Glu Ala Tyr Tyr Ile Ala
    130                 135                 140

Leu Asp Asp Trp Glu Pro Val Pro Glu Asp Met Phe Ser Leu Ser Glu
145                 150                 155                 160

Val Ile Lys Arg Tyr Asp Phe Ala Gln Gln Leu Ala Arg Ala Ser Met
                165                 170                 175
```

```
Pro Glu Phe Lys Lys Lys Gly Tyr Glu Ile Pro Leu Leu Ala Thr Tyr
            180                 185                 190

Ala Asn Ala Ala Asn Val His Leu Leu Leu Met Arg Asp Met Gln Ile
        195                 200                 205

Tyr Gly Glu Arg Trp Gly Ile Pro Lys Glu Asp Ile Glu Leu Tyr Leu
    210                 215                 220

Ser Glu Gln Glu Asn Phe Thr Ser Glu Tyr Thr Asp His Cys Val Lys
225                 230                 235                 240

Tyr Tyr Asn Glu Gly Leu Asn Gln Leu Lys Asn Lys Ser Gly Val Ser
                245                 250                 255

Gly Leu Val Trp Glu Asn Tyr Asn Arg Phe Arg Thr Glu Met Thr Ile
            260                 265                 270

Leu Val Leu Asp Ile Val Ala Val Phe Pro Arg Tyr Asn Val Ile Glu
        275                 280                 285

Tyr Pro Ile Asp Ser Thr Val Glu Leu Thr Arg Thr Ile Tyr Leu Asp
    290                 295                 300

Pro Leu Gly Tyr Thr Gly Asn Ser Asn Asp Glu His Pro Glu Tyr Tyr
305                 310                 315                 320

Ala Ser Thr Lys Ser Phe Ser Ser Ile Glu Ser Arg Ala Ile Pro Ala
                325                 330                 335

Pro Thr Leu Phe Gln Trp Ile Thr Glu Leu Gln Val Tyr Ser Ala Lys
            340                 345                 350

Gly Ser His Gly Ser Thr Tyr Thr Thr Trp Trp Thr Gly His Lys Val
        355                 360                 365

Thr Ala Lys Pro Thr Asn Gly Gly Leu Glu Ser Lys Tyr Asp Phe Gly
    370                 375                 380

Ser Ser Ser Gly Ser Gln Asn Lys Asp Val Phe Ala Leu Asp Gly Lys
385                 390                 395                 400

Asp Val Tyr Asp Ser Gln Ser Met Leu Thr Ser Ile Ser Tyr Ser Gly
                405                 410                 415

Ile Arg Tyr Phe Gly Cys Pro Gln Phe Lys Leu Asn Trp Ile Asn Lys
            420                 425                 430

Asn Asn Glu Leu Ala Glu Gln Ile Phe Asn Tyr Ser Ser Asn Val Gly
        435                 440                 445

Ser Ser Phe Ser Glu Tyr Arg Tyr Ser Lys Asp Glu Leu Pro Ile Glu
    450                 455                 460

Leu Leu Ala Ser Pro Ile Tyr Gly Asp Ile Glu Glu Tyr Ser His Arg
465                 470                 475                 480

Leu Ser His Val Ser Glu Val Ile Lys Asp Tyr Gly Gln Gly Ile Ile
                485                 490                 495

Pro Val Leu Gly Phe Thr His Val Ser Val Ser Arg Asp Asn Arg Ile
            500                 505                 510

Tyr Ser Asp Lys Ile Thr Gln Ile Pro Ala Val Lys Met Tyr Glu Leu
        515                 520                 525

Val Ser Pro Ala Val Val Val Lys Gly Pro Gly Ser Thr Gly Gly Asp
    530                 535                 540

Leu Val Lys Arg Gly Ser Ser Gly Asn Ile Gly Ser Met Asn Val Thr
545                 550                 555                 560

Val Asn Ser Pro Leu Ser Gln Lys Tyr Arg Val Arg Val Arg Tyr Ala
                565                 570                 575

Thr Asn Ala Ser Gly Gln Leu Asn Val Ser Ile Asn Asp Lys Leu Thr
            580                 585                 590

Leu Gln Lys Pro Phe Glu Arg Thr Gly Thr Thr Ile Gly Glu Gly Thr
```

```
        595                 600                 605

Asp Leu Ser Tyr Asp Ser Phe Gly Tyr Leu Glu Tyr Ser Thr Thr Ile
    610                 615                 620

Gln Phe Pro Asn Glu His Pro Lys Ile Thr Phe Asn Leu Ser His Trp
625                 630                 635                 640

Ser Gly Ser Gly Ala Phe Tyr Ile Asp Lys Ile Glu Phe Ile Pro Val
                645                 650                 655

Asp Glu Asn Tyr Asp Glu Arg Val Thr Leu Glu Lys Ala Gln Lys Ala
            660                 665                 670

Val Asn Ala Leu Phe Thr Ala Gly Arg Asn Ala Leu Gln Lys Asp Val
        675                 680                 685

Thr Asp Phe Lys Val Asp Gln Val Ser Ile Leu Val Asp Cys Ile Pro
    690                 695                 700

Gly Glu Leu Tyr Pro Asn Glu Lys Arg Glu Leu Leu Ser Leu Val Lys
705                 710                 715                 720

Tyr Ala Lys Arg Leu Ser Tyr Ser Arg Asn Leu Leu Leu Asp Pro Thr
                725                 730                 735

Phe Asp Ser Ile Asn Ser Pro Asp Glu Asn Gly Trp Tyr Gly Ser Asn
            740                 745                 750

Gly Ile Ala Ile Gly Asn Gly Asn Phe Val Phe Lys Gly Asn Tyr Leu
        755                 760                 765

Ile Phe Ser Gly Thr Asn Asp Thr Gln Tyr Pro Thr Tyr Leu Tyr Gln
    770                 775                 780

Lys Ile Asp Glu Ser Lys Leu Lys Glu Tyr Thr Arg Tyr Lys Leu Arg
785                 790                 795                 800

Gly Phe Ile Glu Ser Ser Gln Asp Leu Glu Ala Tyr Val Ile Arg Tyr
                805                 810                 815

Asp Ala Lys His Glu Thr Leu Asp Val Ser Asn Asn Leu Phe Pro Asp
            820                 825                 830

Ile Ser Pro Val Asn Ala Cys Gly Glu Pro Asn Arg Cys Ala Ala Leu
        835                 840                 845

Gln Tyr Leu Asp Glu Asn Pro Arg Leu Glu Cys Ser Ser Ile Gln Asp
    850                 855                 860

Gly Ile Leu Ser Asp Ser His Ser Phe Ser Leu Asn Ile Asp Thr Gly
865                 870                 875                 880

Ser Ile Asp Tyr Asp Glu Asn Val Gly Ile Trp Val Leu Phe Lys Ile
                885                 890                 895

Ser Thr Pro Glu Gly Tyr Ala Lys Phe Gly Asn Leu Glu Val Ile Glu
            900                 905                 910

Asp Gly Leu Val Ile Gly Glu Ala Leu Ala Arg Val Lys Arg Gln Glu
        915                 920                 925

Thr Lys Trp Arg Asn Lys Leu Thr Gln Leu Arg Thr Glu Thr Gln Ala
    930                 935                 940

Ile Tyr Thr Arg Ala Lys Gln Ala Ile Asp Asn Leu Phe Thr Asn Ala
945                 950                 955                 960

Gln Asp Ser His Leu Lys Ile Gly Ala Thr Phe Ala Ser Ile Val Ala
                965                 970                 975

Ala Arg Lys Ile Val Gln Ser Ile Arg Glu Ala Tyr Met Ser Trp Leu
            980                 985                 990

Ser Ile Val Pro Ser Val Asn Tyr Pro Ile Phe Thr Glu Leu Asn Glu
        995                 1000                1005

Arg Val Gln Arg Ala Phe Arg Leu Tyr Asp Val Arg Asn Val Val Arg
    1010                1015                1020
```

```
Asn Gly Arg Phe Leu Ser Gly Val Ser Asp Trp Ile Val Thr Ser Asp
1025                1030                1035                1040

Val Lys Val Gln Glu Glu Asn Gly Asn Asn Val Leu Val Leu Ser Asn
                1045                1050                1055

Trp Asp Ala Gln Val Leu Gln Cys Leu Asn Leu Tyr Glu Asp His Gly
            1060                1065                1070

Tyr Ile Leu Arg Val Thr Ala Arg Lys Glu Gly Leu Gly Glu Gly Tyr
        1075                1080                1085

Ile Thr Ile Thr Asp Glu Glu Gly His Thr Asp Gln Leu Thr Phe Gly
    1090                1095                1100

Gly Cys Glu Glu Ile Asp Ser Ser Asn Ser Phe Val Ser Thr Gly Tyr
1105                1110                1115                1120

Ile Thr Lys Glu Leu Glu Phe Phe Pro Asp Thr Glu Lys Val Arg Ile
                1125                1130                1135

Glu Ile Gly Glu Thr Glu Gly Thr Phe Gln Val Glu Ser Val Glu Leu
            1140                1145                1150

Phe Leu Met Glu Asp Ile Cys
        1155


<210> SEQ ID NO 20
<211> LENGTH: 3438
<212> TYPE: DNA
<213> ORGANISM: Bacillus thuringiensis
<220> FEATURE:
<221> NAME/KEY: CDS
<222> LOCATION: (1)...(3438)

<400> SEQUENCE: 20

atg aaa aaa att aag ttt aaa tat tgt ata caa gga gac ttg aat atg      48
Met Lys Lys Ile Lys Phe Lys Tyr Cys Ile Gln Gly Asp Leu Asn Met
 1               5                  10                  15

aat caa aaa aac tat gat att ata ggt gct tcg aca aac ggt aca aac      96
Asn Gln Lys Asn Tyr Asp Ile Ile Gly Ala Ser Thr Asn Gly Thr Asn
            20                  25                  30

aaa tta ctt gaa ggt tat aac att ata atc agt ccc tac gaa gct cca     144
Lys Leu Leu Glu Gly Tyr Asn Ile Ile Ile Ser Pro Tyr Glu Ala Pro
        35                  40                  45

aca tcc gtt act aca act att gaa att act gga acc ata cta agc gat     192
Thr Ser Val Thr Thr Thr Ile Glu Ile Thr Gly Thr Ile Leu Ser Asp
     50                  55                  60

tta ggt gtt cca gga gca tca tca gtt agt tta ctt ttg aat aaa ctt     240
Leu Gly Val Pro Gly Ala Ser Ser Val Ser Leu Leu Leu Asn Lys Leu
 65                  70                  75                  80

ata aat cta tta tgg cca aat gat acc aat act gtg tgg ggg aca ttc     288
Ile Asn Leu Leu Trp Pro Asn Asp Thr Asn Thr Val Trp Gly Thr Phe
                 85                  90                  95

gga aaa gaa acc gct gat ctt cta aat gaa gtg tta tct cca aat gat     336
Gly Lys Glu Thr Ala Asp Leu Leu Asn Glu Val Leu Ser Pro Asn Asp
            100                 105                 110

cca gta gta aca gat gca aat act aat tta gca gga cta aat gac tcc     384
Pro Val Val Thr Asp Ala Asn Thr Asn Leu Ala Gly Leu Asn Asp Ser
        115                 120                 125

ctt aac tta tat tta aat gaa ctt gaa ata tgg aaa aaa gac ccc aac     432
Leu Asn Leu Tyr Leu Asn Glu Leu Glu Ile Trp Lys Lys Asp Pro Asn
    130                 135                 140

aac gca act acc caa agg aat gtc aca caa tac ttt gtt agt ttg aat     480
Asn Ala Thr Thr Gln Arg Asn Val Thr Gln Tyr Phe Val Ser Leu Asn
145                 150                 155                 160
```

-continued

```
ttg gat ttt aca cat gat atg cct tca ttt gct gta cct gga tat gaa      528
Leu Asp Phe Thr His Asp Met Pro Ser Phe Ala Val Pro Gly Tyr Glu
                165                 170                 175

acg aag tta tta aca att tat gca caa gct gca aat ctt cat tta ctt      576
Thr Lys Leu Leu Thr Ile Tyr Ala Gln Ala Ala Asn Leu His Leu Leu
            180                 185                 190

tta tta aga gat gct tct agg ttt gga gaa ggt tgg gga ctg act caa      624
Leu Leu Arg Asp Ala Ser Arg Phe Gly Glu Gly Trp Gly Leu Thr Gln
        195                 200                 205

gaa atc ata gat tct aac tat aat aat caa tta aaa ttg aca gaa aaa      672
Glu Ile Ile Asp Ser Asn Tyr Asn Asn Gln Leu Lys Leu Thr Glu Lys
    210                 215                 220

tac acg gac cat tgt gta aag tgg tac aac gca gga tta gaa aaa tta      720
Tyr Thr Asp His Cys Val Lys Trp Tyr Asn Ala Gly Leu Glu Lys Leu
225                 230                 235                 240

aaa gga aat tta act ggg gaa aat tgg tac act tat aat aga ttt cgt      768
Lys Gly Asn Leu Thr Gly Glu Asn Trp Tyr Thr Tyr Asn Arg Phe Arg
                245                 250                 255

aga gaa atg acg tta atg gtg tta gac gta gtt gca tta ttt cca aac      816
Arg Glu Met Thr Leu Met Val Leu Asp Val Val Ala Leu Phe Pro Asn
            260                 265                 270

tat gat aca cga atg tac ccg atc gca acg tca tca gaa ctt aca aga      864
Tyr Asp Thr Arg Met Tyr Pro Ile Ala Thr Ser Ser Glu Leu Thr Arg
        275                 280                 285

atg att tat aca gat cca atc gct tat aca caa agc gat cca tgg tac      912
Met Ile Tyr Thr Asp Pro Ile Ala Tyr Thr Gln Ser Asp Pro Trp Tyr
    290                 295                 300

aag ata aca tct ctt tct ttt tca aat att gaa aac agc gcg att cca      960
Lys Ile Thr Ser Leu Ser Phe Ser Asn Ile Glu Asn Ser Ala Ile Pro
305                 310                 315                 320

agt cct tct ttc ttc aag tgg cta aga tcc gtt tca att aat agc cag     1008
Ser Pro Ser Phe Phe Lys Trp Leu Arg Ser Val Ser Ile Asn Ser Gln
                325                 330                 335

tgg tgg ggc agt ggt cct aat caa acc tac tat tgg gtt gga cat gaa     1056
Trp Trp Gly Ser Gly Pro Asn Gln Thr Tyr Tyr Trp Val Gly His Glu
            340                 345                 350

tta gta tat tct aat tca aat tct aat caa tca ctt aag gtt aaa tat     1104
Leu Val Tyr Ser Asn Ser Asn Ser Asn Gln Ser Leu Lys Val Lys Tyr
        355                 360                 365

gga gac cct aat tct tat att gag ccc cct gat tct ttc agt ttt tct     1152
Gly Asp Pro Asn Ser Tyr Ile Glu Pro Pro Asp Ser Phe Ser Phe Ser
    370                 375                 380

tct acg gat gtt tac aga acc att tct gtt gtt aga aat tca gta agt     1200
Ser Thr Asp Val Tyr Arg Thr Ile Ser Val Val Arg Asn Ser Val Ser
385                 390                 395                 400

aat tat ata gta agt gaa gtt caa ttc aat tca att agt aat aca aat     1248
Asn Tyr Ile Val Ser Glu Val Gln Phe Asn Ser Ile Ser Asn Thr Asn
                405                 410                 415

caa att agt gaa gaa att tat aaa cat caa tca aat tgg agt aga aaa     1296
Gln Ile Ser Glu Glu Ile Tyr Lys His Gln Ser Asn Trp Ser Arg Lys
            420                 425                 430

gaa acc aaa gat tca att aca gaa cta tcc tta gct gct aat ccc cca     1344
Glu Thr Lys Asp Ser Ile Thr Glu Leu Ser Leu Ala Ala Asn Pro Pro
        435                 440                 445

aca aca ttt gga aat gta gca gaa tac agt cat aga tta gca tat att     1392
Thr Thr Phe Gly Asn Val Ala Glu Tyr Ser His Arg Leu Ala Tyr Ile
    450                 455                 460

tca gag gca tac caa agt caa aac cca tca aaa tac cca acc tac att     1440
Ser Glu Ala Tyr Gln Ser Gln Asn Pro Ser Lys Tyr Pro Thr Tyr Ile
465                 470                 475                 480
```

-continued

```
cct gta ttc ggt tgg acg cat aca agc gta cgt tac gat aat aaa att      1488
Pro Val Phe Gly Trp Thr His Thr Ser Val Arg Tyr Asp Asn Lys Ile
                485                 490                 495

ttc ccg gac aaa atc act caa att cca gct gtt aaa agc tct tca gct      1536
Phe Pro Asp Lys Ile Thr Gln Ile Pro Ala Val Lys Ser Ser Ser Ala
            500                 505                 510

caa ggt gga tca tgg aaa aat ata gtg aaa ggt ccc ggg ttt act gga      1584
Gln Gly Gly Ser Trp Lys Asn Ile Val Lys Gly Pro Gly Phe Thr Gly
        515                 520                 525

gga gat gtg aca act gca gtt tcg cca gca act tta acc gac ata ata      1632
Gly Asp Val Thr Thr Ala Val Ser Pro Ala Thr Leu Thr Asp Ile Ile
    530                 535                 540

aaa ata caa gtt act cta gat cca aat tca ctt tca caa aaa tat cgt      1680
Lys Ile Gln Val Thr Leu Asp Pro Asn Ser Leu Ser Gln Lys Tyr Arg
545                 550                 555                 560

gca cga ctt cgc tat gct tcc aat gca ttt gta gca gct act ttg tat      1728
Ala Arg Leu Arg Tyr Ala Ser Asn Ala Phe Val Ala Ala Thr Leu Tyr
                565                 570                 575

aca aat aca agt agt aat tat aat ttt gaa ctt aca aaa ggt aca act      1776
Thr Asn Thr Ser Ser Asn Tyr Asn Phe Glu Leu Thr Lys Gly Thr Thr
            580                 585                 590

gaa cag ttt aca aca tat aat tca tac cag tat gta gat atc cca ggt      1824
Glu Gln Phe Thr Thr Tyr Asn Ser Tyr Gln Tyr Val Asp Ile Pro Gly
        595                 600                 605

tca ata caa ttt aat aat act tct gat aca gtg tct gtt tat ttg cat      1872
Ser Ile Gln Phe Asn Asn Thr Ser Asp Thr Val Ser Val Tyr Leu His
    610                 615                 620

atg gat tca aca act aat gca aac gtt cat gta gat aga att gaa ttc      1920
Met Asp Ser Thr Thr Asn Ala Asn Val His Val Asp Arg Ile Glu Phe
625                 630                 635                 640

att cca gta gat gaa cag tac gat gaa aga gta aca cta gaa aaa gca      1968
Ile Pro Val Asp Glu Gln Tyr Asp Glu Arg Val Thr Leu Glu Lys Ala
                645                 650                 655

cag aaa gcc gtg aat gcc ttg ttt aca gcg gga aga cat gca ctc caa      2016
Gln Lys Ala Val Asn Ala Leu Phe Thr Ala Gly Arg His Ala Leu Gln
            660                 665                 670

aca gat gtg aca gat tac aaa gtg gat caa gtg tca att tta gtg gat      2064
Thr Asp Val Thr Asp Tyr Lys Val Asp Gln Val Ser Ile Leu Val Asp
        675                 680                 685

tgt gta tca ggg gag tta tat cca aat gag aaa cgc gaa cta ctc agt      2112
Cys Val Ser Gly Glu Leu Tyr Pro Asn Glu Lys Arg Glu Leu Leu Ser
    690                 695                 700

tta gtc aaa tac gca aaa cgt ttg agc tat tct cgt aat tta ctc cta      2160
Leu Val Lys Tyr Ala Lys Arg Leu Ser Tyr Ser Arg Asn Leu Leu Leu
705                 710                 715                 720

gat cca aca ttc gat tct atc aat tca tca gat aag aat ggc tgg tac      2208
Asp Pro Thr Phe Asp Ser Ile Asn Ser Ser Asp Lys Asn Gly Trp Tyr
                725                 730                 735

ggg agt aat ggt att gca att agc agt ggg aat ttt gta ttc aaa ggg      2256
Gly Ser Asn Gly Ile Ala Ile Ser Ser Gly Asn Phe Val Phe Lys Gly
            740                 745                 750

aac tat tta atc ttc tca ggt aca aat gat gaa caa tat cca acc tat      2304
Asn Tyr Leu Ile Phe Ser Gly Thr Asn Asp Glu Gln Tyr Pro Thr Tyr
        755                 760                 765

ctc tat caa aaa ata gac gaa tct aag tta aaa gaa tat aca cgt tat      2352
Leu Tyr Gln Lys Ile Asp Glu Ser Lys Leu Lys Glu Tyr Thr Arg Tyr
    770                 775                 780

aaa ctg aga ggc ttt ata gaa aat agt caa gat tta gaa gca tat gtc      2400
Lys Leu Arg Gly Phe Ile Glu Asn Ser Gln Asp Leu Glu Ala Tyr Val
```

-continued

```
785                 790                 795                 800

att cgc tat gat gcc aaa cat gaa aca ttg gat gta tcc aat aat cta      2448
Ile Arg Tyr Asp Ala Lys His Glu Thr Leu Asp Val Ser Asn Asn Leu
                805                 810                 815

tta ccg gat att tct cct gta aat gca tgt gga gaa cca aat cgt tgt      2496
Leu Pro Asp Ile Ser Pro Val Asn Ala Cys Gly Glu Pro Asn Arg Cys
            820                 825                 830

gtg gca tta caa tac ctg gat gaa aac cca aga tta gaa tgt agt tcg      2544
Val Ala Leu Gln Tyr Leu Asp Glu Asn Pro Arg Leu Glu Cys Ser Ser
        835                 840                 845

gtt caa gat ggt att tta tct gat tcg cat tca ttt tct ctc aat ata      2592
Val Gln Asp Gly Ile Leu Ser Asp Ser His Ser Phe Ser Leu Asn Ile
    850                 855                 860

gat aca ggt tct att gat ttc aat gag agc gta gga att tgg gtg ttg      2640
Asp Thr Gly Ser Ile Asp Phe Asn Glu Ser Val Gly Ile Trp Val Leu
865                 870                 875                 880

ttt aaa att tcc aca ccg gaa ggg tat gcg aaa ttt gga aac cta gaa      2688
Phe Lys Ile Ser Thr Pro Glu Gly Tyr Ala Lys Phe Gly Asn Leu Glu
                885                 890                 895

gtg att gaa aat ggc cca gtc atc gga gaa gca tta gcc cgt gtg aaa      2736
Val Ile Glu Asn Gly Pro Val Ile Gly Glu Ala Leu Ala Arg Val Lys
            900                 905                 910

cgc caa gaa aca aag tgg aga aac cag ttg aca caa ctg aga acg gaa      2784
Arg Gln Glu Thr Lys Trp Arg Asn Gln Leu Thr Gln Leu Arg Thr Glu
        915                 920                 925

aca caa gcg att tat aca cga gca aaa caa gcg ctg gat aat ctt ttt      2832
Thr Gln Ala Ile Tyr Thr Arg Ala Lys Gln Ala Leu Asp Asn Leu Phe
    930                 935                 940

gcg aat gca caa gac tct cac tta aaa ata ggt acg aca ttt gcg gca      2880
Ala Asn Ala Gln Asp Ser His Leu Lys Ile Gly Thr Thr Phe Ala Ala
945                 950                 955                 960

att gtg gct gcg cga aag att gtc caa tcc ata cgc gaa gcg tat atg      2928
Ile Val Ala Ala Arg Lys Ile Val Gln Ser Ile Arg Glu Ala Tyr Met
                965                 970                 975

tca tgg tta tct gtt gtt cca ggt gta aat tat cct atc ttt aca gag      2976
Ser Trp Leu Ser Val Val Pro Gly Val Asn Tyr Pro Ile Phe Thr Glu
            980                 985                 990

ttg act gag aga gta cag caa gca ttt caa tta tat gat gta cga aat      3024
Leu Thr Glu Arg Val Gln Gln Ala Phe Gln Leu Tyr Asp Val Arg Asn
        995                 1000                1005

gtc gtg cgt aat ggc caa ttc ctt agt ggc tta tcc gat tgg att gta      3072
Val Val Arg Asn Gly Gln Phe Leu Ser Gly Leu Ser Asp Trp Ile Val
    1010                1015                1020

aca cct gac gtc aag gta caa gaa gac aat ggg aat aac gta ttg gtt      3120
Thr Pro Asp Val Lys Val Gln Glu Asp Asn Gly Asn Asn Val Leu Val
1025                1030                1035                1040

ctt tct aat tgg gat gcg caa gta tta caa tgt ctg aag ctc tat caa      3168
Leu Ser Asn Trp Asp Ala Gln Val Leu Gln Cys Leu Lys Leu Tyr Gln
                1045                1050                1055

gat cgc ggg tat atc tta cgt gta acg gca cgt aag gaa gga ttg gga      3216
Asp Arg Gly Tyr Ile Leu Arg Val Thr Ala Arg Lys Glu Gly Leu Gly
            1060                1065                1070

gaa gga tac gta aca att acg gat gaa gaa ggg aat aca gat caa ttg      3264
Glu Gly Tyr Val Thr Ile Thr Asp Glu Glu Gly Asn Thr Asp Gln Leu
        1075                1080                1085

acg ttt ggt gca tgt gag gag ata gat gca tct aat gcg ttc att tcc      3312
Thr Phe Gly Ala Cys Glu Glu Ile Asp Ala Ser Asn Ala Phe Ile Ser
    1090                1095                1100

aca ggt tat att aca aaa gaa ctg gaa ttc ttc cca gat aca gag aaa      3360
```

-continued

```
Thr Gly Tyr Ile Thr Lys Glu Leu Glu Phe Phe Pro Asp Thr Glu Lys
1105                1110                1115                1120

gtg cgt ata gaa att gga gaa aca gaa gga aca ttc cag gtg gaa agt      3408
Val Arg Ile Glu Ile Gly Glu Thr Glu Gly Thr Phe Gln Val Glu Ser
                1125                1130                1135

gta gaa tta ttc ttg atg gaa gat cta tgt                              3438
Val Glu Leu Phe Leu Met Glu Asp Leu Cys
            1140                1145


<210> SEQ ID NO 21
<211> LENGTH: 1146
<212> TYPE: PRT
<213> ORGANISM: Bacillus thuringiensis

<400> SEQUENCE: 21

Met Lys Lys Ile Lys Phe Lys Tyr Cys Ile Gln Gly Asp Leu Asn Met
 1               5                  10                  15

Asn Gln Lys Asn Tyr Asp Ile Ile Gly Ala Ser Thr Asn Gly Thr Asn
            20                  25                  30

Lys Leu Leu Glu Gly Tyr Asn Ile Ile Ile Ser Pro Tyr Glu Ala Pro
        35                  40                  45

Thr Ser Val Thr Thr Thr Ile Glu Ile Thr Gly Thr Ile Leu Ser Asp
    50                  55                  60

Leu Gly Val Pro Gly Ala Ser Ser Val Ser Leu Leu Leu Asn Lys Leu
65                  70                  75                  80

Ile Asn Leu Leu Trp Pro Asn Asp Thr Asn Thr Val Trp Gly Thr Phe
                85                  90                  95

Gly Lys Glu Thr Ala Asp Leu Leu Asn Glu Val Leu Ser Pro Asn Asp
            100                 105                 110

Pro Val Val Thr Asp Ala Asn Thr Asn Leu Ala Gly Leu Asn Asp Ser
        115                 120                 125

Leu Asn Leu Tyr Leu Asn Glu Leu Glu Ile Trp Lys Lys Asp Pro Asn
    130                 135                 140

Asn Ala Thr Thr Gln Arg Asn Val Thr Gln Tyr Phe Val Ser Leu Asn
145                 150                 155                 160

Leu Asp Phe Thr His Asp Met Pro Ser Phe Ala Val Pro Gly Tyr Glu
                165                 170                 175

Thr Lys Leu Leu Thr Ile Tyr Ala Gln Ala Ala Asn Leu His Leu Leu
            180                 185                 190

Leu Leu Arg Asp Ala Ser Arg Phe Gly Glu Gly Trp Gly Leu Thr Gln
        195                 200                 205

Glu Ile Ile Asp Ser Asn Tyr Asn Asn Gln Leu Lys Leu Thr Glu Lys
    210                 215                 220

Tyr Thr Asp His Cys Val Lys Trp Tyr Asn Ala Gly Leu Glu Lys Leu
225                 230                 235                 240

Lys Gly Asn Leu Thr Gly Glu Asn Trp Tyr Thr Tyr Asn Arg Phe Arg
                245                 250                 255

Arg Glu Met Thr Leu Met Val Leu Asp Val Val Ala Leu Phe Pro Asn
            260                 265                 270

Tyr Asp Thr Arg Met Tyr Pro Ile Ala Thr Ser Ser Glu Leu Thr Arg
        275                 280                 285

Met Ile Tyr Thr Asp Pro Ile Ala Tyr Thr Gln Ser Asp Pro Trp Tyr
    290                 295                 300

Lys Ile Thr Ser Leu Ser Phe Ser Asn Ile Glu Asn Ser Ala Ile Pro
305                 310                 315                 320
```

-continued

```
Ser Pro Ser Phe Phe Lys Trp Leu Arg Ser Val Ser Ile Asn Ser Gln
                325                 330                 335

Trp Trp Gly Ser Gly Pro Asn Gln Thr Tyr Tyr Trp Val Gly His Glu
            340                 345                 350

Leu Val Tyr Ser Asn Ser Asn Ser Asn Gln Ser Leu Lys Val Lys Tyr
        355                 360                 365

Gly Asp Pro Asn Ser Tyr Ile Glu Pro Pro Asp Ser Phe Ser Phe Ser
    370                 375                 380

Ser Thr Asp Val Tyr Arg Thr Ile Ser Val Val Arg Asn Ser Val Ser
385                 390                 395                 400

Asn Tyr Ile Val Ser Glu Val Gln Phe Asn Ser Ile Ser Asn Thr Asn
                405                 410                 415

Gln Ile Ser Glu Glu Ile Tyr Lys His Gln Ser Asn Trp Ser Arg Lys
            420                 425                 430

Glu Thr Lys Asp Ser Ile Thr Glu Leu Ser Leu Ala Ala Asn Pro Pro
        435                 440                 445

Thr Thr Phe Gly Asn Val Ala Glu Tyr Ser His Arg Leu Ala Tyr Ile
    450                 455                 460

Ser Glu Ala Tyr Gln Ser Gln Asn Pro Ser Lys Tyr Pro Thr Tyr Ile
465                 470                 475                 480

Pro Val Phe Gly Trp Thr His Thr Ser Val Arg Tyr Asp Asn Lys Ile
                485                 490                 495

Phe Pro Asp Lys Ile Thr Gln Ile Pro Ala Val Lys Ser Ser Ser Ala
            500                 505                 510

Gln Gly Gly Ser Trp Lys Asn Ile Val Lys Gly Pro Gly Phe Thr Gly
        515                 520                 525

Gly Asp Val Thr Thr Ala Val Ser Pro Ala Thr Leu Thr Asp Ile Ile
    530                 535                 540

Lys Ile Gln Val Thr Leu Asp Pro Asn Ser Leu Ser Gln Lys Tyr Arg
545                 550                 555                 560

Ala Arg Leu Arg Tyr Ala Ser Asn Ala Phe Val Ala Ala Thr Leu Tyr
                565                 570                 575

Thr Asn Thr Ser Ser Asn Tyr Asn Phe Glu Leu Thr Lys Gly Thr Thr
            580                 585                 590

Glu Gln Phe Thr Thr Tyr Asn Ser Tyr Gln Tyr Val Asp Ile Pro Gly
        595                 600                 605

Ser Ile Gln Phe Asn Asn Thr Ser Asp Thr Val Ser Val Tyr Leu His
    610                 615                 620

Met Asp Ser Thr Thr Asn Ala Asn Val His Val Asp Arg Ile Glu Phe
625                 630                 635                 640

Ile Pro Val Asp Glu Gln Tyr Asp Glu Arg Val Thr Leu Glu Lys Ala
                645                 650                 655

Gln Lys Ala Val Asn Ala Leu Phe Thr Ala Gly Arg His Ala Leu Gln
            660                 665                 670

Thr Asp Val Thr Asp Tyr Lys Val Asp Gln Val Ser Ile Leu Val Asp
        675                 680                 685

Cys Val Ser Gly Glu Leu Tyr Pro Asn Glu Lys Arg Glu Leu Leu Ser
    690                 695                 700

Leu Val Lys Tyr Ala Lys Arg Leu Ser Tyr Ser Arg Asn Leu Leu Leu
705                 710                 715                 720

Asp Pro Thr Phe Asp Ser Ile Asn Ser Ser Asp Lys Asn Gly Trp Tyr
                725                 730                 735

Gly Ser Asn Gly Ile Ala Ile Ser Ser Gly Asn Phe Val Phe Lys Gly
```

```
            740                 745                 750

Asn Tyr Leu Ile Phe Ser Gly Thr Asn Asp Glu Gln Tyr Pro Thr Tyr
        755                 760                 765

Leu Tyr Gln Lys Ile Asp Glu Ser Lys Leu Lys Glu Tyr Thr Arg Tyr
    770                 775                 780

Lys Leu Arg Gly Phe Ile Glu Asn Ser Gln Asp Leu Glu Ala Tyr Val
785                 790                 795                 800

Ile Arg Tyr Asp Ala Lys His Glu Thr Leu Asp Val Ser Asn Asn Leu
                805                 810                 815

Leu Pro Asp Ile Ser Pro Val Asn Ala Cys Gly Glu Pro Asn Arg Cys
            820                 825                 830

Val Ala Leu Gln Tyr Leu Asp Glu Asn Pro Arg Leu Glu Cys Ser Ser
        835                 840                 845

Val Gln Asp Gly Ile Leu Ser Asp Ser His Ser Phe Ser Leu Asn Ile
    850                 855                 860

Asp Thr Gly Ser Ile Asp Phe Asn Glu Ser Val Gly Ile Trp Val Leu
865                 870                 875                 880

Phe Lys Ile Ser Thr Pro Glu Gly Tyr Ala Lys Phe Gly Asn Leu Glu
                885                 890                 895

Val Ile Glu Asn Gly Pro Val Ile Gly Glu Ala Leu Ala Arg Val Lys
            900                 905                 910

Arg Gln Glu Thr Lys Trp Arg Asn Gln Leu Thr Gln Leu Arg Thr Glu
        915                 920                 925

Thr Gln Ala Ile Tyr Thr Arg Ala Lys Gln Ala Leu Asp Asn Leu Phe
    930                 935                 940

Ala Asn Ala Gln Asp Ser His Leu Lys Ile Gly Thr Thr Phe Ala Ala
945                 950                 955                 960

Ile Val Ala Ala Arg Lys Ile Val Gln Ser Ile Arg Glu Ala Tyr Met
                965                 970                 975

Ser Trp Leu Ser Val Val Pro Gly Val Asn Tyr Pro Ile Phe Thr Glu
            980                 985                 990

Leu Thr Glu Arg Val Gln Gln Ala Phe Gln Leu Tyr Asp Val Arg Asn
        995                 1000                1005

Val Val Arg Asn Gly Gln Phe Leu Ser Gly Leu Ser Asp Trp Ile Val
    1010                1015                1020

Thr Pro Asp Val Lys Val Gln Glu Asp Asn Gly Asn Asn Val Leu Val
1025                1030                1035                1040

Leu Ser Asn Trp Asp Ala Gln Val Leu Gln Cys Leu Lys Leu Tyr Gln
                1045                1050                1055

Asp Arg Gly Tyr Ile Leu Arg Val Thr Ala Arg Lys Glu Gly Leu Gly
            1060                1065                1070

Glu Gly Tyr Val Thr Ile Thr Asp Glu Glu Gly Asn Thr Asp Gln Leu
        1075                1080                1085

Thr Phe Gly Ala Cys Glu Glu Ile Asp Ala Ser Asn Ala Phe Ile Ser
    1090                1095                1100

Thr Gly Tyr Ile Thr Lys Glu Leu Glu Phe Phe Pro Asp Thr Glu Lys
1105                1110                1115                1120

Val Arg Ile Glu Ile Gly Glu Thr Glu Gly Thr Phe Gln Val Glu Ser
                1125                1130                1135

Val Glu Leu Phe Leu Met Glu Asp Leu Cys
            1140                1145
```

<210> SEQ ID NO 22

<211> LENGTH: 3393
<212> TYPE: DNA
<213> ORGANISM: Bacillus thuringiensis
<220> FEATURE:
<221> NAME/KEY: CDS
<222> LOCATION: (1)...(3393)

<400> SEQUENCE: 22

```
atg aat caa aaa aac tat gat att ata ggt gct tcg aca aac ggt aca       48
Met Asn Gln Lys Asn Tyr Asp Ile Ile Gly Ala Ser Thr Asn Gly Thr
 1               5                  10                  15

aac aaa tta ctt gaa ggt tat aac att ata atc agt ccc tac gaa gct       96
Asn Lys Leu Leu Glu Gly Tyr Asn Ile Ile Ile Ser Pro Tyr Glu Ala
            20                  25                  30

cca aca tcc gtt act aca act att gaa att act gga acc ata cta agc      144
Pro Thr Ser Val Thr Thr Thr Ile Glu Ile Thr Gly Thr Ile Leu Ser
        35                  40                  45

gat tta ggt gtt cca gga gca tca tca gtt agt tta ctt ttg aat aaa      192
Asp Leu Gly Val Pro Gly Ala Ser Ser Val Ser Leu Leu Leu Asn Lys
    50                  55                  60

ctt ata aat cta tta tgg cca aat gat acc aat act gtg tgg ggg aca      240
Leu Ile Asn Leu Leu Trp Pro Asn Asp Thr Asn Thr Val Trp Gly Thr
 65                  70                  75                  80

ttc gga aaa gaa acc gct gat ctt cta aat gaa gtg tta tct cca aat      288
Phe Gly Lys Glu Thr Ala Asp Leu Leu Asn Glu Val Leu Ser Pro Asn
                85                  90                  95

gat cca gta gta aca gat gca aat act aat tta gca gga cta aat gac      336
Asp Pro Val Val Thr Asp Ala Asn Thr Asn Leu Ala Gly Leu Asn Asp
            100                 105                 110

tcc ctt aac tta tat tta aat gaa ctt gaa ata tgg aaa aaa gac ccc      384
Ser Leu Asn Leu Tyr Leu Asn Glu Leu Glu Ile Trp Lys Lys Asp Pro
        115                 120                 125

aac aac gca act acc caa agg aat gtc aca caa tac ttt gtt agt ttg      432
Asn Asn Ala Thr Thr Gln Arg Asn Val Thr Gln Tyr Phe Val Ser Leu
    130                 135                 140

aat ttg gat ttt aca cat gat atg cct tca ttt gct gta cct gga tat      480
Asn Leu Asp Phe Thr His Asp Met Pro Ser Phe Ala Val Pro Gly Tyr
145                 150                 155                 160

gaa acg aag tta tta aca att tat gca caa gct gca aat ctt cat tta      528
Glu Thr Lys Leu Leu Thr Ile Tyr Ala Gln Ala Ala Asn Leu His Leu
                165                 170                 175

ctt tta tta aga gat gct tct agg ttt gga gaa ggt tgg gga ctg act      576
Leu Leu Leu Arg Asp Ala Ser Arg Phe Gly Glu Gly Trp Gly Leu Thr
            180                 185                 190

caa gaa atc ata gat tct aac tat aat aat caa tta aaa ttg aca gaa      624
Gln Glu Ile Ile Asp Ser Asn Tyr Asn Asn Gln Leu Lys Leu Thr Glu
        195                 200                 205

aaa tac acg gac cat tgt gta aag tgg tac aac gca gga tta gaa aaa      672
Lys Tyr Thr Asp His Cys Val Lys Trp Tyr Asn Ala Gly Leu Glu Lys
    210                 215                 220

tta aaa gga aat tta act ggg gaa aat tgg tac act tat aat aga ttt      720
Leu Lys Gly Asn Leu Thr Gly Glu Asn Trp Tyr Thr Tyr Asn Arg Phe
225                 230                 235                 240

cgt aga gaa atg acg tta atg gtg tta gac gta gtt gca tta ttt cca      768
Arg Arg Glu Met Thr Leu Met Val Leu Asp Val Val Ala Leu Phe Pro
                245                 250                 255

aac tat gat aca cga atg tac ccg atc gca acg tca tca gaa ctt aca      816
Asn Tyr Asp Thr Arg Met Tyr Pro Ile Ala Thr Ser Ser Glu Leu Thr
            260                 265                 270

aga atg att tat aca gat cca atc gct tat aca caa agc gat cca tgg      864
Arg Met Ile Tyr Thr Asp Pro Ile Ala Tyr Thr Gln Ser Asp Pro Trp
```

```
        275                 280                 285

tac aag ata aca tct ctt tct ttt tca aat att gaa aac agc gcg att      912
Tyr Lys Ile Thr Ser Leu Ser Phe Ser Asn Ile Glu Asn Ser Ala Ile
    290                 295                 300

cca agt cct tct ttc ttc aag tgg cta aga tcc gtt tca att aat agc      960
Pro Ser Pro Ser Phe Phe Lys Trp Leu Arg Ser Val Ser Ile Asn Ser
305                 310                 315                 320

cag tgg tgg ggc agt ggt cct aat caa acc tac tat tgg gtt gga cat     1008
Gln Trp Trp Gly Ser Gly Pro Asn Gln Thr Tyr Tyr Trp Val Gly His
                325                 330                 335

gaa tta gta tat tct aat tca aat tct aat caa tca ctt aag gtt aaa     1056
Glu Leu Val Tyr Ser Asn Ser Asn Ser Asn Gln Ser Leu Lys Val Lys
            340                 345                 350

tat gga gac cct aat tct tat att gag ccc cct gat tct ttc agt ttt     1104
Tyr Gly Asp Pro Asn Ser Tyr Ile Glu Pro Pro Asp Ser Phe Ser Phe
        355                 360                 365

tct tct acg gat gtt tac aga acc att tct gtt gtt aga aat tca gta     1152
Ser Ser Thr Asp Val Tyr Arg Thr Ile Ser Val Val Arg Asn Ser Val
    370                 375                 380

agt aat tat ata gta agt gaa gtt caa ttc aat tca att agt aat aca     1200
Ser Asn Tyr Ile Val Ser Glu Val Gln Phe Asn Ser Ile Ser Asn Thr
385                 390                 395                 400

aat caa att agt gaa gaa att tat aaa cat caa tca aat tgg agt aga     1248
Asn Gln Ile Ser Glu Glu Ile Tyr Lys His Gln Ser Asn Trp Ser Arg
                405                 410                 415

aaa gaa acc aaa gat tca att aca gaa cta tcc tta gct gct aat ccc     1296
Lys Glu Thr Lys Asp Ser Ile Thr Glu Leu Ser Leu Ala Ala Asn Pro
            420                 425                 430

cca aca aca ttt gga aat gta gca gaa tac agt cat aga tta gca tat     1344
Pro Thr Thr Phe Gly Asn Val Ala Glu Tyr Ser His Arg Leu Ala Tyr
        435                 440                 445

att tca gag gca tac caa agt caa aac cca tca aaa tac cca acc tac     1392
Ile Ser Glu Ala Tyr Gln Ser Gln Asn Pro Ser Lys Tyr Pro Thr Tyr
    450                 455                 460

att cct gta ttc ggt tgg acg cat aca agc gta cgt tac gat aat aaa     1440
Ile Pro Val Phe Gly Trp Thr His Thr Ser Val Arg Tyr Asp Asn Lys
465                 470                 475                 480

att ttc ccg gac aaa atc act caa att cca gct gtt aaa agc tct tca     1488
Ile Phe Pro Asp Lys Ile Thr Gln Ile Pro Ala Val Lys Ser Ser Ser
                485                 490                 495

gct caa ggt gga tca tgg aaa aat ata gtg aaa ggt ccc ggg ttt act     1536
Ala Gln Gly Gly Ser Trp Lys Asn Ile Val Lys Gly Pro Gly Phe Thr
            500                 505                 510

gga gga gat gtg aca act gca gtt tcg cca gca act tta acc gac ata     1584
Gly Gly Asp Val Thr Thr Ala Val Ser Pro Ala Thr Leu Thr Asp Ile
        515                 520                 525

ata aaa ata caa gtt act cta gat cca aat tca ctt tca caa aaa tat     1632
Ile Lys Ile Gln Val Thr Leu Asp Pro Asn Ser Leu Ser Gln Lys Tyr
    530                 535                 540

cgt gca cga ctt cgc tat gct tcc aat gca ttt gta gca gct act ttg     1680
Arg Ala Arg Leu Arg Tyr Ala Ser Asn Ala Phe Val Ala Ala Thr Leu
545                 550                 555                 560

tat aca aat aca agt agt aat tat aat ttt gaa ctt aca aaa ggt aca     1728
Tyr Thr Asn Thr Ser Ser Asn Tyr Asn Phe Glu Leu Thr Lys Gly Thr
                565                 570                 575

act gaa cag ttt aca aca tat aat tca tac cag tat gta gat atc cca     1776
Thr Glu Gln Phe Thr Thr Tyr Asn Ser Tyr Gln Tyr Val Asp Ile Pro
            580                 585                 590

ggt tca ata caa ttt aat aat act tct gat aca gtg tct gtt tat ttg     1824
```

-continued

```
Gly Ser Ile Gln Phe Asn Asn Thr Ser Asp Thr Val Ser Val Tyr Leu
        595                 600                 605

cat atg gat tca aca act aat gca aac gtt cat gta gat aga att gaa      1872
His Met Asp Ser Thr Thr Asn Ala Asn Val His Val Asp Arg Ile Glu
    610                 615                 620

ttc att cca gta gat gaa cag tac gat gaa aga gta aca cta gaa aaa      1920
Phe Ile Pro Val Asp Glu Gln Tyr Asp Glu Arg Val Thr Leu Glu Lys
625                 630                 635                 640

gca cag aaa gcc gtg aat gcc ttg ttt aca gcg gga aga cat gca ctc      1968
Ala Gln Lys Ala Val Asn Ala Leu Phe Thr Ala Gly Arg His Ala Leu
                645                 650                 655

caa aca gat gtg aca gat tac aaa gtg gat caa gtg tca att tta gtg      2016
Gln Thr Asp Val Thr Asp Tyr Lys Val Asp Gln Val Ser Ile Leu Val
            660                 665                 670

gat tgt gta tca ggg gag tta tat cca aat gag aaa cgc gaa cta ctc      2064
Asp Cys Val Ser Gly Glu Leu Tyr Pro Asn Glu Lys Arg Glu Leu Leu
        675                 680                 685

agt tta gtc aaa tac gca aaa cgt ttg agc tat tct cgt aat tta ctc      2112
Ser Leu Val Lys Tyr Ala Lys Arg Leu Ser Tyr Ser Arg Asn Leu Leu
    690                 695                 700

cta gat cca aca ttc gat tct atc aat tca tca gat aag aat ggc tgg      2160
Leu Asp Pro Thr Phe Asp Ser Ile Asn Ser Ser Asp Lys Asn Gly Trp
705                 710                 715                 720

tac ggg agt aat ggt att gca att agc agt ggg aat ttt gta ttc aaa      2208
Tyr Gly Ser Asn Gly Ile Ala Ile Ser Ser Gly Asn Phe Val Phe Lys
                725                 730                 735

ggg aac tat tta atc ttc tca ggt aca aat gat gaa caa tat cca acc      2256
Gly Asn Tyr Leu Ile Phe Ser Gly Thr Asn Asp Glu Gln Tyr Pro Thr
            740                 745                 750

tat ctc tat caa aaa ata gac gaa tct aag tta aaa gaa tat aca cgt      2304
Tyr Leu Tyr Gln Lys Ile Asp Glu Ser Lys Leu Lys Glu Tyr Thr Arg
        755                 760                 765

tat aaa ctg aga ggc ttt ata gaa aat agt caa gat tta gaa gca tat      2352
Tyr Lys Leu Arg Gly Phe Ile Glu Asn Ser Gln Asp Leu Glu Ala Tyr
    770                 775                 780

gtc att cgc tat gat gcc aaa cat gaa aca ttg gat gta tcc aat aat      2400
Val Ile Arg Tyr Asp Ala Lys His Glu Thr Leu Asp Val Ser Asn Asn
785                 790                 795                 800

cta tta ccg gat att tct cct gta aat gca tgt gga gaa cca aat cgt      2448
Leu Leu Pro Asp Ile Ser Pro Val Asn Ala Cys Gly Glu Pro Asn Arg
                805                 810                 815

tgt gtg gca tta caa tac ctg gat gaa aac cca aga tta gaa tgt agt      2496
Cys Val Ala Leu Gln Tyr Leu Asp Glu Asn Pro Arg Leu Glu Cys Ser
            820                 825                 830

tcg gtt caa gat ggt att tta tct gat tcg cat tca ttt tct ctc aat      2544
Ser Val Gln Asp Gly Ile Leu Ser Asp Ser His Ser Phe Ser Leu Asn
        835                 840                 845

ata gat aca ggt tct att gat ttc aat gag agc gta gga att tgg gtg      2592
Ile Asp Thr Gly Ser Ile Asp Phe Asn Glu Ser Val Gly Ile Trp Val
    850                 855                 860

ttg ttt aaa att tcc aca ccg gaa ggg tat gcg aaa ttt gga aac cta      2640
Leu Phe Lys Ile Ser Thr Pro Glu Gly Tyr Ala Lys Phe Gly Asn Leu
865                 870                 875                 880

gaa gtg att gaa aat ggc cca gtc atc gga gaa gca tta gcc cgt gtg      2688
Glu Val Ile Glu Asn Gly Pro Val Ile Gly Glu Ala Leu Ala Arg Val
                885                 890                 895

aaa cgc caa gaa aca aag tgg aga aac cag ttg aca caa ctg aga acg      2736
Lys Arg Gln Glu Thr Lys Trp Arg Asn Gln Leu Thr Gln Leu Arg Thr
            900                 905                 910
```

```
gaa aca caa gcg att tat aca cga gca aaa caa gcg ctg gat aat ctt     2784
Glu Thr Gln Ala Ile Tyr Thr Arg Ala Lys Gln Ala Leu Asp Asn Leu
        915                 920                 925

ttt gcg aat gca caa gac tct cac tta aaa ata ggt acg aca ttt gcg     2832
Phe Ala Asn Ala Gln Asp Ser His Leu Lys Ile Gly Thr Thr Phe Ala
    930                 935                 940

gca att gtg gct gcg cga aag att gtc caa tcc ata cgc gaa gcg tat     2880
Ala Ile Val Ala Ala Arg Lys Ile Val Gln Ser Ile Arg Glu Ala Tyr
945                 950                 955                 960

atg tca tgg tta tct gtt gtt cca ggt gta aat tat cct atc ttt aca     2928
Met Ser Trp Leu Ser Val Val Pro Gly Val Asn Tyr Pro Ile Phe Thr
                965                 970                 975

gag ttg act gag aga gta cag caa gca ttt caa tta tat gat gta cga     2976
Glu Leu Thr Glu Arg Val Gln Gln Ala Phe Gln Leu Tyr Asp Val Arg
            980                 985                 990

aat gtc gtg cgt aat ggc caa ttc ctt agt ggc tta tcc gat tgg att     3024
Asn Val Val Arg Asn Gly Gln Phe Leu Ser Gly Leu Ser Asp Trp Ile
        995                 1000                1005

gta aca cct gac gtc aag gta caa gaa gac aat ggg aat aac gta ttg     3072
Val Thr Pro Asp Val Lys Val Gln Glu Asp Asn Gly Asn Asn Val Leu
    1010                1015                1020

gtt ctt tct aat tgg gat gcg caa gta tta caa tgt ctg aag ctc tat     3120
Val Leu Ser Asn Trp Asp Ala Gln Val Leu Gln Cys Leu Lys Leu Tyr
1025                1030                1035                1040

caa gat cgc ggg tat atc tta cgt gta acg gca cgt aag gaa gga ttg     3168
Gln Asp Arg Gly Tyr Ile Leu Arg Val Thr Ala Arg Lys Glu Gly Leu
                1045                1050                1055

gga gaa gga tac gta aca att acg gat gaa gaa ggg aat aca gat caa     3216
Gly Glu Gly Tyr Val Thr Ile Thr Asp Glu Glu Gly Asn Thr Asp Gln
            1060                1065                1070

ttg acg ttt ggt gca tgt gag gag ata gat gca tct aat gcg ttc att     3264
Leu Thr Phe Gly Ala Cys Glu Glu Ile Asp Ala Ser Asn Ala Phe Ile
        1075                1080                1085

tcc aca ggt tat att aca aaa gaa ctg gaa ttc ttc cca gat aca gag     3312
Ser Thr Gly Tyr Ile Thr Lys Glu Leu Glu Phe Phe Pro Asp Thr Glu
    1090                1095                1100

aaa gtg cgt ata gaa att gga gaa aca gaa gga aca ttc cag gtg gaa     3360
Lys Val Arg Ile Glu Ile Gly Glu Thr Glu Gly Thr Phe Gln Val Glu
1105                1110                1115                1120

agt gta gaa tta ttc ttg atg gaa gat cta tgt                         3393
Ser Val Glu Leu Phe Leu Met Glu Asp Leu Cys
                1125                1130


<210> SEQ ID NO 23
<211> LENGTH: 1131
<212> TYPE: PRT
<213> ORGANISM: Bacillus thuringiensis

<400> SEQUENCE: 23

Met Asn Gln Lys Asn Tyr Asp Ile Ile Gly Ala Ser Thr Asn Gly Thr
 1               5                  10                  15

Asn Lys Leu Leu Glu Gly Tyr Asn Ile Ile Ile Ser Pro Tyr Glu Ala
            20                  25                  30

Pro Thr Ser Val Thr Thr Thr Ile Glu Ile Thr Gly Thr Ile Leu Ser
        35                  40                  45

Asp Leu Gly Val Pro Gly Ala Ser Ser Val Ser Leu Leu Leu Asn Lys
    50                  55                  60

Leu Ile Asn Leu Leu Trp Pro Asn Asp Thr Asn Thr Val Trp Gly Thr
65                  70                  75                  80
```

-continued

```
Phe Gly Lys Glu Thr Ala Asp Leu Leu Asn Glu Val Leu Ser Pro Asn
                85                  90                  95

Asp Pro Val Val Thr Asp Ala Asn Thr Asn Leu Ala Gly Leu Asn Asp
            100                 105                 110

Ser Leu Asn Leu Tyr Leu Asn Glu Leu Glu Ile Trp Lys Lys Asp Pro
        115                 120                 125

Asn Asn Ala Thr Thr Gln Arg Asn Val Thr Gln Tyr Phe Val Ser Leu
    130                 135                 140

Asn Leu Asp Phe Thr His Asp Met Pro Ser Phe Ala Val Pro Gly Tyr
145                 150                 155                 160

Glu Thr Lys Leu Leu Thr Ile Tyr Ala Gln Ala Ala Asn Leu His Leu
                165                 170                 175

Leu Leu Leu Arg Asp Ala Ser Arg Phe Gly Glu Gly Trp Gly Leu Thr
            180                 185                 190

Gln Glu Ile Ile Asp Ser Asn Tyr Asn Asn Gln Leu Lys Leu Thr Glu
        195                 200                 205

Lys Tyr Thr Asp His Cys Val Lys Trp Tyr Asn Ala Gly Leu Glu Lys
    210                 215                 220

Leu Lys Gly Asn Leu Thr Gly Glu Asn Trp Tyr Thr Tyr Asn Arg Phe
225                 230                 235                 240

Arg Arg Glu Met Thr Leu Met Val Leu Asp Val Val Ala Leu Phe Pro
                245                 250                 255

Asn Tyr Asp Thr Arg Met Tyr Pro Ile Ala Thr Ser Ser Glu Leu Thr
            260                 265                 270

Arg Met Ile Tyr Thr Asp Pro Ile Ala Tyr Thr Gln Ser Asp Pro Trp
        275                 280                 285

Tyr Lys Ile Thr Ser Leu Ser Phe Ser Asn Ile Glu Asn Ser Ala Ile
    290                 295                 300

Pro Ser Pro Ser Phe Phe Lys Trp Leu Arg Ser Val Ser Ile Asn Ser
305                 310                 315                 320

Gln Trp Trp Gly Ser Gly Pro Asn Gln Thr Tyr Tyr Trp Val Gly His
                325                 330                 335

Glu Leu Val Tyr Ser Asn Ser Asn Ser Asn Gln Ser Leu Lys Val Lys
            340                 345                 350

Tyr Gly Asp Pro Asn Ser Tyr Ile Glu Pro Pro Asp Ser Phe Ser Phe
        355                 360                 365

Ser Ser Thr Asp Val Tyr Arg Thr Ile Ser Val Val Arg Asn Ser Val
    370                 375                 380

Ser Asn Tyr Ile Val Ser Glu Val Gln Phe Asn Ser Ile Ser Asn Thr
385                 390                 395                 400

Asn Gln Ile Ser Glu Glu Ile Tyr Lys His Gln Ser Asn Trp Ser Arg
                405                 410                 415

Lys Glu Thr Lys Asp Ser Ile Thr Glu Leu Ser Leu Ala Ala Asn Pro
            420                 425                 430

Pro Thr Thr Phe Gly Asn Val Ala Glu Tyr Ser His Arg Leu Ala Tyr
        435                 440                 445

Ile Ser Glu Ala Tyr Gln Ser Gln Asn Pro Ser Lys Tyr Pro Thr Tyr
    450                 455                 460

Ile Pro Val Phe Gly Trp Thr His Thr Ser Val Arg Tyr Asp Asn Lys
465                 470                 475                 480

Ile Phe Pro Asp Lys Ile Thr Gln Ile Pro Ala Val Lys Ser Ser Ser
                485                 490                 495

Ala Gln Gly Gly Ser Trp Lys Asn Ile Val Lys Gly Pro Gly Phe Thr
```

```
            500                 505                 510

Gly Gly Asp Val Thr Thr Ala Val Ser Pro Ala Thr Leu Thr Asp Ile
        515                 520                 525

Ile Lys Ile Gln Val Thr Leu Asp Pro Asn Ser Leu Ser Gln Lys Tyr
    530                 535                 540

Arg Ala Arg Leu Arg Tyr Ala Ser Asn Ala Phe Val Ala Ala Thr Leu
545                 550                 555                 560

Tyr Thr Asn Thr Ser Ser Asn Tyr Asn Phe Glu Leu Thr Lys Gly Thr
                565                 570                 575

Thr Glu Gln Phe Thr Thr Tyr Asn Ser Tyr Gln Tyr Val Asp Ile Pro
            580                 585                 590

Gly Ser Ile Gln Phe Asn Asn Thr Ser Asp Thr Val Ser Val Tyr Leu
        595                 600                 605

His Met Asp Ser Thr Thr Asn Ala Asn Val His Val Asp Arg Ile Glu
    610                 615                 620

Phe Ile Pro Val Asp Glu Gln Tyr Asp Glu Arg Val Thr Leu Glu Lys
625                 630                 635                 640

Ala Gln Lys Ala Val Asn Ala Leu Phe Thr Ala Gly Arg His Ala Leu
                645                 650                 655

Gln Thr Asp Val Thr Asp Tyr Lys Val Asp Gln Val Ser Ile Leu Val
            660                 665                 670

Asp Cys Val Ser Gly Glu Leu Tyr Pro Asn Glu Lys Arg Glu Leu Leu
        675                 680                 685

Ser Leu Val Lys Tyr Ala Lys Arg Leu Ser Tyr Ser Arg Asn Leu Leu
    690                 695                 700

Leu Asp Pro Thr Phe Asp Ser Ile Asn Ser Ser Asp Lys Asn Gly Trp
705                 710                 715                 720

Tyr Gly Ser Asn Gly Ile Ala Ile Ser Ser Gly Asn Phe Val Phe Lys
                725                 730                 735

Gly Asn Tyr Leu Ile Phe Ser Gly Thr Asn Asp Glu Gln Tyr Pro Thr
            740                 745                 750

Tyr Leu Tyr Gln Lys Ile Asp Glu Ser Lys Leu Lys Glu Tyr Thr Arg
        755                 760                 765

Tyr Lys Leu Arg Gly Phe Ile Glu Asn Ser Gln Asp Leu Glu Ala Tyr
    770                 775                 780

Val Ile Arg Tyr Asp Ala Lys His Glu Thr Leu Asp Val Ser Asn Asn
785                 790                 795                 800

Leu Leu Pro Asp Ile Ser Pro Val Asn Ala Cys Gly Glu Pro Asn Arg
                805                 810                 815

Cys Val Ala Leu Gln Tyr Leu Asp Glu Asn Pro Arg Leu Glu Cys Ser
            820                 825                 830

Ser Val Gln Asp Gly Ile Leu Ser Asp Ser His Ser Phe Ser Leu Asn
        835                 840                 845

Ile Asp Thr Gly Ser Ile Asp Phe Asn Glu Ser Val Gly Ile Trp Val
    850                 855                 860

Leu Phe Lys Ile Ser Thr Pro Glu Gly Tyr Ala Lys Phe Gly Asn Leu
865                 870                 875                 880

Glu Val Ile Glu Asn Gly Pro Val Ile Gly Glu Ala Leu Ala Arg Val
                885                 890                 895

Lys Arg Gln Glu Thr Lys Trp Arg Asn Gln Leu Thr Gln Leu Arg Thr
            900                 905                 910

Glu Thr Gln Ala Ile Tyr Thr Arg Ala Lys Gln Ala Leu Asp Asn Leu
        915                 920                 925
```

```
Phe Ala Asn Ala Gln Asp Ser His Leu Lys Ile Gly Thr Thr Phe Ala
    930                 935                 940

Ala Ile Val Ala Ala Arg Lys Ile Val Gln Ser Ile Arg Glu Ala Tyr
945                 950                 955                 960

Met Ser Trp Leu Ser Val Val Pro Gly Val Asn Tyr Pro Ile Phe Thr
                965                 970                 975

Glu Leu Thr Glu Arg Val Gln Gln Ala Phe Gln Leu Tyr Asp Val Arg
            980                 985                 990

Asn Val Val Arg Asn Gly Gln Phe Leu Ser Gly Leu Ser Asp Trp Ile
        995                 1000                1005

Val Thr Pro Asp Val Lys Val Gln Glu Asp Asn Gly Asn Asn Val Leu
    1010                1015                1020

Val Leu Ser Asn Trp Asp Ala Gln Val Leu Gln Cys Leu Lys Leu Tyr
1025                1030                1035                1040

Gln Asp Arg Gly Tyr Ile Leu Arg Val Thr Ala Arg Lys Glu Gly Leu
                1045                1050                1055

Gly Glu Gly Tyr Val Thr Ile Thr Asp Glu Glu Gly Asn Thr Asp Gln
            1060                1065                1070

Leu Thr Phe Gly Ala Cys Glu Glu Ile Asp Ala Ser Asn Ala Phe Ile
        1075                1080                1085

Ser Thr Gly Tyr Ile Thr Lys Glu Leu Glu Phe Phe Pro Asp Thr Glu
    1090                1095                1100

Lys Val Arg Ile Glu Ile Gly Glu Thr Glu Gly Thr Phe Gln Val Glu
1105                1110                1115                1120

Ser Val Glu Leu Phe Leu Met Glu Asp Leu Cys
                1125                1130


<210> SEQ ID NO 24
<211> LENGTH: 1002
<212> TYPE: DNA
<213> ORGANISM: Bacillus thuringiensis
<220> FEATURE:
<221> NAME/KEY: CDS
<222> LOCATION: (1)...(1002)

<400> SEQUENCE: 24

atg gtg aga gtc tat cca gac ttt gat gag atg ata agg gaa gct gct       48
Met Val Arg Val Tyr Pro Asp Phe Asp Glu Met Ile Arg Glu Ala Ala
 1               5                  10                  15

cga aaa tgg tca gaa gca aat gga ttg cta ttt caa aag gtg tcg tat       96
Arg Lys Trp Ser Glu Ala Asn Gly Leu Leu Phe Gln Lys Val Ser Tyr
            20                  25                  30

gcg gat cct tta acc aat gcg gat aca atc agt cta agt gtc aaa ttc      144
Ala Asp Pro Leu Thr Asn Ala Asp Thr Ile Ser Leu Ser Val Lys Phe
        35                  40                  45

aaa gat atc gga tgc cta gaa gaa tgc gtc gaa gta gaa aaa ata agc      192
Lys Asp Ile Gly Cys Leu Glu Glu Cys Val Glu Val Glu Lys Ile Ser
     50                  55                  60

att cca caa aat ttt acg aat aat acg gat caa aaa caa aaa gaa aca      240
Ile Pro Gln Asn Phe Thr Asn Asn Thr Asp Gln Lys Gln Lys Glu Thr
 65                  70                  75                  80

ttg gaa act ata aca tat gta gaa aat ctg ttg act tgg gaa aat gac      288
Leu Glu Thr Ile Thr Tyr Val Glu Asn Leu Leu Thr Trp Glu Asn Asp
                85                  90                  95

ttt cat ttt gtg ctt cca gga caa aac ttt ctt acg ata cca cgt gtt      336
Phe His Phe Val Leu Pro Gly Gln Asn Phe Leu Thr Ile Pro Arg Val
            100                 105                 110
```

-continued

```
cct cgt tca gtt cat atg gat att aat cca ggt ttc ctt gtg aat ttt      384
Pro Arg Ser Val His Met Asp Ile Asn Pro Gly Phe Leu Val Asn Phe
        115                 120                 125

ttt ggt aga aat caa cta ttc cat acc aaa ata aga gaa cca cgt ccc      432
Phe Gly Arg Asn Gln Leu Phe His Thr Lys Ile Arg Glu Pro Arg Pro
    130                 135                 140

att cgg gcg gaa gtg ttt tta gaa cca tct agc agt gca tcg att caa      480
Ile Arg Ala Glu Val Phe Leu Glu Pro Ser Ser Ser Ala Ser Ile Gln
145                 150                 155                 160

ctg caa gtg gaa aaa caa cat gtt tct caa ccg tat caa atg gaa tta      528
Leu Gln Val Glu Lys Gln His Val Ser Gln Pro Tyr Gln Met Glu Leu
                165                 170                 175

tca atg cta gga agt att att gtg acg gca caa gat aga gga cag gaa      576
Ser Met Leu Gly Ser Ile Ile Val Thr Ala Gln Asp Arg Gly Gln Glu
            180                 185                 190

caa ggt acg gat cgc tat gtt gag tta aca gat ctc ata cca ttc ctc      624
Gln Gly Thr Asp Arg Tyr Val Glu Leu Thr Asp Leu Ile Pro Phe Leu
        195                 200                 205

tgc ccg cat aaa aac ttt tct tct aaa ggg cgg gca ttg ata ttc ctt      672
Cys Pro His Lys Asn Phe Ser Ser Lys Gly Arg Ala Leu Ile Phe Leu
    210                 215                 220

gaa cag gga acg ttc aag gga ata ttg agt cga aag ata cgt gca tat      720
Glu Gln Gly Thr Phe Lys Gly Ile Leu Ser Arg Lys Ile Arg Ala Tyr
225                 230                 235                 240

gcc aca caa atg ctt cat tgc gac gga aaa aca cta gaa tat gaa att      768
Ala Thr Gln Met Leu His Cys Asp Gly Lys Thr Leu Glu Tyr Glu Ile
                245                 250                 255

cct tta aat aat cca tta cct gaa tct gcc cta cga cct aaa cct atg      816
Pro Leu Asn Asn Pro Leu Pro Glu Ser Ala Leu Arg Pro Lys Pro Met
            260                 265                 270

acg att aac gct aca tca tgt gga tgt tct tct gat aga cca tca gtc      864
Thr Ile Asn Ala Thr Ser Cys Gly Cys Ser Ser Asp Arg Pro Ser Val
        275                 280                 285

gta tct act tcc tct cat cca tcg aat cct aca acc tat tcc cag caa      912
Val Ser Thr Ser Ser His Pro Ser Asn Pro Thr Thr Tyr Ser Gln Gln
    290                 295                 300

cct aaa cct atg acg act aac gct aca tca tgt gga tgt tct gcc tgt      960
Pro Lys Pro Met Thr Thr Asn Ala Thr Ser Cys Gly Cys Ser Ala Cys
305                 310                 315                 320

atg tct gca aca tca aat aaa aat cta tat aca gaa caa taa             1002
Met Ser Ala Thr Ser Asn Lys Asn Leu Tyr Thr Glu Gln
                325                 330


<210> SEQ ID NO 25
<211> LENGTH: 333
<212> TYPE: PRT
<213> ORGANISM: Bacillus thuringiensis

<400> SEQUENCE: 25

Met Val Arg Val Tyr Pro Asp Phe Asp Glu Met Ile Arg Glu Ala Ala
 1               5                  10                  15

Arg Lys Trp Ser Glu Ala Asn Gly Leu Leu Phe Gln Lys Val Ser Tyr
            20                  25                  30

Ala Asp Pro Leu Thr Asn Ala Asp Thr Ile Ser Leu Ser Val Lys Phe
        35                  40                  45

Lys Asp Ile Gly Cys Leu Glu Glu Cys Val Glu Val Glu Lys Ile Ser
    50                  55                  60

Ile Pro Gln Asn Phe Thr Asn Asn Thr Asp Gln Lys Gln Lys Glu Thr
65                  70                  75                  80
```

```
Leu Glu Thr Ile Thr Tyr Val Glu Asn Leu Leu Thr Trp Glu Asn Asp
                85                  90                  95

Phe His Phe Val Leu Pro Gly Gln Asn Phe Leu Thr Ile Pro Arg Val
            100                 105                 110

Pro Arg Ser Val His Met Asp Ile Asn Pro Gly Phe Leu Val Asn Phe
        115                 120                 125

Phe Gly Arg Asn Gln Leu Phe His Thr Lys Ile Arg Glu Pro Arg Pro
    130                 135                 140

Ile Arg Ala Glu Val Phe Leu Glu Pro Ser Ser Ser Ala Ser Ile Gln
145                 150                 155                 160

Leu Gln Val Glu Lys Gln His Val Ser Gln Pro Tyr Gln Met Glu Leu
                165                 170                 175

Ser Met Leu Gly Ser Ile Ile Val Thr Ala Gln Asp Arg Gly Gln Glu
            180                 185                 190

Gln Gly Thr Asp Arg Tyr Val Glu Leu Thr Asp Leu Ile Pro Phe Leu
        195                 200                 205

Cys Pro His Lys Asn Phe Ser Ser Lys Gly Arg Ala Leu Ile Phe Leu
    210                 215                 220

Glu Gln Gly Thr Phe Lys Gly Ile Leu Ser Arg Lys Ile Arg Ala Tyr
225                 230                 235                 240

Ala Thr Gln Met Leu His Cys Asp Gly Lys Thr Leu Glu Tyr Glu Ile
                245                 250                 255

Pro Leu Asn Asn Pro Leu Pro Glu Ser Ala Leu Arg Pro Lys Pro Met
            260                 265                 270

Thr Ile Asn Ala Thr Ser Cys Gly Cys Ser Ser Asp Arg Pro Ser Val
        275                 280                 285

Val Ser Thr Ser Ser His Pro Ser Asn Pro Thr Thr Tyr Ser Gln Gln
    290                 295                 300

Pro Lys Pro Met Thr Thr Asn Ala Thr Ser Cys Gly Cys Ser Ala Cys
305                 310                 315                 320

Met Ser Ala Thr Ser Asn Lys Asn Leu Tyr Thr Glu Gln
                325                 330


<210> SEQ ID NO 26
<211> LENGTH: 1026
<212> TYPE: DNA
<213> ORGANISM: Bacillus thuringiensis
<220> FEATURE:
<221> NAME/KEY: CDS
<222> LOCATION: (1)...(1026)

<400> SEQUENCE: 26

atg aaa aag tct tgt aat cca aat gaa gtg aat cca agt gca tat act       48
Met Lys Lys Ser Cys Asn Pro Asn Glu Val Asn Pro Ser Ala Tyr Thr
 1               5                  10                  15

tta tac aac ttt gat gag tat gta att ggc aat ttt ttc aat gca gtg       96
Leu Tyr Asn Phe Asp Glu Tyr Val Ile Gly Asn Phe Phe Asn Ala Val
            20                  25                  30

caa cac cct ata aat ctt tcc ttc aga gaa gat gaa tgg aat ttt gat      144
Gln His Pro Ile Asn Leu Ser Phe Arg Glu Asp Glu Trp Asn Phe Asp
        35                  40                  45

tca gac tat att cct acc cca act tct gac caa cta act agc cct tgt      192
Ser Asp Tyr Ile Pro Thr Pro Thr Ser Asp Gln Leu Thr Ser Pro Cys
     50                  55                  60

aaa tct gtt cca acc agc gca ccg tgt aaa tat ggt cca atc gat cct      240
Lys Ser Val Pro Thr Ser Ala Pro Cys Lys Tyr Gly Pro Ile Asp Pro
 65                  70                  75                  80
```

-continued

```
tat gag tgg ata gaa tgg cta gac ctc gta gca gaa ggg aca gat tta      288
Tyr Glu Trp Ile Glu Trp Leu Asp Leu Val Ala Glu Gly Thr Asp Leu
                85                  90                  95

tat gaa gaa atc caa aat gca aat aca aaa acc ccg ttt att aat gat      336
Tyr Glu Glu Ile Gln Asn Ala Asn Thr Lys Thr Pro Phe Ile Asn Asp
            100                 105                 110

gaa tat tac ttt aat aat aca tca tct gaa aca caa cca tat cag acc      384
Glu Tyr Tyr Phe Asn Asn Thr Ser Ser Glu Thr Gln Pro Tyr Gln Thr
        115                 120                 125

att tct cat tca gaa aca ttg acc aca acc acg aca aac aca aca aca      432
Ile Ser His Ser Glu Thr Leu Thr Thr Thr Thr Thr Asn Thr Thr Thr
    130                 135                 140

caa gga tgt aaa ata aat cca aaa gtc agt tat tcg aga aaa acg aaa      480
Gln Gly Cys Lys Ile Asn Pro Lys Val Ser Tyr Ser Arg Lys Thr Lys
145                 150                 155                 160

gtt aaa gtc aaa att gtt gat gta gaa aag gga ttt aac acg gaa ata      528
Val Lys Val Lys Ile Val Asp Val Glu Lys Gly Phe Asn Thr Glu Ile
                165                 170                 175

ggg gca gaa tat aac ttt agc gat aca aac aca tac aca gaa aca gca      576
Gly Ala Glu Tyr Asn Phe Ser Asp Thr Asn Thr Tyr Thr Glu Thr Ala
            180                 185                 190

act cgg act gtg aca gtt cca tca atg acg aca tat gtt cca ccc tat      624
Thr Arg Thr Val Thr Val Pro Ser Met Thr Thr Tyr Val Pro Pro Tyr
        195                 200                 205

acc tct gcg tat gtg acg gtc gta tta gaa aga gga tat tat gaa gct      672
Thr Ser Ala Tyr Val Thr Val Val Leu Glu Arg Gly Tyr Tyr Glu Ala
    210                 215                 220

tat aat att cca atc gac acg aat tta tat gga aga ttt gaa ctc atc      720
Tyr Asn Ile Pro Ile Asp Thr Asn Leu Tyr Gly Arg Phe Glu Leu Ile
225                 230                 235                 240

tac acc aac ctc gat ggc agc aac cct cga tcg gcg ggt gtt ctg gat      768
Tyr Thr Asn Leu Asp Gly Ser Asn Pro Arg Ser Ala Gly Val Leu Asp
                245                 250                 255

cta tat cct ttc gta gaa tta att aca aca tgt tgt caa aat tgt agt      816
Leu Tyr Pro Phe Val Glu Leu Ile Thr Thr Cys Cys Gln Asn Cys Ser
            260                 265                 270

cag tgt gtg cca gac atg att cag cct gat cgt gac aat caa aca gtt      864
Gln Cys Val Pro Asp Met Ile Gln Pro Asp Arg Asp Asn Gln Thr Val
        275                 280                 285

cgt ttt act gga aga ggg gat ctt ata tcg gat ttt gca gcg aat act      912
Arg Phe Thr Gly Arg Gly Asp Leu Ile Ser Asp Phe Ala Ala Asn Thr
    290                 295                 300

tta acc gta acg act aca ttt gtt gac aat gca aca gga gca acc gtt      960
Leu Thr Val Thr Thr Thr Phe Val Asp Asn Ala Thr Gly Ala Thr Val
305                 310                 315                 320

tcg caa cac gta gaa tcc gta cca gtt cag tat gga ccc gct acc aca     1008
Ser Gln His Val Glu Ser Val Pro Val Gln Tyr Gly Pro Ala Thr Thr
                325                 330                 335

gta gta aac aca tct aaa                                              1026
Val Val Asn Thr Ser Lys
            340


<210> SEQ ID NO 27
<211> LENGTH: 342
<212> TYPE: PRT
<213> ORGANISM: Bacillus thuringiensis

<400> SEQUENCE: 27

Met Lys Lys Ser Cys Asn Pro Asn Glu Val Asn Pro Ser Ala Tyr Thr
 1               5                  10                  15
```

```
Leu Tyr Asn Phe Asp Glu Tyr Val Ile Gly Asn Phe Phe Asn Ala Val
            20                  25                  30

Gln His Pro Ile Asn Leu Ser Phe Arg Glu Asp Glu Trp Asn Phe Asp
        35                  40                  45

Ser Asp Tyr Ile Pro Thr Pro Thr Ser Asp Gln Leu Thr Ser Pro Cys
    50                  55                  60

Lys Ser Val Pro Thr Ser Ala Pro Cys Lys Tyr Gly Pro Ile Asp Pro
65                  70                  75                  80

Tyr Glu Trp Ile Glu Trp Leu Asp Leu Val Ala Glu Gly Thr Asp Leu
                85                  90                  95

Tyr Glu Glu Ile Gln Asn Ala Asn Thr Lys Thr Pro Phe Ile Asn Asp
            100                 105                 110

Glu Tyr Tyr Phe Asn Asn Thr Ser Ser Glu Thr Gln Pro Tyr Gln Thr
        115                 120                 125

Ile Ser His Ser Glu Thr Leu Thr Thr Thr Thr Thr Asn Thr Thr Thr
    130                 135                 140

Gln Gly Cys Lys Ile Asn Pro Lys Val Ser Tyr Ser Arg Lys Thr Lys
145                 150                 155                 160

Val Lys Val Lys Ile Val Asp Val Glu Lys Gly Phe Asn Thr Glu Ile
                165                 170                 175

Gly Ala Glu Tyr Asn Phe Ser Asp Thr Asn Thr Tyr Thr Glu Thr Ala
            180                 185                 190

Thr Arg Thr Val Thr Val Pro Ser Met Thr Thr Tyr Val Pro Pro Tyr
        195                 200                 205

Thr Ser Ala Tyr Val Thr Val Val Leu Glu Arg Gly Tyr Tyr Glu Ala
    210                 215                 220

Tyr Asn Ile Pro Ile Asp Thr Asn Leu Tyr Gly Arg Phe Glu Leu Ile
225                 230                 235                 240

Tyr Thr Asn Leu Asp Gly Ser Asn Pro Arg Ser Ala Gly Val Leu Asp
                245                 250                 255

Leu Tyr Pro Phe Val Glu Leu Ile Thr Thr Cys Cys Gln Asn Cys Ser
            260                 265                 270

Gln Cys Val Pro Asp Met Ile Gln Pro Asp Arg Asp Asn Gln Thr Val
        275                 280                 285

Arg Phe Thr Gly Arg Gly Asp Leu Ile Ser Asp Phe Ala Ala Asn Thr
    290                 295                 300

Leu Thr Val Thr Thr Thr Phe Val Asp Asn Ala Thr Gly Ala Thr Val
305                 310                 315                 320

Ser Gln His Val Glu Ser Val Pro Val Gln Tyr Gly Pro Ala Thr Thr
                325                 330                 335

Val Val Asn Thr Ser Lys
            340


<210> SEQ ID NO 28
<211> LENGTH: 3009
<212> TYPE: DNA
<213> ORGANISM: Bacillus thuringiensis
<220> FEATURE:
<221> NAME/KEY: CDS
<222> LOCATION: (1)...(3009)

<400> SEQUENCE: 28

atg aaa agg atg aag aaa aag cta gca agt gtt gta acc tgt aca tta        48
Met Lys Arg Met Lys Lys Lys Leu Ala Ser Val Val Thr Cys Thr Leu
 1               5                  10                  15

tta gct cct atg ttt ttg aat ggg aac gta gac act gta ttt gca gat        96
```

-continued

```
Leu Ala Pro Met Phe Leu Asn Gly Asn Val Asp Thr Val Phe Ala Asp
            20                  25                  30

agt aaa aca aat caa att tct tca aca cag gaa aac caa aag aat gag      144
Ser Lys Thr Asn Gln Ile Ser Ser Thr Gln Glu Asn Gln Lys Asn Glu
        35                  40                  45

atg gat cga aaa gga cta ctt ggt tat tat ttt aaa gga aaa gat ttt      192
Met Asp Arg Lys Gly Leu Leu Gly Tyr Tyr Phe Lys Gly Lys Asp Phe
    50                  55                  60

aat aat ctt act ata ttt gct cca aca cgt gag aat act ctt att tat      240
Asn Asn Leu Thr Ile Phe Ala Pro Thr Arg Glu Asn Thr Leu Ile Tyr
65                  70                  75                  80

gat tta gaa aca gcg aat tct tta tta gat aag caa caa caa acc tat      288
Asp Leu Glu Thr Ala Asn Ser Leu Leu Asp Lys Gln Gln Gln Thr Tyr
                85                  90                  95

caa tct att cgt tgg atc ggt tta ata aaa agc aaa aaa gct gga gat      336
Gln Ser Ile Arg Trp Ile Gly Leu Ile Lys Ser Lys Lys Ala Gly Asp
            100                 105                 110

ttt acc ttt caa tta tcg gat gat gag cat gct att ata gaa atc gat      384
Phe Thr Phe Gln Leu Ser Asp Asp Glu His Ala Ile Ile Glu Ile Asp
        115                 120                 125

ggg aaa gtt att tcg caa aaa ggc caa aag aaa caa gtt gtt cat tta      432
Gly Lys Val Ile Ser Gln Lys Gly Gln Lys Lys Gln Val Val His Leu
    130                 135                 140

gaa aaa gat aaa tta gtt ccc atc aaa att gaa tat caa tct gat aaa      480
Glu Lys Asp Lys Leu Val Pro Ile Lys Ile Glu Tyr Gln Ser Asp Lys
145                 150                 155                 160

gcg tta aac cca gat agt caa atg ttt aaa gaa ttg aaa tta ttt aaa      528
Ala Leu Asn Pro Asp Ser Gln Met Phe Lys Glu Leu Lys Leu Phe Lys
                165                 170                 175

ata aat agt caa aaa caa tct cag caa gtg caa caa gac gaa ttg aga      576
Ile Asn Ser Gln Lys Gln Ser Gln Gln Val Gln Gln Asp Glu Leu Arg
            180                 185                 190

aat cct gaa ttt ggt aaa gaa aaa act caa aca tat tta aag aaa gca      624
Asn Pro Glu Phe Gly Lys Glu Lys Thr Gln Thr Tyr Leu Lys Lys Ala
        195                 200                 205

tcg aaa agc agc ttg ttt agc aat aaa agt aaa cga gat ata gat gaa      672
Ser Lys Ser Ser Leu Phe Ser Asn Lys Ser Lys Arg Asp Ile Asp Glu
    210                 215                 220

gat ata gat gag gat aca gat aca gat gga gat gcc att cct gat gta      720
Asp Ile Asp Glu Asp Thr Asp Thr Asp Gly Asp Ala Ile Pro Asp Val
225                 230                 235                 240

tgg gaa gaa aat ggg tat acc atc aaa gga aga gta gct gtt aaa tgg      768
Trp Glu Glu Asn Gly Tyr Thr Ile Lys Gly Arg Val Ala Val Lys Trp
                245                 250                 255

gac gaa gga tta gct gat aag gga tat aaa aag ttt gtt tcc aat cct      816
Asp Glu Gly Leu Ala Asp Lys Gly Tyr Lys Lys Phe Val Ser Asn Pro
            260                 265                 270

ttt aga cag cac act gct ggt gac ccc tat agt gac tat gaa aag gca      864
Phe Arg Gln His Thr Ala Gly Asp Pro Tyr Ser Asp Tyr Glu Lys Ala
        275                 280                 285

tca aaa gat ttg gat tta tct aat gca aaa gaa aca ttt aat cca ttg      912
Ser Lys Asp Leu Asp Leu Ser Asn Ala Lys Glu Thr Phe Asn Pro Leu
    290                 295                 300

gtg gct gct ttt cca agt gtc aat gtt agc ttg gaa aat gtc acc ata      960
Val Ala Ala Phe Pro Ser Val Asn Val Ser Leu Glu Asn Val Thr Ile
305                 310                 315                 320

tca aaa gat gaa aat aaa act gct gaa att gcg tct act tca tcg aat     1008
Ser Lys Asp Glu Asn Lys Thr Ala Glu Ile Ala Ser Thr Ser Ser Asn
                325                 330                 335
```

-continued

```
aat tgg tcc tat aca aat aca gag ggg gca tct att gaa gct gga att      1056
Asn Trp Ser Tyr Thr Asn Thr Glu Gly Ala Ser Ile Glu Ala Gly Ile
            340                 345                 350

gga cca gaa ggt ttg ttg tct ttt gga gta agt gcc aat tat caa cat      1104
Gly Pro Glu Gly Leu Leu Ser Phe Gly Val Ser Ala Asn Tyr Gln His
        355                 360                 365

tct gaa aca gtg gcc aaa gag tgg ggt aca act aag gga gac gca aca      1152
Ser Glu Thr Val Ala Lys Glu Trp Gly Thr Thr Lys Gly Asp Ala Thr
    370                 375                 380

caa tat aat aca gct tca gca gga tat cta aat gcc aat gtt cga tat      1200
Gln Tyr Asn Thr Ala Ser Ala Gly Tyr Leu Asn Ala Asn Val Arg Tyr
385                 390                 395                 400

aat aat gta ggg acg gca gcc att tat gat gtg aaa cct aca acg aat      1248
Asn Asn Val Gly Thr Ala Ala Ile Tyr Asp Val Lys Pro Thr Thr Asn
                405                 410                 415

ttt gta tta gat aag act aca ctc gcg acg att aag gca aaa gaa aat      1296
Phe Val Leu Asp Lys Thr Thr Leu Ala Thr Ile Lys Ala Lys Glu Asn
            420                 425                 430

gcc acg gct gat cat ata ata cca ggg aat agt tac ccg gaa aaa ggg      1344
Ala Thr Ala Asp His Ile Ile Pro Gly Asn Ser Tyr Pro Glu Lys Gly
        435                 440                 445

aaa aat gga att gcg ata act act atg gat gat ttt aac tct cat cct      1392
Lys Asn Gly Ile Ala Ile Thr Thr Met Asp Asp Phe Asn Ser His Pro
    450                 455                 460

att act cta aat aaa caa caa cta gat aag ttg tta tat aat gtt aca      1440
Ile Thr Leu Asn Lys Gln Gln Leu Asp Lys Leu Leu Tyr Asn Val Thr
465                 470                 475                 480

cca ctt atg ttg gaa act acc caa gtt gag ggt acg tat aag aaa aaa      1488
Pro Leu Met Leu Glu Thr Thr Gln Val Glu Gly Thr Tyr Lys Lys Lys
                485                 490                 495

gat gta gat ggt aat atc att act gga ggg aca tgg agt gga gtg aca      1536
Asp Val Asp Gly Asn Ile Ile Thr Gly Gly Thr Trp Ser Gly Val Thr
            500                 505                 510

caa caa att gag gcg caa act gct tct att att gtt gat act gga gag      1584
Gln Gln Ile Glu Ala Gln Thr Ala Ser Ile Ile Val Asp Thr Gly Glu
        515                 520                 525

ggt gtt tcg gaa aaa cgt att gca gca aaa gat tat gat gac ccc gaa      1632
Gly Val Ser Glu Lys Arg Ile Ala Ala Lys Asp Tyr Asp Asp Pro Glu
    530                 535                 540

gat aaa aca ccg tct tta act cta aaa gat gcc ctg aaa att gga tat      1680
Asp Lys Thr Pro Ser Leu Thr Leu Lys Asp Ala Leu Lys Ile Gly Tyr
545                 550                 555                 560

cca gaa gaa att gaa gaa aaa aat gat tta tta tat tat aaa gga aaa      1728
Pro Glu Glu Ile Glu Glu Lys Asn Asp Leu Leu Tyr Tyr Lys Gly Lys
                565                 570                 575

ata ata tct gaa tca agt gtg atg act ttt ctt gat aat gga acc tcc      1776
Ile Ile Ser Glu Ser Ser Val Met Thr Phe Leu Asp Asn Gly Thr Ser
            580                 585                 590

gaa aaa gtt aaa aaa caa atc gag gat aaa act gga aaa ttt aaa gac      1824
Glu Lys Val Lys Lys Gln Ile Glu Asp Lys Thr Gly Lys Phe Lys Asp
        595                 600                 605

gta caa cat ttg tat gat gtg aaa cta aca cct gga atg aat ttt act      1872
Val Gln His Leu Tyr Asp Val Lys Leu Thr Pro Gly Met Asn Phe Thr
    610                 615                 620

att aaa tta gct tca ata tac gat agt gtc gat aat ttt agt ggc agt      1920
Ile Lys Leu Ala Ser Ile Tyr Asp Ser Val Asp Asn Phe Ser Gly Ser
625                 630                 635                 640

caa tca tta ggg gca tta aat agt ata agt aag gtt gct gga gga aat      1968
Gln Ser Leu Gly Ala Leu Asn Ser Ile Ser Lys Val Ala Gly Gly Asn
                645                 650                 655
```

```
aca ggg aaa aat caa tat caa tca tca tct tct aat gcg tat att tct     2016
Thr Gly Lys Asn Gln Tyr Gln Ser Ser Ser Ser Asn Ala Tyr Ile Ser
            660                 665                 670

tta tct tcg agt aca aaa gga gag ttg aat aaa aat act acg tac tat     2064
Leu Ser Ser Ser Thr Lys Gly Glu Leu Asn Lys Asn Thr Thr Tyr Tyr
        675                 680                 685

ctt agc atg tat atg aga gca gat gct gat aca gaa cct acc ata gaa     2112
Leu Ser Met Tyr Met Arg Ala Asp Ala Asp Thr Glu Pro Thr Ile Glu
    690                 695                 700

cta aaa gga gaa aaa tcc aca ata aaa agc caa aaa gtt aaa cta aac     2160
Leu Lys Gly Glu Lys Ser Thr Ile Lys Ser Gln Lys Val Lys Leu Asn
705                 710                 715                 720

aat aag gga tat cag agg gta gat att tta gta gaa aat act gag tcg     2208
Asn Lys Gly Tyr Gln Arg Val Asp Ile Leu Val Glu Asn Thr Glu Ser
            725                 730                 735

aat cca att cat caa att tat gta cac ggt aac aat aag aca aat gtc     2256
Asn Pro Ile His Gln Ile Tyr Val His Gly Asn Asn Lys Thr Asn Val
            740                 745                 750

tat tgg gac gat gtg tct ctt aca gag gta tct gct ata aaa caa gaa     2304
Tyr Trp Asp Asp Val Ser Leu Thr Glu Val Ser Ala Ile Lys Gln Glu
        755                 760                 765

tta ccc gat ata tca gat aaa gag ata caa agg gct cat aca ttt aag     2352
Leu Pro Asp Ile Ser Asp Lys Glu Ile Gln Arg Ala His Thr Phe Lys
    770                 775                 780

aaa gaa cag tta agt tta gat ggt aag tat atg aat gaa ttg aca tta     2400
Lys Glu Gln Leu Ser Leu Asp Gly Lys Tyr Met Asn Glu Leu Thr Leu
785                 790                 795                 800

cac gtt gat tcg tta aaa gac aag aac aat aag ccg gtt cag ttc agt     2448
His Val Asp Ser Leu Lys Asp Lys Asn Asn Lys Pro Val Gln Phe Ser
            805                 810                 815

tat aaa gtg aaa gat ggt gaa aaa gat tta gga act aaa tcc tat aca     2496
Tyr Lys Val Lys Asp Gly Glu Lys Asp Leu Gly Thr Lys Ser Tyr Thr
            820                 825                 830

cct gat aag cag gga aat ata aac att aac ttt cta gat tac aat cgt     2544
Pro Asp Lys Gln Gly Asn Ile Asn Ile Asn Phe Leu Asp Tyr Asn Arg
        835                 840                 845

gga ttt gga att tct aag gat cat aaa att caa att tat gcg gta cgt     2592
Gly Phe Gly Ile Ser Lys Asp His Lys Ile Gln Ile Tyr Ala Val Arg
    850                 855                 860

aaa gac caa gag gtg aaa gta gca gaa cta aaa aac tat aat atg agt     2640
Lys Asp Gln Glu Val Lys Val Ala Glu Leu Lys Asn Tyr Asn Met Ser
865                 870                 875                 880

gga act atc aga ttt agc aat gat gga gaa agt ggc ctt cca gag ata     2688
Gly Thr Ile Arg Phe Ser Asn Asp Gly Glu Ser Gly Leu Pro Glu Ile
            885                 890                 895

tat gga tat att ttc atg act cca gaa ggt caa tat cct gtt tct cct     2736
Tyr Gly Tyr Ile Phe Met Thr Pro Glu Gly Gln Tyr Pro Val Ser Pro
            900                 905                 910

gta gga ggt ata cac caa ata tgg tca aga tat tat aca agc act tac     2784
Val Gly Gly Ile His Gln Ile Trp Ser Arg Tyr Tyr Thr Ser Thr Tyr
        915                 920                 925

aag tgg agt act caa tat agt tat gat ttt gca tcc ttt aat agt gat     2832
Lys Trp Ser Thr Gln Tyr Ser Tyr Asp Phe Ala Ser Phe Asn Ser Asp
    930                 935                 940

ata aaa aca gtt cat ttt aat gga tat gta aag gaa ctg gat gat acg     2880
Ile Lys Thr Val His Phe Asn Gly Tyr Val Lys Glu Leu Asp Asp Thr
945                 950                 955                 960

aat ggc gac gac ata ctg gct tat ctt gaa aat aaa tat gaa tct cat     2928
Asn Gly Asp Asp Ile Leu Ala Tyr Leu Glu Asn Lys Tyr Glu Ser His
```

-continued

```
                965                 970                 975

ggt tta gag ggg agt gta gtg tta gaa gga gat gaa agg ggc agt aat      2976
Gly Leu Glu Gly Ser Val Val Leu Glu Gly Asp Glu Arg Gly Ser Asn
            980                 985                 990

gtg act gtt gaa tat cat ata aaa ttg aaa taa                          3009
Val Thr Val Glu Tyr His Ile Lys Leu Lys
        995                 1000


<210> SEQ ID NO 29
<211> LENGTH: 1002
<212> TYPE: PRT
<213> ORGANISM: Bacillus thuringiensis

<400> SEQUENCE: 29

Met Lys Arg Met Lys Lys Lys Leu Ala Ser Val Val Thr Cys Thr Leu
 1               5                  10                  15

Leu Ala Pro Met Phe Leu Asn Gly Asn Val Asp Thr Val Phe Ala Asp
            20                  25                  30

Ser Lys Thr Asn Gln Ile Ser Ser Thr Gln Glu Asn Gln Lys Asn Glu
        35                  40                  45

Met Asp Arg Lys Gly Leu Leu Gly Tyr Tyr Phe Lys Gly Lys Asp Phe
    50                  55                  60

Asn Asn Leu Thr Ile Phe Ala Pro Thr Arg Glu Asn Thr Leu Ile Tyr
65                  70                  75                  80

Asp Leu Glu Thr Ala Asn Ser Leu Leu Asp Lys Gln Gln Gln Thr Tyr
                85                  90                  95

Gln Ser Ile Arg Trp Ile Gly Leu Ile Lys Ser Lys Lys Ala Gly Asp
            100                 105                 110

Phe Thr Phe Gln Leu Ser Asp Asp Glu His Ala Ile Ile Glu Ile Asp
        115                 120                 125

Gly Lys Val Ile Ser Gln Lys Gly Gln Lys Lys Gln Val Val His Leu
    130                 135                 140

Glu Lys Asp Lys Leu Val Pro Ile Lys Ile Glu Tyr Gln Ser Asp Lys
145                 150                 155                 160

Ala Leu Asn Pro Asp Ser Gln Met Phe Lys Glu Leu Lys Leu Phe Lys
                165                 170                 175

Ile Asn Ser Gln Lys Gln Ser Gln Gln Val Gln Gln Asp Glu Leu Arg
            180                 185                 190

Asn Pro Glu Phe Gly Lys Glu Lys Thr Gln Thr Tyr Leu Lys Lys Ala
        195                 200                 205

Ser Lys Ser Ser Leu Phe Ser Asn Lys Ser Lys Arg Asp Ile Asp Glu
    210                 215                 220

Asp Ile Asp Glu Asp Thr Asp Thr Asp Gly Asp Ala Ile Pro Asp Val
225                 230                 235                 240

Trp Glu Glu Asn Gly Tyr Thr Ile Lys Gly Arg Val Ala Val Lys Trp
                245                 250                 255

Asp Glu Gly Leu Ala Asp Lys Gly Tyr Lys Lys Phe Val Ser Asn Pro
            260                 265                 270

Phe Arg Gln His Thr Ala Gly Asp Pro Tyr Ser Asp Tyr Glu Lys Ala
        275                 280                 285

Ser Lys Asp Leu Asp Leu Ser Asn Ala Lys Glu Thr Phe Asn Pro Leu
    290                 295                 300

Val Ala Ala Phe Pro Ser Val Asn Val Ser Leu Glu Asn Val Thr Ile
305                 310                 315                 320

Ser Lys Asp Glu Asn Lys Thr Ala Glu Ile Ala Ser Thr Ser Ser Asn
```

-continued

```
                325                 330                 335

Asn Trp Ser Tyr Thr Asn Thr Glu Gly Ala Ser Ile Glu Ala Gly Ile
            340                 345                 350

Gly Pro Glu Gly Leu Leu Ser Phe Gly Val Ser Ala Asn Tyr Gln His
        355                 360                 365

Ser Glu Thr Val Ala Lys Glu Trp Gly Thr Thr Lys Gly Asp Ala Thr
    370                 375                 380

Gln Tyr Asn Thr Ala Ser Ala Gly Tyr Leu Asn Ala Asn Val Arg Tyr
385                 390                 395                 400

Asn Asn Val Gly Thr Ala Ala Ile Tyr Asp Val Lys Pro Thr Thr Asn
                405                 410                 415

Phe Val Leu Asp Lys Thr Thr Leu Ala Thr Ile Lys Ala Lys Glu Asn
            420                 425                 430

Ala Thr Ala Asp His Ile Ile Pro Gly Asn Ser Tyr Pro Glu Lys Gly
        435                 440                 445

Lys Asn Gly Ile Ala Ile Thr Thr Met Asp Asp Phe Asn Ser His Pro
    450                 455                 460

Ile Thr Leu Asn Lys Gln Gln Leu Asp Lys Leu Leu Tyr Asn Val Thr
465                 470                 475                 480

Pro Leu Met Leu Glu Thr Thr Gln Val Glu Gly Thr Tyr Lys Lys Lys
                485                 490                 495

Asp Val Asp Gly Asn Ile Ile Thr Gly Gly Thr Trp Ser Gly Val Thr
            500                 505                 510

Gln Gln Ile Glu Ala Gln Thr Ala Ser Ile Ile Val Asp Thr Gly Glu
        515                 520                 525

Gly Val Ser Glu Lys Arg Ile Ala Ala Lys Asp Tyr Asp Asp Pro Glu
    530                 535                 540

Asp Lys Thr Pro Ser Leu Thr Leu Lys Asp Ala Leu Lys Ile Gly Tyr
545                 550                 555                 560

Pro Glu Glu Ile Glu Glu Lys Asn Asp Leu Leu Tyr Tyr Lys Gly Lys
                565                 570                 575

Ile Ile Ser Glu Ser Ser Val Met Thr Phe Leu Asp Asn Gly Thr Ser
            580                 585                 590

Glu Lys Val Lys Lys Gln Ile Glu Asp Lys Thr Gly Lys Phe Lys Asp
        595                 600                 605

Val Gln His Leu Tyr Asp Val Lys Leu Thr Pro Gly Met Asn Phe Thr
    610                 615                 620

Ile Lys Leu Ala Ser Ile Tyr Asp Ser Val Asp Asn Phe Ser Gly Ser
625                 630                 635                 640

Gln Ser Leu Gly Ala Leu Asn Ser Ile Ser Lys Val Ala Gly Gly Asn
                645                 650                 655

Thr Gly Lys Asn Gln Tyr Gln Ser Ser Ser Ser Asn Ala Tyr Ile Ser
            660                 665                 670

Leu Ser Ser Ser Thr Lys Gly Glu Leu Asn Lys Asn Thr Thr Tyr Tyr
        675                 680                 685

Leu Ser Met Tyr Met Arg Ala Asp Ala Asp Thr Glu Pro Thr Ile Glu
    690                 695                 700

Leu Lys Gly Glu Lys Ser Thr Ile Lys Ser Gln Lys Val Lys Leu Asn
705                 710                 715                 720

Asn Lys Gly Tyr Gln Arg Val Asp Ile Leu Val Glu Asn Thr Glu Ser
                725                 730                 735

Asn Pro Ile His Gln Ile Tyr Val His Gly Asn Asn Lys Thr Asn Val
            740                 745                 750
```

```
Tyr Trp Asp Asp Val Ser Leu Thr Glu Val Ser Ala Ile Lys Gln Glu
        755                 760                 765

Leu Pro Asp Ile Ser Asp Lys Glu Ile Gln Arg Ala His Thr Phe Lys
    770                 775                 780

Lys Glu Gln Leu Ser Leu Asp Gly Lys Tyr Met Asn Glu Leu Thr Leu
785                 790                 795                 800

His Val Asp Ser Leu Lys Asp Lys Asn Asn Lys Pro Val Gln Phe Ser
                805                 810                 815

Tyr Lys Val Lys Asp Gly Glu Lys Asp Leu Gly Thr Lys Ser Tyr Thr
            820                 825                 830

Pro Asp Lys Gln Gly Asn Ile Asn Ile Asn Phe Leu Asp Tyr Asn Arg
        835                 840                 845

Gly Phe Gly Ile Ser Lys Asp His Lys Ile Gln Ile Tyr Ala Val Arg
    850                 855                 860

Lys Asp Gln Glu Val Lys Val Ala Glu Leu Lys Asn Tyr Asn Met Ser
865                 870                 875                 880

Gly Thr Ile Arg Phe Ser Asn Asp Gly Glu Ser Gly Leu Pro Glu Ile
                885                 890                 895

Tyr Gly Tyr Ile Phe Met Thr Pro Glu Gly Gln Tyr Pro Val Ser Pro
            900                 905                 910

Val Gly Gly Ile His Gln Ile Trp Ser Arg Tyr Tyr Thr Ser Thr Tyr
        915                 920                 925

Lys Trp Ser Thr Gln Tyr Ser Tyr Asp Phe Ala Ser Phe Asn Ser Asp
    930                 935                 940

Ile Lys Thr Val His Phe Asn Gly Tyr Val Lys Glu Leu Asp Asp Thr
945                 950                 955                 960

Asn Gly Asp Asp Ile Leu Ala Tyr Leu Glu Asn Lys Tyr Glu Ser His
                965                 970                 975

Gly Leu Glu Gly Ser Val Val Leu Glu Gly Asp Glu Arg Gly Ser Asn
            980                 985                 990

Val Thr Val Glu Tyr His Ile Lys Leu Lys
        995                 1000


<210> SEQ ID NO 30
<211> LENGTH: 1347
<212> TYPE: DNA
<213> ORGANISM: Bacillus thuringiensis
<220> FEATURE:
<221> NAME/KEY: CDS
<222> LOCATION: (1)...(1347)

<400> SEQUENCE: 30

atg cat aaa caa aca ata aaa aat tta tct att tgc ata gca act gta        48
Met His Lys Gln Thr Ile Lys Asn Leu Ser Ile Cys Ile Ala Thr Val
 1               5                  10                  15

tca cta tta gga caa tac ttt ata tcc tct act acg gta tac gct gct        96
Ser Leu Leu Gly Gln Tyr Phe Ile Ser Ser Thr Thr Val Tyr Ala Ala
            20                  25                  30

gaa aat caa att aac tca tta aat cta aaa gta gag caa att cta gat       144
Glu Asn Gln Ile Asn Ser Leu Asn Leu Lys Val Glu Gln Ile Leu Asp
        35                  40                  45

ttt gga aga gat aaa gag aaa gca aaa gaa tgg gcc gat act tac ttt       192
Phe Gly Arg Asp Lys Glu Lys Ala Lys Glu Trp Ala Asp Thr Tyr Phe
     50                  55                  60

aaa gat tgg aag aaa aca att aat aat gaa caa aaa aaa ctt tta aat       240
Lys Asp Trp Lys Lys Thr Ile Asn Asn Glu Gln Lys Lys Leu Leu Asn
 65                  70                  75                  80
```

-continued

```
gat att aaa cgc tta aca caa tta aat gaa aaa ata ggt aaa ttc gat      288
Asp Ile Lys Arg Leu Thr Gln Leu Asn Glu Lys Ile Gly Lys Phe Asp
                 85                  90                  95

caa aat tca gag atg ttt tct aaa aaa gat aaa gag gat ata gat aaa      336
Gln Asn Ser Glu Met Phe Ser Lys Lys Asp Lys Glu Asp Ile Asp Lys
            100                 105                 110

ata gac aaa gct ttg aat aat aaa aat gca aaa tta acc aaa tct ttg      384
Ile Asp Lys Ala Leu Asn Asn Lys Asn Ala Lys Leu Thr Lys Ser Leu
        115                 120                 125

aat gtg tat aaa aat ttg aat ggc aaa gat tta gga tat gta gaa ggt      432
Asn Val Tyr Lys Asn Leu Asn Gly Lys Asp Leu Gly Tyr Val Glu Gly
    130                 135                 140

tat ttt aat gta ccg aat tcc cca aat aaa ata gat aga aca aaa tat      480
Tyr Phe Asn Val Pro Asn Ser Pro Asn Lys Ile Asp Arg Thr Lys Tyr
145                 150                 155                 160

aat aaa tta gtt aat gag ttt aag tat ggg gct atc aat aca ttc atg      528
Asn Lys Leu Val Asn Glu Phe Lys Tyr Gly Ala Ile Asn Thr Phe Met
                165                 170                 175

aat aca gac tta aca caa gat act aca aat aaa tca aca cct att ttg      576
Asn Thr Asp Leu Thr Gln Asp Thr Thr Asn Lys Ser Thr Pro Ile Leu
            180                 185                 190

ctt tca ttg aag cta cca aaa gga aca aaa ata gga caa tta aat gaa      624
Leu Ser Leu Lys Leu Pro Lys Gly Thr Lys Ile Gly Gln Leu Asn Glu
        195                 200                 205

gaa cat ata ata aca gac aga aac tta gga att gaa ata aaa aaa aca      672
Glu His Ile Ile Thr Asp Arg Asn Leu Gly Ile Glu Ile Lys Lys Thr
    210                 215                 220

agt att att gtt gaa aaa gga aga gaa gtt att aaa cta gaa gga gac      720
Ser Ile Ile Val Glu Lys Gly Arg Glu Val Ile Lys Leu Glu Gly Asp
225                 230                 235                 240

gta gta cca aaa act aaa att caa gaa aaa gta aaa aaa gca gaa agt      768
Val Val Pro Lys Thr Lys Ile Gln Glu Lys Val Lys Lys Ala Glu Ser
                245                 250                 255

gat ttg aat caa aaa ttt aaa gaa ata acg ggt tta aaa caa aac tta      816
Asp Leu Asn Gln Lys Phe Lys Glu Ile Thr Gly Leu Lys Gln Asn Leu
            260                 265                 270

cta agt ctg aaa ata gat aat cta tat aca tca gct agc att gac aga      864
Leu Ser Leu Lys Ile Asp Asn Leu Tyr Thr Ser Ala Ser Ile Asp Arg
        275                 280                 285

acg gaa aca gtt ata aaa caa tta gtc agc aat gta cca aac aat tta      912
Thr Glu Thr Val Ile Lys Gln Leu Val Ser Asn Val Pro Asn Asn Leu
    290                 295                 300

ttg tta aat ata atg aaa aat atg aat aat aaa aca tta ttt act att      960
Leu Leu Asn Ile Met Lys Asn Met Asn Asn Lys Thr Leu Phe Thr Ile
305                 310                 315                 320

aca gat aaa att cta ata ccc ggc aag gaa ggt gta tta ggt tat tat     1008
Thr Asp Lys Ile Leu Ile Pro Gly Lys Glu Gly Val Leu Gly Tyr Tyr
                325                 330                 335

gat acc att tct aaa aca tta ttt ata caa att gat cat ttg ggg cat     1056
Asp Thr Ile Ser Lys Thr Leu Phe Ile Gln Ile Asp His Leu Gly His
            340                 345                 350

aaa aac aat gaa gga aat gac act aat act ctt ctt cat gaa ttt ggt     1104
Lys Asn Asn Glu Gly Asn Asp Thr Asn Thr Leu Leu His Glu Phe Gly
        355                 360                 365

cat gct gta gat cat ttg gca aaa ggg gag ata caa tca aaa tct agt     1152
His Ala Val Asp His Leu Ala Lys Gly Glu Ile Gln Ser Lys Ser Ser
    370                 375                 380

aag ttc att gaa ata ttt aat cga gag aga ggt aat att aca ata gaa     1200
Lys Phe Ile Glu Ile Phe Asn Arg Glu Arg Gly Asn Ile Thr Ile Glu
```

```
385                 390                 395                 400

cca tat att aaa caa gat gca gcg gaa ttt ttt gca ggt gtt ttt aat      1248
Pro Tyr Ile Lys Gln Asp Ala Ala Glu Phe Phe Ala Gly Val Phe Asn
                405                 410                 415

tac tta tat tca cct aaa ata tca gat aga gaa caa att caa aaa gaa      1296
Tyr Leu Tyr Ser Pro Lys Ile Ser Asp Arg Glu Gln Ile Gln Lys Glu
            420                 425                 430

gca cct gat gct tgt aaa ttt atc cga aat tta ata cat ggt cta cat      1344
Ala Pro Asp Ala Cys Lys Phe Ile Arg Asn Leu Ile His Gly Leu His
        435                 440                 445

tga                                                                  1347


<210> SEQ ID NO 31
<211> LENGTH: 448
<212> TYPE: PRT
<213> ORGANISM: Bacillus thuringiensis

<400> SEQUENCE: 31

Met His Lys Gln Thr Ile Lys Asn Leu Ser Ile Cys Ile Ala Thr Val
 1               5                  10                  15

Ser Leu Leu Gly Gln Tyr Phe Ile Ser Ser Thr Thr Val Tyr Ala Ala
            20                  25                  30

Glu Asn Gln Ile Asn Ser Leu Asn Leu Lys Val Glu Gln Ile Leu Asp
        35                  40                  45

Phe Gly Arg Asp Lys Glu Lys Ala Lys Glu Trp Ala Asp Thr Tyr Phe
    50                  55                  60

Lys Asp Trp Lys Lys Thr Ile Asn Asn Glu Gln Lys Lys Leu Leu Asn
65                  70                  75                  80

Asp Ile Lys Arg Leu Thr Gln Leu Asn Glu Lys Ile Gly Lys Phe Asp
                85                  90                  95

Gln Asn Ser Glu Met Phe Ser Lys Lys Asp Lys Glu Asp Ile Asp Lys
            100                 105                 110

Ile Asp Lys Ala Leu Asn Asn Lys Asn Ala Lys Leu Thr Lys Ser Leu
        115                 120                 125

Asn Val Tyr Lys Asn Leu Asn Gly Lys Asp Leu Gly Tyr Val Glu Gly
    130                 135                 140

Tyr Phe Asn Val Pro Asn Ser Pro Asn Lys Ile Asp Arg Thr Lys Tyr
145                 150                 155                 160

Asn Lys Leu Val Asn Glu Phe Lys Tyr Gly Ala Ile Asn Thr Phe Met
                165                 170                 175

Asn Thr Asp Leu Thr Gln Asp Thr Thr Asn Lys Ser Thr Pro Ile Leu
            180                 185                 190

Leu Ser Leu Lys Leu Pro Lys Gly Thr Lys Ile Gly Gln Leu Asn Glu
        195                 200                 205

Glu His Ile Ile Thr Asp Arg Asn Leu Gly Ile Glu Ile Lys Lys Thr
    210                 215                 220

Ser Ile Ile Val Glu Lys Gly Arg Glu Val Ile Lys Leu Glu Gly Asp
225                 230                 235                 240

Val Val Pro Lys Thr Lys Ile Gln Glu Lys Val Lys Lys Ala Glu Ser
                245                 250                 255

Asp Leu Asn Gln Lys Phe Lys Glu Ile Thr Gly Leu Lys Gln Asn Leu
            260                 265                 270

Leu Ser Leu Lys Ile Asp Asn Leu Tyr Thr Ser Ala Ser Ile Asp Arg
        275                 280                 285

Thr Glu Thr Val Ile Lys Gln Leu Val Ser Asn Val Pro Asn Asn Leu
```

```
    290                 295                 300

Leu Leu Asn Ile Met Lys Asn Met Asn Asn Lys Thr Leu Phe Thr Ile
305                 310                 315                 320

Thr Asp Lys Ile Leu Ile Pro Gly Lys Glu Gly Val Leu Gly Tyr Tyr
                325                 330                 335

Asp Thr Ile Ser Lys Thr Leu Phe Ile Gln Ile Asp His Leu Gly His
            340                 345                 350

Lys Asn Asn Glu Gly Asn Asp Thr Asn Thr Leu Leu His Glu Phe Gly
        355                 360                 365

His Ala Val Asp His Leu Ala Lys Gly Glu Ile Gln Ser Lys Ser Ser
    370                 375                 380

Lys Phe Ile Glu Ile Phe Asn Arg Glu Arg Gly Asn Ile Thr Ile Glu
385                 390                 395                 400

Pro Tyr Ile Lys Gln Asp Ala Ala Glu Phe Phe Ala Gly Val Phe Asn
                405                 410                 415

Tyr Leu Tyr Ser Pro Lys Ile Ser Asp Arg Glu Gln Ile Gln Lys Glu
            420                 425                 430

Ala Pro Asp Ala Cys Lys Phe Ile Arg Asn Leu Ile His Gly Leu His
        435                 440                 445


<210> SEQ ID NO 32
<211> LENGTH: 1113
<212> TYPE: DNA
<213> ORGANISM: Paenibacillus popilliae
<220> FEATURE:
<221> NAME/KEY: CDS
<222> LOCATION: (1)...(1113)

<400> SEQUENCE: 32

atg aat aaa tta att aaa gta gaa gaa aat aaa aca cct caa acc caa       48
Met Asn Lys Leu Ile Lys Val Glu Glu Asn Lys Thr Pro Gln Thr Gln
 1               5                  10                  15

act ata tac act agt ttt aac gca acc gat att ggt ttt gca tcg aat       96
Thr Ile Tyr Thr Ser Phe Asn Ala Thr Asp Ile Gly Phe Ala Ser Asn
            20                  25                  30

tca gat ata aaa gat gga ttt cta aat ttt gat gag caa aaa ata aat      144
Ser Asp Ile Lys Asp Gly Phe Leu Asn Phe Asp Glu Gln Lys Ile Asn
        35                  40                  45

aca att ata aaa tat tta aaa atg gga aat ttc cca gat ttt cga gtg      192
Thr Ile Ile Lys Tyr Leu Lys Met Gly Asn Phe Pro Asp Phe Arg Val
    50                  55                  60

ggg aat ttg tta cca tcc gaa cca cat tcc aca gta aat gct ttc ttt      240
Gly Asn Leu Leu Pro Ser Glu Pro His Ser Thr Val Asn Ala Phe Phe
 65                  70                  75                  80

aca caa agg cga att tta ata gag tta gag gtt ccg gct ggt act tat      288
Thr Gln Arg Arg Ile Leu Ile Glu Leu Glu Val Pro Ala Gly Thr Tyr
                85                  90                  95

ctt gcg cat tta gga aac ggt caa acc att ttc cct tta gat tat gga      336
Leu Ala His Leu Gly Asn Gly Gln Thr Ile Phe Pro Leu Asp Tyr Gly
            100                 105                 110

atg aag tta act gat cag gcg gga acg att att gga aag caa gta cta      384
Met Lys Leu Thr Asp Gln Ala Gly Thr Ile Ile Gly Lys Gln Val Leu
        115                 120                 125

aaa ttg aaa gca ctt gtt gtc ccg aag gat gat att ctg aaa gaa act      432
Lys Leu Lys Ala Leu Val Val Pro Lys Asp Asp Ile Leu Lys Glu Thr
    130                 135                 140

aat gtg cag atg ttc att tta tac aaa tca ata tcc aat ata ttg cgt      480
Asn Val Gln Met Phe Ile Leu Tyr Lys Ser Ile Ser Asn Ile Leu Arg
145                 150                 155                 160
```

```
tct aag gga ttt gat gaa aag gat ata gaa agc ctg aaa gct cag tgc      528
Ser Lys Gly Phe Asp Glu Lys Asp Ile Glu Ser Leu Lys Ala Gln Cys
                165                 170                 175

atg ttt ata ttt tca ggc cct aat gta ttg ttg gca ata gaa aat tct      576
Met Phe Ile Phe Ser Gly Pro Asn Val Leu Leu Ala Ile Glu Asn Ser
            180                 185                 190

caa agt gca atg ctt gat tta cta act aat gag tat ata cca aat aat      624
Gln Ser Ala Met Leu Asp Leu Leu Thr Asn Glu Tyr Ile Pro Asn Asn
        195                 200                 205

tta tta aga gat aca ttg tta aaa tta aaa caa cac gcg ggg att gct      672
Leu Leu Arg Asp Thr Leu Leu Lys Leu Lys Gln His Ala Gly Ile Ala
    210                 215                 220

ttt cta agt gtg cct att tgt atg gat aaa gcg att gcc ggg agt aca      720
Phe Leu Ser Val Pro Ile Cys Met Asp Lys Ala Ile Ala Gly Ser Thr
225                 230                 235                 240

tca ttt cct aaa aat ggc gat aaa cct aat atg agt ata atc cca acc      768
Ser Phe Pro Lys Asn Gly Asp Lys Pro Asn Met Ser Ile Ile Pro Thr
                245                 250                 255

cat caa tct tta ctg agc cag ttg gat gaa cat ata agt aca tca cgt      816
His Gln Ser Leu Leu Ser Gln Leu Asp Glu His Ile Ser Thr Ser Arg
            260                 265                 270

aca tta cat cat gaa ttt ggt cat gta ata gat cga gaa att cta aat      864
Thr Leu His His Glu Phe Gly His Val Ile Asp Arg Glu Ile Leu Asn
        275                 280                 285

ggg att tct tcc act cca gag ttt aaa gcg ctg ttt gaa aaa gaa aaa      912
Gly Ile Ser Ser Thr Pro Glu Phe Lys Ala Leu Phe Glu Lys Glu Lys
    290                 295                 300

aat aat att aca gaa ata aat acg tat gcc aac tat gca aaa acg aat      960
Asn Asn Ile Thr Glu Ile Asn Thr Tyr Ala Asn Tyr Ala Lys Thr Asn
305                 310                 315                 320

tca caa gaa ttt ttt gca gag gtt ttt aaa tct atg gtt tcc atg ggg     1008
Ser Gln Glu Phe Phe Ala Glu Val Phe Lys Ser Met Val Ser Met Gly
                325                 330                 335

aat gag aaa tat cca tca agt tat tat cgt gat tct att gag aaa gaa     1056
Asn Glu Lys Tyr Pro Ser Ser Tyr Tyr Arg Asp Ser Ile Glu Lys Glu
            340                 345                 350

gct cct gag act gtg aga ttt ata aaa gat aaa ttg aaa gag aaa gga     1104
Ala Pro Glu Thr Val Arg Phe Ile Lys Asp Lys Leu Lys Glu Lys Gly
        355                 360                 365

tat gta ctt                                                         1113
Tyr Val Leu
    370
```

<210> SEQ ID NO 33
<211> LENGTH: 371
<212> TYPE: PRT
<213> ORGANISM: Paenibacillus popilliae

<400> SEQUENCE: 33

```
Met Asn Lys Leu Ile Lys Val Glu Glu Asn Lys Thr Pro Gln Thr Gln
 1               5                  10                  15

Thr Ile Tyr Thr Ser Phe Asn Ala Thr Asp Ile Gly Phe Ala Ser Asn
            20                  25                  30

Ser Asp Ile Lys Asp Gly Phe Leu Asn Phe Asp Glu Gln Lys Ile Asn
        35                  40                  45

Thr Ile Ile Lys Tyr Leu Lys Met Gly Asn Phe Pro Asp Phe Arg Val
    50                  55                  60

Gly Asn Leu Leu Pro Ser Glu Pro His Ser Thr Val Asn Ala Phe Phe
65                  70                  75                  80
```

```
Thr Gln Arg Arg Ile Leu Ile Glu Leu Glu Val Pro Ala Gly Thr Tyr
                85                  90                  95

Leu Ala His Leu Gly Asn Gly Gln Thr Ile Phe Pro Leu Asp Tyr Gly
            100                 105                 110

Met Lys Leu Thr Asp Gln Ala Gly Thr Ile Ile Gly Lys Gln Val Leu
        115                 120                 125

Lys Leu Lys Ala Leu Val Val Pro Lys Asp Asp Ile Leu Lys Glu Thr
    130                 135                 140

Asn Val Gln Met Phe Ile Leu Tyr Lys Ser Ile Ser Asn Ile Leu Arg
145                 150                 155                 160

Ser Lys Gly Phe Asp Glu Lys Asp Ile Glu Ser Leu Lys Ala Gln Cys
                165                 170                 175

Met Phe Ile Phe Ser Gly Pro Asn Val Leu Leu Ala Ile Glu Asn Ser
            180                 185                 190

Gln Ser Ala Met Leu Asp Leu Leu Thr Asn Glu Tyr Ile Pro Asn Asn
        195                 200                 205

Leu Leu Arg Asp Thr Leu Leu Lys Leu Lys Gln His Ala Gly Ile Ala
    210                 215                 220

Phe Leu Ser Val Pro Ile Cys Met Asp Lys Ala Ile Ala Gly Ser Thr
225                 230                 235                 240

Ser Phe Pro Lys Asn Gly Asp Lys Pro Asn Met Ser Ile Ile Pro Thr
                245                 250                 255

His Gln Ser Leu Leu Ser Gln Leu Asp Glu His Ile Ser Thr Ser Arg
            260                 265                 270

Thr Leu His His Glu Phe Gly His Val Ile Asp Arg Glu Ile Leu Asn
        275                 280                 285

Gly Ile Ser Ser Thr Pro Glu Phe Lys Ala Leu Phe Glu Lys Glu Lys
    290                 295                 300

Asn Asn Ile Thr Glu Ile Asn Thr Tyr Ala Asn Tyr Ala Lys Thr Asn
305                 310                 315                 320

Ser Gln Glu Phe Phe Ala Glu Val Phe Lys Ser Met Val Ser Met Gly
                325                 330                 335

Asn Glu Lys Tyr Pro Ser Ser Tyr Tyr Arg Asp Ser Ile Glu Lys Glu
            340                 345                 350

Ala Pro Glu Thr Val Arg Phe Ile Lys Asp Lys Leu Lys Glu Lys Gly
        355                 360                 365

Tyr Val Leu
    370
```

<210> SEQ ID NO 34
<211> LENGTH: 987
<212> TYPE: DNA
<213> ORGANISM: Bacillus thuringiensis
<220> FEATURE:
<221> NAME/KEY: CDS
<222> LOCATION: (1)...(987)

<400> SEQUENCE: 34

```
atg gtg aga gac tat cct gat ttt gat ggg atg ata aga aaa gcc gct       48
Met Val Arg Asp Tyr Pro Asp Phe Asp Gly Met Ile Arg Lys Ala Ala
 1               5                  10                  15

cga aag tgg gca gaa gca aac aga ttg aca ttc caa gat att tcg tat       96
Arg Lys Trp Ala Glu Ala Asn Arg Leu Thr Phe Gln Asp Ile Ser Tyr
            20                  25                  30

gca gat cct tta acc aat tca gat aca atc agt cta aat gcc aaa ttc      144
Ala Asp Pro Leu Thr Asn Ser Asp Thr Ile Ser Leu Asn Ala Lys Phe
```

```
        35                  40                  45

aaa gat atc gga tgc ccc gaa gaa tgt gtc gaa tta gaa aaa ata agc       192
Lys Asp Ile Gly Cys Pro Glu Glu Cys Val Glu Leu Glu Lys Ile Ser
     50                  55                  60

gtc gca caa gct ttt acg aat aat acg ggg caa caa caa aaa gaa aca       240
Val Ala Gln Ala Phe Thr Asn Asn Thr Gly Gln Gln Gln Lys Glu Thr
 65                  70                  75                  80

ttt aca acc gca aca ttt gta gaa gat gag tat act tgg gag aat gac       288
Phe Thr Thr Ala Thr Phe Val Glu Asp Glu Tyr Thr Trp Glu Asn Asp
                 85                  90                  95

tat cat ttt gtg ctt cca gga caa aac ttc ctt ata atg ccc cgt ctt       336
Tyr His Phe Val Leu Pro Gly Gln Asn Phe Leu Ile Met Pro Arg Leu
            100                 105                 110

cct cgg tca gct cat agg gat att aat cca ggt ttc ctt gtg aat ttc       384
Pro Arg Ser Ala His Arg Asp Ile Asn Pro Gly Phe Leu Val Asn Phe
        115                 120                 125

ttt ggt caa aat caa caa ttt cat act aaa atg aga gat cta cgt cca       432
Phe Gly Gln Asn Gln Gln Phe His Thr Lys Met Arg Asp Leu Arg Pro
    130                 135                 140

att aac ggg gaa gta ttt tta gaa cca tct agc agt gca aca att caa       480
Ile Asn Gly Glu Val Phe Leu Glu Pro Ser Ser Ser Ala Thr Ile Gln
145                 150                 155                 160

ctg caa gtg gaa aaa caa tat att tct caa ccg tat gaa att gaa tta       528
Leu Gln Val Glu Lys Gln Tyr Ile Ser Gln Pro Tyr Glu Ile Glu Leu
                165                 170                 175

tcg ata cta gga agt att att gtg ata gca cga gat ggg cag aac cga       576
Ser Ile Leu Gly Ser Ile Ile Val Ile Ala Arg Asp Gly Gln Asn Arg
            180                 185                 190

agc agt gag aac tat gtt caa tta aca gat ctc atg cca ctt ctc tgc       624
Ser Ser Glu Asn Tyr Val Gln Leu Thr Asp Leu Met Pro Leu Leu Cys
        195                 200                 205

cct tgt aaa aac ttt ttt tgt aga ggg cga gcg ttg gta ttc gtt gaa       672
Pro Cys Lys Asn Phe Phe Cys Arg Gly Arg Ala Leu Val Phe Val Glu
    210                 215                 220

cag gga acg ttc aag gga gta ttg agc cga gcg ata cgt gca tac gtc       720
Gln Gly Thr Phe Lys Gly Val Leu Ser Arg Ala Ile Arg Ala Tyr Val
225                 230                 235                 240

aca caa acg ctt cac aaa gac gga aaa acg cta gaa tat gaa att cct       768
Thr Gln Thr Leu His Lys Asp Gly Lys Thr Leu Glu Tyr Glu Ile Pro
                245                 250                 255

tta aac gca tca cct gac agg gaa agc gaa ttc tcc cca caa cct ttg       816
Leu Asn Ala Ser Pro Asp Arg Glu Ser Glu Phe Ser Pro Gln Pro Leu
            260                 265                 270

gca gca aga tgt atc tca gac gaa gaa tcg aat ggg aac cct tcg att       864
Ala Ala Arg Cys Ile Ser Asp Glu Glu Ser Asn Gly Asn Pro Ser Ile
        275                 280                 285

ttg tca tcg aga cca tcg aat cct aca gcc tat tcc cag caa cct atg       912
Leu Ser Ser Arg Pro Ser Asn Pro Thr Ala Tyr Ser Gln Gln Pro Met
    290                 295                 300

aca act gac tct aca tcc tgt gga tgt tct tct tgt atg tct gaa aaa       960
Thr Thr Asp Ser Thr Ser Cys Gly Cys Ser Ser Cys Met Ser Glu Lys
305                 310                 315                 320

tca aat aac aat cta tat ata aat cag                                   987
Ser Asn Asn Asn Leu Tyr Ile Asn Gln
                325
```

<210> SEQ ID NO 35
<211> LENGTH: 329
<212> TYPE: PRT
<213> ORGANISM: Bacillus thuringiensis

<400> SEQUENCE: 35

```
Met Val Arg Asp Tyr Pro Asp Phe Asp Gly Met Ile Arg Lys Ala Ala
 1               5                  10                  15

Arg Lys Trp Ala Glu Ala Asn Arg Leu Thr Phe Gln Asp Ile Ser Tyr
            20                  25                  30

Ala Asp Pro Leu Thr Asn Ser Asp Thr Ile Ser Leu Asn Ala Lys Phe
        35                  40                  45

Lys Asp Ile Gly Cys Pro Glu Glu Cys Val Glu Leu Glu Lys Ile Ser
    50                  55                  60

Val Ala Gln Ala Phe Thr Asn Asn Thr Gly Gln Gln Gln Lys Glu Thr
65                  70                  75                  80

Phe Thr Thr Ala Thr Phe Val Glu Asp Glu Tyr Thr Trp Glu Asn Asp
                85                  90                  95

Tyr His Phe Val Leu Pro Gly Gln Asn Phe Leu Ile Met Pro Arg Leu
            100                 105                 110

Pro Arg Ser Ala His Arg Asp Ile Asn Pro Gly Phe Leu Val Asn Phe
        115                 120                 125

Phe Gly Gln Asn Gln Gln Phe His Thr Lys Met Arg Asp Leu Arg Pro
    130                 135                 140

Ile Asn Gly Glu Val Phe Leu Glu Pro Ser Ser Ser Ala Thr Ile Gln
145                 150                 155                 160

Leu Gln Val Glu Lys Gln Tyr Ile Ser Gln Pro Tyr Glu Ile Glu Leu
                165                 170                 175

Ser Ile Leu Gly Ser Ile Ile Val Ile Ala Arg Asp Gly Gln Asn Arg
            180                 185                 190

Ser Ser Glu Asn Tyr Val Gln Leu Thr Asp Leu Met Pro Leu Leu Cys
        195                 200                 205

Pro Cys Lys Asn Phe Phe Cys Arg Gly Arg Ala Leu Val Phe Val Glu
    210                 215                 220

Gln Gly Thr Phe Lys Gly Val Leu Ser Arg Ala Ile Arg Ala Tyr Val
225                 230                 235                 240

Thr Gln Thr Leu His Lys Asp Gly Lys Thr Leu Glu Tyr Glu Ile Pro
                245                 250                 255

Leu Asn Ala Ser Pro Asp Arg Glu Ser Glu Phe Ser Pro Gln Pro Leu
            260                 265                 270

Ala Ala Arg Cys Ile Ser Asp Glu Glu Ser Asn Gly Asn Pro Ser Ile
        275                 280                 285

Leu Ser Ser Arg Pro Ser Asn Pro Thr Ala Tyr Ser Gln Gln Pro Met
    290                 295                 300

Thr Thr Asp Ser Thr Ser Cys Gly Cys Ser Ser Cys Met Ser Glu Lys
305                 310                 315                 320

Ser Asn Asn Asn Leu Tyr Ile Asn Gln
                325
```

<210> SEQ ID NO 36
<211> LENGTH: 1071
<212> TYPE: DNA
<213> ORGANISM: Bacillus thuringiensis
<220> FEATURE:
<221> NAME/KEY: CDS
<222> LOCATION: (1)...(1071)

<400> SEQUENCE: 36

```
atg aaa aag tct tgt aat ccc aag aaa gta aat cct aac gaa gtg aat       48
Met Lys Lys Ser Cys Asn Pro Lys Lys Val Asn Pro Asn Glu Val Asn
```

-continued

```
 1               5                   10                  15

cca aca gaa ttt att tta tac gac ttg gat aac tat tta aat cat att       96
Pro Thr Glu Phe Ile Leu Tyr Asp Leu Asp Asn Tyr Leu Asn His Ile
            20                  25                  30

ttg cat aat gta cag tac gac cct gtg aat ctg tcc agt atg tac gac      144
Leu His Asn Val Gln Tyr Asp Pro Val Asn Leu Ser Ser Met Tyr Asp
        35                  40                  45

ggt tat aag cca tca ggt ggt tgg aat ttt gat gga aaa ttc tat cct      192
Gly Tyr Lys Pro Ser Gly Gly Trp Asn Phe Asp Gly Lys Phe Tyr Pro
    50                  55                  60

acc cca act tct agc caa ata cct aac gct tgc gta cca tac ggt aca      240
Thr Pro Thr Ser Ser Gln Ile Pro Asn Ala Cys Val Pro Tyr Gly Thr
65                  70                  75                  80

tac aaa cct tat tgt aaa tat gaa cca tat caa agt ggt act tgg gtt      288
Tyr Lys Pro Tyr Cys Lys Tyr Glu Pro Tyr Gln Ser Gly Thr Trp Val
                85                  90                  95

gta gat aca tcc gct tta atc gca gaa ggg aca gat ata tat gaa gaa      336
Val Asp Thr Ser Ala Leu Ile Ala Glu Gly Thr Asp Ile Tyr Glu Glu
            100                 105                 110

atc gaa tcc atg gct cta gaa acc cct att att gcg gat aga cat gaa      384
Ile Glu Ser Met Ala Leu Glu Thr Pro Ile Ile Ala Asp Arg His Glu
        115                 120                 125

tat aat aat aac tca tct tta gaa caa tcc tat gtg acc cct gcc tat      432
Tyr Asn Asn Asn Ser Ser Leu Glu Gln Ser Tyr Val Thr Pro Ala Tyr
    130                 135                 140

tca gaa aca acg act aca act acg aca aat aca aca aca cac gga tgt      480
Ser Glu Thr Thr Thr Thr Thr Thr Thr Asn Thr Thr Thr His Gly Cys
145                 150                 155                 160

aaa gta aat cca aaa atc agt tat tcg cgt aaa tcg aaa tat aaa gtt      528
Lys Val Asn Pro Lys Ile Ser Tyr Ser Arg Lys Ser Lys Tyr Lys Val
                165                 170                 175

ggt att aag gat aca gaa aat gga ttt aac ctg gaa tta ggg gca gaa      576
Gly Ile Lys Asp Thr Glu Asn Gly Phe Asn Leu Glu Leu Gly Ala Glu
            180                 185                 190

tat aac ttc agc aat aca aac tca aac acg gct acg aca act cgg act      624
Tyr Asn Phe Ser Asn Thr Asn Ser Asn Thr Ala Thr Thr Thr Arg Thr
        195                 200                 205

gtg aca ttt cca tca ttt acg aca aaa gtg cca ccc tat acc act acg      672
Val Thr Phe Pro Ser Phe Thr Thr Lys Val Pro Pro Tyr Thr Thr Thr
    210                 215                 220

att gtg acg gtc ata tta aac aaa gga aca tat gcc aat tat aat gtt      720
Ile Val Thr Val Ile Leu Asn Lys Gly Thr Tyr Ala Asn Tyr Asn Val
225                 230                 235                 240

cca gtc caa acg aat tta ttt ggg aga ttt ctc act cat cac ggc caa      768
Pro Val Gln Thr Asn Leu Phe Gly Arg Phe Leu Thr His His Gly Gln
                245                 250                 255

ggc atg gat cca aac gac tcg cgt acg tac aat tat ttt gac cta tat      816
Gly Met Asp Pro Asn Asp Ser Arg Thr Tyr Asn Tyr Phe Asp Leu Tyr
            260                 265                 270

cct tgc gta gaa tta aat caa aca tgc tgt gca gca tca tct tgt agc      864
Pro Cys Val Glu Leu Asn Gln Thr Cys Cys Ala Ala Ser Ser Cys Ser
        275                 280                 285

gaa tgt gta aca gac atg gtg caa gct ctt cct gac aat ctt acg gtt      912
Glu Cys Val Thr Asp Met Val Gln Ala Leu Pro Asp Asn Leu Thr Val
    290                 295                 300

cgt ttt aat gga aca ggg tca ttt ata gcg gat gtt gca tcg aat aac      960
Arg Phe Asn Gly Thr Gly Ser Phe Ile Ala Asp Val Ala Ser Asn Asn
305                 310                 315                 320

ttt gtc att act act gaa gag gtt gac aat gca aca gga gta acc att     1008
```

-continued

```
Phe Val Ile Thr Thr Glu Glu Val Asp Asn Ala Thr Gly Val Thr Ile
            325                 330                 335

tcg aaa aaa aca gaa tac gta ccc gct att tac gga ccc ccg acc aca     1056
Ser Lys Lys Thr Glu Tyr Val Pro Ala Ile Tyr Gly Pro Pro Thr Thr
            340                 345                 350

aca gta acc aca tct                                                 1071
Thr Val Thr Thr Ser
        355


<210> SEQ ID NO 37
<211> LENGTH: 357
<212> TYPE: PRT
<213> ORGANISM: Bacillus thuringiensis

<400> SEQUENCE: 37

Met Lys Lys Ser Cys Asn Pro Lys Lys Val Asn Pro Asn Glu Val Asn
 1               5                  10                  15

Pro Thr Glu Phe Ile Leu Tyr Asp Leu Asp Asn Tyr Leu Asn His Ile
            20                  25                  30

Leu His Asn Val Gln Tyr Asp Pro Val Asn Leu Ser Ser Met Tyr Asp
        35                  40                  45

Gly Tyr Lys Pro Ser Gly Gly Trp Asn Phe Asp Gly Lys Phe Tyr Pro
    50                  55                  60

Thr Pro Thr Ser Ser Gln Ile Pro Asn Ala Cys Val Pro Tyr Gly Thr
65                  70                  75                  80

Tyr Lys Pro Tyr Cys Lys Tyr Glu Pro Tyr Gln Ser Gly Thr Trp Val
                85                  90                  95

Val Asp Thr Ser Ala Leu Ile Ala Glu Gly Thr Asp Ile Tyr Glu Glu
            100                 105                 110

Ile Glu Ser Met Ala Leu Glu Thr Pro Ile Ile Ala Asp Arg His Glu
        115                 120                 125

Tyr Asn Asn Asn Ser Ser Leu Glu Gln Ser Tyr Val Thr Pro Ala Tyr
    130                 135                 140

Ser Glu Thr Thr Thr Thr Thr Thr Thr Asn Thr Thr Thr His Gly Cys
145                 150                 155                 160

Lys Val Asn Pro Lys Ile Ser Tyr Ser Arg Lys Ser Lys Tyr Lys Val
                165                 170                 175

Gly Ile Lys Asp Thr Glu Asn Gly Phe Asn Leu Glu Leu Gly Ala Glu
            180                 185                 190

Tyr Asn Phe Ser Asn Thr Asn Ser Asn Thr Ala Thr Thr Thr Arg Thr
        195                 200                 205

Val Thr Phe Pro Ser Phe Thr Thr Lys Val Pro Pro Tyr Thr Thr Thr
    210                 215                 220

Ile Val Thr Val Ile Leu Asn Lys Gly Thr Tyr Ala Asn Tyr Asn Val
225                 230                 235                 240

Pro Val Gln Thr Asn Leu Phe Gly Arg Phe Leu Thr His His Gly Gln
                245                 250                 255

Gly Met Asp Pro Asn Asp Ser Arg Thr Tyr Asn Tyr Phe Asp Leu Tyr
            260                 265                 270

Pro Cys Val Glu Leu Asn Gln Thr Cys Cys Ala Ala Ser Ser Cys Ser
        275                 280                 285

Glu Cys Val Thr Asp Met Val Gln Ala Leu Pro Asp Asn Leu Thr Val
    290                 295                 300

Arg Phe Asn Gly Thr Gly Ser Phe Ile Ala Asp Val Ala Ser Asn Asn
305                 310                 315                 320
```

-continued

```
Phe Val Ile Thr Thr Glu Glu Val Asp Asn Ala Thr Gly Val Thr Ile
                325                 330                 335

Ser Lys Lys Thr Glu Tyr Val Pro Ala Ile Tyr Gly Pro Pro Thr Thr
            340                 345                 350

Thr Val Thr Thr Ser
        355


<210> SEQ ID NO 38
<211> LENGTH: 292
<212> TYPE: PRT
<213> ORGANISM: Bacillus sphaericus

<400> SEQUENCE: 38

Met Lys Arg Thr Lys Leu Leu Phe Tyr Ile Met Ile Ala Ser Phe Leu
 1               5                  10                  15

Phe Val Asn Gly Ser Ile Tyr Thr Ala Lys Ala Thr Thr Ile Asp Glu
            20                  25                  30

Asn Asn Leu Asp Ile Ile Lys Gln Gln Gly Val Ser Ile Glu Asp Ile
        35                  40                  45

Asp Arg Lys Ile Asp Asn Met Ile Ala Ser Ile Pro Pro Leu Phe Gly
    50                  55                  60

Phe Leu Pro Tyr Ser Arg Phe Pro Tyr Ile Phe Gly Glu Ser Val Asp
65                  70                  75                  80

Val Ser Gly Ile Asn Ile Glu Asn Thr Asn Val Thr Ser Val Val Pro
                85                  90                  95

Leu Phe Ile Gly Ser Asn Thr Phe Glu Asn Thr Thr Asp Arg Thr Met
            100                 105                 110

Thr Phe Asn Thr Val Ser Phe Ser Lys Ser Ile Thr Asp Ser Thr Thr
        115                 120                 125

Thr Gln Thr Leu Asn Gly Phe Lys Thr Ala Phe Glu Ala Ser Gly Lys
    130                 135                 140

Val Gly Ile Pro Leu Val Ala Glu Gly Gln Ile Lys Thr Thr Leu Glu
145                 150                 155                 160

Tyr Asn Phe Ser His Thr Asn Ser Asn Thr Thr Ser Val Thr Thr Thr
                165                 170                 175

Tyr Thr Val Pro Pro Gln Pro Ile Pro Val Pro Pro His Thr Lys Thr
            180                 185                 190

Arg Thr Asp Val Tyr Leu Asn Gln Val Ser Ile Ser Gly Asn Val Glu
        195                 200                 205

Ile Tyr Ala Asp Ala Ile Thr Gly Ile Lys Ala Glu Ser Ser Gly Thr
    210                 215                 220

Val Ile Ser Ile Gly Asp Gly Leu Asn Leu Ala Ser Asn Thr Tyr Gly
225                 230                 235                 240

Leu Ile Arg Ser Pro Gln Asp Pro Asp Arg Val Arg Ala Ile Gly Ser
                245                 250                 255

Gly Lys Phe Asn Leu Ile His Gly Ala Asp Phe Thr Ala Ile Thr Tyr
            260                 265                 270

Asp Ile Thr Ser Gly Glu Ala Ser Ala Arg Ile Ile Asp Val Lys Glu
        275                 280                 285

Ile Ser Phe Lys
    290


<210> SEQ ID NO 39
<211> LENGTH: 362
<212> TYPE: PRT
<213> ORGANISM: Bacillus sphaericus
```

<400> SEQUENCE: 39

```
Ser Phe Ile Pro Thr Glu Gly Lys Tyr Ile Arg Val Met Asp Phe Tyr
 1               5                  10                  15

Asn Ser Glu Tyr Pro Phe Cys Ile His Ala Pro Ser Ala Pro Asn Gly
            20                  25                  30

Asp Ile Met Thr Glu Ile Cys Ser Arg Glu Asn Asn Gln Tyr Phe Ile
        35                  40                  45

Phe Phe Pro Thr Asp Asp Gly Arg Val Ile Ile Ala Asn Arg His Asn
    50                  55                  60

Gly Ser Val Phe Thr Gly Glu Ala Thr Ser Val Val Ser Asp Ile Tyr
65                  70                  75                  80

Thr Gly Ser Pro Ser Gln Phe Phe Arg Glu Val Lys Arg Thr Met Ser
                85                  90                  95

Thr Tyr Tyr Leu Ala Ile Gln Asn Pro Glu Ser Ala Thr Asp Val Arg
            100                 105                 110

Ala Leu Glu Pro Asn Ser His Glu Leu Pro Ser Arg Leu Tyr Phe Thr
        115                 120                 125

Asn Asn Ile Glu Asn Asn Ser Asn Ile Leu Ile Ser Asn Lys Glu Gln
    130                 135                 140

Ile Tyr Leu Thr Leu Pro Ser Leu Pro Glu Asn Glu Gln Tyr Pro Lys
145                 150                 155                 160

Thr Pro Val Leu Ser Gly Ile Asp Asp Ile Gly Pro Asn Gln Ser Glu
                165                 170                 175

Lys Ser Ile Ile Gly Ser Thr Leu Ile Pro Cys Ile Met Val Ser Asp
            180                 185                 190

Phe Ile Ser Leu Gly Glu Arg Met Lys Thr Thr Pro Tyr Tyr Tyr Val
        195                 200                 205

Lys His Thr Gln Tyr Trp Gln Ser Met Trp Ser Ala Leu Phe Pro Pro
    210                 215                 220

Gly Ser Lys Glu Thr Lys Thr Glu Lys Ser Gly Ile Thr Asp Thr Ser
225                 230                 235                 240

Gln Ile Ser Met Thr Asp Gly Ile Asn Val Ser Ile Gly Ala Asp Phe
                245                 250                 255

Gly Leu Lys Phe Gly Asn Lys Thr Phe Gly Ile Lys Gly Gly Phe Thr
            260                 265                 270

Tyr Asp Thr Lys Thr Gln Ile Thr Asn Thr Ser Gln Leu Leu Ile Glu
        275                 280                 285

Thr Thr Tyr Thr Arg Glu Tyr Thr Asn Thr Glu Asn Phe Pro Val Arg
    290                 295                 300

Tyr Thr Gly Tyr Val Leu Ala Ser Glu Phe Thr Leu His Arg Ser Asp
305                 310                 315                 320

Gly Thr Gln Val Asn Thr Ile Pro Trp Val Ala Leu Asn Asp Asn Tyr
                325                 330                 335

Thr Thr Ile Ala Arg Tyr Pro His Phe Ala Ser Glu Pro Leu Leu Gly
            340                 345                 350

Asn Thr Lys Ile Ile Thr Asp Asp Gln Asn
        355                 360
```

<210> SEQ ID NO 40
<211> LENGTH: 327
<212> TYPE: PRT
<213> ORGANISM: Bacillus sphaericus

<400> SEQUENCE: 40

```
Met Met Lys Asn Lys Ala Lys Val Ile Leu Met Gly Ala Thr Ile Gly
 1               5                  10                  15

Leu Ser Leu Leu Ser Ser Pro Ile Ala Met Ala Ala Asn Gly Asp Ser
            20                  25                  30

Asn Val Lys Glu Asn Gln Ser Ile Ala Asn Phe Ser Pro Val Lys Asn
        35                  40                  45

Ser Phe Pro Asp Ala Ala Asn Gly Ser Arg Phe Leu Val Asn Tyr Tyr
    50                  55                  60

Gly Arg Tyr Leu Thr Ser Asn Gly Leu Gly Ser Ile Gly Lys His Pro
65                  70                  75                  80

Glu Asn Ile Asp Phe Glu Val Lys Asn Thr Tyr Gly Lys Leu Ser Met
                85                  90                  95

Glu Pro Gln Val Ile Ser Gln Asn Pro Leu Trp Ala Gly Gln Ser Asp
            100                 105                 110

Leu Arg Asn Asp Thr Asp Arg Asp Gln Thr Leu Ser Ser Gln Glu Phe
        115                 120                 125

Arg Lys Ser Phe Ser Asn Thr Thr Thr Ala Thr Thr Glu His Gly Phe
    130                 135                 140

Met Phe Gly Thr Glu Thr Ser Leu Ala Thr Gly Ile Pro Phe Leu Ala
145                 150                 155                 160

Glu Gly Lys Ile Thr Leu Lys Ala Glu Tyr Asn Phe Ser Ser Ser Gln
                165                 170                 175

Ala Asn Glu Thr Ser Glu Thr Val Glu Tyr Val Ala Pro Ser Gln Ser
            180                 185                 190

Ile Val Val Pro Pro His Thr Ile Ala Arg Val Val Ala Val Leu Glu
        195                 200                 205

Ile Lys Lys Ile Lys Gly Glu Met Asp Ile Tyr Ala Glu Val Gly Leu
    210                 215                 220

Asn Lys Glu Lys Phe Gly Tyr Glu Glu Leu Pro Ile Ser Ser Met Gly
225                 230                 235                 240

Gly Leu Lys Trp Val Ser Leu Gly Ser Ile Tyr Glu Glu Ala Tyr Asn
                245                 250                 255

Gln Ala Lys Leu Ser Gly Thr His Glu Phe Pro Asp Ile Lys Ile Ile
            260                 265                 270

Ser Arg Ser Val Asn Asn Pro Asp Tyr Phe Leu Ala Ser Gly Lys Gly
        275                 280                 285

Arg Phe Glu Ser Glu Tyr Gly Ser Leu Phe Asn Val Gln Val Glu Tyr
    290                 295                 300

Ile Ser Thr Lys Ser Asn Glu Val Ile Lys Thr Glu Asn Leu Met Val
305                 310                 315                 320

Ser Pro Thr Ile Ile Ser Glu
                325
```

<210> SEQ ID NO 41
<211> LENGTH: 79
<212> TYPE: PRT
<213> ORGANISM: Bacillus thuringiensis

<400> SEQUENCE: 41

```
Met Ser Ala Asp Gly Thr Thr Ser Phe Ser Gln Asn Phe Glu Leu Pro
 1               5                  10                  15

Lys Asp Thr Val Pro Ala Thr Pro Lys Gly Asp Ala Lys Thr Val Glu
            20                  25                  30

Arg Thr Glu Gly Thr Gly Thr Asp Ser Gly Glu Gly Lys Met Val Glu
```

```
        35                  40                  45

Thr Lys Val Gly Ser Pro Leu Asn Asn Glu Lys Val Gln Lys Leu Leu
    50                  55                  60

Lys Glu Gln Lys Val Gln Val Gln Ile Leu Gly Lys Glu Lys Trp
65                  70                  75


<210> SEQ ID NO 42
<211> LENGTH: 316
<212> TYPE: PRT
<213> ORGANISM: Bacillus thuringiensis

<400> SEQUENCE: 42

Met Tyr Met Ala Glu Ile Lys Arg Leu Asp Tyr Tyr Leu Gly Ala Leu
 1               5                  10                  15

Pro Phe Gly Asn Phe Tyr Val Asp Asp Cys Asp Thr Leu Lys Asn Phe
            20                  25                  30

Ile Asp Ser Leu Leu Asp Gly Lys Pro Ser Thr Met Asn Asn Thr Pro
        35                  40                  45

Leu Thr Gly Asn Val Asn Val Thr Asn Gln Ser Val Thr Ile Leu Asp
    50                  55                  60

Asp Leu Asp Ser Ile Ala Thr Leu Thr Pro Glu Tyr Val Tyr Asp Asn
65                  70                  75                  80

Tyr Phe Ser Asn Asp Thr Ser Thr Glu Lys Thr Tyr Gln Thr Leu Ser
                85                  90                  95

Phe Glu Lys Asp Val Gln Thr Thr Val Ser Thr Thr Val Thr His Gly
            100                 105                 110

Phe Gln Ile Gly Gly Lys Leu Gly Ala Glu Val Lys Gly Ser Val Ser
        115                 120                 125

Ile Pro Phe Val Ala Asp Gly Gly Val Thr Val Ser Ala Glu Ile Ser
    130                 135                 140

Gly Gln Tyr Asn Phe Ser Ser Ala Asp Thr Glu Thr Thr Thr Thr Ser
145                 150                 155                 160

Gln Lys Leu Ile Ile Pro Ser Gln Ser Gly Asn Ile Arg Pro Gly Tyr
                165                 170                 175

Thr Thr Arg Val Gln Ile Met Leu Ala Lys Ile Asn Ile Pro Gln Thr
            180                 185                 190

Ala Val His Phe Ser Gly Ser Met Ser Gly Thr Val His Arg Asp Pro
        195                 200                 205

Ile Pro Ser Ser Val Ile Gly Leu Val Asp Tyr Asp Leu Tyr Asp Glu
    210                 215                 220

Val Arg Ser Leu Glu Asn Asn Cys Ser Asn Ser Thr Val Gly Arg Asp
225                 230                 235                 240

Thr Gly Leu Val Leu Asn Asn Ala Asn Gln Ser Val Asp Phe Ser Gly
                245                 250                 255

Ser Gly Phe Phe Thr Gly Ser Ile Thr Ala Phe Asn Phe Tyr Val Lys
            260                 265                 270

Ile Thr Glu Tyr Pro Ile Asn Asn Ser Ser Gln Glu Asn Ile Arg Trp
        275                 280                 285

Tyr Ser Ile Glu Pro Lys Val Leu Asn Gln Ser Ile Ile Arg His Arg
    290                 295                 300

Phe Pro Ser Asn Ser Ser Val Asn Thr Cys Asn Cys
305                 310                 315


<210> SEQ ID NO 43
<211> LENGTH: 525
```

<212> TYPE: PRT
<213> ORGANISM: Bacillus thuringiensis

<400> SEQUENCE: 43

```
Met Ala Gln Ser Glu Phe Asn Gln Asn Leu Arg Glu Gln Gly Gln Ser
 1               5                  10                  15

Arg Ala Arg Val Ile Ile Leu Arg Val Asn Asn Pro Gly Tyr Asn Thr
            20                  25                  30

Asn Thr Leu Asp Ile Ala Asp Ile Glu Asp Ile Ile His Leu Pro Gln
        35                  40                  45

Ala Ile Glu Leu Ala Asn Ala Phe Gln Ser Ala Leu Val Pro Thr Thr
    50                  55                  60

Ser Asn Phe Gly Glu Asp Thr Leu Arg Phe Asp Val Glu Arg Gly Leu
65                  70                  75                  80

Gly Ile Ala Thr His Val Tyr Pro Arg Ala Ile Asn Val Asn Tyr Val
                85                  90                  95

Thr Arg Thr Leu Ser Gln Thr Asn Asn Gln Val Gln Ser Met Ile Asn
            100                 105                 110

Lys Val Ile Glu Glu Leu Lys Ser Leu Leu Gly Ile Asn Leu Ala Asn
        115                 120                 125

Ser Val Leu Gln Gln Leu Thr Thr Val Ile Thr Glu Thr Phe Thr Asn
    130                 135                 140

Leu Tyr Val Gln Gln Gln Ser Ala Trp Leu Phe Trp Gly Arg Gln Thr
145                 150                 155                 160

Ser Ser Gln Thr Asn Tyr Thr Tyr Asn Ile Val Phe Ala Ile Gln Asn
                165                 170                 175

Ala Gln Thr Gly Ser Phe Met Lys Ala Ile Pro Ile Gly Phe Glu Ile
            180                 185                 190

Ser Ala Tyr Ile Ala Arg Glu Arg Leu Leu Phe Phe Asn Ile Gln Asp
        195                 200                 205

Tyr Ala Ser Tyr Ser Val Lys Ile His Ala Ile Gln Val Met Gln Pro
    210                 215                 220

Leu Ile His Glu Ser Phe Gln Pro Leu Arg Gly Ile Phe Asn Ile Ile
225                 230                 235                 240

Thr Ser Val Asn Asn Arg Ser Ala Ile Gln Ile Thr Glu Tyr Tyr Asp
                245                 250                 255

Glu Asn Thr His Asp Tyr Pro Val Lys Leu Trp Asp Tyr Asn Asn Ile
            260                 265                 270

Ile Asn Gln Lys Trp Ile Leu Val Phe Asn Gln Thr Thr Arg Ala Tyr
        275                 280                 285

Ser Ile Gln Asn Leu Ile Ala Arg Tyr Leu Val Leu Thr Trp Asp Ser
    290                 295                 300

Thr Pro Gly Ser Asn Lys Val Phe Ala Ser Thr Asn Arg Trp Asn Asp
305                 310                 315                 320

Ser Gln Phe Trp Ile Leu Glu Ser Thr Ala Asp Gly Ser Ile Phe Leu
                325                 330                 335

Thr Asn Met Lys Asp Thr Gln Phe Val Leu Glu Ile Glu Asn Ser Ser
            340                 345                 350

Thr Thr Asn Gly Thr Asn Val Ile Val Asn Arg Lys Asn Asn Asn Ala
        355                 360                 365

Gln Gln Lys Phe Tyr Leu Asn Lys Val Asn Gln Glu Phe Gln Asp Gly
    370                 375                 380

Val Tyr Lys Ile Lys Thr Ala Leu Asn Asn Ser Ser Val Leu Gln Met
385                 390                 395                 400
```

Ser Glu Asp Tyr Phe Gly Tyr Thr Ser Asp Tyr Phe Val Lys Leu Trp
405 410 415

Thr Asn Asn Asn Asn Asp Ile Asn Gln Lys Trp Ile Phe Glu Phe Asp
420 425 430

Ser Thr Lys Ser Ala Tyr Gln Ile Lys Ser Gln Arg Asp Pro Ser Leu
435 440 445

Val Leu Ala Trp Thr Trp Ser Val Pro Thr Val Lys Leu Pro Ile Pro
450 455 460

Asn Asn Asp Asp His Leu Trp Phe Leu Gln Asn Ala Gly Ser Gly Thr
465 470 475 480

Tyr Tyr Phe Val Asn Met Thr Asp Thr Arg Tyr Val Leu Glu Val Ala
485 490 495

Ser Ser Ser Thr Thr Asn Gly Thr Ile Leu Thr Ile Asn Lys Arg Asn
500 505 510

Gly Asn Leu Asn Gln Lys Phe Leu Leu Asp Met Ile Asn
515 520 525

<210> SEQ ID NO 44
<211> LENGTH: 340
<212> TYPE: PRT
<213> ORGANISM: Bacillus cereus

<400> SEQUENCE: 44

Met Ala Ile Met Asn Asp Ile Ala Gln Asp Ala Ala Arg Ala Trp Asp
1 5 10 15

Ile Ile Ala Gly Pro Phe Ile Arg Pro Gly Thr Thr Pro Thr Asn Arg
20 25 30

Gln Leu Phe Asn Tyr Gln Ile Gly Asn Ile Glu Val Glu Pro Gly Asn
35 40 45

Leu Asn Phe Ser Val Val Pro Glu Leu Asp Phe Ser Val Ser Gln Asp
50 55 60

Leu Phe Asn Asn Thr Ser Val Gln Gln Ser Gln Thr Ala Ser Phe Asn
65 70 75 80

Glu Ser Arg Thr Glu Thr Thr Ser Thr Ala Val Thr His Gly Val Lys
85 90 95

Ser Gly Val Thr Val Ser Ala Ser Ala Lys Phe Asn Ala Lys Ile Leu
100 105 110

Val Lys Ser Ile Glu Gln Thr Ile Thr Thr Thr Val Ser Thr Glu Tyr
115 120 125

Asn Phe Ser Ser Thr Thr Thr Arg Thr Asn Thr Val Thr Arg Gly Trp
130 135 140

Ser Ile Ala Gln Pro Val Leu Val Pro Pro His Ser Arg Val Thr Ala
145 150 155 160

Thr Leu Gln Ile Tyr Lys Gly Asp Phe Thr Val Pro Val Leu Leu Ser
165 170 175

Leu Arg Val Tyr Gly Gln Thr Gly Thr Leu Ala Gly Asn Pro Ser Phe
180 185 190

Pro Ser Leu Tyr Ala Ala Thr Tyr Glu Asn Thr Leu Leu Gly Arg Ile
195 200 205

Arg Glu His Ile Ala Pro Pro Ala Leu Phe Arg Ala Ser Asn Ala Tyr
210 215 220

Ile Ser Asn Gly Val Gln Ala Ile Trp Arg Gly Thr Ala Thr Thr Arg
225 230 235 240

Val Ser Gln Gly Leu Tyr Ser Val Val Arg Ile Asp Glu Arg Pro Leu

```
                245                 250                 255

Ala Gly Tyr Ser Gly Glu Thr Arg Thr Tyr Tyr Leu Pro Val Thr Leu
            260                 265                 270

Ser Asn Ser Ser Gln Ile Leu Thr Pro Gly Ser Leu Gly Ser Glu Ile
        275                 280                 285

Pro Ile Ile Asn Pro Val Pro Asn Ala Ser Cys Lys Lys Glu Asn Ser
    290                 295                 300

Pro Ile Ile Ile His His Asp Arg Glu Lys His Arg Glu Arg Asp Tyr
305                 310                 315                 320

Asp Lys Glu His Ile Cys His Asp Gln Ala Glu Lys Tyr Glu Arg Asp
                325                 330                 335

Tyr Asp Lys Glu
            340


<210> SEQ ID NO 45
<211> LENGTH: 1131
<212> TYPE: PRT
<213> ORGANISM: Bacillus thuringiensis

<400> SEQUENCE: 45

Met Asn Gln Lys Asn Tyr Glu Ile Ile Gly Ala Ser Thr Asn Gly Thr
 1               5                  10                  15

Ile Glu Leu Pro Glu Asp Tyr Asn Thr Ile Val Ser Pro Tyr Asp Ala
            20                  25                  30

Pro Ala Ser Val Thr Thr Thr Ile Glu Ile Thr Gly Thr Ile Leu Ser
        35                  40                  45

Asp Leu Gly Val Pro Gly Ala Ser Ser Val Ser Leu Leu Leu Asn Lys
    50                  55                  60

Leu Ile Asn Leu Leu Trp Pro Asn Asp Thr Asn Thr Val Trp Gly Thr
65                  70                  75                  80

Phe Gly Lys Glu Thr Ala Asp Leu Leu Asn Glu Val Leu Ser Pro Asp
                85                  90                  95

Asp Pro Val Val Lys Asp Ala Asn Thr Ile Leu Lys Gly Ile Asn Gly
            100                 105                 110

Ser Leu Asn Leu Tyr Leu Asn Ala Leu Glu Ile Trp Lys Lys Asp Pro
        115                 120                 125

Asn Asn Leu Thr Thr Ile Glu Asn Val Thr Asp Tyr Phe Arg Ser Leu
    130                 135                 140

Asn Val Val Phe Thr His Asp Met Pro Ser Phe Ala Val Pro Gly Tyr
145                 150                 155                 160

Glu Thr Lys Leu Leu Thr Ile Tyr Ala Gln Ala Ala Asn Leu His Leu
                165                 170                 175

Leu Leu Leu Arg Asp Ala Ser Arg Phe Gly Glu Gly Trp Gly Leu Thr
            180                 185                 190

Gln Glu Ile Ile Asn Thr Asn Tyr Asn Asp Gln Leu Arg Leu Thr Ala
        195                 200                 205

Glu Tyr Thr Asp His Cys Val Lys Trp Tyr Asn Ala Gly Leu Glu Lys
    210                 215                 220

Leu Lys Gly Asn Leu Thr Gly Glu Asn Trp Tyr Thr Tyr Asn Arg Phe
225                 230                 235                 240

Arg Arg Glu Met Thr Leu Met Val Leu Asp Val Val Ala Leu Phe Pro
                245                 250                 255

Asn Tyr Asp Thr Arg Met Tyr Pro Ile Gly Thr Ser Ser Glu Leu Thr
            260                 265                 270
```

-continued

Arg Met Ile Tyr Thr Asp Pro Ile Ala Tyr Thr Gln Ser Asp Pro Trp
275 280 285

Tyr Lys Ile Thr Ser Leu Ser Phe Ser Asn Ile Glu Asn Ser Ala Ile
290 295 300

Pro Ser Pro Ser Phe Phe Arg Trp Leu Lys Ser Val Ser Ile Asn Ser
305 310 315 320

Gln Trp Trp Gly Ser Gly Pro Ser Gln Thr Tyr Tyr Trp Val Gly His
325 330 335

Glu Leu Val Tyr Ser Asn Ser Asn Ser Asn Gln Ser Leu Lys Val Lys
340 345 350

Tyr Gly Asp Pro Asn Ser Phe Ile Glu Pro Pro Asp Ser Phe Ser Phe
355 360 365

Ser Ser Thr Asp Val Tyr Arg Thr Ile Ser Val Val Arg Asn Ser Val
370 375 380

Ser Asn Tyr Ile Val Ser Glu Val Arg Phe Asn Ser Ile Ser Ser Thr
385 390 395 400

Asn Gln Ile Ser Glu Glu Ile Tyr Lys His Gln Ser Asn Trp Ser Arg
405 410 415

Gln Glu Thr Lys Asp Ser Ile Thr Glu Leu Ser Leu Ala Ala Asn Pro
420 425 430

Pro Thr Thr Phe Gly Asn Val Ala Glu Tyr Ser His Arg Leu Ala Tyr
435 440 445

Ile Ser Glu Ala Tyr Gln Ser His Asn Pro Ser Lys Tyr Pro Thr Tyr
450 455 460

Ile Pro Val Phe Gly Trp Thr His Thr Ser Val Arg Tyr Asp Asn Lys
465 470 475 480

Ile Phe Pro Asp Lys Ile Thr Gln Ile Pro Ala Val Lys Ser Ser Ser
485 490 495

Ala Gln Gly Gly Ser Trp Lys Asn Ile Val Lys Gly Pro Gly Phe Thr
500 505 510

Gly Gly Asp Val Thr Thr Ala Val Ser Pro Ala Thr Val Thr Asp Ile
515 520 525

Ile Lys Ile Gln Val Thr Leu Asp Pro Asn Ser Leu Ser Gln Lys Tyr
530 535 540

Arg Ala Arg Leu Arg Tyr Ala Ser Asn Ala Phe Val Pro Ala Thr Leu
545 550 555 560

Tyr Thr Asn Thr Ser Ser Asn Tyr Asn Phe Glu Leu Lys Lys Gly Thr
565 570 575

Thr Glu Gln Phe Thr Thr Tyr Asn Ser Tyr Gln Tyr Val Asp Ile Pro
580 585 590

Gly Ser Ile Gln Phe Asn Asn Thr Ser Asp Thr Val Ser Val Tyr Leu
595 600 605

His Met Asp Ser Thr Ser Asn Val Asn Val His Val Asp Arg Ile Glu
610 615 620

Phe Ile Pro Ile Asp Glu Asn Tyr Asp Glu Arg Phe Gln Leu Glu Lys
625 630 635 640

Ala Gln Lys Ala Val Asn Ala Leu Phe Thr Ala Gly Arg Asn Ala Leu
645 650 655

Gln Thr Asp Val Thr Asp Tyr Lys Val Asp Gln Val Ser Ile Leu Val
660 665 670

Asp Cys Val Ser Gly Glu Leu Tyr Pro Asn Glu Lys Arg Glu Leu Leu
675 680 685

Ser Leu Val Lys Tyr Ala Lys Arg Leu Ser Tyr Ser Arg Asn Leu Leu

```
    690                 695                 700

Leu Asp Pro Thr Phe Asp Ser Ile Asn Ser Pro Glu Glu Asn Gly Trp
705                 710                 715                 720

Tyr Gly Ser Asn Gly Ile Ala Ile Gly Ser Gly Asn Ile Val Phe Lys
                725                 730                 735

Gly Asn Tyr Leu Ile Phe Ser Gly Thr Asn Asp Glu Gln Tyr Pro Thr
            740                 745                 750

Tyr Leu Tyr Gln Lys Ile Asp Glu Thr Lys Leu Lys Glu Tyr Thr Arg
        755                 760                 765

Tyr Lys Leu Arg Gly Phe Ile Glu Ser Ser Gln Asp Leu Glu Ala Tyr
    770                 775                 780

Val Ile Arg Tyr Asp Ala Lys His Gln Thr Met Asp Val Ser Asn Asn
785                 790                 795                 800

Leu Phe Ser Asp Ile Thr Pro Val Asn Ala Cys Gly Glu Pro Asn Arg
                805                 810                 815

Cys Ala Ala Leu Pro Tyr Leu Asp Glu Asn Pro Arg Leu Glu Cys Ser
            820                 825                 830

Ser Ile Gln Asp Gly Ile Leu Ser Asp Ser His Ser Phe Ser Leu His
        835                 840                 845

Ile Asp Thr Gly Ser Ile Asp Phe Asn Glu Asn Val Gly Ile Trp Val
    850                 855                 860

Leu Phe Lys Ile Ser Thr Pro Glu Gly Tyr Ala Arg Phe Gly Asn Leu
865                 870                 875                 880

Glu Val Ile Glu Asp Gly Pro Val Ile Gly Glu Ala Leu Ala Arg Val
                885                 890                 895

Lys Arg Gln Glu Thr Lys Trp Arg Asn Lys Leu Thr Gln Leu Arg Thr
            900                 905                 910

Glu Thr Gln Ala Ile Tyr Thr Arg Ala Lys Gln Ala Ile Asp Asn Leu
        915                 920                 925

Phe Thr Asn Ala Gln Asp Ser His Leu Lys Ile Gly Ala Thr Phe Ala
    930                 935                 940

Ser Ile Val Ala Ala Arg Lys Ile Val Gln Ser Ile Arg Glu Ala Tyr
945                 950                 955                 960

Met Ser Trp Leu Ser Ile Val Pro Gly Val Asn Tyr Pro Ile Val Thr
                965                 970                 975

Glu Leu Asn Glu Arg Ile Gln Gln Ala Phe Gln Leu Tyr Asp Val Arg
            980                 985                 990

Asn Val Val Arg Asn Gly Arg Phe Gln Ser Gly Thr Ser Asp Trp Ile
        995                 1000                1005

Val Thr Ser Asp Val Arg Val Gln Glu Glu Asn Gly Asn Asn Val Leu
    1010                1015                1020

Val Leu Ser Asn Trp Asp Ala Gln Val Leu Gln Cys Met Thr Leu Tyr
1025                1030                1035                1040

Gln Asp Arg Gly Tyr Ile Leu Arg Val Thr Ala Arg Lys Glu Gly Leu
                1045                1050                1055

Gly Glu Gly Tyr Val Thr Ile Thr Asp Glu Glu Gly Asn Thr Asp Gln
            1060                1065                1070

Leu Arg Phe Gly Gly Cys Glu Glu Ile Asp Ala Ser Asn Ser Phe Val
        1075                1080                1085

Ser Thr Gly Tyr Met Thr Lys Glu Leu Glu Phe Phe Pro Asp Thr Glu
    1090                1095                1100

Lys Val Arg Ile Glu Ile Gly Glu Thr Glu Gly Thr Phe Gln Val Glu
1105                1110                1115                1120
```

```
Ser Val Glu Leu Phe Leu Met Glu Asp Leu Cys
                1125                1130


<210> SEQ ID NO 46
<211> LENGTH: 1138
<212> TYPE: PRT
<213> ORGANISM: Bacillus thuringiensis

<400> SEQUENCE: 46

Met Asn Leu Asn Asn Leu Asp Gly Tyr Glu Asp Ser Asn Arg Thr Leu
 1               5                  10                  15

Asn Asn Ser Leu Asn Tyr Pro Thr Gln Lys Ala Leu Ser Pro Ser Leu
            20                  25                  30

Lys Asn Met Asn Tyr Gln Asp Phe Leu Ser Ile Thr Glu Arg Glu Gln
        35                  40                  45

Pro Glu Ala Leu Ala Ser Gly Asn Thr Ala Ile Asn Thr Val Val Ser
    50                  55                  60

Val Thr Gly Ala Thr Leu Ser Ala Leu Gly Val Pro Gly Ala Ser Phe
65                  70                  75                  80

Ile Thr Asn Phe Tyr Leu Lys Ile Ala Gly Leu Leu Trp Pro Glu Asn
                85                  90                  95

Gly Lys Ile Trp Asp Glu Phe Met Thr Glu Val Glu Ala Leu Ile Asp
            100                 105                 110

Gln Lys Ile Glu Glu Tyr Val Arg Asn Lys Ala Ile Ala Glu Leu Asp
        115                 120                 125

Gly Leu Gly Ser Ala Leu Asp Lys Tyr Gln Lys Ala Leu Ala Asp Trp
    130                 135                 140

Leu Gly Lys Gln Asp Asp Pro Glu Ala Ile Leu Ser Val Ala Thr Glu
145                 150                 155                 160

Phe Arg Ile Ile Asp Ser Leu Phe Glu Phe Ser Met Pro Ser Phe Lys
                165                 170                 175

Val Thr Gly Tyr Glu Ile Pro Leu Leu Thr Val Tyr Ala Gln Ala Ala
            180                 185                 190

Asn Leu His Leu Ala Leu Leu Arg Asp Ser Thr Leu Tyr Gly Asp Lys
        195                 200                 205

Trp Gly Phe Thr Gln Asn Asn Ile Glu Glu Asn Tyr Asn Arg Gln Lys
    210                 215                 220

Lys Arg Ile Ser Glu Tyr Ser Asp His Cys Thr Lys Trp Tyr Asn Ser
225                 230                 235                 240

Gly Leu Ser Arg Leu Asn Gly Ser Thr Tyr Glu Gln Trp Ile Asn Tyr
                245                 250                 255

Asn Arg Phe Arg Arg Glu Met Ile Leu Met Ala Leu Asp Leu Val Ala
            260                 265                 270

Val Phe Pro Phe His Asp Pro Arg Arg Tyr Ser Met Glu Thr Ser Thr
        275                 280                 285

Gln Leu Thr Arg Glu Val Tyr Thr Asp Pro Val Ser Leu Ser Ile Ser
    290                 295                 300

Asn Pro Asp Ile Gly Pro Ser Phe Ser Gln Met Glu Asn Thr Ala Ile
305                 310                 315                 320

Arg Thr Pro His Leu Val Asp Tyr Leu Asp Glu Leu Tyr Ile Tyr Thr
                325                 330                 335

Ser Lys Tyr Lys Ala Phe Ser His Glu Ile Gln Pro Asp Leu Phe Tyr
            340                 345                 350

Trp Ser Ala His Lys Val Ser Phe Lys Lys Ser Glu Gln Ser Asn Leu
```

```
        355                 360                 365

Tyr Thr Thr Gly Ile Tyr Gly Lys Thr Ser Gly Tyr Ile Ser Ser Gly
    370                 375                 380

Ala Tyr Ser Phe His Gly Asn Asp Ile Tyr Arg Thr Leu Ala Ala Pro
385                 390                 395                 400

Ser Val Val Val Tyr Pro Tyr Thr Gln Asn Tyr Gly Val Glu Gln Val
                405                 410                 415

Glu Phe Tyr Gly Val Lys Gly His Val His Tyr Arg Gly Asp Asn Lys
            420                 425                 430

Tyr Asp Leu Thr Tyr Asp Ser Ile Asp Gln Leu Pro Pro Asp Gly Glu
        435                 440                 445

Pro Ile His Glu Lys Tyr Thr His Arg Leu Cys His Ala Thr Ala Ile
    450                 455                 460

Phe Lys Ser Thr Pro Asp Tyr Asp Asn Ala Thr Ile Pro Ile Phe Ser
465                 470                 475                 480

Trp Thr His Arg Ser Ala Glu Tyr Tyr Asn Arg Ile Tyr Pro Asn Lys
                485                 490                 495

Ile Thr Lys Ile Pro Ala Val Lys Met Tyr Lys Leu Asp Asp Pro Ser
            500                 505                 510

Thr Val Val Lys Gly Pro Gly Phe Thr Gly Gly Asp Leu Val Lys Arg
        515                 520                 525

Gly Ser Thr Gly Tyr Ile Gly Asp Ile Lys Ala Thr Val Asn Ser Pro
    530                 535                 540

Leu Ser Gln Lys Tyr Arg Val Arg Val Arg Tyr Ala Thr Asn Val Ser
545                 550                 555                 560

Gly Gln Phe Asn Val Tyr Ile Asn Asp Lys Ile Thr Leu Gln Thr Lys
                565                 570                 575

Phe Gln Asn Thr Val Glu Thr Ile Gly Glu Gly Lys Asp Leu Thr Tyr
            580                 585                 590

Gly Ser Phe Gly Tyr Ile Glu Tyr Ser Thr Thr Ile Gln Phe Pro Asp
        595                 600                 605

Glu His Pro Lys Ile Thr Leu His Leu Ser Asp Leu Ser Asn Asn Ser
    610                 615                 620

Ser Phe Tyr Val Asp Ser Ile Glu Phe Ile Pro Val Asp Val Asn Tyr
625                 630                 635                 640

Ala Glu Lys Glu Lys Leu Glu Lys Ala Gln Lys Ala Val Asn Thr Leu
                645                 650                 655

Phe Thr Glu Gly Arg Asn Ala Leu Gln Lys Asp Val Thr Asp Tyr Lys
            660                 665                 670

Val Asp Gln Val Ser Ile Leu Val Asp Cys Ile Ser Gly Asp Leu Tyr
        675                 680                 685

Pro Asn Glu Lys Arg Glu Leu Gln Asn Leu Val Lys Tyr Ala Lys Arg
    690                 695                 700

Leu Ser Tyr Ser Arg Asn Leu Leu Leu Asp Pro Thr Phe Asp Ser Ile
705                 710                 715                 720

Asn Ser Ser Glu Glu Asn Gly Trp Tyr Gly Ser Asn Gly Ile Val Ile
                725                 730                 735

Gly Asn Gly Asp Phe Val Phe Lys Gly Asn Tyr Leu Ile Phe Ser Gly
            740                 745                 750

Thr Asn Asp Thr Gln Tyr Pro Thr Tyr Leu Tyr Gln Lys Ile Asp Glu
        755                 760                 765

Ser Lys Leu Lys Glu Tyr Thr Arg Tyr Lys Leu Lys Gly Phe Ile Glu
    770                 775                 780
```

Ser Ser Gln Asp Leu Glu Ala Tyr Val Ile Arg Tyr Asp Ala Lys His
785 790 795 800

Arg Thr Leu Asp Val Ser Asp Asn Leu Leu Pro Asp Ile Leu Pro Glu
805 810 815

Asn Thr Cys Gly Glu Pro Asn Arg Cys Ala Ala Gln Gln Tyr Leu Asp
820 825 830

Glu Asn Pro Ser Pro Glu Cys Ser Ser Met Gln Asp Gly Ile Leu Ser
835 840 845

Asp Ser His Ser Phe Ser Leu Asn Ile Asp Thr Gly Ser Ile Asn His
850 855 860

Asn Glu Asn Leu Gly Ile Trp Val Leu Phe Lys Ile Ser Thr Leu Glu
865 870 875 880

Gly Tyr Ala Lys Phe Gly Asn Leu Glu Val Ile Glu Asp Gly Pro Val
885 890 895

Ile Gly Glu Ala Leu Ala Arg Val Lys Arg Gln Glu Thr Lys Trp Arg
900 905 910

Asn Lys Leu Ala Gln Leu Thr Thr Glu Thr Gln Ala Ile Tyr Thr Arg
915 920 925

Ala Lys Gln Ala Leu Asp Asn Leu Phe Ala Asn Ala Gln Asp Ser His
930 935 940

Leu Lys Arg Asp Val Thr Phe Ala Glu Ile Ala Ala Ala Arg Lys Ile
945 950 955 960

Val Gln Ser Ile Arg Glu Ala Tyr Met Ser Trp Leu Ser Val Val Pro
965 970 975

Gly Val Asn His Pro Ile Phe Thr Glu Leu Ser Gly Arg Val Gln Arg
980 985 990

Ala Phe Gln Leu Tyr Asp Val Arg Asn Val Val Arg Asn Gly Arg Phe
995 1000 1005

Leu Asn Gly Leu Ser Asp Trp Ile Val Thr Ser Asp Val Lys Val Gln
1010 1015 1020

Glu Glu Asn Gly Asn Asn Val Leu Val Leu Asn Asn Trp Asp Ala Gln
1025 1030 1035 1040

Val Leu Gln Asn Val Lys Leu Tyr Gln Asp Arg Gly Tyr Ile Leu His
1045 1050 1055

Val Thr Ala Arg Lys Ile Gly Ile Gly Glu Gly Tyr Ile Thr Ile Thr
1060 1065 1070

Asp Glu Glu Gly His Thr Asp Gln Leu Arg Phe Thr Ala Cys Glu Glu
1075 1080 1085

Ile Asp Ala Ser Asn Ala Phe Ile Ser Gly Tyr Ile Thr Lys Glu Leu
1090 1095 1100

Glu Phe Phe Pro Asp Thr Glu Lys Val His Ile Glu Ile Gly Glu Thr
1105 1110 1115 1120

Glu Gly Ile Phe Leu Val Glu Ser Ile Glu Leu Phe Leu Met Glu Glu
1125 1130 1135

Leu Cys

<210> SEQ ID NO 47
<211> LENGTH: 326
<212> TYPE: PRT
<213> ORGANISM: Bacillus thuringiensis

<400> SEQUENCE: 47

Met Val Arg Glu Tyr Pro Asp Leu Asp Ser Met Ile Arg Glu Ala Ala
1 5 10 15

```
Gln Lys Trp Ser Glu Asp Asn Gly Leu Gln Phe Gln Lys Val Ser Phe
            20                  25                  30

Lys Asp Pro Phe Thr Asn Arg Asp Thr Ile Arg Met Ser Val Lys Phe
        35                  40                  45

Lys Asp Ile Gly Cys Pro Glu Glu Cys Leu Glu Thr Glu Thr Val Lys
    50                  55                  60

Leu Ser Gln Ala Phe Thr Asn Asn Thr Gly Gln Pro Lys Lys Glu Thr
65                  70                  75                  80

Val Asn Thr Val Thr Tyr Val Glu Asn Gln Leu Thr Trp Glu Asn Asp
                85                  90                  95

Phe His Phe Lys Leu Pro Gly Gln Asn Phe Leu Ile Leu Pro Arg Ile
            100                 105                 110

Pro Gln Ser Val Arg Met Asp Ile Asn Pro Gly Phe Leu Val Asn Phe
        115                 120                 125

Phe Gly Asp Asn Glu Leu Phe Ser Thr Asn Met Arg Asp Arg Arg Pro
    130                 135                 140

Ile Gln Ala Asp Val Phe Val Glu Pro Gly Ser Ser Ala Ala Ile Gln
145                 150                 155                 160

Leu Lys Val Glu Lys Leu His Val Thr Gln Pro Tyr Glu Ile Glu Leu
                165                 170                 175

Ser Ile Leu Gly Ser Ile Ile Val Thr Ala Gln Gly Ala Glu Arg Tyr
            180                 185                 190

Val Asp Val Thr Asp Leu Leu Pro Phe Leu Cys Leu Ser Lys Asn Leu
        195                 200                 205

Ser Ser Arg Gly Arg Ala Leu Ile Phe Leu Glu Gln Gly Thr Phe Lys
    210                 215                 220

Gly Ile Leu Asn Arg Lys Ile Arg Gly Tyr Ala Leu Gln Thr Arg His
225                 230                 235                 240

Cys Asp Gly Lys Thr Ile Glu Tyr Glu Ile Pro Leu Asn Asn Arg Pro
                245                 250                 255

Pro Val Ser Ala Arg Pro Leu Asn Pro Ala Thr Thr Ala Gln Gln Ser
            260                 265                 270

Arg Lys Thr Asn Asp Ser Ser Cys Gly Cys Ser Ser Asp Arg Pro Pro
        275                 280                 285

Val Gly Ile Tyr Leu Leu Ser Thr Ile Glu Ser Asn Asn Leu Phe Ser
    290                 295                 300

Ala Thr Glu Ala Asp Glu Gly Cys Arg Phe Ile Met Trp Met Cys Cys
305                 310                 315                 320

Leu Phe Val Cys Ile Lys
                325


<210> SEQ ID NO 48
<211> LENGTH: 335
<212> TYPE: PRT
<213> ORGANISM: Bacillus thuringiensis

<400> SEQUENCE: 48

Met Lys Lys Ser Cys Asp Pro Asn Pro Val Asn Gln Ser Thr Thr Thr
 1               5                  10                  15

Thr Phe Asp Leu Asp Asp Phe Leu Leu Asn Asn Met Phe Asn Val Thr
            20                  25                  30

Leu Gln Pro Ala Asn Ile Trp Tyr Tyr Gln Asp Glu Trp Pro Tyr Glu
        35                  40                  45

Ser Pro Tyr Val Pro Thr Pro Thr Ser Asp Asp Leu Ser Lys Gly Cys
```

```
    50                  55                  60

Trp Phe Asp Ala Tyr Val Pro Thr Cys Arg Tyr Asp His Ala Pro Gly
65                  70                  75                  80

Tyr Thr Ala Asn Thr Ser Gly Leu Met Ala Glu Gly Thr Asp Leu Thr
                85                  90                  95

Glu Glu Ile Asp Ser Val Ala Tyr Ala Thr Pro Tyr Ile Ala Asp Ser
            100                 105                 110

Tyr Thr Phe Thr Asn Asp Gly Pro Ile Thr Gln Glu Tyr Gln Thr Leu
        115                 120                 125

Ala Tyr Glu Gln Ala Val Glu Thr Ser Thr Ser Asn Thr Thr Thr His
    130                 135                 140

Gly Cys Arg Val Gly Ser Thr Phe Gly Tyr Ser Arg Asn Ser Thr Phe
145                 150                 155                 160

Thr Ala Lys Ile Arg Asp Thr Glu Lys Gly Phe His Leu Asp Val Gly
                165                 170                 175

Ala Glu Tyr Asp Phe Thr Asn Thr Asn Thr Phe Thr Thr Ser Thr Thr
            180                 185                 190

Thr Asn Val Leu Val Pro Ser Gln Val Ile Thr Val Pro Ser Tyr Cys
        195                 200                 205

Thr Ala Tyr Val Thr Met Val Leu Asn Lys Ala Thr Tyr Ala Lys Ala
    210                 215                 220

Asp Val Pro Leu Ile Thr Thr Leu Ser Gly Arg Phe Phe Ile Asp Glu
225                 230                 235                 240

Thr Asp Asn Ser Asp Glu Tyr Phe Asp Ile Tyr Pro Tyr Val Glu Leu
                245                 250                 255

Val Thr Thr Cys Cys Thr Gly Asn Cys Ser Gln Cys Val Thr Asp Gln
            260                 265                 270

Leu Gln Leu Asp Ala Val Asn Arg Thr Val Ile Phe Asp Gly Leu Gly
        275                 280                 285

Ser Phe Glu Ala Asn Ile Ala Ser Asn Glu Leu Ile Val Arg Thr Lys
    290                 295                 300

Leu Val Asp Asn Val Thr Gly Ala Thr Ile Ser Glu Gln Ala Gly Arg
305                 310                 315                 320

Val Pro Val Val Tyr Gly Pro Ser Thr Thr Lys Val Thr Thr Ser
                325                 330                 335


<210> SEQ ID NO 49
<211> LENGTH: 875
<212> TYPE: PRT
<213> ORGANISM: Clostridium perfringens

<400> SEQUENCE: 49

Met Asn Ile Gln Ile Lys Asn Val Phe Ser Phe Leu Thr Leu Thr Ala
 1               5                  10                  15

Met Ile Ser Gln Thr Leu Ser Tyr Asn Val Tyr Ala Gln Thr Thr Thr
            20                  25                  30

Gln Asn Asp Thr Asn Gln Lys Glu Glu Ile Thr Asn Glu Asn Thr Leu
        35                  40                  45

Ser Ser Asn Gly Leu Met Gly Tyr Tyr Phe Ala Asp Glu His Phe Lys
    50                  55                  60

Asp Leu Glu Leu Met Ala Pro Ile Lys Asn Gly Asp Leu Lys Phe Glu
65                  70                  75                  80

Glu Lys Lys Val Asp Lys Leu Leu Thr Glu Asp Asn Ser Ser Ile Lys
                85                  90                  95
```

```
Ser Ile Arg Trp Thr Gly Arg Ile Ile Pro Ser Glu Asp Gly Glu Tyr
            100                 105                 110

Ile Leu Ser Thr Asp Arg Asn Asp Val Leu Met Gln Ile Asn Ala Lys
        115                 120                 125

Gly Asp Ile Ala Lys Thr Leu Lys Val Asn Met Lys Lys Gly Gln Ala
    130                 135                 140

Tyr Asn Ile Arg Ile Glu Ile Gln Asp Lys Asn Leu Gly Ser Ile Asp
145                 150                 155                 160

Asn Leu Ser Val Pro Lys Leu Tyr Trp Glu Leu Asn Gly Asn Lys Thr
                165                 170                 175

Val Ile Pro Glu Glu Asn Leu Phe Phe Arg Asp Tyr Ser Lys Ile Asp
            180                 185                 190

Glu Asn Asp Pro Phe Ile Pro Asn Asn Asn Phe Phe Asp Val Arg Phe
        195                 200                 205

Phe Ser Ala Ala Trp Glu Asp Glu Asp Leu Asp Thr Asp Asn Asp Asn
    210                 215                 220

Ile Pro Asp Ala Tyr Glu Lys Asn Gly Tyr Thr Ile Lys Asp Ser Ile
225                 230                 235                 240

Ala Val Lys Trp Asn Asp Ser Phe Ala Glu Gln Gly Tyr Lys Lys Tyr
                245                 250                 255

Val Ser Ser Tyr Leu Glu Ser Asn Thr Ala Gly Asp Pro Tyr Thr Asp
            260                 265                 270

Tyr Gln Lys Ala Ser Gly Ser Ile Asp Lys Ala Ile Lys Leu Glu Ala
        275                 280                 285

Arg Asp Pro Leu Val Ala Ala Tyr Pro Val Val Gly Val Gly Met Glu
    290                 295                 300

Asn Leu Ile Ile Ser Thr Asn Glu His Ala Ser Ser Asp Gln Gly Lys
305                 310                 315                 320

Thr Val Ser Arg Ala Thr Thr Asn Ser Lys Thr Asp Ala Asn Thr Val
                325                 330                 335

Gly Val Ser Ile Ser Ala Gly Tyr Gln Asn Gly Phe Thr Gly Asn Ile
            340                 345                 350

Thr Thr Ser Tyr Ser His Thr Thr Asp Asn Ser Thr Ala Val Gln Asp
        355                 360                 365

Ser Asn Gly Glu Ser Trp Asn Thr Gly Leu Ser Ile Asn Lys Gly Glu
    370                 375                 380

Ser Ala Tyr Ile Asn Ala Asn Val Arg Tyr Tyr Asn Thr Gly Thr Ala
385                 390                 395                 400

Pro Met Tyr Lys Val Thr Pro Thr Thr Asn Leu Val Leu Asp Gly Glu
                405                 410                 415

Thr Leu Ala Thr Ile Lys Ala Gln Asp Asn Gln Ile Gly Asn Asn Leu
            420                 425                 430

Ser Pro Asn Glu Thr Tyr Pro Lys Lys Gly Leu Ser Pro Leu Ala Leu
        435                 440                 445

Asn Thr Met Asp Gln Phe Asn Ala Arg Leu Ile Pro Ile Asn Tyr Asp
    450                 455                 460

Gln Leu Lys Lys Leu Asp Ser Gly Lys Gln Ile Lys Leu Glu Thr Thr
465                 470                 475                 480

Gln Val Ser Gly Asn Tyr Gly Thr Lys Asn Ser Gln Gly Gln Ile Ile
                485                 490                 495

Thr Glu Gly Asn Ser Trp Ser Asn Tyr Ile Ser Gln Ile Asp Ser Val
            500                 505                 510

Ser Ala Ser Ile Ile Leu Asp Thr Gly Ser Gln Thr Phe Glu Arg Arg
```

```
        515                 520                 525

Val Ala Ala Lys Glu Gln Gly Asn Pro Glu Asp Lys Thr Pro Glu Ile
    530                 535                 540

Thr Ile Gly Glu Ala Ile Lys Lys Ala Phe Ser Ala Thr Lys Asn Gly
545                 550                 555                 560

Glu Leu Leu Tyr Phe Asn Gly Ile Pro Ile Asp Glu Ser Cys Val Glu
                565                 570                 575

Leu Ile Phe Asp Asp Asn Thr Ser Glu Ile Ile Lys Glu Gln Leu Lys
            580                 585                 590

Tyr Leu Asp Asp Lys Lys Ile Tyr Asn Val Lys Leu Glu Arg Gly Met
        595                 600                 605

Asn Ile Leu Ile Lys Val Pro Ser Tyr Phe Thr Asn Phe Asp Glu Tyr
    610                 615                 620

Asn Asn Phe Pro Ala Ser Trp Ser Asn Ile Asp Thr Lys Asn Gln Asp
625                 630                 635                 640

Gly Leu Gln Ser Val Ala Asn Lys Leu Ser Gly Glu Thr Lys Ile Ile
                645                 650                 655

Ile Pro Met Ser Lys Leu Lys Pro Tyr Lys Arg Tyr Val Phe Ser Gly
            660                 665                 670

Tyr Ser Lys Asp Pro Ser Thr Ser Asn Ser Ile Thr Val Asn Ile Lys
        675                 680                 685

Ser Lys Glu Gln Lys Thr Asp Tyr Leu Val Pro Glu Lys Asp Tyr Thr
    690                 695                 700

Lys Phe Ser Tyr Glu Phe Glu Thr Thr Gly Lys Asp Ser Ser Asp Ile
705                 710                 715                 720

Glu Ile Thr Leu Thr Ser Ser Gly Val Ile Phe Leu Asp Asn Leu Ser
                725                 730                 735

Ile Thr Glu Leu Asn Ser Thr Pro Glu Ile Leu Lys Glu Pro Glu Ile
            740                 745                 750

Lys Val Pro Ser Asp Gln Glu Ile Leu Asp Ala His Asn Lys Tyr Tyr
        755                 760                 765

Ala Asp Ile Lys Leu Asp Thr Asn Thr Gly Asn Thr Tyr Ile Asp Gly
    770                 775                 780

Ile Tyr Phe Glu Pro Thr Gln Thr Asn Lys Glu Ala Leu Asp Tyr Ile
785                 790                 795                 800

Gln Lys Tyr Arg Val Glu Ala Thr Leu Gln Tyr Ser Gly Phe Lys Asp
                805                 810                 815

Ile Gly Thr Lys Asp Lys Glu Ile Arg Asn Tyr Leu Gly Asp Gln Asn
            820                 825                 830

Gln Pro Lys Thr Asn Tyr Ile Asn Phe Arg Ser Tyr Phe Thr Ser Gly
        835                 840                 845

Glu Asn Val Met Thr Tyr Lys Lys Leu Arg Ile Tyr Ala Val Thr Pro
    850                 855                 860

Asp Asn Arg Glu Leu Leu Val Leu Ser Val Asn
865                 870                 875


<210> SEQ ID NO 50
<211> LENGTH: 871
<212> TYPE: PRT
<213> ORGANISM: Brevibacillus laterosporus

<400> SEQUENCE: 50

Met Lys Tyr Met Lys Lys Gly Leu Ser Ser Val Val Ile Gly Thr Leu
 1               5                  10                  15
```

-continued

```
Phe Ala Ser Met Phe Leu Asn Gly Asn Val Asn Ala Val Tyr Ala Asn
            20                  25                  30

Ser Lys Thr Asn Gln Ile Ala Thr Thr Thr Gln Ala Ser Lys Asp Asn
        35                  40                  45

Gln Ile Asp Arg Glu Gly Leu Leu Gly Tyr Tyr Phe Lys Gly Lys Asp
    50                  55                  60

Phe Asn Asp Leu Thr Leu Phe Ala Pro Thr Arg Asp Asn Thr Leu Ile
65                  70                  75                  80

Tyr Asp Gln Gln Thr Ala Asn Thr Leu Val Asp Gln Lys His Gln Glu
                85                  90                  95

Tyr His Ser Ile Arg Trp Ile Gly Leu Ile Gln Ser Ser Ala Thr Gly
            100                 105                 110

Asp Phe Thr Phe Lys Leu Ser Asp Asp Glu Asn Ala Ile Ile Glu Leu
        115                 120                 125

Asp Gly Lys Val Ile Ser Glu Lys Gly Asn Asn Lys Gln Ser Val His
    130                 135                 140

Leu Glu Lys Gly Gln Leu Val Gln Ile Lys Ile Glu Tyr Gln Ser Asp
145                 150                 155                 160

Asp Ala Leu His Ile Asp Asn Lys Ile Phe Lys Glu Leu Lys Leu Phe
                165                 170                 175

Lys Ile Asp Ser Gln Asn His Ser Gln Gln Val Gln Gln Asp Glu Leu
            180                 185                 190

Arg Asn Pro Glu Phe Asn Lys Lys Glu Thr Gln Val Phe Leu Lys Lys
        195                 200                 205

Ala Ser Lys Thr Asn Leu Phe Thr Gln Lys Thr Lys Arg Asp Ile Asp
    210                 215                 220

Glu Asp Thr Asp Thr Asp Gly Asp Ser Ile Pro Asp Val Trp Glu Glu
225                 230                 235                 240

Asn Gly Tyr Thr Ile Gln Asn Lys Val Ala Val Lys Trp Asp Asp Ser
                245                 250                 255

Leu Ala Ser Lys Gly Tyr Gln Lys Phe Thr Ser Asn Pro Leu Glu Ala
            260                 265                 270

His Thr Val Gly Asp Pro Tyr Ser Asp Tyr Glu Lys Ala Ala Arg Asp
        275                 280                 285

Met Pro Leu Ser Asn Ala Lys Glu Thr Phe Asn Pro Leu Val Ala Ala
    290                 295                 300

Phe Pro Ser Val Asn Val Ser Leu Glu Lys Val Ile Leu Ser Lys Asn
305                 310                 315                 320

Glu Asp Leu Ser His Ser Val Glu Ser Ser Gln Ser Thr Asn Trp Ser
                325                 330                 335

Tyr Thr Asn Thr Glu Gly Val Asn Val Asn Ala Gly Trp Ser Gly Leu
            340                 345                 350

Gly Pro Ser Phe Gly Val Ser Val Asn Tyr Gln His Ser Glu Thr Val
        355                 360                 365

Ala Asn Glu Trp Gly Ser Ala Thr Asn Asp Gly Thr His Ile Asn Gly
    370                 375                 380

Ala Glu Ser Ala Tyr Leu Asn Ala Asn Val Arg Tyr Asn Asn Val Gly
385                 390                 395                 400

Thr Gly Ala Ile Tyr Glu Thr Lys Pro Thr Thr Ser Phe Ile Leu Asp
                405                 410                 415

Gly Thr Thr Ile Gly Thr Ile Lys Ala Lys Glu Asn Thr Thr Ala Leu
            420                 425                 430

Thr Ile Leu Pro Asp Gln Ser Tyr Pro Glu Lys Gly Lys Asn Gly Ile
```

-continued

```
        435                 440                 445

Ala Ile Asn Thr Met Asp Asp Phe Asn Ser Arg Pro Ile Pro Leu Asn
    450                 455                 460

Lys Glu Gln Leu Asn Thr Tyr Leu Ser Asn Lys Lys Pro Ile Leu Leu
465                 470                 475                 480

Glu Thr Asp Gln Val Glu Gly Lys Tyr Ala Ile Lys Asp Thr Asn Gly
                485                 490                 495

Asn Ile Thr Ile Ala Gly Asp Trp Asn Gly Ile Thr Asp Glu Ile Ser
            500                 505                 510

Ala Lys Thr Ala Ser Ile Ile Val Asp Asn Gly Asn Gln Met Ser Glu
        515                 520                 525

Lys Arg Val Ala Ala Lys Asp Tyr Thr Asn Pro Glu Asp Lys Thr Pro
    530                 535                 540

Asn Leu Ser Val Lys Glu Ala Leu Lys Leu Ala Tyr Pro Asp Glu Ile
545                 550                 555                 560

Glu Glu Lys Asp Gly Leu Leu Phe Tyr Asn Asp Gln Pro Ile Phe Glu
                565                 570                 575

Ala Ser Val Gln Ser Tyr Val Asp Glu Tyr Thr Ala Lys Gln Ile Arg
            580                 585                 590

Lys Gln Leu Asn Asp Ser Thr Gly Ser Phe Lys Asp Val Lys Asn Leu
        595                 600                 605

Tyr Asp Val Lys Leu Glu Pro Lys Met Asn Phe Thr Ile Lys Thr Ser
    610                 615                 620

Thr Leu Tyr Asp Gly Gly Glu Ser Asp Asn Thr Lys Ile Gly Asn Trp
625                 630                 635                 640

Tyr Tyr Thr Tyr Val Val Asn Gly Gly Asn Thr Gly Lys Lys Gln Tyr
                645                 650                 655

Arg Ser Ala Asn Lys Gly Ala Phe Thr Glu Leu Ser Thr Glu Ser Lys
            660                 665                 670

Asn Lys Leu Lys Lys Asn Ile Asp Tyr Tyr Val Ser Leu Tyr Met Lys
        675                 680                 685

Ala Asp Ser Lys Val Ser Val Asp Ile Glu Ile Asp Gly Lys Gln Glu
    690                 695                 700

Ser Ile Val Thr Asp Asn Ile Thr Leu Asp His Val Gly Tyr Gln Arg
705                 710                 715                 720

Ile Asn Ile Leu Val Pro Asn Leu Glu Gly Asn Glu Ile Asn Thr Ile
                725                 730                 735

Ser Ile Lys Gly Asp Gly Gln Thr Asn Val Tyr Trp Asp Asp Val Ser
            740                 745                 750

Phe Val Glu Val Gly Ala Glu Glu Ile Glu Tyr Lys Asp Pro Val Pro
        755                 760                 765

Gln Phe Asp Ile Ile Glu Gly Asp Phe Asp Phe Phe Gly Asp Pro Leu
    770                 775                 780

Ala Val Lys Tyr His Asp Ala Thr Tyr Phe Ile Asp Ser Pro Leu Ile
785                 790                 795                 800

Thr Gln Thr Pro Gly Thr Phe Ser Phe Thr Tyr Lys Val Ile Gly Glu
                805                 810                 815

Gln Thr Lys Thr Val Leu Asp Ser Gly Ser Gly Lys Asn Ala Asn Arg
            820                 825                 830

Ile Asn Leu Asp Phe Lys Asn Val Lys Ser Asp Arg Ser Phe Leu Tyr
        835                 840                 845

Thr Leu Ser Cys Lys Asp Asp Leu Trp Gly Ser Thr Arg Thr Ala Val
    850                 855                 860
```

```
Val Arg Ile Phe Ala Val Asp
865                 870


<210> SEQ ID NO 51
<211> LENGTH: 785
<212> TYPE: PRT
<213> ORGANISM: Brevibacillus laterosporus

<400> SEQUENCE: 51

Met Thr Tyr Met Lys Lys Lys Leu Val Ser Val Val Thr Cys Ala Leu
 1               5                  10                  15

Leu Ala Pro Met Phe Leu Asn Gly Asn Val Asn Pro Val Tyr Ala Asp
            20                  25                  30

Asn Gln Thr Asn Gln Leu Ser Thr Ala Gln Glu Asn Gln Glu Lys Glu
        35                  40                  45

Val Asp Arg Lys Gly Leu Leu Gly Tyr Tyr Phe Lys Gly Lys Glu Phe
    50                  55                  60

Asn His Leu Thr Leu Phe Ala Pro Thr Arg Asp Asn Thr Leu Ile Tyr
65                  70                  75                  80

Asp Gln Gln Thr Val Asp Phe Leu Leu Asp Lys Lys Gln Gln Glu Tyr
                85                  90                  95

Gln Ser Ile Arg Trp Ile Gly Leu Ile Gln Ser Lys Glu Thr Gly Asp
            100                 105                 110

Phe Thr Phe Asn Leu Ser Asp Asp Lys Asn Ala Ile Ile Glu Ile Asp
        115                 120                 125

Gly Lys Thr Ile Ser His Lys Gly Gln Asn Lys Gln Val Val His Leu
    130                 135                 140

Glu Lys Gly Lys Leu Val Pro Ile Lys Ile Glu Tyr Gln Ser Asp Gln
145                 150                 155                 160

Ile Val Asn Arg Asp Ser Lys Ile Phe Lys Glu Phe Lys Leu Phe Lys
                165                 170                 175

Val Asp Ser Gln Gln Gln Ser His Gln Val Gln Leu Asp Glu Leu Arg
            180                 185                 190

Asn Pro Glu Phe Asn Lys Lys Glu Thr Gln Gln Phe Leu Glu Lys Ala
        195                 200                 205

Ser Lys Thr Asn Ile Phe Thr Gln Asn Met Lys Arg Asp Glu Asp Ala
    210                 215                 220

Thr Asp Thr Asp Gly Asp Ser Ile Pro Asp Leu Trp Glu Glu Asn Gly
225                 230                 235                 240

Tyr Thr Ile Gln Asn Lys Val Ala Val Lys Trp Asp Asp Ser Phe Ala
                245                 250                 255

Ala Lys Gly Tyr Thr Lys Phe Val Ser Asn Pro Phe Asp Ser His Thr
            260                 265                 270

Val Gly Asp Pro Tyr Thr Asp Tyr Glu Lys Ala Ala Arg Asp Leu Asp
        275                 280                 285

Leu Ala Asn Ala Lys Glu Thr Phe Asn Pro Leu Val Ala Ala Phe Pro
    290                 295                 300

Ser Val Asn Val Asn Leu Glu Lys Val Ile Leu Ser Pro Asn Glu Asp
305                 310                 315                 320

Leu Ser Asn Ser Val Glu Ser His Ser Ser Thr Asn Trp Ser Tyr Thr
                325                 330                 335

Asn Thr Glu Gly Ala Ser Ile Glu Ala Gly Ser Gly Pro Leu Gly Ile
            340                 345                 350

Ser Tyr Gly Val Ser Ala Asn Tyr Gln His Ser Glu Thr Val Ala Lys
```

```
        355                 360                 365

Glu Trp Gly Thr Ser Thr Gly Asn Thr Ser Gln Phe Asn Thr Ala Ser
    370                 375                 380

Ala Gly Tyr Leu Asn Ala Asn Val Arg Tyr Asn Asn Val Gly Thr Gly
385                 390                 395                 400

Ala Ile Tyr Glu Val Lys Pro Thr Thr Gly Phe Val Leu Asp Asn Asp
                405                 410                 415

Thr Val Ala Thr Ile Thr Ala Lys Ser Asn Ser Thr Ala Leu Ser Ile
            420                 425                 430

Ser Pro Gly Glu Ser Tyr Pro Lys Lys Gly Gln Asn Gly Ile Ala Ile
        435                 440                 445

Asn Thr Met Asp Asp Phe Asn Ser His Pro Ile Thr Leu Asn Lys Gln
    450                 455                 460

Gln Leu Asp Gln Ile Phe Asn Asn Lys Pro Leu Met Leu Glu Thr Asn
465                 470                 475                 480

Gln Ala Asp Gly Val Tyr Lys Ile Lys Asp Thr Ser Gly Asn Ile Val
                485                 490                 495

Thr Gly Gly Glu Trp Asn Gly Val Ile Gln Gln Ile Gln Ala Lys Thr
            500                 505                 510

Ala Ser Ile Ile Val Asp Thr Gly Glu Gly Val Ser Glu Lys Arg Val
        515                 520                 525

Ala Ala Lys Asp Tyr Asp Asn Pro Glu Asp Lys Thr Pro Ser Leu Ser
    530                 535                 540

Leu Lys Glu Ala Leu Lys Leu Gly Tyr Pro Glu Glu Ile Lys Glu Lys
545                 550                 555                 560

Asp Gly Leu Leu Tyr Tyr Asn Asp Lys Pro Ile Tyr Glu Ser Ser Val
                565                 570                 575

Met Thr Tyr Leu Asp Glu Asn Thr Ala Lys Glu Val Lys Glu Gln Leu
            580                 585                 590

Asn Asp Ile Thr Gly Lys Phe Lys Asp Val Lys Gln Leu Phe Asp Val
        595                 600                 605

Lys Leu Thr Pro Lys Met Asn Phe Thr Ile Lys Leu Ala Thr Leu Tyr
    610                 615                 620

Asp Gly Ala Glu Asp Gly Ser Ser Pro Thr Asp Val Gly Ile Ser Ser
625                 630                 635                 640

Pro Leu Gly Glu Trp Ala Phe Lys Pro Asp Ile Asn Asn Val Glu Gly
                645                 650                 655

Gly Asn Thr Gly Lys Arg Gln Tyr Gln Leu Ser Lys Asn Lys Asp Gly
            660                 665                 670

Tyr Tyr Tyr Gly Met Leu Ala Leu Ser Pro Glu Val Ser Asn Lys Leu
        675                 680                 685

Lys Lys Asn Tyr Gln Tyr Tyr Ile Ser Met Ser Ile Lys Ala Asp Ala
    690                 695                 700

Gly Val Glu Pro Thr Val Thr Val Met Asp Asn Leu Leu Asn Gly Ile
705                 710                 715                 720

Val Asp Lys Lys Leu Lys Leu Ser Ser Asn Gly Tyr Gln Arg Phe Asp
                725                 730                 735

Ile Leu Val Asp Asn Ser Glu Ser His Pro Ile Asn Val Met Val Ile
            740                 745                 750

Asp Leu Gly Val Ser Ser Gln Asp Tyr Asn Asn Tyr Ser Lys Asn Ile
        755                 760                 765

Tyr Ile Asp Asp Ile Thr Ile Thr Glu Val Ser Ala Met Lys Val Lys
    770                 775                 780
```

Asn
785

<210> SEQ ID NO 52
<211> LENGTH: 462
<212> TYPE: PRT
<213> ORGANISM: Bacillus cereus

<400> SEQUENCE: 52

```
Met Lys Arg Met Glu Gly Lys Leu Phe Met Val Ser Lys Lys Leu Gln
 1               5                  10                  15

Val Val Thr Lys Thr Val Leu Leu Ser Thr Val Phe Ser Ile Ser Leu
            20                  25                  30

Leu Asn Asn Glu Val Ile Lys Ala Glu Gln Leu Asn Ile Asn Ser Gln
        35                  40                  45

Ser Lys Tyr Thr Asn Leu Gln Asn Leu Lys Ile Thr Asp Lys Val Glu
    50                  55                  60

Asp Phe Lys Glu Asp Lys Glu Lys Ala Lys Glu Trp Gly Lys Glu Lys
65                  70                  75                  80

Glu Lys Glu Trp Lys Leu Thr Ala Thr Glu Lys Gly Lys Met Asn Asn
                85                  90                  95

Phe Leu Asp Asn Lys Asn Asp Ile Lys Thr Asn Tyr Lys Glu Ile Thr
            100                 105                 110

Phe Ser Met Ala Gly Ser Phe Glu Asp Glu Ile Lys Asp Leu Lys Glu
        115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
    210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Lys Gly Val Glu Cys Leu
                245                 250                 255

Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
        275                 280                 285

Lys Asp Leu Thr Asp Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
```

```
        355                 360                 365

Asp Phe Glu Glu Gln Phe Leu Asn Thr Ile Lys Glu Asp Lys Gly Tyr
    370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
        435                 440                 445

Gly Val Lys Arg Tyr Val Val Asp Ala Thr Leu Leu Thr Asn
    450                 455                 460


<210> SEQ ID NO 53
<211> LENGTH: 775
<212> TYPE: PRT
<213> ORGANISM: Bacillus thuringiensis

<400> SEQUENCE: 53

Met Lys Asn Met Lys Lys Lys Leu Ala Ser Val Val Thr Cys Thr Leu
 1               5                  10                  15

Leu Ala Pro Met Phe Leu Asn Gly Asn Val Asn Ala Val Tyr Ala Asp
            20                  25                  30

Ser Lys Thr Asn Gln Ile Ser Thr Thr Gln Lys Asn Gln Gln Lys Glu
        35                  40                  45

Met Asp Arg Lys Gly Leu Leu Gly Tyr Tyr Phe Lys Gly Lys Asp Phe
    50                  55                  60

Ser Asn Leu Thr Met Phe Ala Pro Thr Arg Asp Asn Thr Leu Ile Tyr
65                  70                  75                  80

Asp Gln Gln Thr Ala Asn Lys Leu Leu Asp Lys Lys Gln Gln Gln Tyr
                85                  90                  95

Gln Ser Ile Arg Trp Ile Gly Leu Ile Gln Ser Lys Glu Lys Gly Asp
            100                 105                 110

Phe Thr Phe Asn Leu Ser Glu Asp Glu Gln Ala Ile Ile Glu Ile Asp
        115                 120                 125

Gly Lys Ile Ile Ser Asn Lys Gly Lys Glu Lys Gln Val Val His Leu
    130                 135                 140

Glu Lys Glu Lys Leu Val Pro Ile Lys Ile Glu Tyr Gln Ser Asp Thr
145                 150                 155                 160

Lys Phe Asn Ile Asp Ser Lys Thr Phe Lys Glu Phe Lys Leu Phe Lys
                165                 170                 175

Ile Asp Ser Gln Asn Gln Ser Gln Gln Val Lys Arg Asp Glu Leu Arg
            180                 185                 190

Asn Pro Glu Phe Asn Lys Lys Glu Ser Arg Glu Phe Leu Ala Lys Ala
        195                 200                 205

Ser Lys Thr Asn Phe Phe Met Gln Lys Met Lys Arg Asp Ile Asp Glu
    210                 215                 220

Asp Thr Asp Thr Asp Gly Asp Ser Ile Pro Asp Leu Trp Glu Glu Asn
225                 230                 235                 240

Gly Tyr Thr Ile Gln Asn Lys Val Ala Val Lys Trp Asp Asp Lys Phe
                245                 250                 255

Ala Gln Gln Gly Tyr Val Lys Tyr Leu Ser Ser Pro Tyr Gln Ala His
            260                 265                 270
```

-continued

```
Thr Val Gly Asp Pro Tyr Thr Asp Trp Glu Lys Ala Ala Gly Asp Ile
        275                 280                 285

Pro Lys Ser Asn Ala Ala Ala Thr Arg Asn Pro Leu Val Ala Ala Phe
    290                 295                 300

Pro Ser Ile Asn Val Asp Met Arg Lys Met Ile Leu Ser Lys Asp Ser
305                 310                 315                 320

Asn Leu Ser Asn Ser Ala Glu Ala His Ser Asn Asn Ser Tyr Thr Tyr
                325                 330                 335

Ala Asn Ser Glu Gly Ala Ser Ile Glu Ala Gly Phe Gly Pro Lys Gly
            340                 345                 350

Phe Ser Phe Gly Val Ser Ala Asn Tyr Gln His Thr Glu Thr Val Gly
        355                 360                 365

Ser Asp Trp Gly Asn Ser Lys Ser Asn Thr Glu Gln Phe Asn Ser Ala
    370                 375                 380

Ser Ala Gly Tyr Leu Asn Ala Asn Val His Tyr Asn Asn Val Gly Thr
385                 390                 395                 400

Gly Gly Ile Tyr Asp Ala Gln Pro Thr Thr Ser Phe Ile Leu Gln Asp
                405                 410                 415

Ser Thr Ile Ala Thr Ile Thr Ala Lys Ser Asn Ala Thr Ala Leu Ser
            420                 425                 430

Ile Pro Ser Gly Asp Arg Tyr Pro Ala Ser Lys Glu Gly Ile Ser Leu
        435                 440                 445

Lys Thr Met Asp Asp Phe Asn Ser His Pro Ile Thr Leu Asn Lys Pro
    450                 455                 460

Gln Leu Asp Ala Val Leu Asn Asn Glu Val Ile Lys Ile Asn Thr Asp
465                 470                 475                 480

Gln Thr Asp Gly Arg Tyr Gly Ile Ile Gly Val Asp Gly Lys Ala Glu
                485                 490                 495

Ile Gly Asp Arg Trp Ser Pro Ile Ile Asp Glu Ile Lys Gly Arg Thr
            500                 505                 510

Ala Ser Ile Ile Ile Asp Pro Ala Asp Gly Lys Ala Leu Glu Thr Arg
        515                 520                 525

Ile Ala Ala Lys Asp Tyr Lys Asn Pro Glu Asp Lys Thr Pro Ser Leu
    530                 535                 540

Thr Ile Lys Glu Gly Leu Lys Ile Ala Tyr Pro Glu Ser Ile Ser Glu
545                 550                 555                 560

Asp Lys Asp Gly Ile Leu Phe Tyr Glu Tyr Lys Asn Asp Glu Gly Lys
                565                 570                 575

Val Thr Lys Lys Gln Leu Ser Glu Glu Asn Ile Met Pro Tyr Leu Asp
            580                 585                 590

Glu Asp Thr Ser Lys Glu Phe Glu Arg Gln Leu Ser Asp Gly Ser Ala
        595                 600                 605

Lys Gly Leu Tyr Asp Ile Lys Leu Thr Pro Lys Met Asn Ile Thr Ile
    610                 615                 620

Arg Leu Ala Thr Val Thr Leu Gly Phe Asp Asp Gln Phe Ser Ala Tyr
625                 630                 635                 640

Pro Trp Glu Asn Ala Thr Trp Ser Asp Lys Phe Gly Asn Leu Arg Leu
                645                 650                 655

Gly Ser Leu Ala Ile Pro Gln Glu Ser Lys Tyr Thr Ile Pro Lys Asp
            660                 665                 670

Lys Val Lys Pro Asn Tyr Asp Tyr Leu Ile Thr Gly Tyr Ile Lys His
        675                 680                 685

Asp Phe Thr Thr Asp Asn Glu Ser Leu Gly Ile Val Ala Phe Thr Lys
```

690 695 700

Lys Asp Asn Phe Glu Met Trp Asn Met Gly Thr Ser Ile Phe Ser Gln
705 710 715 720

Asn Ser Gly Gly Glu Phe Lys Lys Phe Thr Ile Lys Thr Gln Asn Ile
725 730 735

Ser Gly Asp Tyr Ile Leu Asp Ser Ile Gln Leu Met Lys Arg Asn Asn
740 745 750

Asp Val Asn Lys Ile Asp Ser Tyr Leu Asp Asp Ile Ser Ile Ile Pro
755 760 765

Ile Gly Pro Asn Lys Ser Arg
770 775

<210> SEQ ID NO 54
<211> LENGTH: 126
<212> TYPE: PRT
<213> ORGANISM: Bacillus thuringiensis

<400> SEQUENCE: 54

Met Thr Val Tyr Asn Ala Thr Phe Thr Ile Asn Phe Tyr Asn Glu Gly
1 5 10 15

Glu Trp Gly Gly Pro Glu Pro Tyr Gly Tyr Ile Lys Ala Tyr Leu Thr
20 25 30

Asn Pro Asp His Asp Phe Glu Ile Trp Lys Gln Asp Asp Trp Gly Lys
35 40 45

Ser Thr Pro Glu Arg Ser Thr Tyr Thr Gln Thr Ile Lys Ile Ser Ser
50 55 60

Asp Thr Gly Ser Pro Ile Asn Gln Met Cys Phe Tyr Gly Asp Val Lys
65 70 75 80

Glu Tyr Asp Val Gly Asn Ala Asp Asp Ile Leu Ala Tyr Pro Ser Gln
85 90 95

Lys Val Cys Ser Thr Pro Gly Val Thr Val Arg Leu Asp Gly Asp Glu
100 105 110

Lys Gly Ser Tyr Val Thr Ile Lys Tyr Ser Leu Thr Pro Ala
115 120 125

<210> SEQ ID NO 55
<211> LENGTH: 462
<212> TYPE: PRT
<213> ORGANISM: Bacillus cereus

<400> SEQUENCE: 55

Met Lys Arg Met Glu Gly Lys Leu Phe Met Val Ser Lys Lys Leu Gln
1 5 10 15

Val Val Thr Lys Thr Val Leu Leu Ser Thr Val Phe Ser Ile Ser Leu
20 25 30

Leu Asn Asn Glu Val Ile Lys Ala Glu Gln Leu Asn Ile Asn Ser Gln
35 40 45

Ser Lys Tyr Thr Asn Leu Gln Asn Leu Lys Ile Thr Asp Lys Val Glu
50 55 60

Asp Phe Lys Glu Asp Lys Glu Lys Ala Lys Glu Trp Gly Lys Glu Lys
65 70 75 80

Glu Lys Glu Trp Lys Leu Thr Ala Thr Glu Lys Gly Lys Met Asn Asn
85 90 95

Phe Leu Asp Asn Lys Asn Asp Ile Lys Thr Asn Tyr Lys Glu Ile Thr
100 105 110

Phe Ser Met Ala Gly Ser Phe Glu Asp Glu Ile Lys Asp Leu Lys Glu

```
        115                 120                 125

Ile Asp Lys Met Phe Asp Lys Thr Asn Leu Ser Asn Ser Ile Ile Thr
    130                 135                 140

Tyr Lys Asn Val Glu Pro Thr Thr Ile Gly Phe Asn Lys Ser Leu Thr
145                 150                 155                 160

Glu Gly Asn Thr Ile Asn Ser Asp Ala Met Ala Gln Phe Lys Glu Gln
                165                 170                 175

Phe Leu Asp Arg Asp Ile Lys Phe Asp Ser Tyr Leu Asp Thr His Leu
            180                 185                 190

Thr Ala Gln Gln Val Ser Ser Lys Glu Arg Val Ile Leu Lys Val Thr
        195                 200                 205

Val Pro Ser Gly Lys Gly Ser Thr Thr Pro Thr Lys Ala Gly Val Ile
    210                 215                 220

Leu Asn Asn Ser Glu Tyr Lys Met Leu Ile Asp Asn Gly Tyr Met Val
225                 230                 235                 240

His Val Asp Lys Val Ser Lys Val Val Lys Lys Gly Val Glu Cys Leu
                245                 250                 255

Gln Ile Glu Gly Thr Leu Lys Lys Ser Leu Asp Phe Lys Asn Asp Ile
            260                 265                 270

Asn Ala Glu Ala His Ser Trp Gly Met Lys Asn Tyr Glu Glu Trp Ala
        275                 280                 285

Lys Asp Leu Thr Asp Ser Gln Arg Glu Ala Leu Asp Gly Tyr Ala Arg
    290                 295                 300

Gln Asp Tyr Lys Glu Ile Asn Asn Tyr Leu Arg Asn Gln Gly Gly Ser
305                 310                 315                 320

Gly Asn Glu Lys Leu Asp Ala Gln Ile Lys Asn Ile Ser Asp Ala Leu
                325                 330                 335

Gly Lys Lys Pro Ile Pro Glu Asn Ile Thr Val Tyr Arg Trp Cys Gly
            340                 345                 350

Met Pro Glu Phe Gly Tyr Gln Ile Ser Asp Pro Leu Pro Ser Leu Lys
        355                 360                 365

Asp Phe Glu Glu Gln Phe Leu Asn Thr Ile Lys Glu Asp Lys Gly Tyr
    370                 375                 380

Met Ser Thr Ser Leu Ser Ser Glu Arg Leu Ala Ala Phe Gly Ser Arg
385                 390                 395                 400

Lys Ile Ile Leu Arg Leu Gln Val Pro Lys Gly Ser Thr Gly Ala Tyr
                405                 410                 415

Leu Ser Ala Ile Gly Gly Phe Ala Ser Glu Lys Glu Ile Leu Leu Asp
            420                 425                 430

Lys Asp Ser Lys Tyr His Ile Asp Lys Val Thr Glu Val Ile Ile Lys
        435                 440                 445

Gly Val Lys Arg Tyr Val Val Asp Ala Thr Leu Leu Thr Asn
    450                 455                 460


<210> SEQ ID NO 56
<211> LENGTH: 457
<212> TYPE: PRT
<213> ORGANISM: Brevibacillus laterosporus

<400> SEQUENCE: 56

Met Ile Val Ile Ile Phe Thr Asn Val Lys Gly Gly Asn Glu Leu Lys
 1               5                  10                  15

Lys Asn Phe Tyr Lys Asn Leu Ile Cys Met Ser Ala Leu Leu Leu Ala
            20                  25                  30
```

```
Met Pro Ile Ser Ser Asn Val Thr Tyr Ala Tyr Gly Ser Glu Lys Val
        35                  40                  45

Asp Tyr Leu Val Lys Thr Thr Asn Asn Thr Glu Asp Phe Lys Glu Asp
    50                  55                  60

Lys Glu Lys Ala Lys Glu Trp Gly Lys Glu Lys Glu Lys Glu Trp Lys
65                  70                  75                  80

Leu Thr Val Thr Glu Lys Thr Arg Met Asn Asn Phe Leu Asp Asn Lys
                85                  90                  95

Asn Asp Ile Lys Lys Asn Tyr Lys Glu Ile Thr Phe Ser Met Ala Gly
            100                 105                 110

Ser Phe Glu Asp Glu Ile Lys Asp Leu Lys Glu Ile Asp Lys Met Phe
        115                 120                 125

Asp Lys Ala Asn Leu Ser Ser Ser Ile Val Thr Tyr Lys Asn Val Glu
    130                 135                 140

Pro Ser Thr Ile Gly Phe Asn Lys Pro Leu Thr Glu Gly Asn Thr Ile
145                 150                 155                 160

Asn Thr Asp Val Gln Ala Gln Phe Lys Glu Gln Phe Leu Gly Lys Asp
                165                 170                 175

Ile Lys Phe Asp Ser Tyr Leu Asp Thr His Leu Thr Ala Gln Asn Val
            180                 185                 190

Ser Ser Lys Glu Arg Ile Ile Leu Gln Val Thr Val Pro Ser Gly Lys
        195                 200                 205

Gly Ser Thr Ile Pro Thr Lys Ala Gly Val Ile Leu Asn Asn Asn Glu
    210                 215                 220

Tyr Lys Met Leu Ile Asp Asn Gly Tyr Val Leu His Val Asp Asn Ile
225                 230                 235                 240

Ser Lys Val Val Lys Lys Gly Tyr Glu Cys Leu Gln Ile Gln Gly Thr
                245                 250                 255

Leu Lys Lys Ser Leu Asp Phe Lys Asn Asp Ile Asn Ala Glu Ala His
            260                 265                 270

Arg Trp Gly Met Lys Asn Tyr Glu Gly Trp Ala Lys Asn Leu Thr Asp
        275                 280                 285

Pro Gln Arg Glu Ala Leu Asp Gly Tyr Ala Arg Gln Asp Tyr Lys Gln
    290                 295                 300

Ile Asn Asp Tyr Leu Arg Asn Gln Gly Gly Ser Gly Asn Glu Lys Leu
305                 310                 315                 320

Asp Thr Gln Ile Lys Asn Ile Ser Glu Ala Leu Glu Lys Gln Pro Ile
                325                 330                 335

Pro Glu Asn Ile Thr Val Tyr Arg Trp Cys Gly Met Ala Glu Phe Gly
            340                 345                 350

Tyr Gln Ile Ser Asp Pro Leu Pro Ser Leu Lys Glu Met Glu Glu Lys
        355                 360                 365

Phe Leu Asn Thr Met Lys Glu Asp Lys Gly Tyr Met Ser Thr Ser Leu
    370                 375                 380

Ser Ser Glu Arg Leu Ser Ala Phe Gly Ser Arg Lys Phe Ile Leu Arg
385                 390                 395                 400

Leu Gln Val Pro Lys Gly Ser Thr Gly Ala Tyr Leu Ser Ala Ile Gly
                405                 410                 415

Gly Phe Ala Ser Glu Lys Glu Ile Leu Ile Asp Lys Asp Ser Asn Tyr
            420                 425                 430

His Ile Asp Lys Ile Thr Glu Val Val Ile Lys Gly Val Lys Arg Tyr
        435                 440                 445

Val Val Asp Ala Thr Leu Leu Thr Lys
```

450 455

<210> SEQ ID NO 57
<211> LENGTH: 454
<212> TYPE: PRT
<213> ORGANISM: Clostridium perfringens

<400> SEQUENCE: 57

Met Lys Lys Val Asn Lys Ser Ile Ser Val Phe Leu Ile Leu Tyr Leu
1 5 10 15

Ile Leu Thr Ser Ser Phe Pro Ser Tyr Thr Tyr Ala Gln Asp Leu Gln
20 25 30

Ile Ala Ser Asn Tyr Ile Thr Asp Arg Ala Phe Ile Glu Arg Pro Glu
35 40 45

Asp Phe Leu Lys Asp Lys Glu Asn Ala Ile Gln Trp Glu Lys Lys Glu
50 55 60

Ala Glu Arg Val Glu Lys Asn Leu Asp Thr Leu Glu Lys Glu Ala Leu
65 70 75 80

Glu Leu Tyr Lys Lys Asp Ser Glu Gln Ile Ser Asn Tyr Ser Gln Thr
85 90 95

Arg Gln Tyr Phe Tyr Asp Tyr Gln Ile Glu Ser Asn Pro Arg Glu Lys
100 105 110

Glu Tyr Lys Asn Leu Arg Asn Ala Ile Ser Lys Asn Lys Ile Asp Lys
115 120 125

Pro Ile Asn Val Tyr Tyr Phe Glu Ser Pro Glu Lys Phe Ala Phe Asn
130 135 140

Lys Glu Ile Arg Thr Glu Asn Gln Asn Glu Ile Ser Leu Glu Lys Phe
145 150 155 160

Asn Glu Leu Lys Glu Thr Ile Gln Asp Lys Leu Phe Lys Gln Asp Gly
165 170 175

Phe Lys Asp Val Ser Leu Tyr Glu Pro Gly Asn Gly Asp Glu Lys Pro
180 185 190

Thr Pro Leu Leu Ile His Leu Lys Leu Pro Lys Asn Thr Gly Met Leu
195 200 205

Pro Tyr Ile Asn Ser Asn Asp Val Lys Thr Leu Ile Glu Gln Asp Tyr
210 215 220

Ser Ile Lys Ile Asp Lys Ile Val Arg Ile Val Ile Glu Gly Lys Gln
225 230 235 240

Tyr Ile Lys Ala Glu Ala Ser Ile Val Asn Ser Leu Asp Phe Lys Asp
245 250 255

Asp Val Ser Lys Gly Asp Leu Trp Gly Lys Glu Asn Tyr Ser Asp Trp
260 265 270

Ser Asn Lys Leu Thr Pro Asn Glu Leu Ala Asp Val Asn Asp Tyr Met
275 280 285

Arg Gly Gly Tyr Thr Ala Ile Asn Asn Tyr Leu Ile Ser Asn Gly Pro
290 295 300

Leu Asn Asn Pro Asn Pro Glu Leu Asp Ser Lys Val Asn Asn Ile Glu
305 310 315 320

Asn Ala Leu Lys Leu Thr Pro Ile Pro Ser Asn Leu Ile Val Tyr Arg
325 330 335

Arg Ser Gly Pro Gln Glu Phe Gly Leu Thr Leu Thr Ser Pro Glu Tyr
340 345 350

Asp Phe Asn Lys Ile Glu Asn Ile Asp Ala Phe Lys Glu Lys Trp Glu
355 360 365

-continued

```
Gly Lys Val Ile Thr Tyr Pro Asn Phe Ile Ser Thr Ser Ile Gly Ser
    370                 375                 380

Val Asn Met Ser Ala Phe Ala Lys Arg Lys Ile Ile Leu Arg Ile Asn
385                 390                 395                 400

Ile Pro Lys Asp Ser Pro Gly Ala Tyr Leu Ser Ala Ile Pro Gly Tyr
                405                 410                 415

Ala Gly Glu Tyr Glu Val Leu Leu Asn His Gly Ser Lys Phe Lys Ile
            420                 425                 430

Asn Lys Val Asp Ser Tyr Lys Asp Gly Thr Val Thr Lys Leu Ile Leu
        435                 440                 445

Asp Ala Thr Leu Ile Asn
    450
```

<210> SEQ ID NO 58
<211> LENGTH: 4
<212> TYPE: PRT
<213> ORGANISM: Artificial Sequence
<220> FEATURE:
<223> OTHER INFORMATION: endoplasmic reticulum retention sequence

<400> SEQUENCE: 58

```
Lys Asp Glu Leu
1
```

<210> SEQ ID NO 59
<211> LENGTH: 12
<212> TYPE: DNA
<213> ORGANISM: Artificial Sequence
<220> FEATURE:
<223> OTHER INFORMATION: nucleotide sequence upstream of the ATG start site of axmi-011

<400> SEQUENCE: 59

```
gtgatgaaaa aa                                                         12
```

<210> SEQ ID NO 60
<211> LENGTH: 969
<212> TYPE: DNA
<213> ORGANISM: Bacillus thuringiensis
<220> FEATURE:
<221> NAME/KEY: CDS
<222> LOCATION: (1)...(969)

<400> SEQUENCE: 60

```
gtg atg aaa aaa atg aat aaa aaa cct atg gta gcg ttg ata tta gcc       48
Met Met Lys Lys Met Asn Lys Lys Pro Met Val Ala Leu Ile Leu Ala
 1               5                  10                  15

act tcg att ggt ata cct tgt aca ttt aca cct gga agt gca tta gca       96
Thr Ser Ile Gly Ile Pro Cys Thr Phe Thr Pro Gly Ser Ala Leu Ala
            20                  25                  30

gca gaa aat att cag act agt gtt aat gaa aat gta aaa gtt ggt att      144
Ala Glu Asn Ile Gln Thr Ser Val Asn Glu Asn Val Lys Val Gly Ile
        35                  40                  45

aca gat gtt caa tct gaa ttg aat aag ata gga gac tat tat tat agt      192
Thr Asp Val Gln Ser Glu Leu Asn Lys Ile Gly Asp Tyr Tyr Tyr Ser
     50                  55                  60

aat aac tta gca aat acg act ata aaa cct cct cat cat tgg gat tat      240
Asn Asn Leu Ala Asn Thr Thr Ile Lys Pro Pro His His Trp Asp Tyr
 65                  70                  75                  80

aca ctt aaa aaa aat cct gat aaa gtt gga aca aat ttg gat ttt agt      288
Thr Leu Lys Lys Asn Pro Asp Lys Val Gly Thr Asn Leu Asp Phe Ser
                 85                  90                  95
```

```
att act ggt act gct agt aaa cta aat tat gat agt gta act cct ata      336
Ile Thr Gly Thr Ala Ser Lys Leu Asn Tyr Asp Ser Val Thr Pro Ile
            100                 105                 110

tac att ggg cat aat gaa ttt aat aat gat tca gat cag cct caa aaa      384
Tyr Ile Gly His Asn Glu Phe Asn Asn Asp Ser Asp Gln Pro Gln Lys
        115                 120                 125

ttt aca act tct aaa ttt act aaa gct gta aca gag gga aca aca agt      432
Phe Thr Thr Ser Lys Phe Thr Lys Ala Val Thr Glu Gly Thr Thr Ser
    130                 135                 140

acc gta aca aat gga ttt aga tta gga aat cca ggt tta aac tta ttt      480
Thr Val Thr Asn Gly Phe Arg Leu Gly Asn Pro Gly Leu Asn Leu Phe
145                 150                 155                 160

act att cca tta att tta agt gat ggt atg aaa att aat gcg gaa ttt      528
Thr Ile Pro Leu Ile Leu Ser Asp Gly Met Lys Ile Asn Ala Glu Phe
                165                 170                 175

aac tct tct act tca gaa tct caa caa aaa tcg gaa aca aaa aca ata      576
Asn Ser Ser Thr Ser Glu Ser Gln Gln Lys Ser Glu Thr Lys Thr Ile
            180                 185                 190

gaa gca tca cct caa aac ata gaa gtt cca gca cat aaa aaa tat aaa      624
Glu Ala Ser Pro Gln Asn Ile Glu Val Pro Ala His Lys Lys Tyr Lys
        195                 200                 205

gta gat gtt gta ttg gaa caa aca agc tat tgg gca gat gtt aca ttt      672
Val Asp Val Val Leu Glu Gln Thr Ser Tyr Trp Ala Asp Val Thr Phe
    210                 215                 220

aca ggt gaa gga att aat ctt aat act act ata aat gca act gga ata      720
Thr Gly Glu Gly Ile Asn Leu Asn Thr Thr Ile Asn Ala Thr Gly Ile
225                 230                 235                 240

cat act ggg cat atg gga atg cag gag tca aga aaa ttt tct tgg aac      768
His Thr Gly His Met Gly Met Gln Glu Ser Arg Lys Phe Ser Trp Asn
                245                 250                 255

aaa aat acc att gaa tta ttt aat gga cta aaa caa gag caa aaa aat      816
Lys Asn Thr Ile Glu Leu Phe Asn Gly Leu Lys Gln Glu Gln Lys Asn
            260                 265                 270

aat ata cat ggg att aaa ttt agt aat ggg aaa atg aat gca aac gga      864
Asn Ile His Gly Ile Lys Phe Ser Asn Gly Lys Met Asn Ala Asn Gly
        275                 280                 285

aca ggt aaa gtt gaa ggt att ttt ggt agt aat cta gtt gta aag gta      912
Thr Gly Lys Val Glu Gly Ile Phe Gly Ser Asn Leu Val Val Lys Val
    290                 295                 300

aat gat gtt aca gat cca tta aat cct atc cta gta atg act aaa agt      960
Asn Asp Val Thr Asp Pro Leu Asn Pro Ile Leu Val Met Thr Lys Ser
305                 310                 315                 320

tta aaa taa                                                          969
Leu Lys
```

<210> SEQ ID NO 61
<211> LENGTH: 322
<212> TYPE: PRT
<213> ORGANISM: Bacillus thuringiensis

<400> SEQUENCE: 61

```
Met Met Lys Lys Met Asn Lys Lys Pro Met Val Ala Leu Ile Leu Ala
 1               5                  10                  15

Thr Ser Ile Gly Ile Pro Cys Thr Phe Thr Pro Gly Ser Ala Leu Ala
            20                  25                  30

Ala Glu Asn Ile Gln Thr Ser Val Asn Glu Asn Val Lys Val Gly Ile
        35                  40                  45

Thr Asp Val Gln Ser Glu Leu Asn Lys Ile Gly Asp Tyr Tyr Tyr Ser
    50                  55                  60
```

-continued

```
Asn Asn Leu Ala Asn Thr Thr Ile Lys Pro Pro His His Trp Asp Tyr
65                  70                  75                  80

Thr Leu Lys Lys Asn Pro Asp Lys Val Gly Thr Asn Leu Asp Phe Ser
                85                  90                  95

Ile Thr Gly Thr Ala Ser Lys Leu Asn Tyr Asp Ser Val Thr Pro Ile
            100                 105                 110

Tyr Ile Gly His Asn Glu Phe Asn Asn Asp Ser Asp Gln Pro Gln Lys
        115                 120                 125

Phe Thr Thr Ser Lys Phe Thr Lys Ala Val Thr Glu Gly Thr Thr Ser
    130                 135                 140

Thr Val Thr Asn Gly Phe Arg Leu Gly Asn Pro Gly Leu Asn Leu Phe
145                 150                 155                 160

Thr Ile Pro Leu Ile Leu Ser Asp Gly Met Lys Ile Asn Ala Glu Phe
                165                 170                 175

Asn Ser Ser Thr Ser Glu Ser Gln Gln Lys Ser Glu Thr Lys Thr Ile
            180                 185                 190

Glu Ala Ser Pro Gln Asn Ile Glu Val Pro Ala His Lys Lys Tyr Lys
        195                 200                 205

Val Asp Val Val Leu Glu Gln Thr Ser Tyr Trp Ala Asp Val Thr Phe
    210                 215                 220

Thr Gly Glu Gly Ile Asn Leu Asn Thr Thr Ile Asn Ala Thr Gly Ile
225                 230                 235                 240

His Thr Gly His Met Gly Met Gln Glu Ser Arg Lys Phe Ser Trp Asn
                245                 250                 255

Lys Asn Thr Ile Glu Leu Phe Asn Gly Leu Lys Gln Glu Gln Lys Asn
            260                 265                 270

Asn Ile His Gly Ile Lys Phe Ser Asn Gly Lys Met Asn Ala Asn Gly
        275                 280                 285

Thr Gly Lys Val Glu Gly Ile Phe Gly Ser Asn Leu Val Val Lys Val
    290                 295                 300

Asn Asp Val Thr Asp Pro Leu Asn Pro Ile Leu Val Met Thr Lys Ser
305                 310                 315                 320

Leu Lys
```

<210> SEQ ID NO 62
<211> LENGTH: 6
<212> TYPE: DNA
<213> ORGANISM: Artificial Sequence
<220> FEATURE:
<223> OTHER INFORMATION: ribosomal binding sequence

<400> SEQUENCE: 62 gtgatg 6

<210> SEQ ID NO 63
<211> LENGTH: 5
<212> TYPE: DNA
<213> ORGANISM: Artificial Sequence
<220> FEATURE:
<223> OTHER INFORMATION: ribosomal binding sequence

<400> SEQUENCE: 63 ggaga 5

FAMILY OF PESTICIDAL PROTEINS AND METHODS FOR THEIR USE

CROSS REFERENCE TO RELATED APPLICATION

This application is a continuation of U.S. patent application Ser. No. 11/763,947, filed Jun. 15, 2007, which claims the benefit of U.S. Provisional Application Ser. Nos. 60/814,007, filed Jun. 15, 2006; 60/813,859, filed Jun. 15, 2006; 60/814,420, filed Jun. 16, 2006; 60/814,212, filed Jun. 16, 2006; and 60/814,989, filed Jun. 20, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA039US01NSEQLIST.txt", created on Jun. 24, 2011, and having a size of 305 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Because of the devastation that insects can confer, and the improvement in yield by controlling insect pests, there is a continual need to discover new forms of pesticidal toxins.

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise transformed bacteria, plants, plant cells, tissues, and seeds.

In particular, isolated nucleic acid molecules are provided that encode a pesticidal protein. Additionally, amino acid sequences corresponding to the pesticidal protein are encompassed. In particular, the present invention provides for an isolated nucleic acid molecule comprising a nucleotide sequence encoding the amino acid sequence shown in SEQ ID NO:2, 4, 6, 7, 9, 11, 13, 15, 17, 19, 21, 23, 25, 27, 29, 31, 33, 35, 37 or 61, a nucleotide sequence set forth in SEQ ID NO:1, 3, 5, 8, 10, 12, 14, 16, 18, 20, 22, 24, 26, 28, 30, 32, 34, 36, or 60, or the delta-endotoxin nucleotide sequence of the DNA insert of the plasmid deposited in a bacterial host as Accession No. NRRL B-30961, B-30955, B-30956, B-30957, B-30958, B-30942, B-30939, B-30941, B-50047, B-30959, B-30960, B-30943, or B-50048, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DESCRIPTION OF FIGURES

FIG. 1 shows an alignment of AXMI-022 with the Iota1b from *Clostridium perfringens* (SEQ ID NO:49), Isp1A from *Brevibacillus laterosporus* (SEQ ID NO:50), Isp1B from *Brevibacillus laterosporus* (SEQ ID NO:51), Vip1Ab from *Bacillus thuringiensis* (SEQ ID NO:52), and Vip1Ac from *Bacillus thuringiensis* (SEQ ID NO:53).

FIG. 2 shows an alignment of AXMI-022 with Vip1Ab (SEQ ID NO:52).

FIG. 3 shows an alignment of AXMI-022 with Cry 37Aa1 from *Bacillus thuringiensis* (SEQ ID NO:54).

FIG. 4 shows an alignment of AXMI-023 with the Vip2 pesticidal protein (SEQ ID NO:55), Isp2a from *Brevibacillus laterosporus* (SEQ ID NO:56) and Iota toxin component Ia from *Clostridium perfringens* (SEQ ID NO:57).

DETAILED DESCRIPTION

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of *Bacillus* or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling. The proteins find use in controlling or killing lepidopteran, coleopteran, dipteran, and nematode pest populations and for producing compositions with pesticidal activity.

Plasmids containing the nucleotide sequences of the invention were deposited in the permanent collection of the Agricultural Research Service Culture Collection, Northern Regional Research Laboratory (NRRL), 1815 North University Street, Peoria, Ill. 61604, United States of America, in accordance with Table 1. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. §1.808, sample(s) of the deposit with the ATCC. This deposit was made merely as a convenience for those of skill in the art and is not an admission that a deposit is required under 35 U.S.C. §112.

TABLE 1

| Microorganism Deposit | | | | |
|---|---|---|---|---|
| Gene | Strain | Clone | NRRL number | Deposit Date |
| axmi-011 | ATX13008 | pAX4600 | B-30961 | Jul. 21, 2006 |
| axmi-012 | ATX13026 | pAX012 | B-30955 | Jul. 21, 2006 |
| axmi-013 | ATX13002 | pAX013 | B-30956 | Jul. 21, 2006 |
| axmi-015 | ATX13026 | pAX015 | B-30957 | Jul. 21, 2006 |
| axmi-019 | ATX14875 | pAX019 | B-30958 | Jul. 21, 2006 |
| axmi-044 | ATX14759 | pAX2599 | B-30942 | Jun. 15, 2006 |
| axmi-037 | ATX1489 | pAX2558 | B-30939 | Jun. 15, 2006 |
| axmi-043 | ATX15398 | pAX2597 | B-30941 | Jun. 15, 2006 |
| axmi-033 | ATX14833 | pAX4341 | B-50047 | May 29, 2007 |
| axmi-034 | ATX14833 | pAX4341 | B-50047 | May 29, 2007 |
| axmi-022 | ATX13045 | pAX022 | B-30959 | Jul. 21, 2006 |
| axmi-023 | ATX13045 | pAX023 | B-30960 | Jul. 21, 2006 |
| axmi-041 | ATX21738 | pAX4310 | B-30943 | Jun. 15, 2006 |
| axmi-063 | ATX12972 | pAX5036 | B-50048 | May 29, 2007 |
| axmi-064 | ATX12972 | pAX5036 | B-50048 | May 29, 2007 |

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, *Bacillus* sp., *Clostridium bifermentans* and *Paenibacillus popilliae*. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Pesticidal proteins encompass delta-endotoxins. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiensis* toxin nomenclature," at www.biols.susx.ac.uk/Home/Neil_Crickmore/Bt/index.

Also provided herein are nucleotide sequences encoding polypeptides with homology to several other known classes of pesticidal protein toxins. For example, axmi-011, axmi-012, axmi-015, axmi-032, axmi-044, axmi-033, axmi-034, axmi-022, axmi-063, and axmi-064 demonstrate homology to pesticidal binary toxins such as VIP, Bin, and MTX toxins. The VIP1/VIP2 toxins (see, for example, U.S. Pat. No. 5,770,696, herein incorporated by reference in its entirety) are binary pesticidal toxins that exhibit strong activity on insects by a mechanism believed to involve receptor-mediated endocytosis followed by cellular toxification, similar to the mode of action of other binary ("A/B") toxins. A/B toxins such as VIP, C2, CDT, CST, or the *B. anthracis* edema and lethal toxins initially interact with target cells via a specific, receptor-mediated binding of "B" components as monomers.

These monomers then form homoheptamers. The "B" heptamer-receptor complex then acts as a docking platform that subsequently binds and allows the translocation of an enzymatic "A" component(s) into the cytosol via receptor-mediated endocytosis. Once inside the cell's cytosol,"A" components inhibit normal cell function by, for example, ADP-ribosylation of G-actin, or increasing intracellular levels of cyclic AMP (cAMP). See Barth et al. (2004) *Microbiol Mol Biol Rev* 68:373-402, herein incorporated by reference in its entirety.

Aside from the A/B type binary toxins, other types of binary toxins that act as pesticidal proteins are known in the art. Cry34Ab1 and Cry35Ab1 comprise a binary toxin with pesticidal activity that was identified from strain PS149B1 (Ellis et al. (2002) *Appl Environ Microbiol.* 68:1137-45, herein incorporated by reference in its entirety). These toxins have molecular masses of approximately 14 and 44 kDa, respectively. Other binary toxins with similar organization and homology to Cry34Aa and Cry34Ab have been identified (Baum et al. (2004) *Appl Environ Microbiol.* 70:4889-98, herein incorporated by reference in its entirety).

BinA and BinB are proteins from *Bacillus sphaericus* that comprise a mosquitocidal binary toxin protein (Baumann et al. (1991) *Micriobiol. Rev.* 55:425-36). Cry35 exhibits amino acid similarity to these BinA and BinB proteins. Cry36 (ET69) and Cry38 (ET75) (International Patent Application No. WO/00/66742-B, herein incorporated by reference in its entirety) are independently isolated peptides that also exhibit amino acid similarity to BinA and BinB, and thus are likely to comprise binary toxins.

Cry23 (also known as cryET33; U.S. Pat. No. 6,063,756, herein incorporated by reference in its entirety) and Cry37 (also known as cryET34; U.S. Pat. No. 6,063,756, herein incorporated by reference in its entirety) also appear to be binary pesticidal toxins. Cry23 also exhibits homology to MTX2 and MTX3 toxins. The term "MTX" is used in the art to delineate a set of pesticidal proteins that are produced by *Bacillus sphaericus*. The first of these, often referred to in the art as MTX1, is synthesized as a parasporal crystal which is toxic to mosquitoes. The major components of the crystal are two proteins of 51 and 42 kDa, Since the presence of both proteins are required for toxicity, MTX1 is considered a "binary" toxin (Baumann et al. (1991) *Microbiol. Rev.* 55:425-436).

By analysis of different *Bacillus sphaericus* strains with differing toxicities, two new classes of MTX toxins have been identified. MTX2 and MTX3 represent separate, related classes of pesticidal toxins that exhibit pesticidal activity. See, for example, Baumann et al. (1991) *Microbiol. Rev.* 55:425-436, herein incorporated by reference in its entirety. MTX2 is a 100-kDa toxin. More recently MTX3 has been identified as a separate toxin, though the amino acid sequence of MTX3 from *B. sphaericus* is 38% identitical to the MTX2 toxin of *B. sphaericus* SSII-1 (Liu, et al. (1996) *Appl. Environ. Microbiol.* 62: 2174-2176).

Thus, provided herein are novel isolated nucleotide sequences that confer pesticidal activity. These isolated nucleotide sequences encode polypeptides with homology to known delta-endotoxins or binary toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated nucleic acid molecule encoding a pesticidal protein can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A pesticidal protein that is substantially free of cellular material includes preparations of protein having less than about 30%, 20%, 10%, or 5% (by dry weight) of non-pesticidal protein (also referred to herein as a "contaminating protein").

Nucleotide sequences encoding the proteins of the present invention include the sequence set forth in SEQ ID NO:1, 3, 5, 8, 10, 12, 14, 16, 18, 20, 22, 24, 26, 28, 30, 32, 34, 36, or 60, or the nucleotide sequence deposited in a bacterial host as Accession No. NRRL B-30961, B-30955, B-30956, B-30957, B-30958, B-30942, B-30939, B-30941, B-50047, B-30959, B-30960, B-30943, or B-50048, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the pesticidal protein encoded by this nucleotide sequence are set forth in SEQ ID NO:2, 4, 6, 7, 9, 11, 13, 15, 17, 19, 21, 23, 25, 27, 29, 31, 33, 35, 37 or 61.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein (for example, 957 nucleotides for SEQ ID NO:1; 927 nucleotides for SEQ ID NO:3, 1017 nucleotides for SEQ ID NO:5; 1422 nucleotides for SEQ ID NO:8, 1053 nucleotides for SEQ ID NO:10; 1062 nucleotides for SEQ ID NO:12, 942 nucleotides for SEQ ID NO:14, etc.) depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. By "retains activity" is intended that the fragment will have at least about 30%, at least about 50%, at least about 70%, 80%, 90%, 95% or higher of the pesticidal activity of the pesticidal protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention (for example, 318 amino acids for SEQ ID NO:2, 308 amino acids for SEQ ID NO:4, 338 amino acids for SEQ ID NO:6, 296 amino acids for SEQ ID NO:7, 473 amino acids for SEQ ID NO:9, 351 amino acids for SEQ ID NO:11, 353 amino acids for SEQ ID NO:13, and 314 amino acids for SEQ ID NO:15, etc.).

Preferred pesticidal proteins of the present invention are encoded by a nucleotide sequence sufficiently identical to the nucleotide sequence of SEQ ID NO:1, 3, 5, 8, 10, 12, 14, 16, 18, 20, 22, 24, 26, 28, 30, 32, 34, 36, or 60. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in "jelly-roll" formation (de Maagd et al., 2001, supra). Domains II and III are involved in receptor recognition and binding, and are therefore considered determinants of toxin specificity.

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical between all proteins contained in the alignment in FIG. 1, 2, 3, or 4). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment in FIG. 1, 2, 3, or 4). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal protein sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:2, 4, 6, 7, 9, 11, 13, 15, 17, 19, 21, 23, 25, 27, 29, 31, 33, 35, 37 or 61. Fragments, biologically active portions, and variants thereof are also provided, and may be used to practice the methods of the present invention.

"Fragments" or "biologically active portions" include polypeptide fragments comprising amino acid sequences sufficiently identical to the amino acid sequence set forth in SEQ ID NO:2, 4, 6, 7, 9, 11, 13, 15, 17, 19, 21, 23, 25, 27, 29, 31, 33, 35, 37 or 61, and that exhibit pesticidal activity (for example, SEQ ID NO:7). A biologically active portion of a pesticidal protein can be a polypeptide that is, for example, 10, 25, 50, 100, 150, 200, 250 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 4, 6, 7, 9, 11, 13, 15, 17, 19, 21, 23, 25, 27, 29, 31, 33, 35, 37 or 61. The invention encompasses other fragments, however, such as any fragment in the protein greater than about 10, 20, 30, 50, 100, 150, 200, 250, or 300 amino acids.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of SEQ ID NO:2, 4, 6, 7, 9, 11, 13, 15, 17, 19, 21, 23, 25, 27, 29, 31, 33, 35, 37 or 61. Variants also include polypeptides encoded by a nucleic acid molecule that hybridizes to the nucleic acid molecule of SEQ ID NO:1, 3, 5, 8, 10, 12, 14, 16, 18, 20, 22, 24, 26, 28, 30, 32, 34, 36, or 60, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:2, 4, 6, 7, 9, 11, 13, 15, 17, 19, 21, 23, 25, 27, 29, 31, 33, 35, 37 or 61, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}P$ target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape., etc.).

Use in Pesticidal Control

General methods for employing strains comprising a nucleotide sequence of the present invention, or a variant thereof, in pesticide control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm;

*Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctate*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; zygogramma exclamationis, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabs*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise introducing into a plant or plant cell a polynucleotide comprising a pesticidal sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

The following examples are offered by way of illustration and not by way of limitation.

EXPERIMENTAL

Example 1

Extraction of Plasmid DNA

Strains ATX14759, ATX14875, ATX13008, ATX13002, ATX9387, ATX13045, ATX21738, ATX14833, ATX1489, ATX15398 and ATX12972 were selected for analysis. Pure cultures of each strain were grown in large quantities of rich media. The cultures were centrifuged to harvest the cell pellet. The cell pellet was then prepared by treatment with SDS by methods known in the art, resulting in breakage of the cell wall and release of DNA. Proteins and large genomic DNA were then precipitated by a high salt concentration. The plasmid DNA was then precipitated with ethanol. In several instances, the plasmid DNA was separated from any remaining chromosomal DNA by high-speed centrifugation through a cesium chloride gradient. Alternatively, the plasmid DNA was purified by binding to a resin, as known in the art. For each strain, the quality of the DNA was checked by visualization on an agarose gel by methods known in the art.

Example 2

Cloning of Genes

DNA libraries were prepared from the plasmid DNA or each strain. This may be achieved in many ways as known in the art. For, example, the purified plasmid DNA can be sheared into 5-10 kb sized fragments and the 5' and 3' single stranded overhangs repaired using T4 DNA polymerase and Klenow fragment in the presence of all four dNTPs, as known in the art. Phosphates can then be attached to the 5' ends by treatment with T4 polynucleotide kinase, as known in the art. The repaired DNA fragments can then be ligated overnight into a standard high copy vector (i.e. pBLUESCRIPT™ SK+), suitably prepared to accept the inserts as known in the art (for example by digestion with a restriction enzyme producing blunt ends).

The quality of the resulting DNA libraries was analyzed by digesting a subset of clones with a restriction enzyme known to have a cleavage site flanking the cloning site. A high percentage of clones were determined to contain inserts, ideally with an average insert size of 5-6 kb.

Example 3

High Throughput Sequencing of Library Plates

Once the DNA library quality was checked and confirmed, colonies were grown in a rich broth in 2 ml 96-well blocks overnight at 37° C., typically at a shaking speed of 350 rpm. The blocks were centrifuged to harvest the cells to the bottom of the block. The blocks were then prepared by standard alkaline lysis prep in a high throughput format.

The end sequences of clones from this library were then determined for a large number of clones from each block in the following manner: The DNA sequence of each clone chosen for analysis was determined using the fluorescent dye terminator sequencing technique (Applied Biosystems), by methods known in the art using an automated DNA sequencing machine, and standard oligonucleotide primers that anneal to the plasmid vector in the region flanking the insert.

Example 4

Assembly and Screening of Sequencing Data

DNA sequences obtained were compiled into an assembly project and aligned together to form contigs. This can be done efficiently using a computer program, such as Vector NTI, or alternatively by using the Phred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further.

Example 5 axmi-037

From strain ATX1489, clone pAX2558 was found to contain an open reading frame with homology to "cry" type delta-endotoxins. This open reading frame was designated as axmi-037 (SEQ ID NO:16). Inspection of the axmi-037 open reading frame suggests that more than one start codon may be present. The two predicted start codons are the ATG codon beginning at nucleotide position 1 of SEQ ID NO:16, and a downstream ATG codon (represented by SEQ ID NO:18). The ATG at nucleotide 77 of SEQ ID NO:16 has a ribosome binding site sequence (5'-G-G-A-G-G-3'), located at nucleotide positions 63-67 of SEQ ID NO:16. Based on the presence of this strong ribosome binding consensus sequence immediately upstream of this second start site, and the homology of the two predicted proteins to other endotoxins, the translation product of the downstream start site is herein designated AXMI-037 (SEQ ID NO:19). The longer translation product, beginning at the ATG at nucleotide position 1 of SEQ ID NO:16, is designated AXMI-37-2 (and set forth in SEQ ID NO:17). pAX2558 was deposited with the ARS Patent Strain Collection on Jun. 15, 2006, and assigned NRRL B-30939. AXMI-37-2 exhibits 60% amino acid identity to the Cry7Aa1 endotoxin.

Example 6 axmi-019

From strain ATX14875, a clone was found to contain an open reading frame with homology to MTX family toxins. This open reading frame was designated as axmi-019 (SEQ ID NO:10), and the encoded protein was designated AXMI-019 (SEQ ID NO:11). By searching of public databases of protein sequences, such as the GenPept database, the C-terminal region of AXMI-019 (starting at approximately amino acid 123 of SEQ ID NO:11) was found to have low homology to a class of toxins including *Bacillus thuringiensis serovar darmstadiensis* Cry14-4 toxin (SEQ ID NO:42; encoded by GENBANK® ID AAV70918.1), and the *Bacillus sphaericus* MTX2 protein (SEQ ID NO:16, GENBANK® ID AAC44124.1).

Example 7 axmi-011, axmi-012 and axmi-015

From strain ATX13008, three individual clones were found to contain open reading frames with homology to MTX-like toxins. These open reading frames were designated axmi-011 (SEQ ID NO:1), axmi-012 (SEQ ID NO:3), and axmi-015 (SEQ ID NO:8), and the encoded proteins are designated AXMI-011 (SEQ ID NO:2), AXMI-012 (SEQ ID NO:4), and AXMI-015 (SEQ ID NO:9), respectively. By searching of public databases of protein sequences, AXMI-011 was found to have low homology to a class of toxins including MTX2 (SEQ ID NO:16); AXMI-015 was found to have low homology (about 35% amino acid identify over 178 amino acids) to a mosquitocidal toxin from *Bacillus thuringiensis* israelensis RBTH 02046 (SEQ ID NO:41, GENBANK® ID gi|75761628:1-79; AXMI-012 was found to have homology (29% over 217 amino acids) to a class of toxins including the p42 binary toxin of *Bacillus sphaericus* (SEQ ID NO:39; GENBANK® ID CAA73761).

Inspection of the axmi-011 coding region reveals the existence of an alternate translational start site 12 nucleotides upstream of the ATG start of axmi-011. This open reading frame contains a 5' extension of the following twelve nucleotides

```
5'-G-T-G-A-T-G-A-A-A-A-A-A-3'    (SEQ ID NO: 59)
```

immediately upstream and adjacent to the axmi-11 open reading frame. This open reading frame is herein designated as axmi-011(long) (SEQ ID NO:60). Translation of axmi-011 utilizing the putative GTG start would result in a modified AXMI-011 protein that contains an N-terminal extension of four amino acids (amino acid residues 1 through 4 of SEQ ID NO:61).

Analysis of the DNA context surrounding the two potential start sites reveals a sequence with a good match to the consensus for a ribosome binding site 5' G-T-G-A-T-G-3' (SEQ ID NO:62) positioned from −10 to −6 nt relative to the ATG start codon of SEQ ID NO:1. This is a proper position for a bacterial ribosome binding site. No obvious homology to the consensus ribosome start site is observed in the position 15 nt upstream of the putative GTG start site. Thus, the protein initiated from the ATG start codon is designated AXMI-011 (SEQ ID NO:2). The protein encoded by translation initiated at the GTG start codon is designated AXMI-011(LONG) (SEQ ID NO:61).

Example 8 axmi-032

From strain ATX9387, a plasmid was found to contain an open reading frame with homology to pesticidal toxins. This open reading frame was designated as axmi-032 (SEQ ID NO:12), and the encoded protein was designated AXMI-032 (SEQ ID NO:13). By searching of public databases of protein sequences, such as the GenPept database, AXMI-032 was found to have homology to a class of toxins including a presumed binary toxin from *Bacillus thuringiensis* (SEQ ID NO:43; GENBANK® Accession No. CAD30104.1) which is a possible two-domain toxin from *Bacillus thuringiensis serovar israelensis.*

Example 9 axmi-013

From strain ATX13002, a clone was found to contain an open reading frame with homology to "cry" type delta-endotoxins. This open reading frame was designated as axmi-013 (SEQ ID NO:5), and the encoded protein was designated AXMI-013 (SEQ ID NO:6). By searching of public databases of protein sequences, the C-terminal region of AXMI-013 was found to have 52% identity with the MTX3 toxin (SEQ ID NO:40: GENBANK® ID AAB36661).

Example 10

Expression of AXMI-013 in *Bacillus*

The insecticidal AXMI-013 gene is amplified by PCR and cloned into the *Bacillus* expression vector pAX916 by methods well known in the art. The resulting clone is assayed for expression of AXMI-013 protein after transformation into cells of a cry(−) *Bacillus thuringiensis* strain. A *Bacillus* strain containing the axmi-013 clone and expressing the AXMI-013 insecticidal protein is grown in, for example, CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation is evident by microscopic examination. Samples are prepared, and analyzed by polyacrylamide gel electrophoresis (PAGE). AXMI-013 is tested for insecticidal activity in bioassays against important insect pests.

Inspection of the predicted amino acid sequence of AXMI-013 (SEQ ID NO:6) suggested that the N-terminus of the full-length AXMI-013 protein may comprise a signal peptide for secretion. The predicted site of cleavage was estimated to be between the alanine at position 27 and lysine at position 28 of SEQ ID NO:6. Similarly, MTX3 (SEQ ID NO:40) is predicted to possess a secretion signal peptide at its N-terminus (Liu, et al. (1996) *Appl. Environ. Microbiol.* 62:2174-2176).

The expressed AXMI-013 protein was excised from a polyacrylamide gel and subjected to N-terminal sequence analysis as known in the art. The N-terminal sequence identified by this analysis corresponded to a N-terminal truncation of the AXMI-013 protein, resulting in a truncated peptide with an N-terminus corresponding to the glutamine (Q) at amino acid position 40 of SEQ ID NO:6. This truncated protein is referred to herein as AXMI-013(Q), and the amino acid sequence of this protein is provided in SEQ ID NO:7. As known in the art, prediction of the exact site of cleavage is somewhat difficult. Nonetheless, the cleavage at approximately amino acid position 40 of SEQ ID NO:6 suggests that either (1) AXMI-013 is further processed after initial cleavage at amino acid positions 27/28, or AXMI-013 has a novel secretion signal. In order to confirm this, one skilled in the art may make gene fusion constructs utilizing (1) a heterologous protein and (2) using increasing length portions of AXMI-013. One can then test for secretion of the marker protein and determine the processing sites by N-terminal sequencing. Other methods to determine the extent of the signal sequence are known in the art.

Example 11 axmi-023 and axmi-041

From strain ATX13045, a plasmid clone was found to contain an open reading frame with homology to "cry" type delta-endotoxins. This open reading frame was designated as axmi-023 (SEQ ID NO:30), and the encoded protein was designated AXMI-023 (SEQ ID NO:31). BLAST search of the non-redundant 'nr' database demonstrates that AXMI-023 has low amino acid identity (less than 30% amino acid identity) with the VIP2 protein toxin, as well as several other presumed or known toxins. (GENBANK® Accession No. AA086513.1, SEQ ID NO:55)

From strain ATX21738, a plasmid clone was found to contain an open reading frame with homology to "cry" type delta-endotoxins. This open reading frame was designated as axmi-041 (SEQ ID NO:32), and the encoded protein was designated AXMI-041 (SEQ ID NO:33). pAX4310 was deposited with the ARS Patent Strain Collection on Jun. 15, 2006, and assigned NRRL B-30943. AXMI-041 is 21% identical to AXMI-023, and similarly exhibits low amino acid identity (less than 30% amino acid identity) with the VIP2 protein toxin, as well as several other presumed or known toxins. A search of DNA and protein databases with the DNA sequences and amino acid sequences of AXMI-023 and AXMI-041 revealed that they are homologous to known pesticidal proteins. FIG. 4 shows an alignment of AXMI-023 with the Vip2 pesticidal protein (SEQ ID NO:55), and several related toxins. AXMI-041 also shows homology with this class of toxins.

Example 12

AXMI-022 Defines a Novel Class of Pesticidal Proteins

From strain ATX13045, a plasmid clone was found to contain an open reading frame with homology to known insect toxins. This open reading frame was designated as axmi-022 (SEQ ID NO:28), and the encoded protein was designated AXMI-022 (SEQ ID NO:29).

The amino acid sequence of AXMI-022 is 64.9% identical to Vip1A(b) (SEQ ID NO:52; see also U.S. Pat. No. 5,770,696, herein incorporated by reference in its entirety) throughout the length of Vip1A(b), and has significant amino acid identity with several other binary protein toxins. Further analysis of AXMI-022 revealed the following features of this polypeptide:

AXMI-022 is significantly longer than other binary proteins to which it shares homology, and encodes a peptide of 1,003 amino acids. For example, the Vip1A(b) protein is 834 amino acids in length;

Inspection of the DNA region surrounding the axmi-022 open reading frame shows no evidence for a second ORF encoding a toxin domain. The genes encoding binary toxins are typically physically closely linked. Most often, both the toxin and the receptor protein are organized as adjacent open reading frames, and are often transcriptionally linked in an operon.

The receptor binding region of AXMI-022 (from about amino acid 640 to about amino acid 770 of SEQ ID NO:29) is different from other binary toxins. The region of AXMI-022 corresponding to the region of binary proteins involved in receptor binding is quite different in AXMI-022 compared to other binary proteins. This is suggestive that AXMI-022 binds to a different receptor than other binary proteins The C-terminal 133 amino acids of AXMI-022 (starting about amino acid 870 of SEQ ID NO:29) show amino acid homology to the Cry37Aa binary protein (SEQ ID NO:54; GENBANK® Accession No. AAF76376; U.S. Pat. No. 6,063,756, herein incorporated by reference in its entirety). This region has homology to Cry37Aa at a sequence identity of about 36%. Cry37Aa is in a different class of binary toxins than the Vip1-type toxins. Cry37Aa belongs to the Cry34 family, which forms a binary toxin with the Cry35 family. Cry34Ab1 is principally responsible for forming pores in lipid membranes, while Cry35Ab1 enhances the formation of pores (Masson, et al. (2004) *Biochemistry* 43:12349-57).

Thus, AXMI-022 appears to be a novel type of "single peptide" binary toxin, having homology to multiple classes of binary proteins, with a receptor-binding component from one class of binary toxins directly fused to a toxin component from a different class of binary toxins. This organization of domains has not been previously predicted in the art.

Example 13 axmi-043

From strain ATX15398, pAX2597 was found to contain an open reading frame with homology to "cry" type delta-endotoxins. This open reading frame was designated as axmi-043. pAX2597 was deposited with the ARS Patent Strain Collection on Jun. 15, 2006, and assigned NRRL B-30941. Inspection of the axmi-043 open reading frame suggests that more than one start codon may be present. The ATG at position 46 of SEQ ID NO:20 has a ribosome binding site (5' G-G-A-G-A-3') (SEQ ID NO:63) starting at nucleotide 33 of SEQ ID NO:20. Based on the presence of this strong ribosome binding consensus sequence immediately upstream of this second start site, and the homology of the two predicted proteins to other endotoxins, we herein designate the translation product of the internal start site (represented by SEQ ID NO:22) as AXMI-043 (SEQ ID NO:23), and the longer protein as AXMI-043-2 (SEQ ID NO:21). AXMI-043 exhibits 93% amino acid identity to the AXMI-028 endotoxin, and AXMI-43-2 is 90% identical to AXMI-028 (SEQ ID NO:45 of this application, see also U.S. patent application Ser. No. 11/416,261, herein incorporated by reference in its entirety). AXMI-043 appears to be a "full-length endotoxin," and contains a C-terminal region (after the aspartic residue at position 629 of the AXMI-043 amino acid sequence) often referred to in the art as a non-toxic domain or a "crystal domain." AXMI-043 exhibits 54% amino acid identity with the Cry7Aa1 endotoxin (SEQ ID NO:46) throughout the full length of the protein.

Example 14 axmi-44

From strain ATX14759, pAX2599 was found to contain an open reading frame with homology to "cry" type delta-endotoxins. This open reading frame was designated as axmi-044 (SEQ ID NO:14), and the encoded protein was designated AXMI-044 (SEQ ID NO:15). pAX2599 was deposited with the ARS Patent Strain Collection on Jun. 15, 2006, and assigned Accession No. NRRL B-30942. By searching of public databases of protein sequences, such as the GenPept database maintained by the NCBI (National Center for Biotechnology Information) AXMI-044 was found to have low homology to the cry-15Aa/cry33 family of toxins (SEQ ID NO:44, GENBANK® ID 8928022), and to MTX2 (SEQ ID NO:38).

Example 15 axmi-033 and axmi-034

From strain ATX14833, a plasmid clone was found to contain two open reading frames with homology to insect toxins. The first open reading frame was designated as axmi-033 (SEQ ID NO:24), and the encoded protein was designated AXMI-033 (SEQ ID NO:25). AXMI-33 exhibits 61% amino acid identity to the 326 amino acid CryC35 insect toxin (SEQ ID NO:47, encoded by GENBANK® reference CAA63374). The second open reading frame was designated as axmi-034 (SEQ ID NO:26), and the encoded protein was designated AXMI-034 (SEQ ID NO:27). AXMI-34 exhibits 45% amino acid identity with the CryC53 endotoxin. (SEQ ID NO:48, encoded by GENBANK® reference CAA67205).

axmi-033 and axmi-034 appear to comprise an operon. The ATG start of axmi-034 is immediately 3' to, and in close proximity of (15 nucleotides immediately downstream of), the TAA stop codon of axmi-033. This organization is well known in the art to suggest that two genes comprise an operon. Thus, the AXMI-033 and AXMI-034 proteins are likely to be co-expressed in their native strain. It is likely that the activities of the two proteins expressed together may be synergistic and superior to the activity of the proteins expressed separately. pAX4341, a clone containing both axmi-033 and axmi-034 open reading frames, was deposited with the ARS Patent Strain Collection on May 29, 2007, and assigned accession number NRRL B-50047.

Example 16 axmi-063 and axmi-064

From strain ATX12972, a plasmid clone was found to contain two open reading frames with homology to insect toxins. The first open reading frame was designated as axmi-063 (SEQ ID NO:34), and the encoded protein was designated AXMI-063 (SEQ ID NO:35). AXMI-63 exhibits 53.1% amino acid identity to the CryC35 insect toxin (SEQ ID NO:47, encoded by GENBANK® reference CAA63374). The second open reading frame was designated as axmi-064 (SEQ ID NO:36), and the encoded protein was designated AXMI-064 (SEQ ID NO:37). AXMI-64 exhibits 44.3% amino acid identity with the CryC53 endotoxin (SEQ ID NO:48, encoded by GENBANK® reference CAA67205).

axmi-063 and axmi-064 appear to comprise an operon. The ATG start of axmi-064 is immediately 3' to, and in close proximity of, the TAA stop codon of axmi-063. This is an organization well known in the art to suggest that two genes comprise an operon. Thus, the AXMI-063 and AXMI-064 proteins are likely to be co-expressed in their native strain. It is likely that the activities of the two proteins expressed together may be synergistic and superior to the activity of the proteins expressed separately. pAX5036, a clone containing both axmi-063 and axmi-064 open reading frames, was deposited with the ARS Patent Strain Collection on May 29, 2007, and assigned NRRL B-50048.

AXMI-033/AXMI-034 are similar to AXMI-063/AXMI-064. Analysis of the amino acid sequence of AXMI-033, AXMI-043, AXMI-063, and AXMI-064 reveals that AXMI-033 and AXMI-063 share significant amino acid identity, and are 69% identical. Similarly AXMI-034 and AXMI-064 share significant amino acid similarity (52% identical).

Example 17

Homology of AXMI-011, AXMI-012, AXMI-013, AXMI-015, AXMI-032, and AXMI-044 to Known Pesticidal Protein Genes A search of protein databases with the amino acid sequences of the proteins of the invention reveal that they are homologous to known pesticidal proteins. Comparison of the amino acid sequences of the proteins of the invention to the non-redundant (nr) database maintained by the NCBI using the BLAST algorithm revealed the following proteins as having the strongest block of amino acid identity to the sequences of the invention (Table 2). Thus, the proteins of the invention are “pesticidal proteins.”

TABLE 2

Amino Acid Identity of AXMI-011, AXMI-012, AXMI-013, AXMI-015, AXMI-032, and AXMI-044 to mosquito toxins in public databases

| PROTEIN | Highest Blast Hit (nr) | % Identity in block |
|---|---|---|
| AXMI-011 | MTX2 | 28% |
| AXMI-012 | P42 component of binary toxin | 29% |
| AXMI-013 | MTX3 | 52% |
| AXMI-015 | RBTH_02046 | 35% |
| AXMI-019 | Cry14-4, MTX2 | 35%, 30% |
| AXMI-032 | GENBANK ® ID CAD30104.1 | 19% |
| AXMI-044 | cry15Aa, MTX2 | 30%, 30% |

Example 18

Additional Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests* and *Journal of Economic Entomology* or by discussion with members of the Entomological Society of America (ESA).

Example 19

Vectoring of axmi Genes for Plant Expression

The coding regions of the invention are connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

In one aspect of the invention, synthetic DNA sequences are designed and generated. These synthetic sequences have altered nucleotide sequence relative to the parent sequence, but encode proteins that are essentially identical to the parent AXMI protein.

In another aspect of the invention, modified versions of the synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (GENEBANK® ID GI:14276838, Miller et al. (2001) *Plant Physiology* 127: 594-606) is known in the art to result in endoplasmic reticulum targeting of heterologous proteins. If the resulting fusion protein also contains an endoplasmic reticulum retention sequence comprising the peptide N-terminus-lysine-aspartic acid-glutamic acid-leucine (i.e., the "KDEL" motif (SEQ ID NO:58)) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Thus, this gene encodes a fusion protein that contains the N-terminal thirty-one amino acids of the acid phosphatase gene from the White Lupin *Lupinus albus* (GENBANK® ID GI:14276838, Miller et al., 2001, supra) fused to the N-terminus of the AXMI sequence, as well as the KDEL sequence at the C-terminus. Thus, the resulting protein is predicted to be targeted the plant endoplasmic reticulum upon expression in a plant cell.

The plant expression cassettes described above are combined with an appropriate plant selectable marker to aid in the selection of transformed cells and tissues, and ligated into plant transformation vectors. These may include binary vectors from *Agrobacterium*-mediated transformation or simple plasmid vectors for aerosol or biolistic transformation.

Example 20

Vectoring of axmi Genes for Plant Expression

The coding region DNA of the axmi genes of the invention are operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

Example 21

Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials
DN62A5S Media

| Components | Per Liter | Source |
|---|---|---|
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 22

Transformation of the Pesticidal Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

Example 23

Soil Infestation of Plants Expressing a Gene of the Invention with Western Corn Rootworm Transgenic plants containing an axmi gene of the invention under the control of a plant promoter are tested for resistance to infestation by Western corn rootworm (WCRW). Plantlets are transplanted from tissue culture media to root trainer (clamshell) pots known in the art to be useful for growth of plantlets in soil. Plants are grown for about 2 weeks in a greeenhouse. Transgenic plants, as well as untransformed controls, are infested with approximately 1,000 WCRW eggs. WCRW eggs are preincubated such that eggs are at the point of hatching when infested onto the plants. Plants are held for about four weeks, or until controls exhibited obvious damage due to the rootworms. At this stage, plants are pulled from pots, roots are washed, and damage evaluated. Several independent events are examined for reduced damage from WCRW infestation relative to non-transformed control plants.

The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An expression construct comprising a nucleotide sequence selected from the group consisting of:

a) the nucleotide sequence of SEQ ID NO:1 or 60, or a complement thereof;

b) a nucleotide sequence that encodes a polypeptide comprising the amino acid sequence of SEQ ID NO:2 or 61; and c) the nucleotide sequence of the DNA insert of the plasmid deposited as Accession No. NRRL B-30961, or a complement thereof;

wherein said nucleotide sequence is operably linked to a heterologous promoter.

2. The expression construct of claim 1, wherein said heterologous promoter is capable of directing expression of the nucleotide sequence in a plant cell.

3. The expression construct of claim 1, wherein said nucleotide sequence is a synthetic sequence that has been designed for expression in a plant.

4. A vector comprising the expression construct of claim 1.

5. The vector of claim 4, further comprising a nucleic acid molecule encoding a heterologous polypeptide.

6. A host cell that contains the expression construct of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the expression construct of claim 1.

12. A fusion protein with pesticidal activity said protein comprising heterologous signal or leader sequence operably linked to a polypeptide selected from the group consisting of:

a) a polypeptide comprising the amino acid sequence of SEQ ID NO:2 or 61;

b) the polypeptide that is encoded by the nucleotide sequence of SEQ ID NO: 1 or 60; and c) the polypeptide encoded by the nucleotide sequence of the DNA insert of the plasmid deposited as Accession No. NRRL B-30961.

13. A composition comprising the fusion protein of claim 12.

14. The composition of claim 13, wherein said composition is selected from the group consisting of a powder, dust, pellet, granule, spray, emulsion, colloid, and solution.

15. The composition of claim 13, wherein said composition is prepared by desiccation, lyophilization, homogenization, extraction, filtration, centrifugation, sedimentation, or concentration of a culture of bacterial cells.

16. The composition of claim 13, comprising from about 1% to about 99% by weight of said fusion protein.

17. A method for killing or controlling a lepidopteran pest population, said method comprising contacting said population with a pesticidally-effective amount of the fusion protein of claim 12.

18. A method for producing a polypeptide with pesticidal activity, said method comprising culturing the host cell of claim 6 under conditions in which the nucleotide sequence encoding the polypeptide is expressed.

19. A plant or plant cell having stably incorporated into its genome a DNA construct comprising a nucleotide sequence that encodes a protein having pesticidal activity against a lepidopteran pest, wherein said nucleotide sequence is selected from the group consisting of:

a) the nucleotide sequence of SEQ ID NO: 1 or 60;

b) a nucleotide sequence that encodes a polypeptide comprising the amino acid sequence of SEQ ID NO:2 or 61; and c) the nucleotide sequence of the DNA insert of the plasmid deposited as Accession No. NRRL B-30961;

wherein said nucleotide sequence is operably linked to a promoter that drives expression of a coding sequence in a plant cell.

20. The plant or plant cell of claim 19, which is a plant cell.

21. A method for protecting a plant from a pest, said method comprising introducing into the genome of said plant or cell thereof at least one expression vector comprising a nucleotide sequence that encodes a pesticidal polypeptide, wherein said nucleotide sequence is selected from the group consisting of:

a) the nucleotide sequence of SEQ ID NO: 1 or 60;

b) a nucleotide sequence that encodes a polypeptide comprising the amino acid sequence of SEQ ID NO:2 or 61; and c) the nucleotide sequence of the DNA insert of the plasmid deposited as Accession No. NRRL B-30961.

* * * * *